(12) United States Patent
Gupta et al.

(10) Patent No.: US 12,291,562 B2
(45) Date of Patent: May 6, 2025

(54) REAGENTS AND ASSAYS USING MODIFIED INTEGRIN DOMAINS

(71) Applicants: Rush University Medical Center, Chicago, IL (US); 149 Bio, LLC, Miami, FL (US)

(72) Inventors: Vineet Gupta, Chicago, IL (US); Antonio J. Barbosa, Ave Maria, FL (US)

(73) Assignees: Rush University Medical Center, Chicago, IL (US); 149 Bio, LLC, Miami, FL (US)

( * ) Notice: Subject to any disclaimer, the term of this patent is extended or adjusted under 35 U.S.C. 154(b) by 683 days.

(21) Appl. No.: 17/599,625

(22) PCT Filed: Mar. 31, 2020

(86) PCT No.: PCT/US2020/025898
§ 371 (c)(1),
(2) Date: Sep. 29, 2021

(87) PCT Pub. No.: WO2020/205827
PCT Pub. Date: Oct. 8, 2020

(65) Prior Publication Data
US 2022/0204585 A1    Jun. 30, 2022

Related U.S. Application Data

(60) Provisional application No. 62/827,461, filed on Apr. 1, 2019.

(51) Int. Cl.
*C07K 14/705* (2006.01)
*A61K 38/00* (2006.01)

(52) U.S. Cl.
CPC ........ *C07K 14/70553* (2013.01); *A61K 38/00* (2013.01); *C07K 2319/21* (2013.01); *C07K 2319/50* (2013.01)

(58) Field of Classification Search
CPC .......... C07K 14/70553; C07K 2319/21; C07K 2319/50; A61K 38/00
See application file for complete search history.

(56) References Cited

U.S. PATENT DOCUMENTS

| | | |
|---|---|---|
| 4,522,811 A | 6/1985 | Eppstein et al. |
| 4,526,938 A | 7/1985 | Churchill et al. |
| 4,873,192 A | 10/1989 | Kunkel |
| 4,880,078 A | 11/1989 | Inoue et al. |
| 5,128,326 A | 7/1992 | Balazs et al. |
| 5,290,540 A | 3/1994 | Prince et al. |
| 5,374,548 A | 12/1994 | Caras |
| 5,399,331 A | 3/1995 | Loughrey et al. |
| 5,416,016 A | 5/1995 | Low et al. |
| 5,591,828 A | 1/1997 | Bosslet et al. |
| 5,679,377 A | 10/1997 | Bernstein et al. |
| 5,855,913 A | 1/1999 | Hanes et al. |
| 5,874,064 A | 2/1999 | Edwards et al. |
| 5,912,015 A | 6/1999 | Bernstein et al. |
| 5,916,597 A | 6/1999 | Lee et al. |
| 5,934,272 A | 8/1999 | Lloyd et al. |
| 5,985,309 A | 11/1999 | Edwards et al. |
| 5,985,320 A | 11/1999 | Edwards et al. |
| 5,989,463 A | 11/1999 | Tracy et al. |
| 6,005,079 A | 12/1999 | Casterman et al. |
| 6,019,968 A | 2/2000 | Platz et al. |
| 6,316,024 B1 | 11/2001 | Allen et al. |
| 6,350,466 B1 | 2/2002 | Li et al. |
| 7,064,180 B2 | 6/2006 | Arnaout et al. |
| 8,241,627 B2 | 8/2012 | Springer et al. |
| 2005/0260192 A1 | 11/2005 | Springer et al. |

FOREIGN PATENT DOCUMENTS

| | | |
|---|---|---|
| EP | 404097 B1 | 9/1996 |
| WO | 9105548 A1 | 5/1991 |
| WO | 9219244 A2 | 11/1992 |
| WO | 9301161 A1 | 1/1993 |
| WO | 9404678 A1 | 3/1994 |
| WO | 9425591 A1 | 11/1994 |
| WO | 9620698 A2 | 7/1996 |
| WO | 9732572 A2 | 9/1997 |
| WO | 9744013 A1 | 11/1997 |
| WO | 9831346 A1 | 7/1998 |
| WO | 9915154 A1 | 4/1999 |
| WO | 9920253 A1 | 4/1999 |
| WO | 9966903 A2 | 12/1999 |
| WO | 2002/09737 A1 | 2/2002 |
| WO | 02088346 A2 | 11/2002 |
| WO | 13165613 A1 | 11/2013 |

OTHER PUBLICATIONS

Michishita et al, A Novel Divalent Cation-Binding Site in the A Domain of the beta2 Integrin CR3 (CD11b/CD18) Is Essential for Ligand Binding, Cell, 1993, 72, pp. 857-867.*
Integrin alpha-M isoform 2 precursor [*Homo sapiens*], from https://www.ncbi.nlm.nih.gov/protein/NP_000623, 2024, pp. 1-6.*
Amann et al., (1988) Gene 69:301-315.
Arnaout MA, Biology and structure of leukocyte β 2 integrins and their role in inflammation. F1000Res. Oct. 4, 2016;5. pii: F1000 Faculty Rev-2433.
Baert et al, (2003) New Engl. J. Med. 348:601-608.
Bajic G, Yatime L, Sim RB, Vorup-Jensen T, Andersen GR. Structural insight on the recognition of surface-bound opsonins by the integrin I domain of complement receptor 3. PNAS. 2013;110:16426-16431.
Baldari, et al., (1987) EMBO J. 6:229-234).
Barton SJ, Travis MA, Askari JA, Buckley PA, Craig SE, Humphries MJ, Mould AP. Novel activating and inactivating mutations in the integrin beta1 subunit A domain. Biochem J. Jun. 1, 2004;380(Pt 2):401-7.

(Continued)

*Primary Examiner* — Li N Komatsu
(74) *Attorney, Agent, or Firm* — Barnes & Thornburg LLP

(57) ABSTRACT

Modified integrin polypeptides are provided. Methods of identifying binding agents that bind to a modified integrin polypeptide are also provided.

9 Claims, 4 Drawing Sheets
Specification includes a Sequence Listing.

(56) References Cited

OTHER PUBLICATIONS

Beniaminovitz et al, (2000) New Engl. J. Med. 342:613-619.
Bloemen et al, (1995) FEBS Lett. 357: 140.
Briscoe et al, (1995) Am. J. Physiol. 1233: 134.
Buchwald et al., (1980), Surgery 88:507.
Chafen Lu, Motomu Shimaoka, Qun Zang, Junichi Takagi, and Timothy A. Springer, Locking in alternate conformations of the integrin αLβ2 I domain with disulfide bonds reveals functional relationships among integrin domains, PNAS Feb. 27, 2001 98 (5) 2393-2398.
Challita et al., J Viral. 69(2):748-55 (1995).
Chen J, Yang W, Kim M, Carman CV, Springer TA Regulation of outside-in signaling and affinity by the beta2 I domain of integrin alphaLbeta2, Proc Natl Acad Sci U S A. Aug. 29, 2006;103(35):13062-7. Epub Aug. 18, 2006.
Chen J, Salas A, Springer TA (2003) Bistable regulation of integrin adhesiveness by a bipolar metal ion cluster. Nat Struct Biol 10:995-1001.
Chin JW, Expanding and reprogramming the genetic code of cells and animals. Annu Rev Biochem. 2014;83:379-408. doi: 10.1146/annurev-biochem-060713-035737. Epub Feb. 10, 2014.
Chothia, C. and Lesk, AM., J Mal. Biol., 196(4): 901-917 (1987).
Chothia, C. et al., Nature, 342: 877-883 (1989).
Cleek et al., (1997) Pro. Int'l. Symp. Control. Rel. Bioact. Mater. 24:853-854.
Dayhoff et al., (1978) Atlas of Protein Sequence and Structure (Natl. Biomed. Res. Found., Washington, D.C.), pp. 345-352.
Dong X, et al. (2017) Force interacts with macromolecular structure in activation of TGF-β. Nature 542:55-59.
During et al, (1989) Ann. Neurol. 25:351.
Eppstein et al, (1985) Proc. Natl. Acad. Sci. USA 82:3688-3692.
Ghosh et al, (2003) New Engl. J. Med. 348:24-32.
Gupta V., Gylling A., Alonso, J.-L., Sugimori T., Ianakiev, P., Xiong J.-P. and Arnaout M. A., The β-tail domain (βTD) regulates physiologic ligand binding to integrin CD11b/CD18, Blood, Apr. 15, 2007;109(8):3513-20. Epub Dec. 14, 2006 (DOI 10.1182/blood-2005-11-056689).
Herold et al, (2002) New Engl. J. Med. 346: 1692-1698.
Holliger et al., PNAS USA 90: 6444-6448 (1993).
Howard et al, (1989) J. Neurosurg. 7 1:105).
Hu X, Kang S, Lefort C, Kim M, Jin MM. Combinatorial libraries against libraries for selecting neoepitope activation-specific antibodies. Proc Natl Acad Sci U S A. Apr. 6, 2010;107(14):6252-7. doi: 10.1073/pnas.0914358107. Epub Mar. 22, 2010.
Huang et al., J Biol Chem, vol. 270, (1995), pp. 19008-19016.
Hudson et al., Nat. Med. 9:129-134 (2003).
Humphries, J. D., Schofield, N. R., Mostafavi-Pour, Z., Green, L. J., Garratt, A. N., Mould, A. P. and Humphries, M. J. (2005). Dual functionality of the anti-beta1 integrin antibody, 12G10, exemplifies agonistic signalling from the ligand binding pocket of integrin adhesion receptors. J. Biol. Chem. 280, 10234-10243.
Hwang et al., (1980) Proc. Natl. Acad. Sci. USA 77:4030-4034.
Hynes RO. Integrins: versatility, modulation, and signaling in cell adhesion. Cell. Apr. 3, 1992;69(1):11-25.
International Preliminary Report on Patentability, issued in PCT/US2020/025898, dated Oct. 14, 2021.
International Search Report, issued in PCT/US2020/025898, dated Aug. 27, 2020.
J. J. Killion; I. J. Fidler (1994) Immunomethods 4:273.
Jin M, Song G, Carman CV, Kim YS, Astrof NS, Shimaoka M, Wittrup DK, Springer TA. Directed evolution to probe protein allostery and integrin I domains of 200,000-fold higher affinity. Proc. Natl. Acad. Sci. U.S.A. 103 5758-5763 (2006).
K. Keinanen; M. L. Laukkanen (1994) FEBS Lett. 346: 123.
Koch-Nolte, et al., FASEB J, 21: 3490-3498 (2007).
Kunkel 1985, Proc. Natl. Acad. Sci. USA. 82: 488-492.
Kunkel et al., 1987, Methods in Enzymol, 154: 367-382.
Kurjan and Herskowitz, (1982) Cell 30:933-943.
Lahti M, Bligt E, Niskanen H, Parkash V, Brandt AM, Jokinen J, Patrikainen P, Käpylä J, Heino J, Salminen TA. Structure of collagen receptor integrin α(1)I domain carrying the activating mutation E317A. J Biol Chem. Dec. 16, 2011;286(50):43343-51.
Lam et al, (1997) Proc. Int'l. Symp. Control Rel. Bioact. Mater. 24:759-760.
Landy, Current Opinion in Biotechnology 3:699-707 (1993).
Langer (1982) Chem. Tech. 12:98-105.
Langer et al., (1981) J. Biomed. Mater. Res. 15: 267-277.
Langer, (1990), Science 249: 1527-1533.
Levy et al., (1985) Science 228: 190.
Li R, Rieu P, Griffith DL, Scott D, Arnaout MA. Two functional states of the CD11b A-domain: correlations with key features of two Mn2+-complexed crystal structures. J Cell Biol 1998;143(6):1523-1534.
Lipsky et al, (2000) New Engl. J. Med. 343: 1594-1602.
Liu et al, (1999) J. Neurol. Neurosurg. Psych. 67:451-456.
Luckow and Summers (1989) Virology 170:31-39.
Luo BH, Karanicolas J, Harmacek LD, Baker D, Springer TA, Rationally designed integrin beta3 mutants stabilized in the high affinity conformation. J Biol Chem. Feb. 6, 2009;284(6):3917-24. doi: 10.1074/jbc.M806312200. Epub Nov. 19, 2008.
Luo BH, Takagi J, Springer TA, Locking the beta3 integrin I-like domain into high and low affinity conformations with disulfides, J Biol Chem. Mar. 12, 2004;279(11):10215-21. Epub Dec. 16, 2003.
Luo B-H, Carman CV, Springer TA (2007) Structural basis of integrin regulation and signaling. Annu Rev Immunol 25:619-647.
Mahalingam B, Ajroud K, Alonso JL, Anand S, Adair BD, Horenstein AL, Malavasi F, Xiong JP, Arnaout MA. Stable coordination of the inhibitory Ca2+ ion at the metal ion-dependent adhesion site in integrin CD11b/CD18 by an antibody-derived ligand aspartate: implications for integrin regulation and structure-based drug design. J Immunol. Dec. 15, 2011;187(12):6393-401.
McCleverty CJ, Liddington RC. Engineered allosteric mutants of the integrin alphaMbeta2 I domain: structural and functional studies. Biochem J. May 15, 2003;372(Pt 1):121-7.
Milgrom et al., (1999) New Engl. J. Med. 341 : 1966-1973.
Ning et al, (1996), Radiotherapy & Oncology 39: 179-189.
Owais et al., (1995) Antimicrob. Agents Chemother. 39: 180.
Pluckthun, in The Pharmacology of Monoclonal Antibodies, vol. 113, Rosenburg and Moore eds., (Springer-Verlag, New York, 1994), pp. 269-315.
Portielji et al., (2003) Cancer Immunol. Immunother. 52: 133-144.
Ranade, (1989) J. Clin. Pharmacol. 29:685.
Langer and Peppas, (1983) J. Macromol. Sci. Rev. Macromol. Chem. 23:61.
Riechmann L. et al., J Immunol. Methods 231:25-38 (1999).
Samy KP, Anderson DJ, Lo DJ, Mulvihill MS, Song M, Farris AB, Parker BS, MacDonald AL, Lu C, Springer TA, Kachlany SC, Reimann KA, How T, Leopardi FV, Franke KS, Williams KD, Collins BH, Kirk AD. Selective Targeting of High-Affinity LFA-1 Does Not Augment Costimulation Blockade in a Nonhuman Primate Renal Transplantation Model. Am J Transplant. May 2017;17(5):1193-1203. doi: 10.1111/ajt.14141. Epub Jan. 27, 2017.
Saudek et al, (1989) N. Engl. J. Med. 321 :574.
Schreier et al, (1994) J. Biol. Chem. 269:9090.
Schultz et al., (1987) Gene 54:113-123.
Sefton, (1987) CRC Crit. Ref Biomed. Eng. 14:201-240.
Sen M, Springer TA (2016) Leukocyte integrin αLβ2 headpiece structures: The αI domain, the pocket for the internal ligand, and concerted movements of its loops. Proc Natl Acad Sci USA 113:2940-2945.
Shimaoka M, Kim M, Cohen EH, Yang W, Astrof N, Peer D, Salas A, Ferrand A, Springer TA. AL-57, a ligand-mimetic antibody to integrin LFA-1, reveals chemokine-induced affinity up-regulation in lymphocytes. Proc Natl Acad Sci U S A. Sep. 19, 2006;103(38):13991-6. Epub Sep. 8, 2006.
Shimaoka M, Lu C, Palframan RT, von Andrian UH, McCormack A, Takagi J, Springer TA. Reversibly locking a protein fold in an active conformation with a disulfide bond: integrin alphaL I domains with high affinity and antagonist activity in vivo. Proc Natl Acad Sci U S A. May 22, 2001;98(11):6009-14. Epub May 15, 2001.

(56) References Cited

OTHER PUBLICATIONS

Shimaoka M, Lu C, Salas A, Xiao T, Takagi J, Springer TA. Stabilizing the integrin alpha M inserted domain in alternative conformations with a range of engineered disulfide bonds. Proc Natl Acad Sci U S A. Dec. 24, 2002;99(26):16737-41. Epub Dec. 4, 2002.
Sidman et al., (1983) Biopolymers 22:547-556.
Sirin et al., 2003, Gene, 323:67.
Slamon et al, (2001) New Engl. J. Med. 344:783-792.
Smith et al. (1983) Mol. Cell. Biol. 3:2156-2165.
Smith, D. B. and Johnson, K. S. (1988) Gene 67:31-40.
Song et al, (1995) PDA Journal of Pharmaceutical Science & Technology 50:372-397.
Su Y, et al. (2016) Relating conformation to function in integrin α5β1. Proc Natl Acad Sci USA 113:E3872-E3881.
Suchanek M, Radzikowska A, Thiele C. Photo-leucine and photo-methionine allow identification of protein-protein interactions in living cells. Nat Methods. Apr. 2005;2(4):261-7. Epub Mar. 23, 2005.
Takagi 2002 Biochemistry, 41, 4339-4347.
Takagi J, Erickson HP, Springer TA (2001) C-terminal opening mimics 'inside-out' activation of integrin α5β1. Nat Struct Biol 8:412-416.
Umezawa et al, (1988) Biochem. Biophys. Res. Commun. 153: 1038.
Wada et al., (1992) Nucleic Acids Res. 20:2111-2118.
Wu, TT and Kabat, E. A., J Exp Med. 132(2):211-50, (1970).
Xia W, Springer TA (2014) Metal ion and ligand binding of integrin α5β1. Proc Natl Acad Sci USA 111:17863-17868.
Xie C, et al. (2010) Structure of an integrin with an αI domain, complement receptor type 4. EMBO J 29:666-679.
Xiong JP, Li R, Essafi M, Stehle T, Arnaout MA. An isoleucine-based allosteric switch controls affinity and shape shifting in integrin CD11b A-domain. J Biol Chem. 2000;275:38762-38767.
Xu S, Wang J, Wang JH, Springer TA (2017) Distinct recognition of complement iC3b by integrins αXβ2 and αMβ2. Proc Natl Acad Sci USA 114:3403-3408.
Yang et al, (2003) New Engl. J. Med. 349:427-434.
Zhang C., Liu J., Jiang X., Haydar N., Zhang C., Shan H., and Zhu J. (2013) Modulation of integrin activation and signaling by α1/α1'-helix unbending at the junction. J. Cell Sci. 126, 5735-5747.
Zhang K, Chen J, The regulation of integrin function by divalent cations, Cell Adh Migr. Jan.-Feb. 2012;6(1):20-9.
Zhengli Wang, Aye Myat Myat Thinn, and Jieqing Zhu A pivotal role for a conserved bulky residue at the α1-helix of the αI integrin domain in ligand binding, J Biol Chem. Dec. 15, 2017; 292(50): 20756-20768.
Ajroud, Kaouther, et al. "Binding affinity of metal ions to the CD11b A-domain is regulated by integrin activation and ligands." Journal of Biological Chemistry 279.24 (2004): 25483-25488.
Krukonis, Eric S., and Ralph R. Isberg. "Integrin β1-chain residues involved in substrate recognition and specificity of binding to invasin." Cellular microbiology 2.3 (2000): 219-230.
Supplementary European Search Report for European Patent Application No. EP20783344.1, dated Apr. 21, 2023.
Valdramidou, Dimitra et al. "Distinct roles of β1 metal ion-dependent adhesion site (MIDAS), adjacent to MIDAS (ADMIDAS), and ligand-associated metal-binding site (LIMBS) cation-binding sites in ligand recognition by integrin α2β1." Journal of Biological Chemistry 283.47 (2008): 32704-32714.

\* cited by examiner

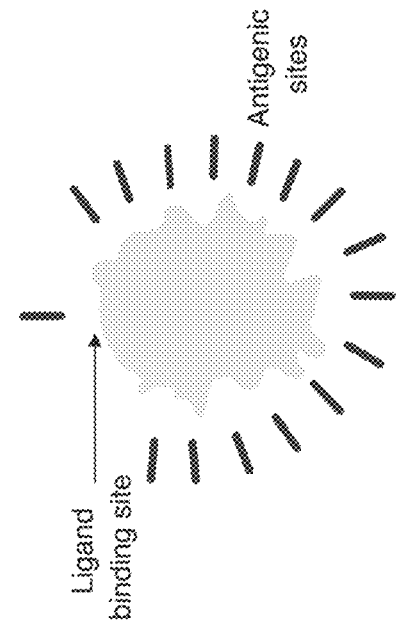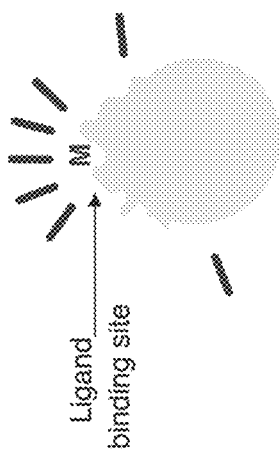

FIG.3 Alignment of βA-domains

SEQUENCE LISTING

<160> NUMBER OF SEQ ID NOS: 86

<210> SEQ ID NO 1
<211> LENGTH: 1135
<212> TYPE: PRT
<213> ORGANISM: Artificial Sequence
<220> FEATURE:
<223> OTHER INFORMATION: CD11b A domain

<400> SEQUENCE: 1

```
Phe Asn Leu Asp Thr Glu Asn Ala Met Thr Phe Gln Glu Asn Ala Arg
1               5                   10                  15

Gly Phe Gly Gln Ser Val Val Gln Leu Gln Gly Ser Arg Val Val Val
            20                  25                  30

Gly Ala Pro Gln Glu Ile Val Ala Ala Asn Gln Arg Gly Ser Leu Tyr
        35                  40                  45

Gln Cys Asp Tyr Ser Thr Gly Ser Cys Glu Pro Ile Arg Leu Gln Val
    50                  55                  60

Pro Val Glu Ala Val Asn Met Ser Leu Gly Leu Ser Leu Ala Ala Thr
65                  70                  75                  80

Thr Ser Pro Pro Gln Leu Leu Ala Cys Gly Pro Thr Val His Gln Thr
                85                  90                  95

Cys Ser Glu Asn Thr Tyr Val Lys Gly Leu Cys Phe Leu Phe Gly Ser
            100                 105                 110

Asn Leu Arg Gln Gln Pro Gln Lys Phe Pro Glu Ala Leu Arg Gly Cys
        115                 120                 125

Pro Gln Glu Asp Ser Asp Ile Ala Phe Leu Ile Asp Gly Ser Gly Ser
    130                 135                 140

Ile Ile Pro His Asp Phe Arg Arg Met Lys Glu Phe Val Ser Thr Val
145                 150                 155                 160

Met Glu Gln Leu Lys Lys Ser Lys Thr Leu Phe Ser Leu Met Gln Tyr
                165                 170                 175

Ser Glu Glu Phe Arg Ile His Phe Thr Phe Lys Glu Phe Gln Asn Asn
            180                 185                 190

Pro Asn Pro Arg Ser Leu Val Lys Pro Ile Thr Gln Leu Leu Gly Arg
        195                 200                 205

Thr His Thr Ala Thr Gly Ile Arg Lys Val Val Arg Glu Leu Phe Asn
    210                 215                 220

Ile Thr Asn Gly Ala Arg Lys Asn Ala Phe Lys Ile Leu Val Val Ile
225                 230                 235                 240

Thr Asp Gly Glu Lys Phe Gly Asp Pro Leu Gly Tyr Glu Asp Val Ile
                245                 250                 255

Pro Glu Ala Asp Arg Glu Gly Val Ile Arg Tyr Val Ile Gly Val Gly
            260                 265                 270

Asp Ala Phe Arg Ser Glu Lys Ser Arg Gln Glu Leu Asn Thr Ile Ala
        275                 280                 285

Ser Lys Pro Pro Arg Asp His Val Phe Gln Val Asn Asn Phe Glu Ala
    290                 295                 300

Leu Lys Thr Ile Gln Asn Gln Leu Arg Glu Lys Ile Phe Ala Ile Glu
305                 310                 315                 320

Gly Thr Gln Thr Gly Ser Ser Ser Phe Glu His Glu Met Ser Gln
                325                 330                 335

Glu Gly Phe Ser Ala Ala Ile Thr Ser Asn Gly Pro Leu Leu Ser Thr
            340                 345                 350

Val Gly Ser Tyr Asp Trp Ala Gly Gly Val Phe Leu Tyr Thr Ser Lys
```

```
            355                 360                 365
Glu Lys Ser Thr Phe Ile Asn Met Thr Arg Val Asp Ser Asp Met Asn
370                 375                 380

Asp Ala Tyr Leu Gly Tyr Ala Ala Ile Ile Leu Arg Asn Arg Val
385                 390                 395                 400

Gln Ser Leu Val Leu Gly Ala Pro Arg Tyr Gln His Ile Gly Leu Val
                    405                 410                 415

Ala Met Phe Arg Gln Asn Thr Gly Met Trp Glu Ser Asn Ala Asn Val
                420                 425                 430

Lys Gly Thr Gln Ile Gly Ala Tyr Phe Gly Ala Ser Leu Cys Ser Val
                435                 440                 445

Asp Val Asp Ser Asn Gly Ser Thr Asp Leu Val Leu Ile Gly Ala Pro
            450                 455                 460

His Tyr Tyr Glu Gln Thr Arg Gly Gly Gln Val Ser Val Cys Pro Leu
465                 470                 475                 480

Pro Arg Gly Arg Ala Arg Trp Gln Cys Asp Ala Val Leu Tyr Gly Glu
                    485                 490                 495

Gln Gly Gln Pro Trp Gly Arg Phe Gly Ala Ala Leu Thr Val Leu Gly
                500                 505                 510

Asp Val Asn Gly Asp Lys Leu Thr Asp Val Ala Ile Gly Ala Pro Gly
                515                 520                 525

Glu Glu Asp Asn Arg Gly Ala Val Tyr Leu Phe His Gly Thr Ser Gly
                530                 535                 540

Ser Gly Ile Ser Pro Ser His Ser Gln Arg Ile Ala Gly Ser Lys Leu
545                 550                 555                 560

Ser Pro Arg Leu Gln Tyr Phe Gly Gln Ser Leu Ser Gly Gly Gln Asp
                    565                 570                 575

Leu Thr Met Asp Gly Leu Val Asp Leu Thr Val Gly Ala Gln Gly His
                580                 585                 590

Val Leu Leu Leu Arg Ser Gln Pro Val Leu Arg Val Lys Ala Ile Met
                595                 600                 605

Glu Phe Asn Pro Arg Glu Val Ala Arg Asn Val Phe Glu Cys Asn Asp
610                 615                 620

Gln Val Val Lys Gly Lys Glu Ala Gly Glu Val Arg Val Cys Leu His
625                 630                 635                 640

Val Gln Lys Ser Thr Arg Asp Arg Leu Arg Glu Gly Gln Ile Gln Ser
                    645                 650                 655

Val Val Thr Tyr Asp Leu Ala Leu Asp Ser Gly Arg Pro His Ser Arg
                660                 665                 670

Ala Val Phe Asn Glu Thr Lys Asn Ser Thr Arg Arg Gln Thr Gln Val
                675                 680                 685

Leu Gly Leu Thr Gln Thr Cys Glu Thr Leu Lys Leu Gln Leu Pro Asn
                690                 695                 700

Cys Ile Glu Asp Pro Val Ser Pro Ile Val Leu Arg Leu Asn Phe Ser
705                 710                 715                 720

Leu Val Gly Thr Pro Leu Ser Ala Phe Gly Asn Leu Arg Pro Val Leu
                    725                 730                 735

Ala Glu Asp Ala Gln Arg Leu Phe Thr Ala Leu Phe Pro Phe Glu Lys
                740                 745                 750

Asn Cys Gly Asn Asp Asn Ile Cys Gln Asp Asp Leu Ser Ile Thr Phe
                755                 760                 765

Ser Phe Met Ser Leu Asp Cys Leu Val Val Gly Gly Pro Arg Glu Phe
770                 775                 780
```

Asn Val Thr Val Thr Val Arg Asn Asp Gly Glu Asp Ser Tyr Arg Thr
785                 790                 795                 800

Gln Val Thr Phe Phe Pro Leu Asp Leu Ser Tyr Arg Lys Val Ser
            805                 810                 815

Thr Leu Gln Asn Gln Arg Ser Gln Arg Ser Trp Arg Leu Ala Cys Glu
        820                 825                 830

Ser Ala Ser Ser Thr Glu Val Ser Gly Ala Leu Lys Ser Thr Ser Cys
            835                 840                 845

Ser Ile Asn His Pro Ile Phe Pro Glu Asn Ser Glu Val Thr Phe Asn
        850                 855                 860

Ile Thr Phe Asp Val Asp Ser Lys Ala Ser Leu Gly Asn Lys Leu Leu
865                 870                 875                 880

Leu Lys Ala Asn Val Thr Ser Glu Asn Asn Met Pro Arg Thr Asn Lys
                885                 890                 895

Thr Glu Phe Gln Leu Glu Leu Pro Val Lys Tyr Ala Val Tyr Met Val
            900                 905                 910

Val Thr Ser His Gly Val Ser Thr Lys Tyr Leu Asn Phe Thr Ala Ser
        915                 920                 925

Glu Asn Thr Ser Arg Val Met Gln His Gln Tyr Gln Val Ser Asn Leu
    930                 935                 940

Gly Gln Arg Ser Leu Pro Ile Ser Leu Val Phe Leu Val Pro Val Arg
945                 950                 955                 960

Leu Asn Gln Thr Val Ile Trp Asp Arg Pro Gln Val Thr Phe Ser Glu
            965                 970                 975

Asn Leu Ser Ser Thr Cys His Thr Lys Glu Arg Leu Pro Ser His Ser
            980                 985                 990

Asp Phe Leu Ala Glu Leu Arg Lys Ala Pro Val Val Asn Cys Ser Ile
        995                 1000                1005

Ala Val Cys Gln Arg Ile Gln Cys Asp Ile Pro Phe Phe Gly Ile
    1010                1015                1020

Gln Glu Glu Phe Asn Ala Thr Leu Lys Gly Asn Leu Ser Phe Asp
    1025                1030                1035

Trp Tyr Ile Lys Thr Ser His Asn His Leu Leu Ile Val Ser Thr
    1040                1045                1050

Ala Glu Ile Leu Phe Asn Asp Ser Val Phe Thr Leu Leu Pro Gly
    1055                1060                1065

Gln Gly Ala Phe Val Arg Ser Gln Thr Glu Thr Lys Val Glu Pro
    1070                1075                1080

Phe Glu Val Pro Asn Pro Leu Pro Leu Ile Val Gly Ser Ser Val
    1085                1090                1095

Gly Gly Leu Leu Leu Leu Ala Leu Ile Thr Ala Ala Leu Tyr Lys
    1100                1105                1110

Leu Gly Phe Phe Lys Arg Gln Tyr Lys Asp Met Met Ser Glu Gly
    1115                1120                1125

Gly Pro Pro Gly Ala Glu Gln
    1130                1135

<210> SEQ ID NO 2
<211> LENGTH: 192
<212> TYPE: PRT
<213> ORGANISM: Artificial Sequence
<220> FEATURE:
<223> OTHER INFORMATION: CD11b mutated

<400> SEQUENCE: 2

Pro Gln Glu Asp Ser Asp Ile Ala Phe Leu Ile Asp Gly Ser Gly Ser
1               5                   10                  15

Ile Ile Pro His Asp Phe Arg Arg Met Lys Glu Phe Val Ser Thr Val
                20                  25                  30

Met Glu Gln Leu Lys Lys Ser Lys Thr Leu Phe Ser Leu Met Gln Tyr
        35                  40                  45

Ser Glu Glu Phe Arg Ile His Phe Thr Phe Lys Glu Phe Gln Asn Asn
50                  55                  60

Pro Asn Pro Arg Ser Leu Val Lys Pro Ile Thr Gln Leu Leu Gly Arg
65                  70                  75                  80

Thr His Thr Ala Thr Gly Ile Arg Lys Val Val Arg Glu Leu Phe Asn
                85                  90                  95

Ile Thr Asn Gly Ala Arg Lys Asn Ala Phe Lys Ile Leu Val Val Ile
                100                 105                 110

Thr Asp Gly Glu Lys Phe Gly Asp Pro Leu Gly Tyr Glu Asp Val Ile
                115                 120                 125

Pro Glu Ala Asp Arg Glu Gly Val Ile Arg Tyr Val Ile Gly Val Gly
                130                 135                 140

Asp Ala Phe Arg Ser Glu Lys Ser Arg Gln Glu Leu Asn Thr Ile Ala
145                 150                 155                 160

Ser Lys Pro Pro Arg Asp His Val Phe Gln Val Asn Asn Phe Glu Ala
                165                 170                 175

Leu Lys Thr Ile Gln Asn Gln Leu Arg Glu Lys Ile Phe Ala Ile Glu
                180                 185                 190

<210> SEQ ID NO 3
<211> LENGTH: 192
<212> TYPE: PRT
<213> ORGANISM: Artificial Sequence
<220> FEATURE:
<223> OTHER INFORMATION: CD11b mutated

<400> SEQUENCE: 3

Pro Gln Glu Asp Ser Asp Ile Ala Phe Leu Ile Ala Gly Ser Gly Ser
1               5                   10                  15

Ile Ile Pro His Asp Phe Arg Arg Met Lys Glu Phe Val Ser Thr Val
                20                  25                  30

Met Glu Gln Leu Lys Lys Ser Lys Thr Leu Phe Ser Leu Met Gln Tyr
        35                  40                  45

Ser Glu Glu Phe Arg Ile His Phe Thr Phe Lys Glu Phe Gln Asn Asn
50                  55                  60

Pro Asn Pro Arg Ser Leu Val Lys Pro Ile Thr Gln Leu Leu Gly Arg
65                  70                  75                  80

Thr His Thr Ala Thr Gly Ile Arg Lys Val Val Arg Glu Leu Phe Asn
                85                  90                  95

Ile Thr Asn Gly Ala Arg Lys Asn Ala Phe Lys Ile Leu Val Val Ile
                100                 105                 110

Thr Asp Gly Glu Lys Phe Gly Asp Pro Leu Gly Tyr Glu Asp Val Ile
                115                 120                 125

Pro Glu Ala Asp Arg Glu Gly Val Ile Arg Tyr Val Ile Gly Val Gly
                130                 135                 140

Asp Ala Phe Arg Ser Glu Lys Ser Arg Gln Glu Leu Asn Thr Ile Ala
145                 150                 155                 160

Ser Lys Pro Pro Arg Asp His Val Phe Gln Val Asn Asn Phe Glu Ala
                165                 170                 175

Leu Lys Thr Ile Gln Asn Gln Leu Arg Glu Lys Ile Phe Ala Ile Glu
            180                 185                 190

<210> SEQ ID NO 4
<211> LENGTH: 192
<212> TYPE: PRT
<213> ORGANISM: Artificial Sequence
<220> FEATURE:
<223> OTHER INFORMATION: cd11b mutated

<400> SEQUENCE: 4

Pro Gln Glu Asp Ser Asp Ile Ala Phe Leu Ile Ala Gly Ser Gly Ser
1               5                   10                  15

Ile Ile Pro His Asp Phe Arg Arg Met Lys Glu Phe Val Ser Thr Val
                20                  25                  30

Met Glu Gln Leu Lys Lys Ser Lys Thr Leu Phe Ser Leu Met Gln Tyr
            35                  40                  45

Ser Glu Glu Phe Arg Ile His Phe Thr Phe Lys Glu Phe Gln Asn Asn
        50                  55                  60

Pro Asn Pro Arg Ser Leu Val Lys Pro Ile Thr Gln Leu Leu Gly Arg
65                  70                  75                  80

Thr His Thr Ala Thr Gly Ile Arg Lys Val Val Arg Glu Leu Phe Asn
                85                  90                  95

Ile Thr Asn Gly Ala Arg Lys Asn Ala Phe Lys Ile Leu Val Val Ile
            100                 105                 110

Thr Asp Gly Glu Lys Phe Gly Asp Pro Leu Gly Tyr Glu Asp Val Ile
        115                 120                 125

Pro Glu Ala Asp Arg Glu Gly Val Ile Arg Tyr Val Ile Gly Val Gly
    130                 135                 140

Asp Ala Phe Arg Ser Glu Lys Ser Arg Gln Glu Leu Asn Thr Ile Ala
145                 150                 155                 160

Ser Lys Pro Pro Arg Asp His Val Phe Gln Val Asn Asn Phe Glu Ala
                165                 170                 175

Leu Lys Thr Ile Gln Asn Gln Leu Arg Glu Lys Ala Phe Ala Ile Glu
            180                 185                 190

<210> SEQ ID NO 5
<211> LENGTH: 192
<212> TYPE: PRT
<213> ORGANISM: Artificial Sequence
<220> FEATURE:
<223> OTHER INFORMATION: CD11b mutated

<400> SEQUENCE: 5

Pro Gln Glu Asp Ser Asp Ile Ala Phe Leu Ile Ala Gly Ser Gly Ser
1               5                   10                  15

Ile Ile Pro His Asp Phe Arg Arg Met Lys Glu Phe Val Ser Thr Val
                20                  25                  30

Met Glu Gln Leu Lys Lys Ser Lys Thr Leu Phe Ser Leu Met Gln Tyr
            35                  40                  45

Ser Glu Glu Phe Arg Ile His Phe Thr Phe Lys Glu Phe Gln Asn Asn
        50                  55                  60

Pro Asn Pro Arg Ser Leu Val Lys Pro Ile Thr Gln Leu Leu Gly Arg
65                  70                  75                  80

Thr His Thr Ala Thr Gly Ile Arg Lys Val Val Arg Glu Leu Phe Asn
                85                  90                  95

Ile Thr Asn Gly Ala Arg Lys Asn Ala Phe Lys Ile Leu Val Val Ile

```
                    100                 105                 110

Thr Asp Gly Glu Lys Phe Gly Asp Pro Leu Gly Tyr Glu Asp Val Ile
            115                 120                 125

Pro Glu Ala Asp Arg Glu Gly Val Ile Arg Tyr Val Ile Gly Val Gly
        130                 135                 140

Asp Ala Phe Arg Ser Glu Lys Ser Arg Gln Glu Leu Asn Thr Ile Ala
145                 150                 155                 160

Ser Lys Pro Pro Arg Asp His Val Phe Gln Val Asn Asn Trp Glu Ala
                165                 170                 175

Leu Lys Thr Ile Gln Asn Gln Leu Arg Glu Lys Ile Phe Ala Ile Glu
            180                 185                 190

<210> SEQ ID NO 6
<211> LENGTH: 192
<212> TYPE: PRT
<213> ORGANISM: Artificial Sequence
<220> FEATURE:
<223> OTHER INFORMATION: CD11b mutated

<400> SEQUENCE: 6

Pro Gln Glu Asp Ser Asp Ile Ala Phe Leu Ile Ala Gly Ala Gly Ala
1               5                   10                  15

Ile Ile Pro His Asp Phe Arg Arg Met Lys Glu Phe Val Ser Thr Val
            20                  25                  30

Met Glu Gln Leu Lys Lys Ser Lys Thr Leu Phe Ser Leu Met Gln Tyr
        35                  40                  45

Ser Glu Glu Phe Arg Ile His Phe Thr Phe Lys Glu Phe Gln Asn Asn
50                  55                  60

Pro Asn Pro Arg Ser Leu Val Lys Pro Ile Thr Gln Leu Leu Gly Arg
65                  70                  75                  80

Ala His Thr Ala Thr Gly Ile Arg Lys Val Val Arg Glu Leu Phe Asn
                85                  90                  95

Ile Thr Asn Gly Ala Arg Lys Asn Ala Phe Lys Ile Leu Val Val Ile
            100                 105                 110

Thr Asp Gly Glu Lys Phe Gly Asp Pro Leu Gly Tyr Glu Asp Val Ile
        115                 120                 125

Pro Glu Ala Asp Arg Glu Gly Val Ile Arg Tyr Val Ile Gly Val Gly
        130                 135                 140

Asp Ala Phe Arg Ser Glu Lys Ser Arg Gln Glu Leu Asn Thr Ile Ala
145                 150                 155                 160

Ser Lys Pro Pro Arg Asp His Val Phe Gln Val Asn Asn Phe Glu Ala
                165                 170                 175

Leu Lys Thr Ile Gln Asn Gln Leu Arg Glu Lys Ile Phe Ala Ile Glu
            180                 185                 190

<210> SEQ ID NO 7
<211> LENGTH: 193
<212> TYPE: PRT
<213> ORGANISM: Artificial Sequence
<220> FEATURE:
<223> OTHER INFORMATION: CD11b mutated

<400> SEQUENCE: 7

Ser Pro Gln Glu Asp Ser Asp Ile Ala Phe Leu Ile Asp Gly Ser Gly
1               5                   10                  15

Ser Ile Ile Pro His Asp Phe Arg Arg Met Lys Glu Phe Val Ser Thr
            20                  25                  30
```

```
Val Met Glu Gln Leu Lys Lys Ser Lys Thr Leu Phe Ser Leu Met Gln
         35                  40                  45

Tyr Ser Glu Glu Phe Arg Ile His Phe Thr Phe Lys Glu Phe Gln Asn
 50                  55                  60

Asn Pro Asn Pro Arg Ser Leu Val Lys Pro Ile Thr Gln Leu Leu Gly
 65                  70                  75                  80

Arg Thr His Thr Ala Thr Gly Ile Arg Lys Val Val Arg Glu Leu Phe
                 85                  90                  95

Asn Ile Thr Asn Gly Ala Arg Lys Asn Ala Phe Lys Ile Leu Val Val
                100                 105                 110

Ile Thr Asp Gly Glu Lys Phe Gly Asp Pro Leu Gly Tyr Glu Asp Val
                115                 120                 125

Ile Pro Glu Ala Asp Arg Glu Gly Val Ile Arg Tyr Val Ile Gly Val
130                 135                 140

Gly Asp Ala Phe Arg Ser Glu Lys Ser Arg Gln Glu Leu Asn Thr Ile
145                 150                 155                 160

Ala Ser Lys Pro Pro Arg Asp His Val Phe Gln Val Asn Asn Phe Glu
                165                 170                 175

Ala Leu Lys Thr Ile Gln Asn Gln Leu Arg Glu Lys Ile Phe Ala Ile
                180                 185                 190

Glu

<210> SEQ ID NO 8
<211> LENGTH: 798
<212> TYPE: PRT
<213> ORGANISM: Artificial Sequence
<220> FEATURE:
<223> OTHER INFORMATION: IBTR1

<400> SEQUENCE: 8

Met Asn Leu Gln Pro Ile Phe Trp Ile Gly Leu Ile Ser Ser Val Cys
 1               5                  10                  15

Cys Val Phe Ala Gln Thr Asp Glu Asn Arg Cys Leu Lys Ala Asn Ala
                 20                  25                  30

Lys Ser Cys Gly Glu Cys Ile Gln Ala Gly Pro Asn Cys Gly Trp Cys
             35                  40                  45

Thr Asn Ser Thr Phe Leu Gln Glu Gly Met Pro Thr Ser Ala Arg Cys
 50                  55                  60

Asp Asp Leu Glu Ala Leu Lys Lys Lys Gly Cys Pro Pro Asp Asp Ile
 65                  70                  75                  80

Glu Asn Pro Arg Gly Ser Lys Asp Ile Lys Lys Asn Lys Asn Val Thr
                 85                  90                  95

Asn Arg Ser Lys Gly Thr Ala Glu Lys Leu Lys Pro Glu Asp Ile Thr
                100                 105                 110

Gln Ile Gln Pro Gln Gln Leu Val Leu Arg Leu Arg Ser Gly Glu Pro
                115                 120                 125

Gln Thr Phe Thr Leu Lys Phe Lys Arg Ala Glu Asp Tyr Pro Ile Asp
            130                 135                 140

Leu Tyr Tyr Leu Met Asp Leu Ser Tyr Ser Met Lys Asp Asp Leu Glu
145                 150                 155                 160

Asn Val Lys Ser Leu Gly Thr Asp Leu Met Asn Glu Met Arg Arg Ile
                165                 170                 175

Thr Ser Asp Phe Arg Ile Gly Phe Gly Ser Phe Val Glu Lys Thr Val
                180                 185                 190

Met Pro Tyr Ile Ser Thr Thr Pro Ala Lys Leu Arg Asn Pro Cys Thr
```

-continued

```
            195                 200                 205
Ser Glu Gln Asn Cys Thr Ser Pro Phe Ser Tyr Lys Asn Val Leu Ser
210                 215                 220

Leu Thr Asn Lys Gly Glu Val Phe Asn Glu Leu Val Gly Lys Gln Arg
225                 230                 235                 240

Ile Ser Gly Asn Leu Asp Ser Pro Glu Gly Phe Asp Ala Ile Met
                245                 250                 255

Gln Val Ala Val Cys Gly Ser Leu Ile Gly Trp Arg Asn Val Thr Arg
                260                 265                 270

Leu Leu Val Phe Ser Thr Asp Ala Gly Phe His Phe Ala Gly Asp Gly
                275                 280                 285

Lys Leu Gly Gly Ile Val Leu Pro Asn Asp Gly Gln Cys His Leu Glu
                290                 295                 300

Asn Asn Met Tyr Thr Met Ser His Tyr Tyr Asp Tyr Pro Ser Ile Ala
305                 310                 315                 320

His Leu Val Gln Lys Leu Ser Glu Asn Ile Gln Thr Ile Phe Ala
                325                 330                 335

Val Thr Glu Glu Phe Gln Pro Val Tyr Lys Glu Leu Lys Asn Leu Ile
                340                 345                 350

Pro Lys Ser Ala Val Gly Thr Leu Ser Ala Asn Ser Ser Asn Val Ile
                355                 360                 365

Gln Leu Ile Ile Asp Ala Tyr Asn Ser Leu Ser Ser Glu Val Ile Leu
                370                 375                 380

Glu Asn Gly Lys Leu Ser Glu Gly Val Thr Ile Ser Tyr Lys Ser Tyr
385                 390                 395                 400

Cys Lys Asn Gly Val Asn Gly Thr Gly Glu Asn Gly Arg Lys Cys Ser
                405                 410                 415

Asn Ile Ser Ile Gly Asp Glu Val Gln Phe Glu Ile Ser Ile Thr Ser
                420                 425                 430

Asn Lys Cys Pro Lys Lys Asp Ser Asp Ser Phe Lys Ile Arg Pro Leu
                435                 440                 445

Gly Phe Thr Glu Glu Val Glu Val Ile Leu Gln Tyr Ile Cys Glu Cys
                450                 455                 460

Glu Cys Gln Ser Glu Gly Ile Pro Glu Ser Pro Lys Cys His Glu Gly
465                 470                 475                 480

Asn Gly Thr Phe Glu Cys Gly Ala Cys Arg Cys Asn Glu Gly Arg Val
                485                 490                 495

Gly Arg His Cys Glu Cys Ser Thr Asp Glu Val Asn Ser Glu Asp Met
                500                 505                 510

Asp Ala Tyr Cys Arg Lys Glu Asn Ser Ser Glu Ile Cys Ser Asn Asn
                515                 520                 525

Gly Glu Cys Val Cys Gly Gln Cys Val Cys Arg Lys Arg Asp Asn Thr
                530                 535                 540

Asn Glu Ile Tyr Ser Gly Lys Phe Cys Glu Cys Asp Asn Phe Asn Cys
545                 550                 555                 560

Asp Arg Ser Asn Gly Leu Ile Cys Gly Gly Asn Gly Val Cys Lys Cys
                565                 570                 575

Arg Val Cys Glu Cys Asn Pro Asn Tyr Thr Gly Ser Ala Cys Asp Cys
                580                 585                 590

Ser Leu Asp Thr Ser Thr Cys Glu Ala Ser Asn Gly Gln Ile Cys Asn
                595                 600                 605

Gly Arg Gly Ile Cys Glu Cys Gly Val Cys Lys Cys Thr Asp Pro Lys
610                 615                 620
```

Phe Gln Gly Gln Thr Cys Glu Met Cys Gln Thr Cys Leu Gly Val Cys
625                 630                 635                 640

Ala Glu His Lys Glu Cys Val Gln Cys Arg Ala Phe Asn Lys Gly Glu
            645                 650                 655

Lys Lys Asp Thr Cys Thr Gln Cys Ser Tyr Phe Asn Ile Thr Lys
        660                 665                 670

Val Glu Ser Arg Asp Lys Leu Pro Gln Pro Val Gln Pro Asp Pro Val
    675                 680                 685

Ser His Cys Lys Glu Lys Asp Val Asp Cys Trp Phe Tyr Phe Thr
690                 695                 700

Tyr Ser Val Asn Gly Asn Asn Glu Val Met Val His Val Val Glu Asn
705                 710                 715                 720

Pro Glu Cys Pro Thr Gly Pro Asp Ile Ile Pro Ile Val Ala Gly Val
                725                 730                 735

Val Ala Gly Ile Val Leu Ile Gly Leu Ala Leu Leu Leu Ile Trp Lys
            740                 745                 750

Leu Leu Met Ile Ile His Asp Arg Arg Glu Phe Ala Lys Phe Glu Lys
        755                 760                 765

Glu Lys Met Asn Ala Lys Trp Asp Thr Gly Glu Asn Pro Ile Tyr Lys
    770                 775                 780

Ser Ala Val Thr Thr Val Val Asn Pro Lys Tyr Glu Gly Lys
785                 790                 795

<210> SEQ ID NO 9
<211> LENGTH: 769
<212> TYPE: PRT
<213> ORGANISM: Artificial Sequence
<220> FEATURE:
<223> OTHER INFORMATION: ITB2

<400> SEQUENCE: 9

Met Leu Gly Leu Arg Pro Pro Leu Leu Ala Leu Val Gly Leu Leu Ser
1               5                   10                  15

Leu Gly Cys Val Leu Ser Gln Glu Cys Thr Lys Phe Lys Val Ser Ser
            20                  25                  30

Cys Arg Glu Cys Ile Glu Ser Gly Pro Gly Cys Thr Trp Cys Gln Lys
        35                  40                  45

Leu Asn Phe Thr Gly Pro Gly Asp Pro Asp Ser Ile Arg Cys Asp Thr
    50                  55                  60

Arg Pro Gln Leu Leu Met Arg Gly Cys Ala Ala Asp Asp Ile Met Asp
65                  70                  75                  80

Pro Thr Ser Leu Ala Glu Thr Gln Glu Asp His Asn Gly Gly Gln Lys
                85                  90                  95

Gln Leu Ser Pro Gln Lys Val Thr Leu Tyr Leu Arg Pro Gly Gln Ala
            100                 105                 110

Ala Ala Phe Asn Val Thr Phe Arg Arg Ala Lys Gly Tyr Pro Ile Asp
        115                 120                 125

Leu Tyr Tyr Leu Met Asp Leu Ser Tyr Ser Met Leu Asp Asp Leu Arg
    130                 135                 140

Asn Val Lys Lys Leu Gly Gly Asp Leu Leu Arg Ala Leu Asn Glu Ile
145                 150                 155                 160

Thr Glu Ser Gly Arg Ile Gly Phe Gly Ser Phe Val Asp Lys Thr Val
                165                 170                 175

Leu Pro Phe Val Asn Thr His Pro Asp Lys Leu Arg Asn Pro Cys Pro
            180                 185                 190

-continued

Asn Lys Glu Lys Glu Cys Gln Pro Pro Phe Ala Phe Arg His Val Leu
    195                 200                 205

Lys Leu Thr Asn Asn Ser Asn Gln Phe Gln Thr Glu Val Gly Lys Gln
    210                 215                 220

Leu Ile Ser Gly Asn Leu Asp Ala Pro Glu Gly Gly Leu Asp Ala Met
225                 230                 235                 240

Met Gln Val Ala Ala Cys Pro Glu Glu Ile Gly Trp Arg Asn Val Thr
                245                 250                 255

Arg Leu Leu Val Phe Ala Thr Asp Asp Gly Phe His Phe Ala Gly Asp
            260                 265                 270

Gly Lys Leu Gly Ala Ile Leu Thr Pro Asn Asp Gly Arg Cys His Leu
        275                 280                 285

Glu Asp Asn Leu Tyr Lys Arg Ser Asn Glu Phe Asp Tyr Pro Ser Val
    290                 295                 300

Gly Gln Leu Ala His Lys Leu Ala Glu Asn Asn Ile Gln Pro Ile Phe
305                 310                 315                 320

Ala Val Thr Ser Arg Met Val Lys Thr Tyr Glu Lys Leu Thr Glu Ile
                325                 330                 335

Ile Pro Lys Ser Ala Val Gly Glu Leu Ser Glu Asp Ser Ser Asn Val
            340                 345                 350

Val Gln Leu Ile Lys Asn Ala Tyr Asn Lys Leu Ser Ser Arg Val Phe
        355                 360                 365

Leu Asp His Asn Ala Leu Pro Asp Thr Leu Lys Val Thr Tyr Asp Ser
370                 375                 380

Phe Cys Ser Asn Gly Val Thr His Arg Asn Gln Pro Arg Gly Asp Cys
385                 390                 395                 400

Asp Gly Val Gln Ile Asn Val Pro Ile Thr Phe Gln Val Lys Val Thr
                405                 410                 415

Ala Thr Glu Cys Ile Gln Glu Gln Ser Phe Val Ile Arg Ala Leu Gly
            420                 425                 430

Phe Thr Asp Ile Val Thr Val Gln Val Leu Pro Gln Cys Glu Cys Arg
        435                 440                 445

Cys Arg Asp Gln Ser Arg Asp Arg Ser Leu Cys His Gly Lys Gly Phe
    450                 455                 460

Leu Glu Cys Gly Ile Cys Arg Cys Asp Thr Gly Tyr Ile Gly Lys Asn
465                 470                 475                 480

Cys Glu Cys Gln Thr Gln Gly Arg Ser Ser Gln Glu Leu Glu Gly Ser
                485                 490                 495

Cys Arg Lys Asp Asn Asn Ser Ile Ile Cys Ser Gly Leu Gly Asp Cys
            500                 505                 510

Val Cys Gly Gln Cys Leu Cys His Thr Ser Asp Val Pro Gly Lys Leu
        515                 520                 525

Ile Tyr Gly Gln Tyr Cys Glu Cys Asp Thr Ile Asn Cys Glu Arg Tyr
    530                 535                 540

Asn Gly Gln Val Cys Gly Gly Pro Gly Arg Gly Leu Cys Phe Cys Gly
545                 550                 555                 560

Lys Cys Arg Cys His Pro Gly Phe Glu Gly Ser Ala Cys Gln Cys Glu
                565                 570                 575

Arg Thr Thr Glu Gly Cys Leu Asn Pro Arg Arg Val Glu Cys Ser Gly
            580                 585                 590

Arg Gly Arg Cys Arg Cys Asn Val Cys Glu Cys His Ser Gly Tyr Gln
        595                 600                 605

-continued

```
Leu Pro Leu Cys Gln Glu Cys Pro Gly Cys Pro Ser Pro Cys Gly Lys
    610                 615                 620

Tyr Ile Ser Cys Ala Glu Cys Leu Lys Phe Glu Lys Gly Pro Phe Gly
625                 630                 635                 640

Lys Asn Cys Ser Ala Ala Cys Pro Gly Leu Gln Leu Ser Asn Asn Pro
                645                 650                 655

Val Lys Gly Arg Thr Cys Lys Glu Arg Asp Ser Glu Gly Cys Trp Val
            660                 665                 670

Ala Tyr Thr Leu Glu Gln Gln Asp Gly Met Asp Arg Tyr Leu Ile Tyr
        675                 680                 685

Val Asp Glu Ser Arg Glu Cys Val Ala Gly Pro Asn Ile Ala Ala Ile
690                 695                 700

Val Gly Gly Thr Val Ala Gly Ile Val Leu Ile Gly Ile Leu Leu Leu
705                 710                 715                 720

Val Ile Trp Lys Ala Leu Ile His Leu Ser Asp Leu Arg Glu Tyr Arg
                725                 730                 735

Arg Phe Glu Lys Glu Lys Leu Lys Ser Gln Trp Asn Asn Asp Asn Pro
            740                 745                 750

Leu Phe Lys Ser Ala Thr Thr Thr Val Met Asn Pro Lys Phe Ala Glu
        755                 760                 765

Ser
```

<210> SEQ ID NO 10
<211> LENGTH: 788
<212> TYPE: PRT
<213> ORGANISM: Artificial Sequence
<220> FEATURE:
<223> OTHER INFORMATION: ITB3

<400> SEQUENCE: 10

```
Met Arg Ala Arg Pro Arg Pro Arg Pro Leu Trp Ala Thr Val Leu Ala
1               5                   10                  15

Leu Gly Ala Leu Ala Gly Val Gly Val Gly Gly Pro Asn Ile Cys Thr
            20                  25                  30

Thr Arg Gly Val Ser Ser Cys Gln Gln Cys Leu Ala Val Ser Pro Met
        35                  40                  45

Cys Ala Trp Cys Ser Asp Glu Ala Leu Pro Leu Gly Ser Pro Arg Cys
    50                  55                  60

Asp Leu Lys Glu Asn Leu Leu Lys Asp Asn Cys Ala Pro Glu Ser Ile
65                  70                  75                  80

Glu Phe Pro Val Ser Glu Ala Arg Val Leu Glu Asp Arg Pro Leu Ser
                85                  90                  95

Asp Lys Gly Ser Gly Asp Ser Ser Gln Val Thr Gln Val Ser Pro Gln
            100                 105                 110

Arg Ile Ala Leu Arg Leu Arg Pro Asp Asp Ser Lys Asn Phe Ser Ile
        115                 120                 125

Gln Val Arg Gln Val Glu Asp Tyr Pro Val Asp Ile Tyr Tyr Leu Met
    130                 135                 140

Asp Leu Ser Tyr Ser Met Lys Asp Asp Leu Trp Ser Ile Gln Asn Leu
145                 150                 155                 160

Gly Thr Lys Leu Ala Thr Gln Met Arg Lys Leu Thr Ser Asn Leu Arg
                165                 170                 175

Ile Gly Phe Gly Ala Phe Val Asp Lys Pro Val Ser Pro Tyr Met Tyr
            180                 185                 190

Ile Ser Pro Pro Glu Ala Leu Glu Asn Pro Cys Tyr Asp Met Lys Thr
```

```
            195                 200                 205
Thr Cys Leu Pro Met Phe Gly Tyr Lys His Val Leu Thr Leu Thr Asp
210                 215                 220

Gln Val Thr Arg Phe Asn Glu Glu Val Lys Lys Gln Ser Val Ser Arg
225                 230                 235                 240

Asn Arg Asp Ala Pro Glu Gly Gly Phe Asp Ala Ile Met Gln Ala Thr
                    245                 250                 255

Val Cys Asp Glu Lys Ile Gly Trp Arg Asn Asp Ala Ser His Leu Leu
                260                 265                 270

Val Phe Thr Thr Asp Ala Lys Thr His Ile Ala Leu Asp Gly Arg Leu
            275                 280                 285

Ala Gly Ile Val Gln Pro Asn Asp Gly Gln Cys His Val Gly Ser Asp
        290                 295                 300

Asn His Tyr Ser Ala Ser Thr Thr Met Asp Tyr Pro Ser Leu Gly Leu
305                 310                 315                 320

Met Thr Glu Lys Leu Ser Gln Lys Asn Ile Asn Leu Ile Phe Ala Val
                    325                 330                 335

Thr Glu Asn Val Val Asn Leu Tyr Gln Asn Tyr Ser Glu Leu Ile Pro
                340                 345                 350

Gly Thr Thr Val Gly Val Leu Ser Met Asp Ser Ser Asn Val Leu Gln
            355                 360                 365

Leu Ile Val Asp Ala Tyr Gly Lys Ile Arg Ser Lys Val Glu Leu Glu
    370                 375                 380

Val Arg Asp Leu Pro Glu Glu Leu Ser Leu Ser Phe Asn Ala Thr Cys
385                 390                 395                 400

Leu Asn Asn Glu Val Ile Pro Gly Leu Lys Ser Cys Met Gly Leu Lys
                    405                 410                 415

Ile Gly Asp Thr Val Ser Phe Ser Ile Glu Ala Lys Val Arg Gly Cys
                420                 425                 430

Pro Gln Glu Lys Glu Lys Ser Phe Thr Ile Lys Pro Val Gly Phe Lys
            435                 440                 445

Asp Ser Leu Ile Val Gln Val Thr Phe Asp Cys Asp Cys Ala Cys Gln
        450                 455                 460

Ala Gln Ala Glu Pro Asn Ser His Arg Cys Asn Asn Gly Asn Gly Thr
465                 470                 475                 480

Phe Glu Cys Gly Val Cys Arg Cys Gly Pro Gly Trp Leu Gly Ser Gln
                    485                 490                 495

Cys Glu Cys Ser Glu Glu Asp Tyr Arg Pro Ser Gln Gln Asp Glu Cys
                500                 505                 510

Ser Pro Arg Glu Gly Gln Pro Val Cys Ser Gln Arg Gly Glu Cys Leu
            515                 520                 525

Cys Gly Gln Cys Val Cys His Ser Ser Asp Phe Gly Lys Ile Thr Gly
        530                 535                 540

Lys Tyr Cys Glu Cys Asp Asp Phe Ser Cys Val Arg Tyr Lys Gly Glu
545                 550                 555                 560

Met Cys Ser Gly His Gly Gln Cys Ser Cys Gly Asp Cys Leu Cys Asp
                    565                 570                 575

Ser Asp Trp Thr Gly Tyr Tyr Cys Asn Cys Thr Thr Arg Thr Asp Thr
                580                 585                 590

Cys Met Ser Ser Asn Gly Leu Leu Cys Ser Gly Arg Gly Lys Cys Glu
            595                 600                 605

Cys Gly Ser Cys Val Cys Ile Gln Pro Gly Ser Tyr Gly Asp Thr Cys
        610                 615                 620
```

-continued

```
Glu Lys Cys Pro Thr Cys Pro Asp Ala Cys Thr Phe Lys Lys Glu Cys
625                 630                 635                 640

Val Glu Cys Lys Lys Phe Asp Arg Gly Ala Leu His Asp Glu Asn Thr
            645                 650                 655

Cys Asn Arg Tyr Cys Arg Asp Glu Ile Glu Ser Val Lys Glu Leu Lys
        660                 665                 670

Asp Thr Gly Lys Asp Ala Val Asn Cys Thr Tyr Lys Asn Glu Asp Asp
    675                 680                 685

Cys Val Val Arg Phe Gln Tyr Tyr Glu Asp Ser Ser Gly Lys Ser Ile
690                 695                 700

Leu Tyr Val Val Glu Glu Pro Glu Cys Pro Lys Gly Pro Asp Ile Leu
705                 710                 715                 720

Val Val Leu Leu Ser Val Met Gly Ala Ile Leu Leu Ile Gly Leu Ala
                725                 730                 735

Ala Leu Leu Ile Trp Lys Leu Leu Ile Thr Ile His Asp Arg Lys Glu
            740                 745                 750

Phe Ala Lys Phe Glu Glu Glu Arg Ala Arg Ala Lys Trp Asp Thr Ala
        755                 760                 765

Asn Asn Pro Leu Tyr Lys Glu Ala Thr Ser Thr Phe Thr Asn Ile Thr
    770                 775                 780

Tyr Arg Gly Thr
785

<210> SEQ ID NO 11
<211> LENGTH: 1822
<212> TYPE: PRT
<213> ORGANISM: Artificial Sequence
<220> FEATURE:
<223> OTHER INFORMATION: ITB1-4

<400> SEQUENCE: 11

Met Ala Gly Pro Arg Pro Ser Pro Trp Ala Arg Leu Leu Leu Ala Ala
1               5                   10                  15

Leu Ile Ser Val Ser Leu Ser Gly Thr Leu Ala Asn Arg Cys Lys Lys
                20                  25                  30

Ala Pro Val Lys Ser Cys Thr Glu Cys Val Arg Val Asp Lys Asp Cys
            35                  40                  45

Ala Tyr Cys Thr Asp Glu Met Phe Arg Asp Arg Arg Cys Asn Thr Gln
        50                  55                  60

Ala Glu Leu Leu Ala Ala Gly Cys Gln Arg Glu Ser Ile Val Val Met
65                  70                  75                  80

Glu Ser Ser Phe Gln Ile Thr Glu Glu Thr Gln Ile Asp Thr Thr Leu
                85                  90                  95

Arg Arg Ser Gln Met Ser Pro Gln Gly Leu Arg Val Arg Leu Arg Pro
            100                 105                 110

Gly Glu Glu Arg His Phe Glu Leu Glu Val Phe Glu Pro Leu Glu Ser
        115                 120                 125

Pro Val Asp Leu Tyr Ile Leu Met Asp Phe Ser Asn Ser Met Ser Asp
    130                 135                 140

Asp Leu Asp Asn Leu Lys Lys Met Gly Gln Asn Leu Ala Arg Val Leu
145                 150                 155                 160

Ser Gln Leu Thr Ser Asp Tyr Thr Ile Gly Phe Gly Lys Phe Val Asp
                165                 170                 175

Lys Val Ser Val Pro Gln Thr Asp Met Arg Pro Glu Lys Leu Lys Glu
            180                 185                 190
```

```
Pro Trp Pro Asn Ser Asp Pro Pro Phe Ser Phe Lys Asn Val Ile Ser
        195                 200                 205

Leu Thr Glu Asp Val Asp Glu Phe Arg Asn Lys Leu Gln Gly Glu Arg
    210                 215                 220

Ile Ser Gly Asn Leu Asp Ala Pro Glu Gly Gly Phe Asp Ala Ile Leu
225                 230                 235                 240

Gln Thr Ala Val Cys Thr Arg Asp Ile Gly Trp Arg Pro Asp Ser Thr
                245                 250                 255

His Leu Leu Val Phe Ser Thr Glu Ser Ala Phe His Tyr Glu Ala Asp
                260                 265                 270

Gly Ala Asn Val Leu Ala Gly Ile Met Ser Arg Asn Asp Glu Arg Cys
                275                 280                 285

His Leu Asp Thr Thr Gly Thr Tyr Thr Gln Tyr Arg Thr Gln Asp Tyr
        290                 295                 300

Pro Ser Val Pro Thr Leu Val Arg Leu Leu Ala Lys His Asn Ile Ile
305                 310                 315                 320

Pro Ile Phe Ala Val Thr Asn Tyr Ser Tyr Ser Tyr Glu Lys Leu
                325                 330                 335

His Thr Tyr Phe Pro Val Ser Ser Leu Gly Val Leu Glu Asp Ser
                340                 345                 350

Ser Asn Ile Val Glu Leu Leu Glu Glu Ala Phe Asn Arg Ile Arg Ser
                355                 360                 365

Asn Leu Asp Ile Arg Ala Leu Asp Ser Pro Arg Gly Leu Arg Thr Glu
    370                 375                 380

Val Thr Ser Lys Met Phe Gln Lys Thr Arg Thr Gly Ser Phe His Ile
385                 390                 395                 400

Arg Arg Gly Glu Val Gly Ile Tyr Gln Val Gln Leu Arg Ala Leu Glu
                405                 410                 415

His Val Asp Gly Thr His Val Cys Gln Leu Pro Glu Asp Gln Lys Gly
                420                 425                 430

Asn Ile His Leu Lys Pro Ser Phe Ser Asp Gly Leu Lys Met Asp Ala
        435                 440                 445

Gly Ile Ile Cys Asp Val Cys Thr Cys Glu Leu Gln Lys Glu Val Arg
    450                 455                 460

Ser Ala Arg Cys Ser Phe Asn Gly Asp Phe Val Cys Gly Gln Cys Val
465                 470                 475                 480

Cys Ser Glu Gly Trp Ser Gly Gln Thr Cys Asn Cys Ser Thr Gly Ser
                485                 490                 495

Leu Ser Asp Ile Gln Pro Cys Leu Arg Glu Gly Glu Asp Lys Pro Cys
        500                 505                 510

Ser Gly Arg Gly Glu Cys Gln Cys Gly His Cys Val Cys Tyr Gly Glu
    515                 520                 525

Gly Arg Tyr Glu Gly Gln Phe Cys Glu Tyr Asp Asn Phe Gln Cys Pro
530                 535                 540

Arg Thr Ser Gly Phe Leu Cys Asn Asp Arg Gly Arg Cys Ser Met Gly
545                 550                 555                 560

Gln Cys Val Cys Glu Pro Gly Trp Thr Gly Pro Ser Cys Asp Cys Pro
                565                 570                 575

Leu Ser Asn Ala Thr Cys Ile Asp Ser Asn Gly Gly Ile Cys Asn Gly
            580                 585                 590

Arg Gly His Cys Glu Cys Gly Arg Cys His Cys His Gln Gln Ser Leu
        595                 600                 605
```

-continued

Tyr Thr Asp Thr Ile Cys Glu Ile Asn Tyr Ser Ala Ile His Pro Gly
610                 615                 620

Leu Cys Glu Asp Leu Arg Ser Cys Val Gln Cys Gln Ala Trp Gly Thr
625                 630                 635                 640

Gly Glu Lys Lys Gly Arg Thr Cys Glu Glu Cys Asn Phe Lys Val Lys
        645                 650                 655

Met Val Asp Glu Leu Lys Arg Ala Glu Glu Val Val Arg Cys Ser
            660                 665                 670

Phe Arg Asp Glu Asp Asp Cys Thr Tyr Ser Tyr Thr Met Glu Gly
            675                 680                 685

Asp Gly Ala Pro Gly Pro Asn Ser Thr Val Leu Val His Lys Lys Lys
690                 695                 700

Asp Cys Pro Pro Gly Ser Phe Trp Trp Leu Ile Pro Leu Leu Leu Leu
705                 710                 715                 720

Leu Leu Pro Leu Leu Ala Leu Leu Leu Leu Cys Trp Lys Tyr Cys
            725                 730                 735

Ala Cys Cys Lys Ala Cys Leu Ala Leu Leu Pro Cys Cys Asn Arg Gly
                740                 745                 750

His Met Val Gly Phe Lys Glu Asp His Tyr Met Leu Arg Glu Asn Leu
            755                 760                 765

Met Ala Ser Asp His Leu Asp Thr Pro Met Leu Arg Ser Gly Asn Leu
770                 775                 780

Lys Gly Arg Asp Val Val Arg Trp Lys Val Thr Asn Asn Met Gln Arg
785                 790                 795                 800

Pro Gly Phe Ala Thr His Ala Ala Ser Ile Asn Pro Thr Glu Leu Val
                805                 810                 815

Pro Tyr Gly Leu Ser Leu Arg Leu Ala Arg Leu Cys Thr Glu Asn Leu
            820                 825                 830

Leu Lys Pro Asp Thr Arg Glu Cys Ala Gln Leu Arg Gln Glu Val Glu
        835                 840                 845

Glu Asn Leu Asn Glu Val Tyr Arg Gln Ile Ser Gly Val His Lys Leu
    850                 855                 860

Gln Gln Thr Lys Phe Arg Gln Pro Asn Ala Gly Lys Lys Gln Asp
865                 870                 875                 880

His Thr Ile Val Asp Thr Val Leu Met Ala Pro Arg Ser Ala Lys Pro
            885                 890                 895

Ala Leu Leu Lys Leu Thr Glu Lys Gln Val Glu Arg Ala Phe His
                900                 905                 910

Asp Leu Lys Val Ala Pro Gly Tyr Tyr Thr Leu Thr Ala Asp Gln Asp
        915                 920                 925

Ala Arg Gly Met Val Glu Phe Gln Gly Val Glu Leu Val Asp Val
930                 935                 940

Arg Val Pro Leu Phe Ile Arg Pro Glu Asp Asp Glu Lys Gln Leu
945                 950                 955                 960

Leu Val Glu Ala Ile Asp Val Pro Ala Gly Thr Ala Thr Leu Gly Arg
            965                 970                 975

Arg Leu Val Asn Ile Thr Ile Ile Lys Glu Gln Ala Arg Asp Val Val
            980                 985                 990

Ser Phe Glu Gln Pro Glu Phe Ser Val Ser Arg Gly Asp Gln Val Ala
        995                 1000                1005

Arg Ile Pro Val Ile Arg Arg Val Leu Asp Gly Gly Lys Ser Gln
        1010                1015                1020

Val Ser Tyr Arg Thr Gln Asp Gly Thr Ala Gln Gly Asn Arg Asp

```
                1025                1030                1035

Tyr Ile Pro Val Glu Gly Glu Leu Leu Phe Gln Pro Gly Glu Ala
                1040                1045                1050

Trp Lys Glu Leu Gln Val Lys Leu Leu Glu Leu Gln Glu Val Asp
                1055                1060                1065

Ser Leu Leu Arg Gly Arg Gln Val Arg Arg Phe His Val Gln Leu
                1070                1075                1080

Ser Asn Pro Lys Phe Gly Ala His Leu Gly Gln Pro His Ser Thr
                1085                1090                1095

Thr Ile Ile Ile Arg Asp Pro Asp Glu Leu Asp Arg Ser Phe Thr
                1100                1105                1110

Ser Gln Met Leu Ser Ser Gln Pro Pro His Gly Asp Leu Gly
                1115                1120                1125

Ala Pro Gln Asn Pro Asn Ala Lys Ala Gly Ser Arg Lys Ile
                1130                1135                1140

His Phe Asn Trp Leu Pro Pro Ser Gly Lys Pro Met Gly Tyr Arg
                1145                1150                1155

Val Lys Tyr Trp Ile Gln Gly Asp Ser Glu Ser Glu Ala His Leu
                1160                1165                1170

Leu Asp Ser Lys Val Pro Ser Val Glu Leu Thr Asn Leu Tyr Pro
                1175                1180                1185

Tyr Cys Asp Tyr Glu Met Lys Val Cys Ala Tyr Gly Ala Gln Gly
                1190                1195                1200

Glu Gly Pro Tyr Ser Ser Leu Val Ser Cys Arg Thr His Gln Glu
                1205                1210                1215

Val Pro Ser Glu Pro Gly Arg Leu Ala Phe Asn Val Val Ser Ser
                1220                1225                1230

Thr Val Thr Gln Leu Ser Trp Ala Glu Pro Ala Glu Thr Asn Gly
                1235                1240                1245

Glu Ile Thr Ala Tyr Glu Val Cys Tyr Gly Leu Val Asn Asp Asp
                1250                1255                1260

Asn Arg Pro Ile Gly Pro Met Lys Lys Val Leu Val Asp Asn Pro
                1265                1270                1275

Lys Asn Arg Met Leu Leu Ile Glu Asn Leu Arg Glu Ser Gln Pro
                1280                1285                1290

Tyr Arg Tyr Thr Val Lys Ala Arg Asn Gly Ala Gly Trp Gly Pro
                1295                1300                1305

Glu Arg Glu Ala Ile Ile Asn Leu Ala Thr Gln Pro Lys Arg Pro
                1310                1315                1320

Met Ser Ile Pro Ile Ile Pro Asp Ile Pro Ile Val Asp Ala Gln
                1325                1330                1335

Ser Gly Glu Asp Tyr Asp Ser Phe Leu Met Tyr Ser Asp Asp Val
                1340                1345                1350

Leu Arg Ser Pro Ser Gly Ser Gln Arg Pro Ser Val Ser Asp Asp
                1355                1360                1365

Thr Gly Cys Gly Trp Lys Phe Glu Pro Leu Leu Gly Glu Glu Leu
                1370                1375                1380

Asp Leu Arg Arg Val Thr Trp Arg Leu Pro Pro Glu Leu Ile Pro
                1385                1390                1395

Arg Leu Ser Ala Ser Ser Gly Arg Ser Ser Asp Ala Glu Ala Pro
                1400                1405                1410

His Gly Pro Pro Asp Asp Gly Gly Ala Gly Gly Lys Gly Gly Ser
                1415                1420                1425
```

```
Leu Pro Arg Ser Ala Thr Pro Gly Pro Gly Glu His Leu Val
    1430            1435            1440

Asn Gly Arg Met Asp Phe Ala Phe Pro Gly Ser Thr Asn Ser Leu
    1445            1450            1455

His Arg Met Thr Thr Thr Ser Ala Ala Ala Tyr Gly Thr His Leu
    1460            1465            1470

Ser Pro His Val Pro His Arg Val Leu Ser Thr Ser Ser Thr Leu
    1475            1480            1485

Thr Arg Asp Tyr Asn Ser Leu Thr Arg Ser Glu His Ser His Ser
    1490            1495            1500

Thr Thr Leu Pro Arg Asp Tyr Ser Thr Leu Thr Ser Val Ser Ser
    1505            1510            1515

His Asp Ser Arg Leu Thr Ala Gly Val Pro Asp Thr Pro Thr Arg
    1520            1525            1530

Leu Val Phe Ser Ala Leu Gly Pro Thr Ser Leu Arg Val Ser Trp
    1535            1540            1545

Gln Glu Pro Arg Cys Glu Arg Pro Leu Gln Gly Tyr Ser Val Glu
    1550            1555            1560

Tyr Gln Leu Leu Asn Gly Gly Glu Leu His Arg Leu Asn Ile Pro
    1565            1570            1575

Asn Pro Ala Gln Thr Ser Val Val Val Glu Asp Leu Leu Pro Asn
    1580            1585            1590

His Ser Tyr Val Phe Arg Val Arg Ala Gln Ser Gln Glu Gly Trp
    1595            1600            1605

Gly Arg Glu Arg Glu Gly Val Ile Thr Ile Glu Ser Gln Val His
    1610            1615            1620

Pro Gln Ser Pro Leu Cys Pro Leu Pro Gly Ser Ala Phe Thr Leu
    1625            1630            1635

Ser Thr Pro Ser Ala Pro Gly Pro Leu Val Phe Thr Ala Leu Ser
    1640            1645            1650

Pro Asp Ser Leu Gln Leu Ser Trp Glu Arg Pro Arg Arg Pro Asn
    1655            1660            1665

Gly Asp Ile Val Gly Tyr Leu Val Thr Cys Glu Met Ala Gln Gly
    1670            1675            1680

Gly Gly Pro Ala Thr Ala Phe Arg Val Asp Gly Asp Ser Pro Glu
    1685            1690            1695

Ser Arg Leu Thr Val Pro Gly Leu Ser Glu Asn Val Pro Tyr Lys
    1700            1705            1710

Phe Lys Val Gln Ala Arg Thr Thr Glu Gly Phe Gly Pro Glu Arg
    1715            1720            1725

Glu Gly Ile Ile Thr Ile Glu Ser Gln Asp Gly Gly Pro Phe Pro
    1730            1735            1740

Gln Leu Gly Ser Arg Ala Gly Leu Phe Gln His Pro Leu Gln Ser
    1745            1750            1755

Glu Tyr Ser Ser Ile Thr Thr Thr His Thr Ser Ala Thr Glu Pro
    1760            1765            1770

Phe Leu Val Asp Gly Leu Thr Leu Gly Ala Gln His Leu Glu Ala
    1775            1780            1785

Gly Gly Ser Leu Thr Arg His Val Thr Gln Glu Phe Val Ser Arg
    1790            1795            1800

Thr Leu Thr Thr Ser Gly Thr Leu Ser Thr His Met Asp Gln Gln
    1805            1810            1815
```

Phe Phe Gln Thr
    1820

<210> SEQ ID NO 12
<211> LENGTH: 799
<212> TYPE: PRT
<213> ORGANISM: Artificial Sequence
<220> FEATURE:
<223> OTHER INFORMATION: ITB1-5

<400> SEQUENCE: 12

Met Pro Arg Ala Pro Ala Pro Leu Tyr Ala Cys Leu Leu Gly Leu Cys
1               5                   10                  15

Ala Leu Leu Pro Arg Leu Ala Gly Leu Asn Ile Cys Thr Ser Gly Ser
            20                  25                  30

Ala Thr Ser Cys Glu Glu Cys Leu Leu Ile His Pro Lys Cys Ala Trp
        35                  40                  45

Cys Ser Lys Glu Asp Phe Gly Ser Pro Arg Ser Ile Thr Ser Arg Cys
    50                  55                  60

Asp Leu Arg Ala Asn Leu Val Lys Asn Gly Cys Gly Gly Glu Ile Glu
65                  70                  75                  80

Ser Pro Ala Ser Ser Phe His Val Leu Arg Ser Leu Pro Leu Ser Ser
                85                  90                  95

Lys Gly Ser Gly Ser Ala Gly Trp Asp Val Ile Gln Met Thr Pro Gln
            100                 105                 110

Glu Ile Ala Val Asn Leu Arg Pro Gly Asp Lys Thr Thr Phe Gln Leu
        115                 120                 125

Gln Val Arg Gln Val Glu Asp Tyr Pro Val Asp Leu Tyr Tyr Leu Met
    130                 135                 140

Asp Leu Ser Leu Ser Met Lys Asp Asp Leu Asp Asn Ile Arg Ser Leu
145                 150                 155                 160

Gly Thr Lys Leu Ala Glu Glu Met Arg Lys Leu Thr Ser Asn Phe Arg
                165                 170                 175

Leu Gly Phe Gly Ser Phe Val Asp Lys Asp Ile Ser Pro Phe Ser Tyr
            180                 185                 190

Thr Ala Pro Arg Tyr Gln Thr Asn Pro Cys Ile Gly Tyr Lys Leu Phe
        195                 200                 205

Pro Asn Cys Val Pro Ser Phe Gly Phe Arg His Leu Leu Pro Leu Thr
    210                 215                 220

Asp Arg Val Asp Ser Phe Asn Glu Glu Val Arg Lys Gln Arg Val Ser
225                 230                 235                 240

Arg Asn Arg Asp Ala Pro Glu Gly Gly Phe Asp Ala Val Leu Gln Ala
                245                 250                 255

Ala Val Cys Lys Glu Lys Ile Gly Trp Arg Lys Asp Ala Leu His Leu
            260                 265                 270

Leu Val Phe Thr Thr Asp Asp Val Pro His Ile Ala Leu Asp Gly Lys
        275                 280                 285

Leu Gly Gly Leu Val Gln Pro His Asp Gly Gln Cys His Leu Asn Glu
    290                 295                 300

Ala Asn Glu Tyr Thr Ala Ser Asn Gln Met Asp Tyr Pro Ser Leu Ala
305                 310                 315                 320

Leu Leu Gly Glu Lys Leu Ala Glu Asn Asn Ile Asn Leu Ile Phe Ala
                325                 330                 335

Val Thr Lys Asn His Tyr Met Leu Tyr Lys Asn Phe Thr Ala Leu Ile
            340                 345                 350

```
Pro Gly Thr Thr Val Glu Ile Leu Asp Gly Asp Ser Lys Asn Ile Ile
            355                 360                 365

Gln Leu Ile Ile Asn Ala Tyr Asn Ser Ile Arg Ser Lys Val Glu Leu
    370                 375                 380

Ser Val Trp Asp Gln Pro Glu Asp Leu Asn Leu Phe Phe Thr Ala Thr
385                 390                 395                 400

Cys Gln Asp Gly Val Ser Tyr Pro Gly Gln Arg Lys Cys Glu Gly Leu
                405                 410                 415

Lys Ile Gly Asp Thr Ala Ser Phe Glu Val Ser Leu Glu Ala Arg Ser
            420                 425                 430

Cys Pro Ser Arg His Thr Glu His Val Phe Ala Leu Arg Pro Val Gly
            435                 440                 445

Phe Arg Asp Ser Leu Glu Val Gly Val Thr Tyr Asn Cys Thr Cys Gly
            450                 455                 460

Cys Ser Val Gly Leu Glu Pro Asn Ser Ala Arg Cys Asn Gly Ser Gly
465                 470                 475                 480

Thr Tyr Val Cys Gly Leu Cys Glu Cys Ser Pro Gly Tyr Leu Gly Thr
                485                 490                 495

Arg Cys Glu Cys Gln Asp Gly Glu Asn Gln Ser Val Tyr Gln Asn Leu
            500                 505                 510

Cys Arg Glu Ala Glu Gly Lys Pro Leu Cys Ser Gly Arg Gly Asp Cys
            515                 520                 525

Ser Cys Asn Gln Cys Ser Cys Phe Glu Ser Glu Phe Gly Lys Ile Tyr
            530                 535                 540

Gly Pro Phe Cys Glu Cys Asp Asn Phe Ser Cys Ala Arg Asn Lys Gly
545                 550                 555                 560

Val Leu Cys Ser Gly His Gly Glu Cys His Cys Gly Glu Cys Lys Cys
                565                 570                 575

His Ala Gly Tyr Ile Gly Asp Asn Cys Asn Cys Ser Thr Asp Ile Ser
            580                 585                 590

Thr Cys Arg Gly Arg Asp Gly Gln Ile Cys Ser Glu Arg Gly His Cys
            595                 600                 605

Leu Cys Gly Gln Cys Gln Cys Thr Glu Pro Gly Ala Phe Gly Glu Met
    610                 615                 620

Cys Glu Lys Cys Pro Thr Cys Pro Asp Ala Cys Ser Thr Lys Arg Asp
625                 630                 635                 640

Cys Val Glu Cys Leu Leu Leu His Ser Gly Lys Pro Asp Asn Gln Thr
                645                 650                 655

Cys His Ser Leu Cys Arg Asp Glu Val Ile Thr Trp Val Asp Thr Ile
            660                 665                 670

Val Lys Asp Asp Gln Glu Ala Val Leu Cys Phe Tyr Lys Thr Ala Lys
    675                 680                 685

Asp Cys Val Met Met Phe Thr Tyr Val Glu Leu Pro Ser Gly Lys Ser
            690                 695                 700

Asn Leu Thr Val Leu Arg Glu Pro Glu Cys Gly Asn Thr Pro Asn Ala
705                 710                 715                 720

Met Thr Ile Leu Leu Ala Val Val Gly Ser Ile Leu Leu Val Gly Leu
                725                 730                 735

Ala Leu Leu Ala Ile Trp Lys Leu Leu Val Thr Ile His Asp Arg Arg
            740                 745                 750

Glu Phe Ala Lys Phe Gln Ser Glu Arg Ser Arg Ala Arg Tyr Glu Met
            755                 760                 765

Ala Ser Asn Pro Leu Tyr Arg Lys Pro Ile Ser Thr His Thr Val Asp
```

-continued

```
            770                 775                 780
Phe Thr Phe Asn Lys Phe Asn Lys Ser Tyr Asn Gly Thr Val Asp
785                 790                 795

<210> SEQ ID NO 13
<211> LENGTH: 788
<212> TYPE: PRT
<213> ORGANISM: Artificial Sequence
<220> FEATURE:
<223> OTHER INFORMATION: ITB1-6

<400> SEQUENCE: 13

Met Gly Ile Glu Leu Leu Cys Leu Phe Phe Leu Phe Leu Gly Arg Asn
1               5                   10                  15

Asp His Val Gln Gly Gly Cys Ala Leu Gly Gly Ala Glu Thr Cys Glu
            20                  25                  30

Asp Cys Leu Leu Ile Gly Pro Gln Cys Ala Trp Cys Ala Gln Glu Asn
        35                  40                  45

Phe Thr His Pro Ser Gly Val Gly Glu Arg Cys Asp Thr Pro Ala Asn
    50                  55                  60

Leu Leu Ala Lys Gly Cys Gln Leu Asn Phe Ile Glu Asn Pro Val Ser
65                  70                  75                  80

Gln Val Glu Ile Leu Lys Asn Lys Pro Leu Ser Val Gly Arg Gln Lys
                85                  90                  95

Asn Ser Ser Asp Ile Val Gln Ile Ala Pro Gln Ser Leu Ile Leu Lys
            100                 105                 110

Leu Arg Pro Gly Gly Ala Gln Thr Leu Gln Val His Val Arg Gln Thr
        115                 120                 125

Glu Asp Tyr Pro Val Asp Leu Tyr Tyr Leu Met Asp Leu Ser Ala Ser
    130                 135                 140

Met Asp Asp Asp Leu Asn Thr Ile Lys Glu Leu Gly Ser Arg Leu Ser
145                 150                 155                 160

Lys Glu Met Ser Lys Leu Thr Ser Asn Phe Arg Leu Gly Phe Gly Ser
                165                 170                 175

Phe Val Glu Lys Pro Val Ser Pro Phe Val Lys Thr Thr Pro Glu Glu
            180                 185                 190

Ile Ala Asn Pro Cys Ser Ser Ile Pro Tyr Phe Cys Leu Pro Thr Phe
        195                 200                 205

Gly Phe Lys His Ile Leu Pro Leu Thr Asn Asp Ala Glu Arg Phe Asn
    210                 215                 220

Glu Ile Val Lys Asn Gln Lys Ile Ser Ala Asn Ile Asp Thr Pro Glu
225                 230                 235                 240

Gly Gly Phe Asp Ala Ile Met Gln Ala Ala Val Cys Lys Glu Lys Ile
                245                 250                 255

Gly Trp Arg Asn Asp Ser Leu His Leu Leu Val Phe Val Ser Asp Ala
            260                 265                 270

Asp Ser His Phe Gly Met Asp Ser Lys Leu Ala Gly Ile Val Ile Pro
        275                 280                 285

Asn Asp Gly Leu Cys His Leu Asp Ser Lys Asn Glu Tyr Ser Met Ser
    290                 295                 300

Thr Val Leu Glu Tyr Pro Thr Ile Gly Gln Leu Ile Asp Lys Leu Val
305                 310                 315                 320

Gln Asn Asn Val Leu Leu Ile Phe Ala Val Thr Gln Glu Gln Val His
                325                 330                 335

Leu Tyr Glu Asn Tyr Ala Lys Leu Ile Pro Gly Ala Thr Val Gly Leu
```

```
              340                 345                 350
Leu Gln Lys Asp Ser Gly Asn Ile Leu Gln Leu Ile Ile Ser Ala Tyr
            355                 360                 365
Glu Glu Leu Arg Ser Glu Val Glu Leu Glu Val Leu Gly Asp Thr Glu
            370                 375                 380
Gly Leu Asn Leu Ser Phe Thr Ala Ile Cys Asn Asn Gly Thr Leu Phe
385                 390                 395                 400
Gln His Gln Lys Lys Cys Ser His Met Lys Val Gly Asp Thr Ala Ser
                405                 410                 415
Phe Ser Val Thr Val Asn Ile Pro His Cys Glu Arg Arg Ser Arg His
            420                 425                 430
Ile Ile Ile Lys Pro Val Gly Leu Gly Asp Ala Leu Glu Leu Leu Val
            435                 440                 445
Ser Pro Glu Cys Asn Cys Asp Cys Gln Lys Glu Val Glu Val Asn Ser
            450                 455                 460
Ser Lys Cys His His Gly Asn Gly Ser Phe Gln Cys Gly Val Cys Ala
465                 470                 475                 480
Cys His Pro Gly His Met Gly Pro Arg Cys Glu Cys Gly Glu Asp Met
                485                 490                 495
Leu Ser Thr Asp Ser Cys Lys Glu Ala Pro Asp His Pro Ser Cys Ser
            500                 505                 510
Gly Arg Gly Asp Cys Tyr Cys Gly Gln Cys Ile Cys His Leu Ser Pro
            515                 520                 525
Tyr Gly Asn Ile Tyr Gly Pro Tyr Cys Gln Cys Asp Asn Phe Ser Cys
            530                 535                 540
Val Arg His Lys Gly Leu Leu Cys Gly Gly Asn Gly Asp Cys Asp Cys
545                 550                 555                 560
Gly Glu Cys Val Cys Arg Ser Gly Trp Thr Gly Glu Tyr Cys Asn Cys
                565                 570                 575
Thr Thr Ser Thr Asp Ser Cys Val Ser Glu Asp Gly Val Leu Cys Ser
            580                 585                 590
Gly Arg Gly Asp Cys Val Cys Gly Lys Cys Val Cys Thr Asn Pro Gly
            595                 600                 605
Ala Ser Gly Pro Thr Cys Glu Arg Cys Pro Thr Cys Gly Asp Pro Cys
            610                 615                 620
Asn Ser Lys Arg Ser Cys Ile Glu Cys His Leu Ser Ala Ala Gly Gln
625                 630                 635                 640
Ala Arg Glu Glu Cys Val Asp Lys Cys Lys Leu Ala Gly Ala Thr Ile
                645                 650                 655
Ser Glu Glu Glu Asp Phe Ser Lys Asp Gly Ser Val Ser Cys Ser Leu
            660                 665                 670
Gln Gly Glu Asn Glu Cys Leu Ile Thr Phe Leu Ile Thr Thr Asp Asn
            675                 680                 685
Glu Gly Lys Thr Ile Ile His Ser Ile Asn Glu Lys Asp Cys Pro Lys
            690                 695                 700
Pro Pro Asn Ile Pro Met Ile Met Leu Gly Val Ser Leu Ala Ile Leu
705                 710                 715                 720
Leu Ile Gly Val Val Leu Leu Cys Ile Trp Lys Leu Leu Val Ser Phe
                725                 730                 735
His Asp Arg Lys Glu Val Ala Lys Phe Glu Ala Glu Arg Ser Lys Ala
            740                 745                 750
Lys Trp Gln Thr Gly Thr Asn Pro Leu Tyr Arg Gly Ser Thr Ser Thr
            755                 760                 765
```

Phe Lys Asn Val Thr Tyr Lys His Arg Glu Lys Gln Lys Val Asp Leu
            770                 775                 780

Ser Thr Asp Cys
785

<210> SEQ ID NO 14
<211> LENGTH: 798
<212> TYPE: PRT
<213> ORGANISM: Artificial Sequence
<220> FEATURE:
<223> OTHER INFORMATION: ITB1-7

<400> SEQUENCE: 14

Met Val Ala Leu Pro Met Val Leu Val Leu Leu Val Leu Ser Arg
1               5                   10                  15

Gly Glu Ser Glu Leu Asp Ala Lys Ile Pro Ser Thr Gly Asp Ala Thr
                20                  25                  30

Glu Trp Arg Asn Pro His Leu Ser Met Leu Gly Ser Cys Gln Pro Ala
            35                  40                  45

Pro Ser Cys Gln Lys Cys Ile Leu Ser His Pro Ser Cys Ala Trp Cys
50                  55                  60

Lys Gln Leu Asn Phe Thr Ala Ser Gly Glu Ala Glu Ala Arg Arg Cys
65                  70                  75                  80

Ala Arg Arg Glu Glu Leu Leu Ala Arg Gly Cys Pro Leu Glu Glu Leu
                85                  90                  95

Glu Glu Pro Arg Gly Gln Gln Glu Val Leu Gln Asp Gln Pro Leu Ser
            100                 105                 110

Gln Gly Ala Arg Gly Glu Gly Ala Thr Gln Leu Ala Pro Gln Arg Val
        115                 120                 125

Arg Val Thr Leu Arg Pro Gly Glu Pro Gln Gln Leu Gln Val Arg Phe
130                 135                 140

Leu Arg Ala Glu Gly Tyr Pro Val Asp Leu Tyr Tyr Leu Met Asp Leu
145                 150                 155                 160

Ser Tyr Ser Met Lys Asp Asp Leu Glu Arg Val Arg Gln Leu Gly His
                165                 170                 175

Ala Leu Leu Val Arg Leu Gln Glu Val Thr His Ser Val Arg Ile Gly
            180                 185                 190

Phe Gly Ser Phe Val Asp Lys Thr Val Leu Pro Phe Val Ser Thr Val
        195                 200                 205

Pro Ser Lys Leu Arg His Pro Cys Pro Thr Arg Leu Glu Arg Cys Gln
210                 215                 220

Ser Pro Phe Ser Phe His His Val Leu Ser Leu Thr Gly Asp Ala Gln
225                 230                 235                 240

Ala Phe Glu Arg Glu Val Gly Arg Gln Ser Val Ser Gly Asn Leu Asp
                245                 250                 255

Ser Pro Glu Gly Gly Phe Asp Ala Ile Leu Gln Ala Ala Leu Cys Gln
            260                 265                 270

Glu Gln Ile Gly Trp Arg Asn Val Ser Arg Leu Leu Val Phe Thr Ser
        275                 280                 285

Asp Asp Thr Phe His Thr Ala Gly Asp Gly Lys Leu Gly Gly Ile Phe
290                 295                 300

Met Pro Ser Asp Gly His Cys His Leu Asp Ser Asn Gly Leu Tyr Ser
305                 310                 315                 320

Arg Ser Thr Glu Phe Asp Tyr Pro Ser Val Gly Gln Val Ala Gln Ala
                325                 330                 335

```
Leu Ser Ala Ala Asn Ile Gln Pro Ile Phe Ala Val Thr Ser Ala Ala
            340                 345                 350

Leu Pro Val Tyr Gln Glu Leu Ser Lys Leu Ile Pro Lys Ser Ala Val
            355                 360                 365

Gly Glu Leu Ser Glu Asp Ser Ser Asn Val Val Gln Leu Ile Met Asp
370                 375                 380

Ala Tyr Asn Ser Leu Ser Ser Thr Val Thr Leu Glu His Ser Ser Leu
385                 390                 395                 400

Pro Pro Gly Val His Ile Ser Tyr Glu Ser Gln Cys Glu Gly Pro Glu
                405                 410                 415

Lys Arg Glu Gly Lys Ala Glu Asp Arg Gly Gln Cys Asn His Val Arg
            420                 425                 430

Ile Asn Gln Thr Val Thr Phe Trp Val Ser Leu Gln Ala Thr His Cys
            435                 440                 445

Leu Pro Glu Pro His Leu Leu Arg Leu Arg Ala Leu Gly Phe Ser Glu
            450                 455                 460

Glu Leu Ile Val Glu Leu His Thr Leu Cys Asp Cys Asn Cys Ser Asp
465                 470                 475                 480

Thr Gln Pro Gln Ala Pro His Cys Ser Asp Gly Gln Gly His Leu Gln
                485                 490                 495

Cys Gly Val Cys Ser Cys Ala Pro Gly Arg Leu Gly Arg Leu Cys Glu
            500                 505                 510

Cys Ser Val Ala Glu Leu Ser Ser Pro Asp Leu Glu Ser Gly Cys Arg
            515                 520                 525

Ala Pro Asn Gly Thr Gly Pro Leu Cys Ser Gly Lys Gly His Cys Gln
            530                 535                 540

Cys Gly Arg Cys Ser Cys Ser Gly Gln Ser Ser Gly His Leu Cys Glu
545                 550                 555                 560

Cys Asp Asp Ala Ser Cys Glu Arg His Glu Gly Ile Leu Cys Gly Gly
                565                 570                 575

Phe Gly Arg Cys Gln Cys Gly Val Cys His Cys His Ala Asn Arg Thr
            580                 585                 590

Gly Arg Ala Cys Glu Cys Ser Gly Asp Met Asp Ser Cys Ile Ser Pro
            595                 600                 605

Glu Gly Gly Leu Cys Ser Gly His Gly Arg Cys Lys Cys Asn Arg Cys
            610                 615                 620

Gln Cys Leu Asp Gly Tyr Tyr Gly Ala Leu Cys Asp Gln Cys Pro Gly
625                 630                 635                 640

Cys Lys Thr Pro Cys Glu Arg His Arg Asp Cys Ala Glu Cys Gly Ala
                645                 650                 655

Phe Arg Thr Gly Pro Leu Ala Thr Asn Cys Ser Thr Cys Ala His
            660                 665                 670

Thr Asn Val Thr Leu Ala Leu Ala Pro Ile Leu Asp Asp Gly Trp Cys
            675                 680                 685

Lys Glu Arg Thr Leu Asp Asn Gln Leu Phe Phe Leu Val Glu Asp
            690                 695                 700

Asp Ala Arg Gly Thr Val Val Leu Arg Val Arg Pro Gln Glu Lys Gly
705                 710                 715                 720

Ala Asp His Thr Gln Ala Ile Val Leu Gly Cys Val Gly Gly Ile Val
                725                 730                 735

Ala Val Gly Leu Gly Leu Val Leu Ala Tyr Arg Leu Ser Val Glu Ile
            740                 745                 750
```

-continued

Tyr Asp Arg Arg Glu Tyr Ser Arg Phe Glu Lys Glu Gln Gln Gln Leu
            755                 760                 765

Asn Trp Lys Gln Asp Ser Asn Pro Leu Tyr Lys Ser Ala Ile Thr Thr
770                 775                 780

Thr Ile Asn Pro Arg Phe Gln Glu Ala Asp Ser Pro Thr Leu
785                 790                 795

<210> SEQ ID NO 15
<211> LENGTH: 769
<212> TYPE: PRT
<213> ORGANISM: Artificial Sequence
<220> FEATURE:
<223> OTHER INFORMATION: ITB1-8

<400> SEQUENCE: 15

Met Cys Gly Ser Ala Leu Ala Phe Phe Thr Ala Ala Phe Val Cys Leu
1               5                   10                  15

Gln Asn Asp Arg Arg Gly Pro Ala Ser Phe Leu Trp Ala Ala Trp Val
            20                  25                  30

Phe Ser Leu Val Leu Gly Leu Gly Gln Gly Glu Asp Asn Arg Cys Ala
        35                  40                  45

Ser Ser Asn Ala Ala Ser Cys Ala Arg Cys Leu Ala Leu Gly Pro Glu
50                  55                  60

Cys Gly Trp Cys Val Gln Glu Asp Phe Ile Ser Gly Gly Ser Arg Ser
65                  70                  75                  80

Glu Arg Cys Asp Ile Val Ser Asn Leu Ile Ser Lys Gly Cys Ser Val
                85                  90                  95

Asp Ser Ile Glu Tyr Pro Ser Val His Val Ile Pro Thr Glu Asn
            100                 105                 110

Glu Ile Asn Thr Gln Val Thr Pro Gly Glu Val Ser Ile Gln Leu Arg
        115                 120                 125

Pro Gly Ala Glu Ala Asn Phe Met Leu Lys Val His Pro Leu Lys Lys
130                 135                 140

Tyr Pro Val Asp Leu Tyr Tyr Leu Val Asp Val Ser Ala Ser Met His
145                 150                 155                 160

Asn Asn Ile Glu Lys Leu Asn Ser Val Gly Asn Asp Leu Ser Arg Lys
                165                 170                 175

Met Ala Phe Phe Ser Arg Asp Phe Arg Leu Gly Phe Gly Ser Tyr Val
            180                 185                 190

Asp Lys Thr Val Ser Pro Tyr Ile Ser Ile His Pro Glu Arg Ile His
        195                 200                 205

Asn Gln Cys Ser Asp Tyr Asn Leu Asp Cys Met Pro Pro His Gly Tyr
210                 215                 220

Ile His Val Leu Ser Leu Thr Glu Asn Ile Thr Glu Phe Glu Lys Ala
225                 230                 235                 240

Val His Arg Gln Lys Ile Ser Gly Asn Ile Asp Thr Pro Glu Gly Gly
                245                 250                 255

Phe Asp Ala Met Leu Gln Ala Ala Val Cys Glu Ser His Ile Gly Trp
            260                 265                 270

Arg Lys Glu Ala Lys Arg Leu Leu Leu Val Met Thr Asp Gln Thr Ser
        275                 280                 285

His Leu Ala Leu Asp Ser Lys Leu Ala Gly Ile Val Val Pro Asn Asp
290                 295                 300

Gly Asn Cys His Leu Lys Asn Asn Val Tyr Val Lys Ser Thr Thr Met
305                 310                 315                 320

-continued

```
Glu His Pro Ser Leu Gly Gln Leu Ser Glu Lys Leu Ile Asp Asn Asn
                325                 330                 335

Ile Asn Val Ile Phe Ala Val Gln Gly Lys Gln Phe His Trp Tyr Lys
            340                 345                 350

Asp Leu Leu Pro Leu Leu Pro Gly Thr Ile Ala Gly Glu Ile Glu Ser
                355                 360                 365

Lys Ala Ala Asn Leu Asn Asn Leu Val Val Glu Ala Tyr Gln Lys Leu
370                 375                 380

Ile Ser Glu Val Lys Val Gln Val Glu Asn Gln Val Gln Gly Ile Tyr
385                 390                 395                 400

Phe Asn Ile Thr Ala Ile Cys Pro Asp Gly Ser Arg Lys Pro Gly Met
                405                 410                 415

Glu Gly Cys Arg Asn Val Thr Ser Asn Asp Glu Val Leu Phe Asn Val
                420                 425                 430

Thr Val Thr Met Lys Lys Cys Asp Val Thr Gly Gly Lys Asn Tyr Ala
            435                 440                 445

Ile Ile Lys Pro Ile Gly Phe Asn Glu Thr Ala Lys Ile His Ile His
        450                 455                 460

Arg Asn Cys Ser Cys Gln Cys Glu Asp Asn Arg Gly Pro Lys Gly Lys
465                 470                 475                 480

Cys Val Asp Glu Thr Phe Leu Asp Ser Lys Cys Phe Gln Cys Asp Glu
                485                 490                 495

Asn Lys Cys His Phe Asp Glu Asp Gln Phe Ser Ser Glu Ser Cys Lys
                500                 505                 510

Ser His Lys Asp Gln Pro Val Cys Ser Gly Arg Gly Val Cys Val Cys
            515                 520                 525

Gly Lys Cys Ser Cys His Lys Ile Lys Leu Gly Lys Val Tyr Gly Lys
        530                 535                 540

Tyr Cys Glu Lys Asp Asp Phe Ser Cys Pro Tyr His His Gly Asn Leu
545                 550                 555                 560

Cys Ala Gly His Gly Glu Cys Glu Ala Gly Arg Cys Gln Cys Phe Ser
                565                 570                 575

Gly Trp Glu Gly Asp Arg Cys Gln Cys Pro Ser Ala Ala Ala Gln His
                580                 585                 590

Cys Val Asn Ser Lys Gly Gln Val Cys Ser Gly Arg Gly Thr Cys Val
            595                 600                 605

Cys Gly Arg Cys Glu Cys Thr Asp Pro Arg Ser Ile Gly Arg Phe Cys
        610                 615                 620

Glu His Cys Pro Thr Cys Tyr Thr Ala Cys Lys Glu Asn Trp Asn Cys
625                 630                 635                 640

Met Gln Cys Leu His Pro His Asn Leu Ser Gln Ala Ile Leu Asp Gln
                645                 650                 655

Cys Lys Thr Ser Cys Ala Leu Met Glu Gln Gln His Tyr Val Asp Gln
            660                 665                 670

Thr Ser Glu Cys Phe Ser Ser Pro Ser Tyr Leu Arg Ile Phe Phe Ile
        675                 680                 685

Ile Phe Ile Val Thr Phe Leu Ile Gly Leu Leu Lys Val Leu Ile Ile
        690                 695                 700

Arg Gln Val Ile Leu Gln Trp Asn Ser Asn Lys Ile Lys Ser Ser Ser
705                 710                 715                 720

Asp Tyr Arg Val Ser Ala Ser Lys Lys Asp Lys Leu Ile Leu Gln Ser
                725                 730                 735

Val Cys Thr Arg Ala Val Thr Tyr Arg Arg Glu Lys Pro Glu Glu Ile
```

```
                    740                 745                 750
Lys Met Asp Ile Ser Lys Leu Asn Ala His Glu Thr Phe Arg Cys Asn
            755                 760                 765
Phe

<210> SEQ ID NO 16
<211> LENGTH: 190
<212> TYPE: PRT
<213> ORGANISM: Artificial Sequence
<220> FEATURE:
<223> OTHER INFORMATION: CD11b A-domain CD11bA WT (WT residues 132-321)

<400> SEQUENCE: 16

Asp Ser Asp Ile Ala Phe Leu Ile Asp Gly Ser Gly Ser Ile Ile Pro
1               5                   10                  15

His Asp Phe Arg Arg Met Lys Glu Phe Val Ser Thr Val Met Glu Gln
            20                  25                  30

Leu Lys Lys Ser Lys Thr Leu Phe Ser Leu Met Gln Tyr Ser Glu Glu
        35                  40                  45

Phe Arg Ile His Phe Thr Phe Lys Glu Phe Gln Asn Asn Pro Asn Pro
    50                  55                  60

Arg Ser Leu Val Lys Pro Ile Thr Gln Leu Leu Gly Arg Thr His Thr
65                  70                  75                  80

Ala Thr Gly Ile Arg Lys Val Val Arg Glu Leu Phe Asn Ile Thr Asn
                85                  90                  95

Gly Ala Arg Lys Asn Ala Phe Lys Ile Leu Val Val Ile Thr Asp Gly
            100                 105                 110

Glu Lys Phe Gly Asp Pro Leu Gly Tyr Glu Asp Val Ile Pro Glu Ala
        115                 120                 125

Asp Arg Glu Gly Val Ile Arg Tyr Val Ile Gly Val Gly Asp Ala Phe
    130                 135                 140

Arg Ser Glu Lys Ser Arg Gln Glu Leu Asn Thr Ile Ala Ser Lys Pro
145                 150                 155                 160

Pro Arg Asp His Val Phe Gln Val Asn Asn Phe Glu Ala Leu Lys Thr
                165                 170                 175

Ile Gln Asn Gln Leu Arg Glu Lys Ile Phe Ala Ile Glu Gly
            180                 185                 190

<210> SEQ ID NO 17
<211> LENGTH: 190
<212> TYPE: PRT
<213> ORGANISM: Artificial Sequence
<220> FEATURE:
<223> OTHER INFORMATION: CD11b A-domain with designed point mutation
      CD11bA - D140A

<400> SEQUENCE: 17

Asp Ser Asp Ile Ala Phe Leu Ile Ala Gly Ser Gly Ser Ile Ile Pro
1               5                   10                  15

His Asp Phe Arg Arg Met Lys Glu Phe Val Ser Thr Val Met Glu Gln
            20                  25                  30

Leu Lys Lys Ser Lys Thr Leu Phe Ser Leu Met Gln Tyr Ser Glu Glu
        35                  40                  45

Phe Arg Ile His Phe Thr Phe Lys Glu Phe Gln Asn Asn Pro Asn Pro
    50                  55                  60

Arg Ser Leu Val Lys Pro Ile Thr Gln Leu Leu Gly Arg Thr His Thr
65                  70                  75                  80
```

```
Ala Thr Gly Ile Arg Lys Val Val Arg Glu Leu Phe Asn Ile Thr Asn
            85                  90                  95

Gly Ala Arg Lys Asn Ala Phe Lys Ile Leu Val Val Ile Thr Asp Gly
        100                 105                 110

Glu Lys Phe Gly Asp Pro Leu Gly Tyr Glu Asp Val Ile Pro Glu Ala
        115                 120                 125

Asp Arg Glu Gly Val Ile Arg Tyr Val Ile Gly Val Gly Asp Ala Phe
        130                 135                 140

Arg Ser Glu Lys Ser Arg Gln Glu Leu Asn Thr Ile Ala Ser Lys Pro
145                 150                 155                 160

Pro Arg Asp His Val Phe Gln Val Asn Asn Phe Glu Ala Leu Lys Thr
                165                 170                 175

Ile Gln Asn Gln Leu Arg Glu Lys Ile Phe Ala Ile Glu Gly
                180                 185                 190
```

<210> SEQ ID NO 18
<211> LENGTH: 190
<212> TYPE: PRT
<213> ORGANISM: Artificial Sequence
<220> FEATURE:
<223> OTHER INFORMATION: CD11b A-domain with designed point mutations
      CD11bA - D140A/F275S

<400> SEQUENCE: 18

```
Asp Ser Asp Ile Ala Phe Leu Ile Ala Gly Ser Gly Ser Ile Ile Pro
1               5                   10                  15

His Asp Phe Arg Arg Met Lys Glu Phe Val Ser Thr Val Met Glu Gln
            20                  25                  30

Leu Lys Lys Ser Lys Thr Leu Phe Ser Leu Met Gln Tyr Ser Glu Glu
        35                  40                  45

Phe Arg Ile His Phe Thr Phe Lys Glu Phe Gln Asn Asn Pro Asn Pro
50                  55                  60

Arg Ser Leu Val Lys Pro Ile Thr Gln Leu Leu Gly Arg Thr His Thr
65                  70                  75                  80

Ala Thr Gly Ile Arg Lys Val Val Arg Glu Leu Phe Asn Ile Thr Asn
            85                  90                  95

Gly Ala Arg Lys Asn Ala Phe Lys Ile Leu Val Val Ile Thr Asp Gly
        100                 105                 110

Glu Lys Phe Gly Asp Pro Leu Gly Tyr Glu Asp Val Ile Pro Glu Ala
        115                 120                 125

Asp Arg Glu Gly Val Ile Arg Tyr Val Ile Gly Val Gly Asp Ala Ser
        130                 135                 140

Arg Ser Glu Lys Ser Arg Gln Glu Leu Asn Thr Ile Ala Ser Lys Pro
145                 150                 155                 160

Pro Arg Asp His Val Phe Gln Val Asn Asn Phe Glu Ala Leu Lys Thr
                165                 170                 175

Ile Gln Asn Gln Leu Arg Glu Lys Ile Phe Ala Ile Glu Gly
                180                 185                 190
```

<210> SEQ ID NO 19
<211> LENGTH: 190
<212> TYPE: PRT
<213> ORGANISM: Artificial Sequence
<220> FEATURE:
<223> OTHER INFORMATION: CD11b A-domain with designed point mutations
      (underlined) CD11bA - D140A/F275S/F302G

<400> SEQUENCE: 19

```
Asp Ser Asp Ile Ala Phe Leu Ile Ala Gly Ser Gly Ser Ile Ile Pro
1               5                   10                  15

His Asp Phe Arg Arg Met Lys Glu Phe Val Ser Thr Val Met Glu Gln
                20                  25                  30

Leu Lys Lys Ser Lys Thr Leu Phe Ser Leu Met Gln Tyr Ser Glu Glu
                35                  40                  45

Phe Arg Ile His Phe Thr Phe Lys Glu Phe Gln Asn Asn Pro Asn Pro
    50                  55                  60

Arg Ser Leu Val Lys Pro Ile Thr Gln Leu Leu Gly Arg Thr His Thr
65                  70                  75                  80

Ala Thr Gly Ile Arg Lys Val Val Arg Glu Leu Phe Asn Ile Thr Asn
                85                  90                  95

Gly Ala Arg Lys Asn Ala Phe Lys Ile Leu Val Val Ile Thr Asp Gly
                100                 105                 110

Glu Lys Phe Gly Asp Pro Leu Gly Tyr Glu Asp Val Ile Pro Glu Ala
            115                 120                 125

Asp Arg Glu Gly Val Ile Arg Tyr Val Ile Gly Val Gly Asp Ala Ser
        130                 135                 140

Arg Ser Glu Lys Ser Arg Gln Glu Leu Asn Thr Ile Ala Ser Lys Pro
145                 150                 155                 160

Pro Arg Asp His Val Phe Gln Val Asn Asn Gly Glu Ala Leu Lys Thr
                165                 170                 175

Ile Gln Asn Gln Leu Arg Glu Lys Ile Phe Ala Ile Glu Gly
                180                 185                 190

<210> SEQ ID NO 20
<211> LENGTH: 190
<212> TYPE: PRT
<213> ORGANISM: Artificial Sequence
<220> FEATURE:
<223> OTHER INFORMATION: CD11b A-domain with designed point mutation
      (underlined) CD11bA - D242A

<400> SEQUENCE: 20

Asp Ser Asp Ile Ala Phe Leu Ile Asp Gly Ser Gly Ser Ile Ile Pro
1               5                   10                  15

His Asp Phe Arg Arg Met Lys Glu Phe Val Ser Thr Val Met Glu Gln
                20                  25                  30

Leu Lys Lys Ser Lys Thr Leu Phe Ser Leu Met Gln Tyr Ser Glu Glu
                35                  40                  45

Phe Arg Ile His Phe Thr Phe Lys Glu Phe Gln Asn Asn Pro Asn Pro
    50                  55                  60

Arg Ser Leu Val Lys Pro Ile Thr Gln Leu Leu Gly Arg Thr His Thr
65                  70                  75                  80

Ala Thr Gly Ile Arg Lys Val Val Arg Glu Leu Phe Asn Ile Thr Asn
                85                  90                  95

Gly Ala Arg Lys Asn Ala Phe Lys Ile Leu Val Val Ile Thr Ala Gly
                100                 105                 110

Glu Lys Phe Gly Asp Pro Leu Gly Tyr Glu Asp Val Ile Pro Glu Ala
            115                 120                 125

Asp Arg Glu Gly Val Ile Arg Tyr Val Ile Gly Val Gly Asp Ala Phe
        130                 135                 140

Arg Ser Glu Lys Ser Arg Gln Glu Leu Asn Thr Ile Ala Ser Lys Pro
145                 150                 155                 160

Pro Arg Asp His Val Phe Gln Val Asn Asn Phe Glu Ala Leu Lys Thr
                165                 170                 175
```

Ile Gln Asn Gln Leu Arg Glu Lys Ile Phe Ala Ile Glu Gly
            180                 185                 190

<210> SEQ ID NO 21
<211> LENGTH: 190
<212> TYPE: PRT
<213> ORGANISM: Artificial Sequence
<220> FEATURE:
<223> OTHER INFORMATION: CD11b A-domain with designed point mutation
      (underlined) CD11bA - F275S

<400> SEQUENCE: 21

Asp Ser Asp Ile Ala Phe Leu Ile Asp Gly Ser Gly Ser Ile Ile Pro
1               5                   10                  15

His Asp Phe Arg Arg Met Lys Glu Phe Val Ser Thr Val Met Glu Gln
            20                  25                  30

Leu Lys Lys Ser Lys Thr Leu Phe Ser Leu Met Gln Tyr Ser Glu Glu
        35                  40                  45

Phe Arg Ile His Phe Thr Phe Lys Glu Phe Gln Asn Asn Pro Asn Pro
50                  55                  60

Arg Ser Leu Val Lys Pro Ile Thr Gln Leu Leu Gly Arg Thr His Thr
65                  70                  75                  80

Ala Thr Gly Ile Arg Lys Val Val Arg Glu Leu Phe Asn Ile Thr Asn
            85                  90                  95

Gly Ala Arg Lys Asn Ala Phe Lys Ile Leu Val Val Ile Thr Asp Gly
        100                 105                 110

Glu Lys Phe Gly Asp Pro Leu Gly Tyr Glu Asp Val Ile Pro Glu Ala
    115                 120                 125

Asp Arg Glu Gly Val Ile Arg Tyr Val Ile Gly Val Gly Asp Ala Ser
130                 135                 140

Arg Ser Glu Lys Ser Arg Gln Glu Leu Asn Thr Ile Ala Ser Lys Pro
145                 150                 155                 160

Pro Arg Asp His Val Phe Gln Val Asn Asn Phe Glu Ala Leu Lys Thr
            165                 170                 175

Ile Gln Asn Gln Leu Arg Glu Lys Ile Phe Ala Ile Glu Gly
            180                 185                 190

<210> SEQ ID NO 22
<211> LENGTH: 190
<212> TYPE: PRT
<213> ORGANISM: Artificial Sequence
<220> FEATURE:
<223> OTHER INFORMATION: CD11b A-domain with designed point mutations
      (underlined) CD11bA - F275S/F302G

<400> SEQUENCE: 22

Asp Ser Asp Ile Ala Phe Leu Ile Asp Gly Ser Gly Ser Ile Ile Pro
1               5                   10                  15

His Asp Phe Arg Arg Met Lys Glu Phe Val Ser Thr Val Met Glu Gln
            20                  25                  30

Leu Lys Lys Ser Lys Thr Leu Phe Ser Leu Met Gln Tyr Ser Glu Glu
        35                  40                  45

Phe Arg Ile His Phe Thr Phe Lys Glu Phe Gln Asn Asn Pro Asn Pro
50                  55                  60

Arg Ser Leu Val Lys Pro Ile Thr Gln Leu Leu Gly Arg Thr His Thr
65                  70                  75                  80

Ala Thr Gly Ile Arg Lys Val Val Arg Glu Leu Phe Asn Ile Thr Asn
            85                  90                  95

```
Gly Ala Arg Lys Asn Ala Phe Lys Ile Leu Val Val Ile Thr Asp Gly
            100                 105                 110

Glu Lys Phe Gly Asp Pro Leu Gly Tyr Glu Asp Val Ile Pro Glu Ala
        115                 120                 125

Asp Arg Glu Gly Val Ile Arg Tyr Val Ile Gly Val Gly Asp Ala Ser
    130                 135                 140

Arg Ser Glu Lys Ser Arg Gln Glu Leu Asn Thr Ile Ala Ser Lys Pro
145                 150                 155                 160

Pro Arg Asp His Val Phe Gln Val Asn Asn Gly Glu Ala Leu Lys Thr
                165                 170                 175

Ile Gln Asn Gln Leu Arg Glu Lys Ile Phe Ala Ile Glu Gly
            180                 185                 190

<210> SEQ ID NO 23
<211> LENGTH: 190
<212> TYPE: PRT
<213> ORGANISM: Artificial Sequence
<220> FEATURE:
<223> OTHER INFORMATION: CD11b A-domain with designed point mutations
      (underlined) CD11bA - D242A/F275S/F302G

<400> SEQUENCE: 23

Asp Ser Asp Ile Ala Phe Leu Ile Asp Gly Ser Gly Ser Ile Ile Pro
1               5                   10                  15

His Asp Phe Arg Arg Met Lys Glu Phe Val Ser Thr Val Met Glu Gln
            20                  25                  30

Leu Lys Lys Ser Lys Thr Leu Phe Ser Leu Met Gln Tyr Ser Glu Glu
        35                  40                  45

Phe Arg Ile His Phe Thr Phe Lys Glu Phe Gln Asn Asn Pro Asn Pro
    50                  55                  60

Arg Ser Leu Val Lys Pro Ile Thr Gln Leu Leu Gly Arg Thr His Thr
65                  70                  75                  80

Ala Thr Gly Ile Arg Lys Val Val Arg Glu Leu Phe Asn Ile Thr Asn
                85                  90                  95

Gly Ala Arg Lys Asn Ala Phe Lys Ile Leu Val Val Ile Thr Ala Gly
            100                 105                 110

Glu Lys Phe Gly Asp Pro Leu Gly Tyr Glu Asp Val Ile Pro Glu Ala
        115                 120                 125

Asp Arg Glu Gly Val Ile Arg Tyr Val Ile Gly Val Gly Asp Ala Ser
    130                 135                 140

Arg Ser Glu Lys Ser Arg Gln Glu Leu Asn Thr Ile Ala Ser Lys Pro
145                 150                 155                 160

Pro Arg Asp His Val Phe Gln Val Asn Asn Gly Glu Ala Leu Lys Thr
                165                 170                 175

Ile Gln Asn Gln Leu Arg Glu Lys Ile Phe Ala Ile Glu Gly
            180                 185                 190

<210> SEQ ID NO 24
<211> LENGTH: 184
<212> TYPE: PRT
<213> ORGANISM: Artificial Sequence
<220> FEATURE:
<223> OTHER INFORMATION: CD11a A-domain CD11aA WT, WT residues 128-321

<400> SEQUENCE: 24

Gly Asn Val Asp Leu Val Phe Leu Phe Asp Gly Ser Met Ser Leu Gln
1               5                   10                  15
```

```
Pro Asp Glu Phe Gln Lys Ile Leu Asp Phe Met Lys Asp Val Met Lys
            20                  25                  30

Lys Leu Ser Asn Thr Ser Tyr Gln Phe Ala Ala Val Gln Phe Ser Thr
        35                  40                  45

Ser Tyr Lys Thr Glu Phe Asp Phe Ser Asp Tyr Val Lys Arg Lys Asp
    50                  55                  60

Pro Asp Ala Leu Leu Lys His Val Lys His Met Leu Leu Leu Thr Asn
65                  70                  75                  80

Thr Phe Gly Ala Ile Asn Tyr Val Ala Thr Glu Val Phe Arg Glu Glu
                85                  90                  95

Leu Gly Ala Arg Pro Asp Ala Thr Lys Val Leu Ile Ile Ile Thr Asp
                100                 105                 110

Gly Glu Ala Thr Asp Ser Gly Asn Ile Asp Ala Ala Lys Asp Ile Ile
                115                 120                 125

Arg Tyr Ile Ile Gly Ile Gly Lys His Phe Gln Thr Lys Glu Ser Gln
    130                 135                 140

Glu Thr Leu His Lys Phe Ala Ser Lys Pro Ala Ser Glu Phe Val Lys
145                 150                 155                 160

Ile Leu Asp Thr Phe Glu Lys Leu Lys Asp Leu Phe Thr Glu Leu Gln
                165                 170                 175

Lys Lys Ile Tyr Val Ile Glu Gly
                180
```

<210> SEQ ID NO 25
<211> LENGTH: 184
<212> TYPE: PRT
<213> ORGANISM: Artificial Sequence
<220> FEATURE:
<223> OTHER INFORMATION: CD11a A-domain with designed point mutation
      (underlined) CD11aA - D137A

<400> SEQUENCE: 25

```
Gly Asn Val Asp Leu Val Phe Leu Phe Ala Gly Ser Met Ser Leu Gln
1               5                   10                  15

Pro Asp Glu Phe Gln Lys Ile Leu Asp Phe Met Lys Asp Val Met Lys
            20                  25                  30

Lys Leu Ser Asn Thr Ser Tyr Gln Phe Ala Ala Val Gln Phe Ser Thr
        35                  40                  45

Ser Tyr Lys Thr Glu Phe Asp Phe Ser Asp Tyr Val Lys Arg Lys Asp
    50                  55                  60

Pro Asp Ala Leu Leu Lys His Val Lys His Met Leu Leu Leu Thr Asn
65                  70                  75                  80

Thr Phe Gly Ala Ile Asn Tyr Val Ala Thr Glu Val Phe Arg Glu Glu
                85                  90                  95

Leu Gly Ala Arg Pro Asp Ala Thr Lys Val Leu Ile Ile Ile Thr Asp
                100                 105                 110

Gly Glu Ala Thr Asp Ser Gly Asn Ile Asp Ala Ala Lys Asp Ile Ile
                115                 120                 125

Arg Tyr Ile Ile Gly Ile Gly Lys His Phe Gln Thr Lys Glu Ser Gln
    130                 135                 140

Glu Thr Leu His Lys Phe Ala Ser Lys Pro Ala Ser Glu Phe Val Lys
145                 150                 155                 160

Ile Leu Asp Thr Phe Glu Lys Leu Lys Asp Leu Phe Thr Glu Leu Gln
                165                 170                 175

Lys Lys Ile Tyr Val Ile Glu Gly
                180
```

<210> SEQ ID NO 26
<211> LENGTH: 184
<212> TYPE: PRT
<213> ORGANISM: Artificial Sequence
<220> FEATURE:
<223> OTHER INFORMATION: CD11a A-domain with designed point mutation
      (underlined) CD11aA - D238A

<400> SEQUENCE: 26

Gly Asn Val Asp Leu Val Phe Leu Phe Asp Gly Ser Met Ser Leu Gln
1               5                   10                  15

Pro Asp Glu Phe Gln Lys Ile Leu Asp Phe Met Lys Asp Val Met Lys
            20                  25                  30

Lys Leu Ser Asn Thr Ser Tyr Gln Phe Ala Ala Val Gln Phe Ser Thr
        35                  40                  45

Ser Tyr Lys Thr Glu Phe Asp Phe Ser Asp Tyr Val Lys Arg Lys Asp
    50                  55                  60

Pro Asp Ala Leu Leu Lys His Val Lys His Met Leu Leu Leu Thr Asn
65                  70                  75                  80

Thr Phe Gly Ala Ile Asn Tyr Val Ala Thr Glu Val Phe Arg Glu Glu
                85                  90                  95

Leu Gly Ala Arg Pro Asp Ala Thr Lys Val Leu Ile Ile Ile Thr Ala
            100                 105                 110

Gly Glu Ala Thr Asp Ser Gly Asn Ile Asp Ala Ala Lys Asp Ile Ile
        115                 120                 125

Arg Tyr Ile Ile Gly Ile Gly Lys His Phe Gln Thr Lys Glu Ser Gln
    130                 135                 140

Glu Thr Leu His Lys Phe Ala Ser Lys Pro Ala Ser Glu Phe Val Lys
145                 150                 155                 160

Ile Leu Asp Thr Phe Glu Lys Leu Lys Asp Leu Phe Thr Glu Leu Gln
                165                 170                 175

Lys Lys Ile Tyr Val Ile Glu Gly
            180

<210> SEQ ID NO 27
<211> LENGTH: 184
<212> TYPE: PRT
<213> ORGANISM: Artificial Sequence
<220> FEATURE:
<223> OTHER INFORMATION: CD11a A-domain with designed point mutation
      (underlined) CD11aA - F264S

<400> SEQUENCE: 27

Gly Asn Val Asp Leu Val Phe Leu Phe Asp Gly Ser Met Ser Leu Gln
1               5                   10                  15

Pro Asp Glu Phe Gln Lys Ile Leu Asp Phe Met Lys Asp Val Met Lys
            20                  25                  30

Lys Leu Ser Asn Thr Ser Tyr Gln Phe Ala Ala Val Gln Phe Ser Thr
        35                  40                  45

Ser Tyr Lys Thr Glu Phe Asp Phe Ser Asp Tyr Val Lys Arg Lys Asp
    50                  55                  60

Pro Asp Ala Leu Leu Lys His Val Lys His Met Leu Leu Leu Thr Asn
65                  70                  75                  80

Thr Phe Gly Ala Ile Asn Tyr Val Ala Thr Glu Val Phe Arg Glu Glu
                85                  90                  95

Leu Gly Ala Arg Pro Asp Ala Thr Lys Val Leu Ile Ile Ile Thr Asp
            100                 105                 110

Gly Glu Ala Thr Asp Ser Gly Asn Ile Asp Ala Ala Lys Asp Ile Ile
            115                 120                 125

Arg Tyr Ile Ile Gly Ile Gly Lys His Ser Gln Thr Lys Glu Ser Gln
            130                 135                 140

Glu Thr Leu His Lys Phe Ala Ser Lys Pro Ala Ser Glu Phe Val Lys
145                 150                 155                 160

Ile Leu Asp Thr Phe Glu Lys Leu Lys Asp Leu Phe Thr Glu Leu Gln
                165                 170                 175

Lys Lys Ile Tyr Val Ile Glu Gly
            180

<210> SEQ ID NO 28
<211> LENGTH: 184
<212> TYPE: PRT
<213> ORGANISM: Artificial Sequence
<220> FEATURE:
<223> OTHER INFORMATION: CD11a A-domain with designed point mutations
      (underlined) CD11aA - F264S/F291G

<400> SEQUENCE: 28

Gly Asn Val Asp Leu Val Phe Leu Phe Asp Gly Ser Met Ser Leu Gln
1               5                   10                  15

Pro Asp Glu Phe Gln Lys Ile Leu Asp Phe Met Lys Asp Val Met Lys
            20                  25                  30

Lys Leu Ser Asn Thr Ser Tyr Gln Phe Ala Ala Val Gln Phe Ser Thr
        35                  40                  45

Ser Tyr Lys Thr Glu Phe Asp Phe Ser Asp Tyr Val Lys Arg Lys Asp
50                  55                  60

Pro Asp Ala Leu Leu Lys His Val Lys His Met Leu Leu Leu Thr Asn
65                  70                  75                  80

Thr Phe Gly Ala Ile Asn Tyr Val Ala Thr Glu Val Phe Arg Glu Glu
                85                  90                  95

Leu Gly Ala Arg Pro Asp Ala Thr Lys Val Leu Ile Ile Ile Thr Asp
            100                 105                 110

Gly Glu Ala Thr Asp Ser Gly Asn Ile Asp Ala Ala Lys Asp Ile Ile
            115                 120                 125

Arg Tyr Ile Ile Gly Ile Gly Lys His Ser Gln Thr Lys Glu Ser Gln
            130                 135                 140

Glu Thr Leu His Lys Phe Ala Ser Lys Pro Ala Ser Glu Phe Val Lys
145                 150                 155                 160

Ile Leu Asp Thr Gly Glu Lys Leu Lys Asp Leu Phe Thr Glu Leu Gln
                165                 170                 175

Lys Lys Ile Tyr Val Ile Glu Gly
            180

<210> SEQ ID NO 29
<211> LENGTH: 184
<212> TYPE: PRT
<213> ORGANISM: Artificial Sequence
<220> FEATURE:
<223> OTHER INFORMATION: CD11a A-domain with designed point mutations
      (underlined) CD11aA - D137A/F264S/F291G

<400> SEQUENCE: 29

Gly Asn Val Asp Leu Val Phe Leu Phe Ala Gly Ser Met Ser Leu Gln
1               5                   10                  15

Pro Asp Glu Phe Gln Lys Ile Leu Asp Phe Met Lys Asp Val Met Lys
            20                  25                  30

```
Lys Leu Ser Asn Thr Ser Tyr Gln Phe Ala Ala Val Gln Phe Ser Thr
            35                  40                  45

Ser Tyr Lys Thr Glu Phe Asp Phe Ser Asp Tyr Val Lys Arg Lys Asp
        50                  55                  60

Pro Asp Ala Leu Leu Lys His Val Lys His Met Leu Leu Leu Thr Asn
 65                  70                  75                  80

Thr Phe Gly Ala Ile Asn Tyr Val Ala Thr Glu Val Phe Arg Glu Glu
                85                  90                  95

Leu Gly Ala Arg Pro Asp Ala Thr Lys Val Leu Ile Ile Ile Thr Asp
                100                 105                 110

Gly Glu Ala Thr Asp Ser Gly Asn Ile Asp Ala Ala Lys Asp Ile Ile
                115                 120                 125

Arg Tyr Ile Ile Gly Ile Gly Lys His Ser Gln Thr Lys Glu Ser Gln
        130                 135                 140

Glu Thr Leu His Lys Phe Ala Ser Lys Pro Ala Ser Glu Phe Val Lys
145                 150                 155                 160

Ile Leu Asp Thr Gly Glu Lys Leu Lys Asp Leu Phe Thr Glu Leu Gln
                165                 170                 175

Lys Lys Ile Tyr Val Ile Glu Gly
            180

<210> SEQ ID NO 30
<211> LENGTH: 184
<212> TYPE: PRT
<213> ORGANISM: Artificial Sequence
<220> FEATURE:
<223> OTHER INFORMATION: CD11a A-domain with designed point mutations
      (underlined) CD11aA - D238A/F264S/F291G

<400> SEQUENCE: 30

Gly Asn Val Asp Leu Val Phe Leu Phe Asp Gly Ser Met Ser Leu Gln
 1               5                  10                  15

Pro Asp Glu Phe Gln Lys Ile Leu Asp Phe Met Lys Asp Val Met L

```
<210> SEQ ID NO 31
<211> LENGTH: 191
<212> TYPE: PRT
<213> ORGANISM: Artificial Sequence
<220> FEATURE:
<223> OTHER INFORMATION: CD11c A-domain WT 129-319

<400> SEQUENCE: 31

Gln Glu Gln Asp Ile Val Phe Leu Ile Asp Gly Ser Gly Ser Ile Ser
1               5                   10                  15

Ser Arg Asn Phe Ala Thr Met Met Asn Phe Val Arg Ala Val Ile Ser
            20                  25                  30

Gln Phe Gln Arg Pro Ser Thr Gln Phe Ser Leu Met Gln Phe Ser Asn
        35                  40                  45

Lys Phe Gln Thr His Phe Thr Phe Glu Glu Phe Arg Arg Ser Ser Asn
    50                  55                  60

Pro Leu Ser Leu Leu Ala Ser Val His Gln Leu Gln Gly Phe Thr Tyr
65                  70                  75                  80

Thr Ala Thr Ala Ile Gln Asn Val Val His Arg Leu Phe His Ala Ser
                85                  90                  95

Tyr Gly Ala Arg Arg Asp Ala Ala Lys Ile Leu Ile Val Ile Thr Asp
            100                 105                 110

Gly Lys Lys Glu Gly Asp Ser Leu Asp Tyr Lys Asp Val Ile Pro Met
        115                 120                 125

Ala Asp Ala Ala Gly Ile Ile Arg Tyr Ala Ile Gly Val Gly Leu Ala
    130                 135                 140

Phe Gln Asn Arg Asn Ser Trp Lys Glu Leu Asn Asp Ile Ala Ser Lys
145                 150                 155                 160

Pro Ser Gln Glu His Ile Phe Lys Val Glu Asp Phe Asp Ala Leu Lys
                165                 170                 175

Asp Ile Gln Asn Gln Leu Lys Glu Lys Ile Phe Ala Ile Glu Gly
            180                 185                 190

<210> SEQ ID NO 32
<211> LENGTH: 191
<212> TYPE: PRT
<213> ORGANISM: Artificial Sequence
<220> FEATURE:
<223> OTHER INFORMATION: CD11c A-domain with designed point mutation
      (underlined) CD11cA - D138A

<400> SEQUENCE: 32

Gln Glu Gln Asp Ile Val Phe Leu Ile Ala Gly Ser Gly Ser Ile Ser
1               5                   10                  15

Ser Arg Asn Phe Ala Thr Met Met Asn Phe Val Arg Ala Val Ile Ser
            20                  25                  30

Gln Phe Gln Arg Pro Ser Thr Gln Phe Ser Leu Met Gln Phe Ser Asn
        35                  40                  45

Lys Phe Gln Thr His Phe Thr Phe Glu Glu Phe Arg Arg Ser Ser Asn
    50                  55                  60

Pro Leu Ser Leu Leu Ala Ser Val His Gln Leu Gln Gly Phe Thr Tyr
65                  70                  75                  80

Thr Ala Thr Ala Ile Gln Asn Val Val His Arg Leu Phe His Ala Ser
                85                  90                  95

Tyr Gly Ala Arg Arg Asp Ala Ala Lys Ile Leu Ile Val Ile Thr Asp
            100                 105                 110

Gly Lys Lys Glu Gly Asp Ser Leu Asp Tyr Lys Asp Val Ile Pro Met
        115                 120                 125
```

```
Ala Asp Ala Ala Gly Ile Ile Arg Tyr Ala Ile Gly Val Gly Leu Ala
    130                 135                 140

Phe Gln Asn Arg Asn Ser Trp Lys Glu Leu Asn Asp Ile Ala Ser Lys
145                 150                 155                 160

Pro Ser Gln Glu His Ile Phe Lys Val Glu Asp Phe Asp Ala Leu Lys
                165                 170                 175

Asp Ile Gln Asn Gln Leu Lys Glu Lys Ile Phe Ala Ile Glu Gly
            180                 185                 190

<210> SEQ ID NO 33
<211> LENGTH: 191
<212> TYPE: PRT
<213> ORGANISM: Artificial Sequence
<220> FEATURE:
<223> OTHER INFORMATION: CD11c A-domain with designed point mutation
      (underlined) CD11cA - D240A

<400> SEQUENCE: 33

Gln Glu Gln Asp Ile Val Phe Leu Ile Asp Gly Ser Gly Ser Ile Ser
1               5                   10                  15

Ser Arg Asn Phe Ala Thr Met Met Asn Phe Val Arg Ala Val Ile Ser
            20                  25                  30

Gln Phe Gln Arg Pro Ser Thr Gln Phe Ser Leu Met Gln Phe Ser Asn
        35                  40                  45

Lys Phe Gln Thr His Phe Thr Phe Glu Glu Phe Arg Arg Ser Ser Asn
50                  55                  60

Pro Leu Ser Leu Leu Ala Ser Val His Gln Leu Gln Gly Phe Thr Tyr
65                  70                  75                  80

Thr Ala Thr Ala Ile Gln Asn Val Val His Arg Leu Phe His Ala Ser
                85                  90                  95

Tyr Gly Ala Arg Arg Asp Ala Ala Lys Ile Leu Ile Val Ile Thr Ala
            100                 105                 110

Gly Lys Lys Glu Gly Asp Ser Leu Asp Tyr Lys Asp Val Ile Pro Met
        115                 120                 125

Ala Asp Ala Ala Gly Ile Ile Arg Tyr Ala Ile Gly Val Gly Leu Ala
    130                 135                 140

Phe Gln Asn Arg Asn Ser Trp Lys Glu Leu Asn Asp Ile Ala Ser Lys
145                 150                 155                 160

Pro Ser Gln Glu His Ile Phe Lys Val Glu Asp Phe Asp Ala Leu Lys
                165                 170                 175

Asp Ile Gln Asn Gln Leu Lys Glu Lys Ile Phe Ala Ile Glu Gly
            180                 185                 190

<210> SEQ ID NO 34
<211> LENGTH: 191
<212> TYPE: PRT
<213> ORGANISM: Artificial Sequence
<220> FEATURE:
<223> OTHER INFORMATION: CD11c A-domain with designed point mutation
      (underlined) CD11cA - F275S

<400> SEQUENCE: 34

Gln Glu Gln Asp Ile Val Phe Leu Ile Asp Gly Ser Gly Ser Ile Ser
1               5                   10                  15

Ser Arg Asn Phe Ala Thr Met Met Asn Phe Val Arg Ala Val Ile Ser
            20                  25                  30

Gln Phe Gln Arg Pro Ser Thr Gln Phe Ser Leu Met Gln Phe Ser Asn
        35                  40                  45
```

Lys Phe Gln Thr His Phe Thr Phe Glu Glu Phe Arg Arg Ser Ser Asn
 50                  55                  60

Pro Leu Ser Leu Leu Ala Ser Val His Gln Leu Gln Gly Phe Thr Tyr
 65                  70                  75                  80

Thr Ala Thr Ala Ile Gln Asn Val Val His Arg Leu Phe His Ala Ser
                 85                  90                  95

Tyr Gly Ala Arg Arg Asp Ala Ala Lys Ile Leu Ile Val Ile Thr Asp
                100                 105                 110

Gly Lys Lys Glu Gly Asp Ser Leu Asp Tyr Lys Asp Val Ile Pro Met
                115                 120                 125

Ala Asp Ala Ala Gly Ile Ile Arg Tyr Ala Ile Gly Val Gly Leu Ala
                130                 135                 140

Ser Gln Asn Arg Asn Ser Trp Lys Glu Leu Asn Asp Ile Ala Ser Lys
145                 150                 155                 160

Pro Ser Gln Glu His Ile Phe Lys Val Glu Asp Phe Asp Ala Leu Lys
                165                 170                 175

Asp Ile Gln Asn Gln Leu Lys Glu Lys Ile Phe Ala Ile Glu Gly
                180                 185                 190

<210> SEQ ID NO 35
<211> LENGTH: 191
<212> TYPE: PRT
<213> ORGANISM: Artificial Sequence
<220> FEATURE:
<223> OTHER INFORMATION: CD11c A-domain with designed point mutations
      (underlined) CD11cA - F275S/F302G

<400> SEQUENCE: 35

Gln Glu Gln Asp Ile Val Phe Leu Ile Asp Gly Ser Gly Ser Ile Ser
 1                   5                  10                  15

Ser Arg Asn Phe Ala Thr Met Met Asn Phe Val Arg Ala Val Ile Ser
                 20                  25                  30

Gln Phe Gln Arg Pro Ser Thr Gln Phe Ser Leu Met Gln Phe Ser Asn
                 35                  40                  45

Lys Phe Gln Thr His Phe Thr Phe Glu Glu Phe Arg Arg Ser Ser Asn
 50                  55                  60

Pro Leu Ser Leu Leu Ala Ser Val His Gln Leu Gln Gly Phe Thr Tyr
 65                  70                  75                  80

Thr Ala Thr Ala Ile Gln Asn Val Val His Arg Leu Phe His Ala Ser
                 85                  90                  95

Tyr Gly Ala Arg Arg Asp Ala Ala Lys Ile Leu Ile Val Ile Thr Asp
                100                 105                 110

Gly Lys Lys Glu Gly Asp Ser Leu Asp Tyr Lys Asp Val Ile Pro Met
                115                 120                 125

Ala Asp Ala Ala Gly Ile Ile Arg Tyr Ala Ile Gly Val Gly Leu Ala
                130                 135                 140

Ser Gln Asn Arg Asn Ser Trp Lys Glu Leu Asn Asp Ile Ala Ser Lys
145                 150                 155                 160

Pro Ser Gln Glu His Ile Phe Lys Val Glu Asp Gly Asp Ala Leu Lys
                165                 170                 175

Asp Ile Gln Asn Gln Leu Lys Glu Lys Ile Phe Ala Ile Glu Gly
                180                 185                 190

<210> SEQ ID NO 36
<211> LENGTH: 191
<212> TYPE: PRT

<213> ORGANISM: Artificial Sequence
<220> FEATURE:
<223> OTHER INFORMATION: CD11c A-domain with designed point mutations
      (underlined) CD11cA - D240A/F275S/F302G

<400> SEQUENCE: 36

```
Gln Glu Gln Asp Ile Val Phe Leu Ile Asp Gly Ser Gly Ser Ile Ser
1               5                   10                  15

Ser Arg Asn Phe Ala Thr Met Met Asn Phe Val Arg Ala Val Ile Ser
                20                  25                  30

Gln Phe Gln Arg Pro Ser Thr Gln Phe Ser Leu Met Gln Phe Ser Asn
        35                  40                  45

Lys Phe Gln Thr His Phe Thr Phe Glu Glu Phe Arg Arg Ser Ser Asn
    50                  55                  60

Pro Leu Ser Leu Leu Ala Ser Val His Gln Leu Gln Gly Ph

```
                130                 135                 140
Ser Gln Asn Arg Asn Ser Trp Lys Glu Leu Asn Asp Ile Ala Ser Lys
145                 150                 155                 160

Pro Ser Gln Glu His Ile Phe Lys Val Glu Asp Gly Asp Ala Leu Lys
                165                 170                 175

Asp Ile Gln Asn Gln Leu Lys Glu Lys Ile Phe Ala Ile Glu Gly
                180                 185                 190

<210> SEQ ID NO 38
<211> LENGTH: 191
<212> TYPE: PRT
<213> ORGANISM: Artificial Sequence
<220> FEATURE:
<223> OTHER INFORMATION: CD11d A-domain WT: residues 147-337

<400> SEQUENCE: 38

Gln Glu Met Asp Ile Val Phe Leu Ile Asp Gly Ser Gly Ser Ile Asp
1               5                   10                  15

Gln Asn Asp Phe Asn Gln Met Lys Gly Phe Val Gln Ala Val Met Gly
                20                  25                  30

Gln Phe Glu Gly Thr Asp Thr Leu Phe Ala Leu Met Gln Tyr Ser Asn
            35                  40                  45

Leu Leu Lys Ile His Phe Thr Phe Thr Gln Phe Arg Thr Ser Pro Ser
50                  55                  60

Gln Gln Ser Leu Val Asp Pro Ile Val Gln Leu Lys Gly Leu Thr Phe
65                  70                  75                  80

Thr Ala Thr Gly Ile Leu Thr Val Val Thr Gln Leu Phe His His Lys
                85                  90                  95

Asn Gly Ala Arg Lys Ser Ala Lys Lys Ile Leu Ile Val Ile Thr Asp
                100                 105                 110

Gly Gln Lys Tyr Lys Asp Pro Leu Glu Tyr Ser Asp Val Ile Pro Gln
            115                 120                 125

Ala Glu Lys Ala Gly Ile Ile Arg Tyr Ala Ile Gly Val Gly His Ala
        130                 135                 140

Phe Gln Gly Pro Thr Ala Arg Gln Glu Leu Asn Thr Ile Ser Ser Ala
145                 150                 155                 160

Pro Pro Gln Asp His Val Phe Lys Val Asp Asn Phe Ala Ala Leu Gly
                165                 170                 175

Ser Ile Gln Lys Gln Leu Gln Glu Lys Ile Tyr Ala Val Glu Gly
                180                 185                 190

<210> SEQ ID NO 39
<211> LENGTH: 191
<212> TYPE: PRT
<213> ORGANISM: Artificial Sequence
<220> FEATURE:
<223> OTHER INFORMATION: CD11d A-domain with designed point mutation
      (underlined) CD11dA - D156A

<400> SEQUENCE: 39

Gln Glu Met Asp Ile Val Phe Leu Ile Ala Gly Ser Gly Ser Ile Asp
1               5                   10                  15

Gln Asn Asp Phe Asn Gln Met Lys Gly Phe Val Gln Ala Val Met Gly
                20                  25                  30

Gln Phe Glu Gly Thr Asp Thr Leu Phe Ala Leu Met Gln Tyr Ser Asn
            35                  40                  45

Leu Leu Lys Ile His Phe Thr Phe Thr Gln Phe Arg Thr Ser Pro Ser
50                  55                  60
```

```
Gln Gln Ser Leu Val Asp Pro Ile Val Gln Leu Lys Gly Leu Thr Phe
 65                  70                  75                  80

Thr Ala Thr Gly Ile Leu Thr Val Val Thr Gln Leu Phe His His Lys
                 85                  90                  95

Asn Gly Ala Arg Lys Ser Ala Lys Lys Ile Leu Ile Val Ile Thr Asp
            100                 105                 110

Gly Gln Lys Tyr Lys Asp Pro Leu Glu Tyr Ser Asp Val Ile Pro Gln
            115                 120                 125

Ala Glu Lys Ala Gly Ile Ile Arg Tyr Ala Ile Gly Val Gly His Ala
130                 135                 140

Phe Gln Gly Pro Thr Ala Arg Gln Glu Leu Asn Thr Ile Ser Ser Ala
145                 150                 155                 160

Pro Pro Gln Asp His Val Phe Lys Val Asp Asn Phe Ala Ala Leu Gly
                165                 170                 175

Ser Ile Gln Lys Gln Leu Gln Glu Lys Ile Tyr Ala Val Glu Gly
                180                 185                 190

<210> SEQ ID NO 40
<211> LENGTH: 191
<212> TYPE: PRT
<213> ORGANISM: Artificial Sequence
<220> FEATURE:
<223> OTHER INFORMATION: CD11d A-domain with designed point mutations
      (underlined) CD11dA - F291S/F318G

<400> SEQUENCE: 40

Gln Glu Met Asp Ile Val Phe Leu Ile Asp Gly Ser Gly Ser Ile Asp
  1               5                  10                  15

Gln Asn Asp Phe Asn Gln Met Lys Gly Phe Val Gln Ala Val Met Gly
                 20                  25                  30

Gln Phe Glu Gly Thr Asp Thr Leu Phe Ala Leu Met Gln Tyr Ser Asn
                 35                  40                  45

Leu Leu Lys Ile His Phe Thr Phe Thr Gln Phe Arg Thr Ser Pro Ser
 50                  55                  60

Gln Gln Ser Leu Val Asp Pro Ile Val Gln Leu Lys Gly Leu Thr Phe
 65                  70                  75                  80

Thr Ala Thr Gly Ile Leu Thr Val Val Thr Gln Leu Phe His His Lys
                 85                  90                  95

Asn Gly Ala Arg Lys Ser Ala Lys Lys Ile Leu Ile Val Ile Thr Asp
            100                 105                 110

Gly Gln Lys Tyr Lys Asp Pro Leu Glu Tyr Ser Asp Val Ile Pro Gln
            115                 120                 125

Ala Glu Lys Ala Gly Ile Ile Arg Tyr Ala Ile Gly Val Gly His Ala
130                 135                 140

Ser Gln Gly Pro Thr Ala Arg Gln Glu Leu Asn Thr Ile Ser Ser Ala
145                 150                 155                 160

Pro Pro Gln Asp His Val Phe Lys Val Asp Asn Gly Ala Ala Leu Gly
                165                 170                 175

Ser Ile Gln Lys Gln Leu Gln Glu Lys Ile Tyr Ala Val Glu Gly
                180                 185                 190

<210> SEQ ID NO 41
<211> LENGTH: 191
<212> TYPE: PRT
<213> ORGANISM: Artificial Sequence
<220> FEATURE:
<223> OTHER INFORMATION: CD11d A-domain with designed point mutation
```

(underlined) CD11dA - D258A

<400> SEQUENCE: 41

```
Gln Glu Met Asp Ile Val Phe Leu Ile Asp Gly Ser Gly Ser Ile Asp
1               5                   10                  15

Gln Asn Asp Phe Asn Gln Met Lys Gly Phe Val Gln Ala Val Met Gly
            20                  25                  30

Gln Phe Glu Gly Thr Asp Thr Leu Phe Ala Leu Met Gln Tyr Ser Asn
        35                  40                  45

Leu Leu Lys Ile His Phe Thr Phe Thr Gln Phe Arg Thr Ser Pro Ser
    50                  55                  60

Gln Gln Ser Leu Val Asp Pro Ile Val Gln Leu Lys Gly Leu Thr Phe
65                  70                  75                  80

Thr Ala Thr Gly Ile Leu Thr Val Val Thr Gln Leu Phe His His Lys
                85                  90                  95

Asn Gly Ala Arg Lys Ser Ala Lys Lys Ile Leu Ile Val Ile Thr Ala
            100                 105                 110

Gly Gln Lys Tyr Lys Asp Pro Leu Glu Tyr Ser Asp Val Ile Pro Gln
        115                 120                 125

Ala Glu Lys Ala Gly Ile Ile Arg Tyr Ala Ile Gly Val Gly His Ala
    130                 135                 140

Phe Gln Gly Pro Thr Ala Arg Gln Glu Leu Asn Thr Ile Ser Ser Ala
145                 150                 155                 160

Pro Pro Gln Asp His Val Phe Lys Val Asp Asn Phe Ala Ala Leu Gly
                165                 170                 175

Ser Ile Gln Lys Gln Leu Gln Glu Lys Ile Tyr Ala Val Glu Gly
            180                 185                 190
```

<210> SEQ ID NO 42
<211> LENGTH: 191
<212> TYPE: PRT
<213> ORGANISM: Artificial Sequence
<220> FEATURE:
<223> OTHER INFORMATION: CD11d A-domain with designed point mutations
      (underlined) CD11dA - D258A/F291S/F318G

<400> SEQUENCE: 42

```
Gln Glu Met Asp Ile Val Phe Leu Ile Asp Gly Ser Gly Ser Ile Asp
1               5                   10                  15

Gln Asn Asp Phe Asn Gln Met Lys Gly Phe Val Gln Ala Val Met Gly
            20                  25                  30

Gln Phe Glu Gly Thr Asp Thr Leu Phe Ala Leu Met Gln Tyr Ser Asn
        35                  40                  45

Leu Leu Lys Ile His Phe Thr Phe Thr Gln Phe Arg Thr Ser Pro Ser
    50                  55                  60

Gln Gln Ser Leu Val Asp Pro Ile Val Gln Leu Lys Gly Leu Thr Phe
65                  70                  75                  80

Thr Ala Thr Gly Ile Leu Thr Val Val Thr Gln Leu Phe His His Lys
                85                  90                  95

Asn Gly Ala Arg Lys Ser Ala Lys Lys Ile Leu Ile Val Ile Thr Ala
            100                 105                 110

Gly Gln Lys Tyr Lys Asp Pro Leu Glu Tyr Ser Asp Val Ile Pro Gln
        115                 120                 125

Ala Glu Lys Ala Gly Ile Ile Arg Tyr Ala Ile Gly Val Gly His Ala
    130                 135                 140

Ser Gln Gly Pro Thr Ala Arg Gln Glu Leu Asn Thr Ile Ser Ser Ala
```

145            150            155            160
Pro Pro Gln Asp His Val Phe Lys Val Asp Asn Gly Ala Ala Leu Gly
                165            170            175

Ser Ile Gln Lys Gln Leu Gln Glu Lys Ile Tyr Ala Val Glu Gly
                180            185            190

<210> SEQ ID NO 43
<211> LENGTH: 191
<212> TYPE: PRT
<213> ORGANISM: Artificial Sequence
<220> FEATURE:
<223> OTHER INFORMATION: CD11d A-domain with designed point mutations
      (underlined) CD11dA - D156A/F291S/F318G

<400> SEQUENCE: 43

Gln Glu Met Asp Ile Val Phe Leu Ile Ala Gly Ser Gly Ser Ile Asp
1               5                   10                  15

Gln Asn Asp Phe Asn Gln Met Lys Gly Phe Val Gln Ala Val Met Gly
                20                  25                  30

Gln Phe Glu Gly Thr Asp Thr Leu Phe Ala Leu Met Gln Tyr Ser Asn
            35                  40                  45

Leu Leu Lys Ile His Phe Thr Phe Thr Gln Phe Arg Thr Ser Pro Ser
50                  55                  60

Gln Gln Ser Leu Val Asp Pro Ile Val Gln Leu Lys Gly Leu Thr Phe
65                  70                  75                  80

Thr Ala Thr Gly Ile Leu Thr Val Val Thr Gln Leu Phe His His Lys
                85                  90                  95

Asn Gly Ala Arg Lys Ser Ala Lys Ile Leu Ile Val Ile Thr Asp
                100                 105                 110

Gly Gln Lys Tyr Lys Asp Pro Leu Glu Tyr Ser Asp Val Ile Pro Gln
            115                 120                 125

Ala Glu Lys Ala Gly Ile Ile Arg Tyr Ala Ile Gly Val Gly His Ala
        130                 135                 140

Ser Gln Gly Pro Thr Ala Arg Gln Glu Leu Asn Thr Ile Ser Ser Ala
145                 150                 155                 160

Pro Pro Gln Asp His Val Phe Lys Val Asp Asn Gly Ala Ala Leu Gly
                165                 170                 175

Ser Ile Gln Lys Gln Leu Gln Glu Lys Ile Tyr Ala Val Glu Gly
                180                 185                 190

<210> SEQ ID NO 44
<211> LENGTH: 246
<212> TYPE: PRT
<213> ORGANISM: Artificial Sequence
<220> FEATURE:
<223> OTHER INFORMATION: Integrin beta7 (ITGB7) betaI-domain with
      designed point mutation (underlined) and deletions: Beta7-C272S-
      delSDL1-delSDL2

<400> SEQUENCE: 44

Glu Gly Tyr Pro Val Asp Leu Tyr Tyr Leu Met Asp Leu Ser Tyr Ser
1               5                   10                  15

Met Lys Asp Asp Leu Glu Arg Val Arg Gln Leu Gly His Ala Leu Leu
                20                  25                  30

Val Arg Leu Gln Glu Val Thr His Ser Val Arg Ile Gly Phe Gly Ser
            35                  40                  45

Phe Val Asp Lys Thr Val Leu Pro Phe Val Ser Thr Val Pro Ser Lys
50                  55                  60

```
Leu Arg His Pro Cys Pro Thr Arg Leu Glu Arg Cys Gln Ser Pro Phe
 65                  70                  75                  80

Ser Phe His His Val Leu Ser Leu Thr Gly Asp Ala Gln Ala Phe Glu
             85                  90                  95

Arg Glu Val Gly Arg Gln Ser Val Ser Gly Asn Leu Asp Ser Pro Glu
            100                 105                 110

Gly Gly Phe Asp Ala Ile Leu Gln Ala Ala Leu Cys Gln Glu Gln Ile
            115                 120                 125

Gly Trp Arg Asn Val Ser Arg Leu Leu Val Phe Thr Ser Asp Asp Thr
            130                 135                 140

Phe His Thr Ala Gly Asp Gly Lys Leu Gly Gly Ile Phe Met Pro Ser
145                 150                 155                 160

Asp Gly His Cys His Leu Asp Ser Asn Gly Leu Tyr Ser Arg Ser Thr
                165                 170                 175

Glu Phe Asp Tyr Pro Ser Val Gly Gln Val Ala Gln Ala Leu Ser Ala
            180                 185                 190

Ala Asn Ile Gln Pro Ile Phe Ala Val Thr Ser Ala Ala Leu Pro Val
            195                 200                 205

Tyr Gln Glu Leu Ser Lys Leu Ile Pro Lys Ser Ala Val Gly Glu Leu
            210                 215                 220

Ser Glu Asp Ser Ser Asn Val Val Gln Leu Ile Met Asp Ala Tyr Asn
225                 230                 235                 240

Ser Leu Ser Ser Thr Val
                245

<210> SEQ ID NO 45
<211> LENGTH: 183
<212> TYPE: PRT
<213> ORGANISM: Artificial Sequence
<220> FEATURE:
<223> OTHER INFORMATION: residue C272 is replaced with Serine (to remove
      one Cysteine site) and SDL1 (K200-F228) and SDL2 (A296-P329)
      residues are deleted from the WT sequence

<400> SEQUENCE: 45

Glu Gly Tyr Pro Val Asp Leu Tyr Tyr Leu Met Asp Leu Ser Tyr Ser
 1               5                  10                  15

Met Lys Asp Asp Leu Glu Arg Val Arg Gln Leu Gly His Ala Leu Leu
             20                  25                  30

Val Arg Leu Gln Glu Val Thr His Ser Val Arg Ile Gly Phe Gly Ser
             35                  40                  45

Phe Val Asp Ser Phe His His Val Leu Ser Leu Thr Gly Asp Ala Gln
 50                  55                  60

Ala Phe Glu Arg Glu Val Gly Arg Gln Ser Val Ser Gly Asn Leu Asp
 65                  70                  75                  80

Ser Pro Glu Gly Gly Phe Asp Ala Ile Leu Gln Ala Ala Leu Ser Gln
             85                  90                  95

Glu Gln Ile Gly Trp Arg Asn Val Ser Arg Leu Leu Val Phe Thr Ser
            100                 105                 110

Asp Asp Thr Phe His Thr Ser Val Gly Gln Val Ala Gln Ala Leu Ser
            115                 120                 125

Ala Ala Asn Ile Gln Pro Ile Phe Ala Val Thr Ser Ala Ala Leu Pro
            130                 135                 140

Val Tyr Gln Glu Leu Ser Lys Leu Ile Pro Lys Ser Ala Val Gly Glu
145                 150                 155                 160

Leu Ser Glu Asp Ser Ser Asn Val Val Gln Leu Ile Met Asp Ala Tyr
```

```
                    165                 170                 175

Asn Ser Leu Ser Ser Thr Val
            180

<210> SEQ ID NO 46
<211> LENGTH: 183
<212> TYPE: PRT
<213> ORGANISM: Artificial Sequence
<220> FEATURE:
<223> OTHER INFORMATION: beta7Protein1 with additional designed point
      mutation (underlined): beta7Protein1-D159A

<400> SEQUENCE: 46

Glu Gly Tyr Pro Val Asp Leu Tyr Tyr Leu Met Ala Leu Ser Tyr Ser
1               5                   10                  15

Met Lys Asp Asp Leu Glu Arg Val Arg Gln Leu Gly His Ala Leu Leu
            20                  25                  30

Val Arg Leu Gln Glu Val Thr His Ser Val Arg Ile Gly Phe Gly Ser
        35                  40                  45

Phe Val Asp Ser Phe His His Val Leu Ser Leu Thr Gly Asp Ala Gln
    50                  55                  60

Ala Phe Glu Arg Glu Val Gly Arg Gln Ser Val Ser Gly Asn Leu Asp
65                  70                  75                  80

Ser Pro Glu Gly Gly Phe Asp Ala Ile Leu Gln Ala Ala Leu Ser Gln
                85                  90                  95

Glu Gln Ile Gly Trp Arg Asn Val Ser Arg Leu Leu Val Phe Thr Ser
            100                 105                 110

Asp Asp Thr Phe His Thr Ser Val Gly Gln Val Ala Gln Ala Leu Ser
        115                 120                 125

Ala Ala Asn Ile Gln Pro Ile Phe Ala Val Thr Ser Ala Ala Leu Pro
    130                 135                 140

Val Tyr Gln Glu Leu Ser Lys Leu Ile Pro Lys Ser Ala Val Gly Glu
145                 150                 155                 160

Leu Ser Glu Asp Ser Ser Asn Val Val Gln Leu Ile Met Asp Ala Tyr
                165                 170                 175

Asn Ser Leu Ser Ser Thr Val
            180

<210> SEQ ID NO 47
<211> LENGTH: 183
<212> TYPE: PRT
<213> ORGANISM: Artificial Sequence
<220> FEATURE:
<223> OTHER INFORMATION: beta7Protein1 with additional designed point
      mutation (underlined): beta7Protein1- V171A

<400> SEQUENCE: 47

Glu Gly Tyr Pro Val Asp Leu Tyr Tyr Leu Met Asp Leu Ser Tyr Ser
1               5                   10                  15

Met Lys Asp Asp Leu Glu Arg Ala Arg Gln Leu Gly His Ala Leu Leu
            20                  25                  30

Val Arg Leu Gln Glu Val Thr His Ser Val Arg Ile Gly Phe Gly Ser
        35                  40                  45

Phe Val Asp Ser Phe His His Val Leu Ser Leu Thr Gly Asp Ala Gln
    50                  55                  60

Ala Phe Glu Arg Glu Val Gly Arg Gln Ser Val Ser Gly Asn Leu Asp
65                  70                  75                  80

Ser Pro Glu Gly Gly Phe Asp Ala Ile Leu Gln Ala Ala Leu Ser Gln
```

```
                85                  90                  95
Glu Gln Ile Gly Trp Arg Asn Val Ser Arg Leu Leu Val Phe Thr Ser
                100                 105                 110

Asp Asp Thr Phe His Thr Ser Val Gly Gln Val Ala Gln Ala Leu Ser
                115                 120                 125

Ala Ala Asn Ile Gln Pro Ile Phe Ala Val Thr Ser Ala Ala Leu Pro
            130                 135                 140

Val Tyr Gln Glu Leu Ser Lys Leu Ile Pro Lys Ser Ala Val Gly Glu
145                 150                 155                 160

Leu Ser Glu Asp Ser Ser Asn Val Val Gln Leu Ile Met Asp Ala Tyr
                165                 170                 175

Asn Ser Leu Ser Ser Thr Val
            180

<210> SEQ ID NO 48
<211> LENGTH: 183
<212> TYPE: PRT
<213> ORGANISM: Artificial Sequence
<220> FEATURE:
<223> OTHER INFORMATION: beta7Protein1 with additional designed point
      mutation (underlined): beta7Protein1- L381A

<400> SEQUENCE: 48

Glu Gly Tyr Pro Val Asp Leu Tyr Tyr Leu Met Asp Leu Ser Tyr Ser
1               5                   10                  15

Met Lys Asp Asp Leu Glu Arg Val Arg Gln Leu Gly His Ala Leu Leu
                20                  25                  30

Val Arg Leu Gln Glu Val Thr His Ser Val Arg Ile Gly Phe Gly Ser
            35                  40                  45

Phe Val Asp Ser Phe His His Val Leu Ser Leu Thr Gly Asp Ala Gln
        50                  55                  60

Ala Phe Glu Arg Glu Val Gly Arg Gln Ser Val Ser Gly Asn Leu Asp
65                  70                  75                  80

Ser Pro Glu Gly Gly Phe Asp Ala Ile Leu Gln Ala Ala Leu Ser Gln
                85                  90                  95

Glu Gln Ile Gly Trp Arg Asn Val Ser Arg Leu Leu Val Phe Thr Ser
                100                 105                 110

Asp Asp Thr Phe His Thr Ser Val Gly Gln Val Ala Gln Ala Leu Ser
                115                 120                 125

Ala Ala Asn Ile Gln Pro Ile Phe Ala Val Thr Ser Ala Ala Leu Pro
            130                 135                 140

Val Tyr Gln Glu Leu Ser Lys Leu Ile Pro Lys Ser Ala Val Gly Glu
145                 150                 155                 160

Leu Ser Glu Asp Ser Ser Asn Val Val Gln Ala Ile Met Asp Ala Tyr
                165                 170                 175

Asn Ser Leu Ser Ser Thr Val
            180

<210> SEQ ID NO 49
<211> LENGTH: 183
<212> TYPE: PRT
<213> ORGANISM: Artificial Sequence
<220> FEATURE:
<223> OTHER INFORMATION: beta7Protein1 with additional designed point
      mutation (underlined): beta7Protein1- D159A/V171A

<400> SEQUENCE: 49

Glu Gly Tyr Pro Val Asp Leu Tyr Tyr Leu Met Ala Leu Ser Tyr Ser
```

```
                1               5                   10                  15
Met Lys Asp Asp Leu Glu Arg Ala Arg Gln Leu Gly His Ala Leu Leu
                20                  25                  30

Val Arg Leu Gln Glu Val Thr His Ser Val Arg Ile Gly Phe Gly Ser
                35                  40                  45

Phe Val Asp Ser Phe His His Val Leu Ser Leu Thr Gly Asp Ala Gln
                50                  55                  60

Ala Phe Glu Arg Glu Val Gly Arg Gln Ser Val Ser Gly Asn Leu Asp
65                  70                  75                  80

Ser Pro Glu Gly Gly Phe Asp Ala Ile Leu Gln Ala Ala Leu Ser Gln
                    85                  90                  95

Glu Gln Ile Gly Trp Arg Asn Val Ser Arg Leu Leu Val Phe Thr Ser
                100                 105                 110

Asp Asp Thr Phe His Thr Ser Val Gly Gln Val Ala Gln Ala Leu Ser
                115                 120                 125

Ala Ala Asn Ile Gln Pro Ile Phe Ala Val Thr Ser Ala Ala Leu Pro
    130                 135                 140

Val Tyr Gln Glu Leu Ser Lys Leu Ile Pro Lys Ser Ala Val Gly Glu
145                 150                 155                 160

Leu Ser Glu Asp Ser Ser Asn Val Val Gln Leu Ile Met Asp Ala Tyr
                    165                 170                 175

Asn Ser Leu Ser Ser Thr Val
                180

<210> SEQ ID NO 50
<211> LENGTH: 183
<212> TYPE: PRT
<213> ORGANISM: Artificial Sequence
<220> FEATURE:
<223> OTHER INFORMATION: beta7Protein1 with additional designed point
      mutation (underlined): beta7Protein1- D159A/L381A

<400> SEQUENCE: 50

Glu Gly Tyr Pro Val Asp Leu Tyr Tyr Leu Met Ala Leu Ser Tyr Ser
1               5                   10                  15

Met Lys Asp Asp Leu Glu Arg Val Arg Gln Leu Gly His Ala Leu Leu
                20                  25                  30

Val Arg Leu Gln Glu Val Thr His Ser Val Arg Ile Gly Phe Gly Ser
                35                  40                  45

Phe Val Asp Ser Phe His His Val Leu Ser Leu Thr Gly Asp Ala Gln
                50                  55                  60

Ala Phe Glu Arg Glu Val Gly Arg Gln Ser Val Ser Gly Asn Leu Asp
65                  70                  75                  80

Ser Pro Glu Gly Gly Phe Asp Ala Ile Leu Gln Ala Ala Leu Ser Gln
                    85                  90                  95

Glu Gln Ile Gly Trp Arg Asn Val Ser Arg Leu Leu Val Phe Thr Ser
                100                 105                 110

Asp Asp Thr Phe His Thr Ser Val Gly Gln Val Ala Gln Ala Leu Ser
                115                 120                 125

Ala Ala Asn Ile Gln Pro Ile Phe Ala Val Thr Ser Ala Ala Leu Pro
    130                 135                 140

Val Tyr Gln Glu Leu Ser Lys Leu Ile Pro Lys Ser Ala Val Gly Glu
145                 150                 155                 160

Leu Ser Glu Asp Ser Ser Asn Val Val Gln Ala Ile Met Asp Ala Tyr
                    165                 170                 175
```

Asn Ser Leu Ser Ser Thr Val
            180

<210> SEQ ID NO 51
<211> LENGTH: 183
<212> TYPE: PRT
<213> ORGANISM: Artificial Sequence
<220> FEATURE:
<223> OTHER INFORMATION: beta7Protein1 with additional designed point
      mutation (underlined): beta7Protein1- V379A

<400> SEQUENCE: 51

Glu Gly Tyr Pro Val Asp Leu Tyr Tyr Leu Met Asp Leu Ser Tyr Ser
1               5                   10                  15

Met Lys Asp Asp Leu Glu Arg Val Arg Gln Leu Gly His Ala Leu Leu
            20                  25                  30

Val Arg Leu Gln Glu Val Thr His Ser Val Arg Ile Gly Phe Gly Ser
        35                  40                  45

Phe Val Asp Ser Phe His His Val Leu Ser Leu Thr Gly Asp Ala Gln
    50                  55                  60

Ala Phe Glu Arg Glu Val Gly Arg Gln Ser Val Ser Gly Asn Leu Asp
65                  70                  75                  80

Ser Pro Glu Gly Gly Phe Asp Ala Ile Leu Gln Ala Ala Leu Ser Gln
                85                  90                  95

Glu Gln Ile Gly Trp Arg Asn Val Ser Arg Leu Leu Val Phe Thr Ser
            100                 105                 110

Asp Asp Thr Phe His Thr Ser Val Gly Gln Val Ala Gln Ala Leu Ser
        115                 120                 125

Ala Ala Asn Ile Gln Pro Ile Phe Ala Val Thr Ser Ala Ala Leu Pro
    130                 135                 140

Val Tyr Gln Glu Leu Ser Lys Leu Ile Pro Lys Ser Ala Val Gly Glu
145                 150                 155                 160

Leu Ser Glu Asp Ser Ser Asn Val Ala Gln Leu Ile Met Asp Ala Tyr
                165                 170                 175

Asn Ser Leu Ser Ser Thr Val
            180

<210> SEQ ID NO 52
<211> LENGTH: 183
<212> TYPE: PRT
<213> ORGANISM: Artificial Sequence
<220> FEATURE:
<223> OTHER INFORMATION: beta7Protein1 with additional designed point
      mutation (underlined): beta7Protein1- D159A/V379A

<400> SEQUENCE: 52

Glu Gly Tyr Pro Val Asp Leu Tyr Tyr Leu Met Ala Leu Ser Tyr Ser
1               5                   10                  15

Met Lys Asp Asp Leu Glu Arg Val Arg Gln Leu Gly His Ala Leu Leu
            20                  25                  30

Val Arg Leu Gln Glu Val Thr His Ser Val Arg Ile Gly Phe Gly Ser
        35                  40                  45

Phe Val Asp Ser Phe His His Val Leu Ser Leu Thr Gly Asp Ala Gln
    50                  55                  60

Ala Phe Glu Arg Glu Val Gly Arg Gln Ser Val Ser Gly Asn Leu Asp
65                  70                  75                  80

Ser Pro Glu Gly Gly Phe Asp Ala Ile Leu Gln Ala Ala Leu Ser Gln
                85                  90                  95

```
Glu Gln Ile Gly Trp Arg Asn Val Ser Arg Leu Leu Val Phe Thr Ser
                100                 105                 110

Asp Asp Thr Phe His Thr Ser Val Gly Gln Val Ala Gln Ala Leu Ser
            115                 120                 125

Ala Ala Asn Ile Gln Pro Ile Phe Ala Val Thr Ser Ala Ala Leu Pro
        130                 135                 140

Val Tyr Gln Glu Leu Ser Lys Leu Ile Pro Lys Ser Ala Val Gly Glu
145                 150                 155                 160

Leu Ser Glu Asp Ser Ser Asn Val Ala Gln Leu Ile Met Asp Ala Tyr
                165                 170                 175

Asn Ser Leu Ser Ser Thr Val
            180
```

<210> SEQ ID NO 53
<211> LENGTH: 245
<212> TYPE: PRT
<213> ORGANISM: Artificial Sequence
<220> FEATURE:
<223> OTHER INFORMATION: Integrin beta4 (ITGB4) betaI-domain with
      designed point mutation (underlined) and deletions: Beta4-C244S-
      delSDL1-delSDL2

<400> SEQUENCE: 53

```
Leu Glu Ser Pro Val Asp Leu Tyr Ile Leu Met Asp Phe Ser Asn Ser
1               5                   10                  15

Met Ser Asp Asp Leu Asp Asn Leu Lys Lys Met Gly Gln Asn Leu Ala
            20                  25                  30

Arg Val Leu Ser Gln Leu Thr Ser Asp Tyr Thr Ile Gly Phe Gly Lys
        35                  40                  45

Phe Val Asp Lys Val Ser Val Pro Gln Thr Asp Met Arg Pro Glu Lys
50                  55                  60

Leu Lys Glu Pro Trp Pro Asn Ser Asp Pro Pro Phe Ser Phe Lys Asn
65                  70                  75                  80

Val Ile Ser Leu Thr Glu Asp Val Asp Glu Phe Arg Asn Lys Leu Gln
                85                  90                  95

Gly Glu Arg Ile Ser Gly Asn Leu Asp Ala Pro Glu Gly Gly Phe Asp
            100                 105                 110

Ala Ile Leu Gln Thr Ala Val Cys Thr Arg Asp Ile Gly Trp Arg Pro
        115                 120                 125

Asp Ser Thr His Leu Leu Val Phe Ser Thr Glu Ser Ala Phe His Tyr
130                 135                 140

Glu Ala Asp Gly Ala Asn Val Leu Ala Gly Ile Met Ser Arg Asn Asp
145                 150                 155                 160

Glu Arg Cys His Leu Asp Thr Thr Gly Thr Tyr Thr Gln Tyr Arg Thr
                165                 170                 175

Gln Asp Tyr Pro Ser Val Pro Thr Leu Val Arg Leu Leu Ala Lys His
            180                 185                 190

Asn Ile Ile Pro Ile Phe Ala Val Thr Asn Tyr Ser Tyr Ser Tyr Tyr
        195                 200                 205

Glu Lys Leu His Thr Tyr Phe Pro Val Ser Ser Leu Gly Val Leu Gln
210                 215                 220

Glu Asp Ser Ser Asn Ile Val Glu Leu Leu Glu Glu Ala Phe Asn Arg
225                 230                 235                 240

Ile Arg Ser Asn Leu
            245
```

```
<210> SEQ ID NO 54
<211> LENGTH: 184
<212> TYPE: PRT
<213> ORGANISM: Artificial Sequence
<220> FEATURE:
<223> OTHER INFORMATION: residue C244 is replaced with Serine (to remove
      one Cysteine site) and SDL1 (K177-F201) and SDL2 (E269-P305)
      residues are deleted from the WT sequence

<400> SEQUENCE: 54
```

Leu Glu Ser Pro Val Asp Leu Tyr Ile Leu Met Asp Phe Ser Asn Ser
1               5                   10                  15

Met Ser Asp Asp Leu Asp Asn Leu Lys Lys Met Gly Gln Asn Leu Ala
            20                  25                  30

Arg Val Leu Ser Gln Leu Thr Ser Asp Tyr Thr Ile Gly Phe Gly Lys
        35                  40                  45

Phe Val Asp Ser Phe Lys Asn Val Ile Ser Leu Thr Glu Asp Val Asp
    50                  55                  60

Glu Phe Arg Asn Lys Leu Gln Gly Glu Arg Ile Ser Gly Asn Leu Asp
65                  70                  75                  80

Ala Pro Glu Gly Gly Phe Asp Ala Ile Leu Gln Thr Ala Val Ser Thr
                85                  90                  95

Arg Asp Ile Gly Trp Arg Pro Asp Ser Thr His Leu Leu Val Phe Ser
            100                 105                 110

Thr Glu Ser Ala Phe His Tyr Ser Val Pro Thr Leu Val Arg Leu Leu
        115                 120                 125

Ala Lys His Asn Ile Ile Pro Ile Phe Ala Val Thr Asn Tyr Ser Tyr
    130                 135                 140

Ser Tyr Tyr Glu Lys Leu His Thr Tyr Phe Pro Val Ser Ser Leu Gly
145                 150                 155                 160

Val Leu Gln Glu Asp Ser Ser Asn Ile Val Glu Leu Leu Glu Glu Ala
                165                 170                 175

Phe Asn Arg Ile Arg Ser Asn Leu
            180

```
<210> SEQ ID NO 55
<211> LENGTH: 248
<212> TYPE: PRT
<213> ORGANISM: Artificial Sequence
<220> FEATURE:
<223> OTHER INFORMATION: Integrin beta5 (ITGB5) betaI-domain with
      designed point mutation (bolded) and deletions: Beta5-C257S-
      delSDL1-delSDL2 (beta5Protein1)

<400> SEQUENCE: 55
```

Glu Asp Tyr Pro Val Asp Leu Tyr Tyr Leu Met Asp Leu Ser Leu Ser
1               5                   10                  15

Met Lys Asp Asp Leu Asp Asn Ile Arg Ser Leu Gly Thr Lys Leu Ala
            20                  25                  30

Glu Glu Met Arg Lys Leu Thr Ser Asn Phe Arg Leu Gly Phe Gly Ser
        35                  40                  45

Phe Val Asp Lys Asp Ile Ser Pro Phe Ser Tyr Thr Ala Pro Arg Tyr
    50                  55                  60

Gln Thr Asn Pro Cys Ile Gly Tyr Lys Leu Phe Pro Asn Cys Val Pro
65                  70                  75                  80

Ser Phe Gly Phe Arg His Leu Leu Pro Leu Thr Asp Arg Val Asp Ser
                85                  90                  95

Phe Asn Glu Glu Val Arg Lys Gln Arg Val Ser Arg Arg Asp Ala Pro
            100                 105                 110

```
Glu Gly Gly Phe Asp Ala Val Leu Gln Ala Ala Val Cys Lys Glu Lys
        115                 120                 125

Ile Gly Trp Arg Lys Asp Ala Leu His Leu Leu Val Phe Thr Thr Asp
    130                 135                 140

Asp Val Pro His Ile Ala Leu Asp Gly Lys Leu Gly Leu Val Gln
145                 150                 155                 160

Pro His Asp Gly Gln Cys His Leu Asn Glu Ala Asn Glu Tyr Thr Ala
                165                 170                 175

Ser Asn Gln Met Asp Tyr Pro Ser Leu Ala Leu Leu Gly Glu Lys Leu
                180                 185                 190

Ala Glu Asn Asn Ile Asn Leu Ile Phe Ala Val Thr Lys Asn His Tyr
                195                 200                 205

Met Leu Tyr Lys Asn Phe Thr Ala Leu Ile Pro Gly Thr Thr Val Glu
        210                 215                 220

Ile Leu Asp Gly Asp Ser Lys Asn Ile Ile Gln Leu Ile Ile Asn Ala
225                 230                 235                 240

Tyr Asn Ser Ile Arg Ser Lys Val
                245

<210> SEQ ID NO 56
<211> LENGTH: 183
<212> TYPE: PRT
<213> ORGANISM: Artificial Sequence
<220> FEATURE:
<223> OTHER INFORMATION: residue C257 is replaced with Serine (to remove
      one Cysteine site) and SDL1 (K184-F214) and SDL2 (A282-P315)
      residues are deleted from the WT sequence

<400> SEQUENCE: 56

Glu Asp Tyr Pro Val Asp Leu Tyr Tyr Leu Met Asp Leu Ser Leu Ser
1               5                   10                  15

Met Lys Asp Asp Leu Asp Asn Ile Arg Ser Leu Gly Thr Lys Leu Ala
            20                  25                  30

Glu Glu Met Arg Lys Leu Thr Ser Asn Phe Arg Leu Gly Phe Gly Ser
        35                  40                  45

Phe Val Asp Gly Phe Arg His Leu Leu Pro Leu Thr Asp Arg Val Asp
    50                  55                  60

Ser Phe Asn Glu Glu Val Arg Lys Gln Arg Val Ser Arg Arg Asp Ala
65                  70                  75                  80

Pro Glu Gly Gly Phe Asp Ala Val Leu Gln Ala Ala Val Ser Lys Glu
                85                  90                  95

Lys Ile Gly Trp Arg Lys Asp Ala Leu His Leu Leu Val Phe Thr Thr
            100                 105                 110

Asp Asp Val Pro His Ile Ser Leu Ala Leu Leu Gly Glu Lys Leu Ala
        115                 120                 125

Glu Asn Asn Ile Asn Leu Ile Phe Ala Val Thr Lys Asn His Tyr Met
    130                 135                 140

Leu Tyr Lys Asn Phe Thr Ala Leu Ile Pro Gly Thr Thr Val Glu Ile
145                 150                 155                 160

Leu Asp Gly Asp Ser Lys Asn Ile Ile Gln Leu Ile Ile Asn Ala Tyr
                165                 170                 175

Asn Ser Ile Arg Ser Lys Val
            180

<210> SEQ ID NO 57
<211> LENGTH: 248
```

```
<212> TYPE: PRT
<213> ORGANISM: Artificial Sequence
<220> FEATURE:
<223> OTHER INFORMATION: Integrin beta6 (ITGB6) betaI-domain with
      designed point mutation (underlined) and deletions: Beta6-C247S-
      delSDL1-SDL2

<400> SEQUENCE: 57

Thr Glu Asp Tyr Pro Val Asp Leu Tyr Tyr Leu Met Asp Leu Ser Ala
1               5                   10                  15

Ser Met Asp Asp Asp Leu Asn Thr Ile Lys Glu Leu Gly Ser Arg Leu
            20                  25                  30

Ser Lys Glu Met Ser Lys Leu Thr Ser Asn Phe Arg Leu Gly Phe Gly
        35                  40                  45

Ser Phe Val Glu Lys Pro Val Ser Pro Phe Val Lys Thr Thr Pro Glu
    50                  55                  60

Glu Ile Ala Asn Pro Cys Ser Ser Ile Pro Tyr Phe Cys Leu Pro Thr
65                  70                  75                  80

Phe Gly Phe Lys His Ile Leu Pro Leu Thr Asn Asp Ala Glu Arg Phe
                85                  90                  95

Asn Glu Ile Val Lys Asn Gln Lys Ile Ser Ala Asn Ile Asp Thr Pro
            100                 105                 110

Glu Gly Gly Phe Asp Ala Ile Met Gln Ala Ala Val Cys Lys Glu Lys
        115                 120                 125

Ile Gly Trp Arg Asn Asp Ser Leu His Leu Leu Val Phe Val Ser Asp
    130                 135                 140

Ala Asp Ser His Phe Gly Met Asp Ser Lys Leu Ala Gly Ile Val Ile
145                 150                 155                 160

Pro Asn Asp Gly Leu Cys His Leu Asp Ser Lys Asn Glu Tyr Ser Met
                165                 170                 175

Ser Thr Val Leu Glu Tyr Pro Thr Ile Gly Gln Leu Ile Asp Lys Leu
            180                 185                 190

Val Gln Asn Asn Val Leu Leu Ile Phe Ala Val Thr Gln Glu Gln Val
        195                 200                 205

His Leu Tyr Glu Asn Tyr Ala Lys Leu Ile Pro Gly Ala Thr Val Gly
    210                 215                 220

Leu Leu Gln Lys Asp Ser Gly Asn Ile Leu Gln Leu Ile Ile Ser Ala
225                 230                 235                 240

Tyr Glu Glu Leu Arg Ser Glu Val
                245

<210> SEQ ID NO 58
<211> LENGTH: 185
<212> TYPE: PRT
<213> ORGANISM: Artificial Sequence
<220> FEATURE:
<223> OTHER INFORMATION: residue C247 is replaced with Serine (to remove
      one Cysteine site) and SDL1 (K174-F202) and SDL2 (G272-P305)
      residues are deleted from the WT sequence

<400> SEQUENCE: 58

Thr Glu Asp Tyr Pro Val Asp Leu Tyr Tyr Leu Met Asp Leu Ser Ala
1               5                   10                  15

Ser Met Asp Asp Asp Leu Asn Thr Ile Lys Glu Leu Gly Ser Arg Leu
            20                  25                  30

Ser Lys Glu Met Ser Lys Leu Thr Ser Asn Phe Arg Leu Gly Phe Gly
        35                  40                  45

Ser Phe Val Glu Gly Phe Lys His Ile Leu Pro Leu Thr Asn Asp Ala
```

```
                50                  55                  60
Glu Arg Phe Asn Glu Ile Val Lys Asn Gln Lys Ile Ser Ala Asn Ile
 65                  70                  75                  80

Asp Thr Pro Glu Gly Gly Phe Asp Ala Ile Met Gln Ala Ala Val Ser
                     85                  90                  95

Lys Glu Lys Ile Gly Trp Arg Asn Asp Ser Leu His Leu Leu Val Phe
                100                 105                 110

Val Ser Asp Ala Asp Ser His Phe Thr Ile Gly Gln Leu Ile Asp Lys
            115                 120                 125

Leu Val Gln Asn Asn Val Leu Leu Ile Phe Ala Val Thr Gln Glu Gln
        130                 135                 140

Val His Leu Tyr Glu Asn Tyr Ala Lys Leu Ile Pro Gly Ala Thr Val
145                 150                 155                 160

Gly Leu Leu Gln Lys Asp Ser Gly Asn Ile Leu Gln Leu Ile Ile Ser
                165                 170                 175

Ala Tyr Glu Glu Leu Arg Ser Glu Val
                180                 185

<210> SEQ ID NO 59
<211> LENGTH: 247
<212> TYPE: PRT
<213> ORGANISM: Artificial Sequence
<220> FEATURE:
<223> OTHER INFORMATION: Integrin beta8 (ITGB8) betaI-domain with
      designed point mutation (underlined) and deletions: Beta8-C265S-
      delSDL1-SDL2

<400> SEQUENCE: 59

Leu Lys Lys Tyr Pro Val Asp Leu Tyr Tyr Leu Val Asp Val Ser Ala
 1               5                  10                  15

Ser Met His Asn Asn Ile Glu Lys Leu Asn Ser Val Gly Asn Asp Leu
                 20                  25                  30

Ser Arg Lys Met Ala Phe Phe Ser Arg Asp Phe Arg Leu Gly Phe Gly
            35                  40                  45

Ser Tyr Val Asp Lys Thr Val Ser Pro Tyr Ile Ser Ile His Pro Glu
        50                  55                  60

Arg Ile His Asn Gln Cys Ser Asp Tyr Asn Leu Asp Cys Met Pro Pro
 65                  70                  75                  80

His Gly Tyr Ile His Val Leu Ser Leu Thr Glu Asn Ile Thr Glu Phe
                 85                  90                  95

Glu Lys Ala Val His Arg Gln Lys Ile Ser Gly Asn Ile Asp Thr Pro
            100                 105                 110

Glu Gly Gly Phe Asp Ala Met Leu Gln Ala Ala Val Cys Glu Ser His
        115                 120                 125

Ile Gly Trp Arg Lys Glu Ala Lys Arg Leu Leu Val Met Thr Asp
            130                 135                 140

Gln Thr Ser His Leu Ala Leu Asp Ser Lys Leu Ala Gly Ile Val Val
145                 150                 155                 160

Pro Asn Asp Gly Asn Cys His Leu Lys Asn Asn Val Tyr Val Lys Ser
                165                 170                 175

Thr Thr Met Glu His Pro Ser Leu Gly Gln Leu Ser Glu Lys Leu Ile
            180                 185                 190

Asp Asn Asn Ile Asn Val Ile Phe Ala Val Gln Gly Lys Gln Phe His
        195                 200                 205

Trp Tyr Lys Asp Leu Leu Pro Leu Leu Pro Gly Thr Ile Ala Gly Glu
            210                 215                 220
```

```
Ile Glu Ser Lys Ala Ala Asn Leu Asn Asn Leu Val Glu Ala Tyr
225                 230                 235                 240

Gln Lys Leu Ile Ser Glu Val
            245
```

<210> SEQ ID NO 60
<211> LENGTH: 185
<212> TYPE: PRT
<213> ORGANISM: Artificial Sequence
<220> FEATURE:
<223> OTHER INFORMATION: residue C265 is replaced with Serine (to remove
      one Cysteine site) and SDL1 (K193-H221) and SDL2 (A290-P322)
      residues are deleted from the WT sequence

<400> SEQUENCE: 60

```
Leu Lys Lys Tyr Pro Val Asp Leu Tyr Tyr Leu Val Asp Val Ser Ala
1               5                   10                  15

Ser Met His Asn Asn Ile Glu Lys Leu Asn Ser Val Gly Asn Asp Leu
            20                  25                  30

Ser Arg Lys Met Ala Phe Phe Ser Arg Asp Phe Arg Leu Gly Phe Gly
        35                  40                  45

Ser Tyr Val Asp Gly Tyr Ile His Val Leu Ser Leu Thr Glu Asn Ile
    50                  55                  60

Thr Glu Phe Glu Lys Ala Val His Arg Gln Lys Ile Ser Gly Asn Ile
65                  70                  75                  80

Asp Thr Pro Glu Gly Gly Phe Asp Ala Met Leu Gln Ala Ala Val Ser
                85                  90                  95

Glu Ser His Ile Gly Trp Arg Lys Glu Ala Lys Arg Leu Leu Leu Val
            100                 105                 110

Met Thr Asp Gln Thr Ser His Leu Ser Leu Gly Gln Leu Ser Glu Lys
        115                 120                 125

Leu Ile Asp Asn Asn Ile Asn Val Ile Phe Ala Val Gln Gly Lys Gln
    130                 135                 140

Phe His Trp Tyr Lys Asp Leu Leu Pro Leu Leu Pro Gly Thr Ile Ala
145                 150                 155                 160

Gly Glu Ile Glu Ser Lys Ala Ala Asn Leu Asn Asn Leu Val Val Glu
                165                 170                 175

Ala Tyr Gln Lys Leu Ile Ser Glu Val
            180                 185
```

<210> SEQ ID NO 61
<211> LENGTH: 726
<212> TYPE: DNA
<213> ORGANISM: Artificial Sequence
<220> FEATURE:
<223> OTHER INFORMATION: Clone 2

<400> SEQUENCE: 61

```
tcttctgagc tgactcagga ccctgctgtg tctgtggcct tgggacagac agtcaggatc      60
acatgccaag gagacagcct cagaagctat tatgcaagct ggtaccagca gaagccagga     120
caggcccctg tacttgtcat ctatggtaaa acaaccggc cctcagggat cccagaccga     180
ttctctggct ccagctcagg aaacacagct tccttgacca tcactgggc tcaggcggaa     240 gatgaggctg actattactg taactcccgg gacagcagtg gtaaccatct ggtattcggc     300
ggagggacca gctgaccgt cctaggtgag ggtaaatctt ccggatctgg ttccgaatcc     360
aaagctagcc aggttcagct ggtgcagtct ggggctgagg tgaagaagcc tggggcctca     420
```

```
gtgaaggtct cctgcaaggc ttctggatac accttcaccg gctactatat gcactgggtg    480
cgacaggccc ctggacaagg gcttgagtgg atgggatgga tcaaccctaa cagtggtggc    540
acaaactatg cacagaagtt tcagggctgg gtcaccatga ccagggacac gtccatcagc    600
acagcctaca tggagctgag caggctgaga tctgacgaca cggccgtgta ttactgtgcg    660
cgctacatgg ttcggggagg agggattgac tactggggcc agggcaccct ggtcaccgtc    720
tcctca                                                                726

<210> SEQ ID NO 62
<211> LENGTH: 720
<212> TYPE: DNA
<213> ORGANISM: Artificial Sequence
<220> FEATURE:
<223> OTHER INFORMATION: Clone 3
<220> FEATURE:
<221> NAME/KEY: misc_feature
<222> LOCATION: (696)..(696)
<223> OTHER INFORMATION: n is a, c, g, or t

<400> SEQUENCE: 62
tcttctgagc tgactcagga ccctgctgtg tctgtggcct tgggacagac agtcaggatc     60
acatgccaag gagacagcct cagaagctat tatgcaagct ggtaccagca gaagccagga    120
caggcccctg tacttgtcat ctatggtaaa acaaccggc cctcaggat cccagaccga    180 ttctctggct ccacctcagg aaatacagct tccttgacca tcactgggc tcaggcggag    240 gatgaggctg actattactg taactcccgg gacagcagtg gtaaccatct ggtattcggc    300
ggagggacca agctcaccgt cctaggtgag ggtaaatctt ccggatctgg ttccgaatcc    360
aaagctagcc aggtgcagct gcaggagtcg ggcccaggac tggtgaaccc ttcacagacc    420
ctgtccctca cctgcactgt ctctggtggc tccatcagca gtggtggtta ctactggagc    480
tggatccgcc agcacccagg aagggcctg gagtggattg gtacatctc ttacagtggg    540 agcacctact acaaccccctc cctcaagagt cgagttacca tatcagtaga cacatctaag    600
aaccagttct ccctgaagct gagctctgtg actgccgcgg acacggccgt gtattactgt    660
gcgagaggtc ggacttggtt cgaccctggg ggccanggca ccctggtcac cgtctcctca    720

<210> SEQ ID NO 63
<211> LENGTH: 720
<212> TYPE: DNA
<213> ORGANISM: Artificial Sequence
<220> FEATURE:
<223> OTHER INFORMATION: Clone 5

<400> SEQUENCE: 63
tcttctgagc tgactcagga ccctgctgtg tctgtggcct tgggacagac agtcaggatc     60
acatgccaag gagacagcct cagaagctat tatgcaagct ggtaccagca gaagccagga    120
caggcccctg tacttgtcat ctatggtaaa acaaccggc cctcaggat cccagaccga    180 ttctctggct ccacctcggg aaattttgct tccttgacca tcacgggggc tcaggcggaa    240
gatggggctg actattactg tcactcccgg gacagcagtg gcaaccatct ggttttcggc    300 gggggggacca agctcaccgt cctaggtgag ggtaaatctt ccggatctgg ttccgaatcc    360
aaagctagcg aggtgcagct ggtgcagtct ggggcagagg tgaaaaagcc gggggagtct    420
ctgaagatct cctgtaaggg ttctggatac agctttacca gctactggat cggctgggtg    480
cgccagatgc ccgggaaagg cctggagtgg atggggatca tctatcctgg tgactctgat    540
accagataca gcccgtcctt ccaaggccag gtcaccatct cagccgacaa gtccatcagc    600
```

```
accgcctacc tgcagtggag cagcctgaag gcctcggaca ccgccatgta ttactgtgcg    660
agacgtgcta ggggtgcttt tgatatctgg ggccaaggaa ccctggtcac cgtctcctca    720
```

<210> SEQ ID NO 64
<211> LENGTH: 723
<212> TYPE: DNA
<213> ORGANISM: Artificial Sequence
<220> FEATURE:
<223> OTHER INFORMATION: Clone 6

<400> SEQUENCE: 64

```
cagtctgtgc tgactcagcc accctcagcg tctgggaccc ccgggcagag ggtcaccatc     60
tcttgttctg gaagcagctc caacatcgga agtaattatg tatcctggta ccagcagctc    120
ccaggaacag cccccaaact cctcatttat gacaataata gcgaccctc agggattcct    180 gaccgattct ctggctccaa gtctggcacg tcagccaccc tgggcatcac cggactccag    240 actgggacg aggccgatta ttactgcgga acatgggata gcagcctgag tgctctttat    300
gtcttcggag ctgggaccaa gctgaccgtc ctaggtgagg gtaaatcttc cggatctggt    360
tccgaatcca aagctagcca ggtgcagctg caggagtcgg gcccaggact ggtgaagcct    420
tcggagaccc tgtccctcac gtgcagtgtc tctggtggct ccaccagtag ttactactgg    480
agctggatcc ggcagccccc agggaagggg ctggagtgga ttgggtatat ctcgaacagt    540
gggagcacca actacaaccc ctccctcaag agtcgagtca ccatgtcaat agacacgtcc    600
aacaaccagt tctccctgaa gttgagttct gtgaccgccg cagacacggc cgtctattac    660
tgtgcgagcc acttgggagc tacctggcgg tggggccagg gaaccctggt caccgtctcc    720
tca                                                                  723
```

<210> SEQ ID NO 65
<211> LENGTH: 708
<212> TYPE: DNA
<213> ORGANISM: Artificial Sequence
<220> FEATURE:
<223> OTHER INFORMATION: Clone 11

<400> SEQUENCE: 65

```
gaggtgcagc tggtggagtc tgggggaggc gtggtccagc ctgggaggtc cctgagactc     60
tcctgtgcag ccactggatt caccttcagt aactatggca tacactgggt ccgccaggct    120
ccaggcaagg gctggagtg gtggcagtt acatcatatg atggaagtaa taatattat    180 gcagactccg tgaagggccg attcaccatc tccagagaca attccaagaa cacgctgtat    240
ctgcaaatga acagcctgag agttgaggac acggctgtgt attactgtgc caaagatcgt    300
ggttactaca catacgtatt tgactattgg ggccggggaa ccctggtcac cgtctcctca    360
ggcgagggta atcttccgg atctggttcc gaatccaaag ctagcgatgt tgtgatgacc    420
cagactccac tctccctgcc cgtcacccct ggagagccgg ccgccatctc tgcaggtct    480 agtcagagcc tcctgcatag taatggatac aactatttgg attggtacct gcagaagcca    540
gggcagtctc cacagctcct gatctatttg ggttctaatc gggcctccgg ggtccctgac    600
aggttcagtg gcagtggatc aggcacagat tttacactga aaatcagcag agtggaggct    660
gaggatgttg ggtttattta ctgcatgcaa gctgtacaaa ctgtcgac                  708
```

<210> SEQ ID NO 66
<211> LENGTH: 411
<212> TYPE: DNA

<213> ORGANISM: Artificial Sequence
<220> FEATURE:
<223> OTHER INFORMATION: Clone 13

<400> SEQUENCE: 66

```
gaagtgcagc tgctggaaag cggcggtggt ctggttcagc cgggtggcag cctgcgtctg      60
agctgtgcgg cgagcggctt tacctttagc agcgatttaa tgagctgggt gcgtcaggca     120
ccgggcaaag gcctggaatg ggtgagcgcg attagcggca gcggcggcag cacctattat     180
gcggatagcg tgaaaggccg ttttaccatt agccgtgata cagcaaaaa cacccctgtat    240
ctgcagatga acagcctgcg tgcggaagat accgcggtgt attattgcgc gaaaaatgag     300
gttatctttg attattgggg ccagggcacc ctggttaccg ttagcagcgc gagcaccaaa     360
ggcctgagca tgtttgatta ttggggccag ggcaccaaag tggaaattaa a              411
```

<210> SEQ ID NO 67
<211> LENGTH: 720
<212> TYPE: DNA
<213> ORGANISM: Artificial Sequence
<220> FEATURE:
<223> OTHER INFORMATION: Clone 14

<400> SEQUENCE: 67

```
gatgttgtga tgacccagtc tccactctcc ctgcccgcca cccttggaca gccggcctcc      60
atctcctgca ggtctagtca agcctcgta tacactgatg aaacaccta cttgaattgg     120
tttcagcaga ggcccggcca atctccaagg cgcctaattt ataaggtttc taaccgggac     180
tctggggtcc cagacagatt cagcggcagt gggtcaggca ctcatttcac actgaaaatc     240
agcagggtgg aggctgagga tgttggagtt tattactgca tgcaaggtac acactggcct     300
ccgacgttcg gccaagggac caaggtggaa atcaaagagg gtaaatcttc cggatctggt     360
tccgaatcca aagctagcga ggtgcagctg gtgcagtctg ggctgaggt gaagaagcct     420
gggggcctcag tgaaggtctc ctgcaaggct tctggaggca ccttcagcag ctatgctatc     480
agctgggtgc gacaggcccc tggacaaggg cttgagtgga tgggagggat catccctatc     540
tttggtacag caaactacgc acagaagttc cagggcagag tcacgattac cgcggacgaa     600
tccacgagca cagcctacat ggagctgagc agcctgagat ctgaggacac ggccgtgtat     660
tactgtgcga gtagcggggt tgactactgg ggccagggca ccctggtcac cgtctcctca     720
```

<210> SEQ ID NO 68
<211> LENGTH: 375
<212> TYPE: DNA
<213> ORGANISM: Artificial Sequence
<220> FEATURE:
<223> OTHER INFORMATION: Clone 8

<400> SEQUENCE: 68

```
gatgtgcagc tggtggagtc tggggaggc ttggtgcagc tggggggtc tctgagactc       60
tcctgtacag cctctggatt caccttcagt aactatgcca tgaactgggt ccgccaggct     120
ccaggaaagg gctcgagtg gtctcagtt atttcaagta gtggtagtcg cgaaactat      180
gcagactccg tgaaaggccg attcaccatc tccagagaca acgccaagag cacgctgtat     240
ctgcaaatga acagcctgaa acctgaggat acggccgtat attactgtgc aaaggttcga     300
gatgcaggct actacagatg gaacctgaat gaccttgatt accggggcca ggggacccag     360
gtcaccgtct cctca                                                      375
```

```
<210> SEQ ID NO 69
<211> LENGTH: 1179
<212> TYPE: PRT
<213> ORGANISM: Homo sapiens

<400> SEQUENCE: 69

Met Ala Pro Arg Pro Arg Ala Arg Pro Gly Val Ala Val Ala Cys Cys
1               5                   10                  15

Trp Leu Leu Thr Val Val Leu Arg Cys Cys Val Ser Phe Asn Val Asp
            20                  25                  30

Val Lys Asn Ser Met Thr Phe Ser Gly Pro Val Glu Asp Met Phe Gly
        35                  40                  45

Tyr Thr Val Gln Gln Tyr Glu Asn Glu Glu Gly Lys Trp Val Leu Ile
    50                  55                  60

Gly Ser Pro Leu Val Gly Gln Pro Lys Asn Arg Thr Gly Asp Val Tyr
65                  70                  75                  80

Lys Cys Pro Val Gly Arg Gly Glu Ser Leu Pro Cys Val Lys Leu Asp
                85                  90                  95

Leu Pro Val Asn Thr Ser Ile Pro Asn Val Thr Glu Val Lys Glu Asn
            100                 105                 110

Met Thr Phe Gly Ser Thr Leu Val Thr Asn Pro Asn Gly Gly Phe Leu
        115                 120                 125

Ala Cys Gly Pro Leu Tyr Ala Tyr Arg Cys Gly His Leu His Tyr Thr
    130                 135                 140

Thr Gly Ile Cys Ser Asp Val Ser Pro Thr Phe Gln Val Val Asn Ser
145                 150                 155                 160

Ile Ala Pro Val Gln Glu Cys Ser Thr Gln Leu Asp Ile Val Ile Val
                165                 170                 175

Leu Asp Gly Ser Asn Ser Ile Tyr Pro Trp Asp Ser Val Thr Ala Phe
            180                 185                 190

Leu Asn Asp Leu Leu Glu Arg Met Asp Ile Gly Pro Lys Gln Thr Gln
        195                 200                 205

Val Gly Ile Val Gln Tyr Gly Glu Asn Val Thr His Glu Phe Asn Leu
    210                 215                 220

Asn Lys Tyr Ser Ser Thr Glu Glu Val Leu Val Ala Ala Lys Lys Ile
225                 230                 235                 240

Val Gln Arg Gly Gly Arg Gln Thr Met Thr Ala Leu Gly Ile Asp Thr
                245                 250                 255

Ala Arg Lys Glu Ala Phe Thr Glu Ala Arg Gly Ala Arg Arg Gly Val
            260                 265                 270

Lys Lys Val Met Val Ile Val Thr Asp Gly Glu Ser His Asp Asn His
        275                 280                 285

Arg Leu Lys Lys Val Ile Gln Asp Cys Glu Asp Glu Asn Ile Gln Arg
    290                 295                 300

Phe Ser Ile Ala Ile Leu Gly Ser Tyr Asn Arg Gly Asn Leu Ser Thr
305                 310                 315                 320

Glu Lys Phe Val Glu Glu Ile Lys Ser Ile Ala Ser Glu Pro Thr Glu
                325                 330                 335

Lys His Phe Phe Asn Val Ser Asp Glu Leu Ala Leu Val Thr Ile Val
            340                 345                 350

Lys Thr Leu Gly Glu Arg Ile Phe Ala Leu Glu Ala Thr Ala Asp Gln
        355                 360                 365

Ser Ala Ala Ser Phe Glu Met Glu Met Ser Gln Thr Gly Phe Ser Ala
    370                 375                 380
```

-continued

His Tyr Ser Gln Asp Trp Val Met Leu Gly Ala Val Gly Ala Tyr Asp
385                 390                 395                 400

Trp Asn Gly Thr Val Val Met Gln Lys Ala Ser Gln Ile Ile Ile Pro
        405                 410                 415

Arg Asn Thr Thr Phe Asn Val Glu Ser Thr Lys Lys Asn Glu Pro Leu
        420                 425                 430

Ala Ser Tyr Leu Gly Tyr Thr Val Asn Ser Ala Thr Ala Ser Ser Gly
        435                 440                 445

Asp Val Leu Tyr Ile Ala Gly Gln Pro Arg Tyr Asn His Thr Gly Gln
        450                 455                 460

Val Ile Ile Tyr Arg Met Glu Asp Gly Asn Ile Lys Ile Leu Gln Thr
465                 470                 475                 480

Leu Ser Gly Glu Gln Ile Gly Ser Tyr Phe Gly Ser Ile Leu Thr Thr
            485                 490                 495

Thr Asp Ile Asp Lys Asp Ser Asn Thr Asp Ile Leu Leu Val Gly Ala
            500                 505                 510

Pro Met Tyr Met Gly Thr Glu Lys Glu Gln Gly Lys Val Tyr Val
            515                 520                 525

Tyr Ala Leu Asn Gln Thr Arg Phe Glu Tyr Gln Met Ser Leu Glu Pro
530                 535                 540

Ile Lys Gln Thr Cys Cys Ser Ser Arg Gln His Asn Ser Cys Thr Thr
545                 550                 555                 560

Glu Asn Lys Asn Glu Pro Cys Gly Ala Arg Phe Gly Thr Ala Ile Ala
            565                 570                 575

Ala Val Lys Asp Leu Asn Leu Asp Gly Phe Asn Asp Ile Val Ile Gly
            580                 585                 590

Ala Pro Leu Glu Asp Asp His Gly Gly Ala Val Tyr Ile Tyr His Gly
            595                 600                 605

Ser Gly Lys Thr Ile Arg Lys Glu Tyr Ala Gln Arg Ile Pro Ser Gly
            610                 615                 620

Gly Asp Gly Lys Thr Leu Lys Phe Phe Gly Gln Ser Ile His Gly Glu
625                 630                 635                 640

Met Asp Leu Asn Gly Asp Gly Leu Thr Asp Val Thr Ile Gly Gly Leu
            645                 650                 655

Gly Gly Ala Ala Leu Phe Trp Ser Arg Asp Val Ala Val Val Lys Val
            660                 665                 670

Thr Met Asn Phe Glu Pro Asn Lys Val Asn Ile Gln Lys Lys Asn Cys
            675                 680                 685

His Met Glu Gly Lys Glu Thr Val Cys Ile Asn Ala Thr Val Cys Phe
            690                 695                 700

Asp Val Lys Leu Lys Ser Lys Glu Asp Thr Ile Tyr Glu Ala Asp Leu
705                 710                 715                 720

Gln Tyr Arg Val Thr Leu Asp Ser Leu Arg Gln Ile Ser Arg Ser Phe
            725                 730                 735

Phe Ser Gly Thr Gln Glu Arg Lys Val Gln Arg Asn Ile Thr Val Arg
            740                 745                 750

Lys Ser Glu Cys Thr Lys His Ser Phe Tyr Met Leu Asp Lys His Asp
            755                 760                 765

Phe Gln Asp Ser Val Arg Ile Thr Leu Asp Phe Asn Leu Thr Asp Pro
            770                 775                 780

Glu Asn Gly Pro Val Leu Asp Asp Ser Leu Pro Asn Ser Val His Glu
785                 790                 795                 800

Tyr Ile Pro Phe Ala Lys Asp Cys Gly Asn Lys Glu Lys Cys Ile Ser

```
                805                 810                 815
Asp Leu Ser Leu His Val Ala Thr Thr Glu Lys Asp Leu Leu Ile Val
            820                 825                 830

Arg Ser Gln Asn Asp Lys Phe Asn Val Ser Leu Thr Val Lys Asn Thr
            835                 840                 845

Lys Asp Ser Ala Tyr Asn Thr Arg Thr Ile Val His Tyr Ser Pro Asn
        850                 855                 860

Leu Val Phe Ser Gly Ile Glu Ala Ile Gln Lys Asp Ser Cys Glu Ser
865                 870                 875                 880

Asn His Asn Ile Thr Cys Lys Val Gly Tyr Pro Phe Leu Arg Arg Gly
                885                 890                 895

Glu Met Val Thr Phe Lys Ile Leu Phe Gln Phe Asn Thr Ser Tyr Leu
            900                 905                 910

Met Glu Asn Val Thr Ile Tyr Leu Ser Ala Thr Ser Asp Ser Glu Glu
            915                 920                 925

Pro Pro Glu Thr Leu Ser Asp Asn Val Val Asn Ile Ser Ile Pro Val
        930                 935                 940

Lys Tyr Glu Val Gly Leu Gln Phe Tyr Ser Ser Ala Ser Glu Tyr His
945                 950                 955                 960

Ile Ser Ile Ala Ala Asn Glu Thr Val Pro Glu Val Ile Asn Ser Thr
                965                 970                 975

Glu Asp Ile Gly Asn Glu Ile Asn Ile Phe Tyr Leu Ile Arg Lys Ser
            980                 985                 990

Gly Ser Phe Pro Met Pro Glu Leu Lys Leu Ser Ile Ser Phe Pro Asn
        995                 1000                1005

Met Thr Ser Asn Gly Tyr Pro Val Leu Tyr Pro Thr Gly Leu Ser
    1010                1015                1020

Ser Ser Glu Asn Ala Asn Cys Arg Pro His Ile Phe Glu Asp Pro
    1025                1030                1035

Phe Ser Ile Asn Ser Gly Lys Lys Met Thr Thr Ser Thr Asp His
    1040                1045                1050

Leu Lys Arg Gly Thr Ile Leu Asp Cys Asn Thr Cys Lys Phe Ala
    1055                1060                1065

Thr Ile Thr Cys Asn Leu Thr Ser Ser Asp Ile Ser Gln Val Asn
    1070                1075                1080

Val Ser Leu Ile Leu Trp Lys Pro Thr Phe Ile Lys Ser Tyr Phe
    1085                1090                1095

Ser Ser Leu Asn Leu Thr Ile Arg Gly Glu Leu Arg Ser Glu Asn
    1100                1105                1110

Ala Ser Leu Val Leu Ser Ser Ser Asn Gln Lys Arg Glu Leu Ala
    1115                1120                1125

Ile Gln Ile Ser Lys Asp Gly Leu Pro Gly Arg Val Pro Leu Trp
    1130                1135                1140

Val Ile Leu Leu Ser Ala Phe Ala Gly Leu Leu Leu Leu Met Leu
    1145                1150                1155

Leu Ile Leu Ala Leu Trp Lys Ile Gly Phe Phe Lys Arg Pro Leu
    1160                1165                1170

Lys Lys Lys Met Glu Lys
    1175

<210> SEQ ID NO 70
<211> LENGTH: 1181
<212> TYPE: PRT
<213> ORGANISM: Homo sapiens
```

<400> SEQUENCE: 70

| | | | | | | | | | | | | | | |
|---|---|---|---|---|---|---|---|---|---|---|---|---|---|---|
| Met | Gly | Pro | Glu | Arg | Thr | Gly | Ala | Ala | Pro | Leu | Pro | Leu | Leu | Val |
| 1 | | | | 5 | | | | | 10 | | | | | 15 |
| Leu | Ala | Leu | Ser | Gln | Gly | Ile | Leu | Asn | Cys | Cys | Leu | Ala | Tyr | Asn | Val |
| | | | 20 | | | | | 25 | | | | | 30 | | |
| Gly | Leu | Pro | Glu | Ala | Lys | Ile | Phe | Ser | Gly | Pro | Ser | Ser | Glu | Gln | Phe |
| | | 35 | | | | | 40 | | | | | 45 | | | |
| Gly | Tyr | Ala | Val | Gln | Gln | Phe | Ile | Asn | Pro | Lys | Gly | Asn | Trp | Leu | Leu |
| | 50 | | | | | 55 | | | | | 60 | | | | |
| Val | Gly | Ser | Pro | Trp | Ser | Gly | Phe | Pro | Glu | Asn | Arg | Met | Gly | Asp | Val |
| 65 | | | | | 70 | | | | | 75 | | | | | 80 |
| Tyr | Lys | Cys | Pro | Val | Asp | Leu | Ser | Thr | Ala | Thr | Cys | Glu | Lys | Leu | Asn |
| | | | | 85 | | | | | 90 | | | | | 95 | |
| Leu | Gln | Thr | Ser | Thr | Ser | Ile | Pro | Asn | Val | Thr | Glu | Met | Lys | Thr | Asn |
| | | | 100 | | | | | 105 | | | | | 110 | | |
| Met | Ser | Leu | Gly | Leu | Ile | Leu | Thr | Arg | Asn | Met | Gly | Thr | Gly | Gly | Phe |
| | | | 115 | | | | | 120 | | | | | 125 | | |
| Leu | Thr | Cys | Gly | Pro | Leu | Trp | Ala | Gln | Gln | Cys | Gly | Asn | Gln | Tyr | Tyr |
| | 130 | | | | | 135 | | | | | 140 | | | | |
| Thr | Thr | Gly | Val | Cys | Ser | Asp | Ile | Ser | Pro | Asp | Phe | Gln | Leu | Ser | Ala |
| 145 | | | | | 150 | | | | | 155 | | | | | 160 |
| Ser | Phe | Ser | Pro | Ala | Thr | Gln | Pro | Cys | Pro | Ser | Leu | Ile | Asp | Val | Val |
| | | | | 165 | | | | | 170 | | | | | 175 | |
| Val | Val | Cys | Asp | Glu | Ser | Asn | Ser | Ile | Tyr | Pro | Trp | Asp | Ala | Val | Lys |
| | | | 180 | | | | | 185 | | | | | 190 | | |
| Asn | Phe | Leu | Glu | Lys | Phe | Val | Gln | Gly | Leu | Asp | Ile | Gly | Pro | Thr | Lys |
| | | | 195 | | | | | 200 | | | | | 205 | | |
| Thr | Gln | Val | Gly | Leu | Ile | Gln | Tyr | Ala | Asn | Asn | Pro | Arg | Val | Val | Phe |
| | 210 | | | | | 215 | | | | | 220 | | | | |
| Asn | Leu | Asn | Thr | Tyr | Lys | Thr | Lys | Glu | Glu | Met | Ile | Val | Ala | Thr | Ser |
| 225 | | | | | 230 | | | | | 235 | | | | | 240 |
| Gln | Thr | Ser | Gln | Tyr | Gly | Gly | Asp | Leu | Thr | Asn | Thr | Phe | Gly | Ala | Ile |
| | | | | 245 | | | | | 250 | | | | | 255 | |
| Gln | Tyr | Ala | Arg | Lys | Tyr | Ala | Tyr | Ser | Ala | Ala | Ser | Gly | Gly | Arg | Arg |
| | | | 260 | | | | | 265 | | | | | 270 | | |
| Ser | Ala | Thr | Lys | Val | Met | Val | Val | Thr | Asp | Gly | Glu | Ser | His | Asp |
| | | 275 | | | | | 280 | | | | | 285 | | | |
| Gly | Ser | Met | Leu | Lys | Ala | Val | Ile | Asp | Gln | Cys | Asn | His | Asp | Asn | Ile |
| | 290 | | | | | 295 | | | | | 300 | | | | |
| Leu | Arg | Phe | Gly | Ile | Ala | Val | Leu | Gly | Tyr | Leu | Asn | Arg | Asn | Ala | Leu |
| 305 | | | | | 310 | | | | | 315 | | | | | 320 |
| Asp | Thr | Lys | Asn | Leu | Ile | Lys | Glu | Ile | Lys | Ala | Ile | Ala | Ser | Ile | Pro |
| | | | | 325 | | | | | 330 | | | | | 335 | |
| Thr | Glu | Arg | Tyr | Phe | Phe | Asn | Val | Ser | Asp | Glu | Ala | Ala | Leu | Leu | Glu |
| | | | 340 | | | | | 345 | | | | | 350 | | |
| Lys | Ala | Gly | Thr | Leu | Gly | Glu | Gln | Ile | Phe | Ser | Ile | Glu | Gly | Thr | Val |
| | | 355 | | | | | 360 | | | | | 365 | | | |
| Gln | Gly | Gly | Asp | Asn | Phe | Gln | Met | Glu | Met | Ser | Gln | Val | Gly | Phe | Ser |
| | 370 | | | | | 375 | | | | | 380 | | | | |
| Ala | Asp | Tyr | Ser | Ser | Gln | Asn | Asp | Ile | Leu | Met | Leu | Gly | Ala | Val | Gly |
| 385 | | | | | 390 | | | | | 395 | | | | | 400 |
| Ala | Phe | Gly | Trp | Ser | Gly | Thr | Ile | Val | Gln | Lys | Thr | Ser | His | Gly | His |

```
            405                 410                 415
Leu Ile Phe Pro Lys Gln Ala Phe Asp Gln Ile Leu Gln Asp Arg Asn
                420                 425                 430

His Ser Ser Tyr Leu Gly Tyr Ser Val Ala Ala Ile Ser Thr Gly Glu
                435                 440                 445

Ser Thr His Phe Val Ala Gly Ala Pro Arg Ala Asn Tyr Thr Gly Gln
            450                 455                 460

Ile Val Leu Tyr Ser Val Asn Glu Asn Gly Asn Ile Thr Val Ile Gln
465                 470                 475                 480

Ala His Arg Gly Asp Gln Ile Gly Ser Tyr Phe Gly Ser Val Leu Cys
                485                 490                 495

Ser Val Asp Val Asp Lys Asp Thr Ile Thr Asp Val Leu Leu Val Gly
                500                 505                 510

Ala Pro Met Tyr Met Ser Asp Leu Lys Lys Glu Glu Gly Arg Val Tyr
                515                 520                 525

Leu Phe Thr Ile Lys Lys Gly Ile Leu Gly Gln His Gln Phe Leu Glu
                530                 535                 540

Gly Pro Glu Gly Ile Glu Asn Thr Arg Phe Gly Ser Ala Ile Ala Ala
545                 550                 555                 560

Leu Ser Asp Ile Asn Met Asp Gly Phe Asn Asp Val Ile Val Gly Ser
                565                 570                 575

Pro Leu Glu Asn Gln Asn Ser Gly Ala Val Tyr Ile Tyr Asn Gly His
                580                 585                 590

Gln Gly Thr Ile Arg Thr Lys Tyr Ser Gln Lys Ile Leu Gly Ser Asp
                595                 600                 605

Gly Ala Phe Arg Ser His Leu Gln Tyr Phe Gly Arg Ser Leu Asp Gly
                610                 615                 620

Tyr Gly Asp Leu Asn Gly Asp Ser Ile Thr Asp Val Ser Ile Gly Ala
625                 630                 635                 640

Phe Gly Gln Val Val Gln Leu Trp Ser Gln Ser Ile Ala Asp Val Ala
                645                 650                 655

Ile Glu Ala Ser Phe Thr Pro Glu Lys Ile Thr Leu Val Asn Lys Asn
                660                 665                 670

Ala Gln Ile Ile Leu Lys Leu Cys Phe Ser Ala Lys Phe Arg Pro Thr
                675                 680                 685

Lys Gln Asn Asn Gln Val Ala Ile Val Tyr Asn Ile Thr Leu Asp Ala
                690                 695                 700

Asp Gly Phe Ser Ser Arg Val Thr Ser Arg Gly Leu Phe Lys Glu Asn
705                 710                 715                 720

Asn Glu Arg Cys Leu Gln Lys Asn Met Val Val Asn Gln Ala Gln Ser
                725                 730                 735

Cys Pro Glu His Ile Ile Tyr Ile Gln Glu Pro Ser Asp Val Val Asn
                740                 745                 750

Ser Leu Asp Leu Arg Val Asp Ile Ser Leu Glu Asn Pro Gly Thr Ser
                755                 760                 765

Pro Ala Leu Glu Ala Tyr Ser Glu Thr Ala Lys Val Phe Ser Ile Pro
                770                 775                 780

Phe His Lys Asp Cys Gly Glu Asp Gly Leu Cys Ile Ser Asp Leu Val
785                 790                 795                 800

Leu Asp Val Arg Gln Ile Pro Ala Ala Gln Glu Gln Pro Phe Ile Val
                805                 810                 815

Ser Asn Gln Asn Lys Arg Leu Thr Phe Ser Val Thr Leu Lys Asn Lys
                820                 825                 830
```

Arg Glu Ser Ala Tyr Asn Thr Gly Ile Val Val Asp Phe Ser Glu Asn
835                 840                 845

Leu Phe Phe Ala Ser Phe Ser Leu Pro Val Asp Gly Thr Glu Val Thr
850                 855                 860

Cys Gln Val Ala Ala Ser Gln Lys Ser Val Ala Cys Asp Val Gly Tyr
865                 870                 875                 880

Pro Ala Leu Lys Arg Glu Gln Gln Val Thr Phe Thr Ile Asn Phe Asp
            885                 890                 895

Phe Asn Leu Gln Asn Leu Gln Asn Gln Ala Ser Leu Ser Phe Gln Ala
            900                 905                 910

Leu Ser Glu Ser Gln Glu Glu Asn Lys Ala Asp Asn Leu Val Asn Leu
            915                 920                 925

Lys Ile Pro Leu Leu Tyr Asp Ala Glu Ile His Leu Thr Arg Ser Thr
930                 935                 940

Asn Ile Asn Phe Tyr Glu Ile Ser Ser Asp Gly Asn Val Pro Ser Ile
945                 950                 955                 960

Val His Ser Phe Glu Asp Val Gly Pro Lys Phe Ile Phe Ser Leu Lys
            965                 970                 975

Val Thr Thr Gly Ser Val Pro Val Ser Met Ala Thr Val Ile Ile His
            980                 985                 990

Ile Pro Gln Tyr Thr Lys Glu Lys Asn Pro Leu Met Tyr Leu Thr Gly
    995                 1000                1005

Val Gln Thr Asp Lys Ala Gly Asp Ile Ser Cys Asn Ala Asp Ile
    1010                1015                1020

Asn Pro Leu Lys Ile Gly Gln Thr Ser Ser Ser Val Ser Phe Lys
    1025                1030                1035

Ser Glu Asn Phe Arg His Thr Lys Glu Leu Asn Cys Arg Thr Ala
    1040                1045                1050

Ser Cys Ser Asn Val Thr Cys Trp Leu Lys Asp Val His Met Lys
    1055                1060                1065

Gly Glu Tyr Phe Val Asn Val Thr Thr Arg Ile Trp Asn Gly Thr
    1070                1075                1080

Phe Ala Ser Ser Thr Phe Gln Thr Val Gln Leu Thr Ala Ala Ala
    1085                1090                1095

Glu Ile Asn Thr Tyr Asn Pro Glu Ile Tyr Val Ile Glu Asp Asn
    1100                1105                1110

Thr Val Thr Ile Pro Leu Met Ile Met Lys Pro Asp Glu Lys Ala
    1115                1120                1125

Glu Val Pro Thr Gly Val Ile Ile Gly Ser Ile Ile Ala Gly Ile
    1130                1135                1140

Leu Leu Leu Leu Ala Leu Val Ala Ile Leu Trp Lys Leu Gly Phe
    1145                1150                1155

Phe Lys Arg Lys Tyr Glu Lys Met Thr Lys Asn Pro Asp Glu Ile
    1160                1165                1170

Asp Glu Thr Thr Glu Leu Ser Ser
    1175                1180

<210> SEQ ID NO 71
<211> LENGTH: 1051
<212> TYPE: PRT
<213> ORGANISM: Homo sapiens

<400> SEQUENCE: 71

Met Gly Pro Gly Pro Ser Arg Ala Pro Arg Ala Pro Arg Leu Met Leu

-continued

```
1               5                   10                  15
Cys Ala Leu Ala Leu Met Val Ala Ala Gly Gly Cys Val Val Ser Ala
                20                  25                  30

Phe Asn Leu Asp Thr Arg Phe Leu Val Val Lys Glu Ala Gly Asn Pro
                35                  40                  45

Gly Ser Leu Phe Gly Tyr Ser Val Ala Leu His Arg Gln Thr Glu Arg
                50                  55                  60

Gln Gln Arg Tyr Leu Leu Leu Ala Gly Ala Pro Arg Glu Leu Ala Val
65                  70                  75                  80

Pro Asp Gly Tyr Thr Asn Arg Thr Gly Ala Val Tyr Leu Cys Pro Leu
                85                  90                  95

Thr Ala His Lys Asp Asp Cys Glu Arg Met Asn Ile Thr Val Lys Asn
                100                 105                 110

Asp Pro Gly His His Ile Ile Glu Asp Met Trp Leu Gly Val Thr Val
                115                 120                 125

Ala Ser Gln Gly Pro Ala Gly Arg Val Leu Val Cys Ala His Arg Tyr
                130                 135                 140

Thr Gln Val Leu Trp Ser Gly Ser Glu Asp Gln Arg Arg Met Val Gly
145                 150                 155                 160

Lys Cys Tyr Val Arg Gly Asn Asp Leu Glu Leu Asp Ser Ser Asp Asp
                165                 170                 175

Trp Gln Thr Tyr His Asn Glu Met Cys Asn Ser Asn Thr Asp Tyr Leu
                180                 185                 190

Glu Thr Gly Met Cys Gln Leu Gly Thr Ser Gly Gly Phe Thr Gln Asn
                195                 200                 205

Thr Val Tyr Phe Gly Ala Pro Gly Ala Tyr Asn Trp Lys Gly Asn Ser
210                 215                 220

Tyr Met Ile Gln Arg Lys Glu Trp Asp Leu Ser Glu Tyr Ser Tyr Lys
225                 230                 235                 240

Asp Pro Glu Asp Gln Gly Asn Leu Tyr Ile Gly Tyr Thr Met Gln Val
                245                 250                 255

Gly Ser Phe Ile Leu His Pro Lys Asn Ile Thr Ile Val Thr Gly Ala
                260                 265                 270

Pro Arg His Arg His Met Gly Ala Val Phe Leu Leu Ser Gln Glu Ala
                275                 280                 285

Gly Gly Asp Leu Arg Arg Arg Gln Val Leu Glu Gly Ser Gln Val Gly
                290                 295                 300

Ala Tyr Phe Gly Ser Ala Ile Ala Leu Ala Asp Leu Asn Asn Asp Gly
305                 310                 315                 320

Trp Gln Asp Leu Leu Val Gly Ala Pro Tyr Tyr Phe Glu Arg Lys Glu
                325                 330                 335

Glu Val Gly Gly Ala Ile Tyr Val Phe Met Asn Gln Ala Gly Thr Ser
                340                 345                 350

Phe Pro Ala His Pro Ser Leu Leu His Gly Pro Ser Gly Ser Ala
                355                 360                 365

Phe Gly Leu Ser Val Ala Ser Ile Gly Asp Ile Asn Gln Asp Gly Phe
                370                 375                 380

Gln Asp Ile Ala Val Gly Ala Pro Phe Glu Gly Leu Gly Lys Val Tyr
385                 390                 395                 400

Ile Tyr His Ser Ser Ser Lys Gly Leu Leu Arg Gln Pro Gln Gln Val
                405                 410                 415

Ile His Gly Glu Lys Leu Gly Leu Pro Gly Leu Ala Thr Phe Gly Tyr
                420                 425                 430
```

```
Ser Leu Ser Gly Gln Met Asp Val Asp Glu Asn Phe Tyr Pro Asp Leu
        435                 440                 445
Leu Val Gly Ser Leu Ser Asp His Ile Val Leu Arg Ala Arg Pro
    450                 455                 460
Val Ile Asn Ile Val His Lys Thr Leu Val Pro Arg Pro Ala Val Leu
465                 470                 475                 480
Asp Pro Ala Leu Cys Thr Ala Thr Ser Cys Val Gln Val Glu Leu Cys
                485                 490                 495
Phe Ala Tyr Asn Gln Ser Ala Gly Asn Pro Asn Tyr Arg Arg Asn Ile
                500                 505                 510
Thr Leu Ala Tyr Thr Leu Glu Ala Asp Arg Asp Arg Pro Pro Arg
        515                 520                 525
Leu Arg Phe Ala Gly Ser Glu Ser Ala Val Phe His Gly Phe Phe Ser
        530                 535                 540
Met Pro Glu Met Arg Cys Gln Lys Leu Glu Leu Leu Met Asp Asn
545                 550                 555                 560
Leu Arg Asp Lys Leu Arg Pro Ile Ile Ile Ser Met Asn Tyr Ser Leu
                565                 570                 575
Pro Leu Arg Met Pro Asp Arg Pro Arg Leu Gly Leu Arg Ser Leu Asp
            580                 585                 590
Ala Tyr Pro Ile Leu Asn Gln Ala Gln Ala Leu Glu Asn His Thr Glu
        595                 600                 605
Val Gln Phe Gln Lys Glu Cys Gly Pro Asp Asn Lys Cys Glu Ser Asn
    610                 615                 620
Leu Gln Met Arg Ala Ala Phe Val Ser Glu Gln Gln Lys Leu Ser
625                 630                 635                 640
Arg Leu Gln Tyr Ser Arg Asp Val Arg Lys Leu Leu Leu Ser Ile Asn
                645                 650                 655
Val Thr Asn Thr Arg Thr Ser Glu Arg Ser Gly Glu Asp Ala His Glu
            660                 665                 670
Ala Leu Leu Thr Leu Val Val Pro Pro Ala Leu Leu Leu Ser Ser Val
        675                 680                 685
Arg Pro Pro Gly Ala Cys Gln Ala Asn Glu Thr Ile Phe Cys Glu Leu
    690                 695                 700
Gly Asn Pro Phe Lys Arg Asn Gln Arg Met Glu Leu Leu Ile Ala Phe
705                 710                 715                 720
Glu Val Ile Gly Val Thr Leu His Thr Arg Asp Leu Gln Val Gln Leu
                725                 730                 735
Gln Leu Ser Thr Ser Ser His Gln Asp Asn Leu Trp Pro Met Ile Leu
            740                 745                 750
Thr Leu Leu Val Asp Tyr Thr Leu Gln Thr Ser Leu Ser Met Val Asn
        755                 760                 765
His Arg Leu Gln Ser Phe Phe Gly Gly Thr Val Met Gly Glu Ser Gly
    770                 775                 780
Met Lys Thr Val Glu Asp Val Gly Ser Pro Leu Lys Tyr Glu Phe Gln
785                 790                 795                 800
Val Gly Pro Met Gly Glu Gly Leu Val Gly Leu Gly Thr Leu Val Leu
                805                 810                 815
Gly Leu Glu Trp Pro Tyr Glu Val Ser Asn Gly Lys Trp Leu Leu Tyr
            820                 825                 830
Pro Thr Glu Ile Thr Val His Gly Asn Gly Ser Trp Pro Cys Arg Pro
        835                 840                 845
```

```
Pro Gly Asp Leu Ile Asn Pro Leu Asn Leu Thr Leu Ser Asp Pro Gly
    850                 855                 860

Asp Arg Pro Ser Ser Pro Gln Arg Arg Arg Gln Leu Asp Pro Gly
865                 870                 875                 880

Gly Gly Gln Gly Pro Pro Val Thr Leu Ala Ala Lys Lys Ala
                885                 890                 895

Lys Ser Glu Thr Val Leu Thr Cys Ala Thr Gly Arg Ala His Cys Val
            900                 905                 910

Trp Leu Glu Cys Pro Ile Pro Asp Ala Pro Val Val Thr Asn Val Thr
        915                 920                 925

Val Lys Ala Arg Val Trp Asn Ser Thr Phe Ile Glu Asp Tyr Arg Asp
930                 935                 940

Phe Asp Arg Val Arg Val Asn Gly Trp Ala Thr Leu Phe Leu Arg Thr
945                 950                 955                 960

Ser Ile Pro Thr Ile Asn Met Glu Asn Lys Thr Thr Trp Phe Ser Val
                965                 970                 975

Asp Ile Asp Ser Glu Leu Val Glu Glu Leu Pro Ala Glu Ile Glu Leu
            980                 985                 990

Trp Leu Val Leu Val Ala Val Gly Ala Gly Leu Leu Leu Leu Gly Leu
        995                 1000                1005

Ile Ile Leu Leu Leu Trp Lys Cys Gly Phe Phe Lys Arg Ala Arg
    1010                1015                1020

Thr Arg Ala Leu Tyr Glu Ala Lys Arg Gln Lys Ala Glu Met Lys
    1025                1030                1035

Ser Gln Pro Ser Glu Thr Glu Arg Leu Thr Asp Asp Tyr
    1040                1045                1050

<210> SEQ ID NO 72
<211> LENGTH: 1032
<212> TYPE: PRT
<213> ORGANISM: Homo sapiens

<400> SEQUENCE: 72

Met Ala Trp Glu Ala Arg Arg Glu Pro Gly Pro Arg Arg Ala Ala Val
1               5                   10                  15

Arg Glu Thr Val Met Leu Leu Leu Cys Leu Gly Val Pro Thr Gly Arg
                20                  25                  30

Pro Tyr Asn Val Asp Thr Glu Ser Ala Leu Leu Tyr Gln Gly Pro His
            35                  40                  45

Asn Thr Leu Phe Gly Tyr Ser Val Val Leu His Ser His Gly Ala Asn
        50                  55                  60

Arg Trp Leu Leu Val Gly Ala Pro Thr Ala Asn Trp Leu Ala Asn Ala
65                  70                  75                  80

Ser Val Ile Asn Pro Gly Ala Ile Tyr Arg Cys Arg Ile Gly Lys Asn
                85                  90                  95

Pro Gly Gln Thr Cys Glu Gln Leu Gln Leu Gly Ser Pro Asn Gly Glu
            100                 105                 110

Pro Cys Gly Lys Thr Cys Leu Glu Glu Arg Asp Asn Gln Trp Leu Gly
        115                 120                 125

Val Thr Leu Ser Arg Gln Pro Gly Glu Asn Gly Ser Ile Val Thr Cys
    130                 135                 140

Gly His Arg Trp Lys Asn Ile Phe Tyr Ile Lys Asn Glu Asn Lys Leu
145                 150                 155                 160

Pro Thr Gly Gly Cys Tyr Gly Val Pro Pro Asp Leu Arg Thr Glu Leu
                165                 170                 175
```

```
Ser Lys Arg Ile Ala Pro Cys Tyr Gln Asp Tyr Val Lys Lys Phe Gly
            180                 185                 190

Glu Asn Phe Ala Ser Cys Gln Ala Gly Ile Ser Ser Phe Tyr Thr Lys
            195                 200                 205

Asp Leu Ile Val Met Gly Ala Pro Gly Ser Ser Tyr Trp Thr Gly Ser
            210                 215                 220

Leu Phe Val Tyr Asn Ile Thr Thr Asn Lys Tyr Lys Ala Phe Leu Asp
225                 230                 235                 240

Lys Gln Asn Gln Val Lys Phe Gly Ser Tyr Leu Gly Tyr Ser Val Gly
                245                 250                 255

Ala Gly His Phe Arg Ser Gln His Thr Thr Glu Val Val Gly Gly Ala
            260                 265                 270

Pro Gln His Glu Gln Ile Gly Lys Ala Tyr Ile Phe Ser Ile Asp Glu
            275                 280                 285

Lys Glu Leu Asn Ile Leu His Glu Met Lys Gly Lys Lys Leu Gly Ser
            290                 295                 300

Tyr Phe Gly Ala Ser Val Cys Ala Val Asp Leu Asn Ala Asp Gly Phe
305                 310                 315                 320

Ser Asp Leu Leu Val Gly Ala Pro Met Gln Ser Thr Ile Arg Glu Glu
                325                 330                 335

Gly Arg Val Phe Val Tyr Ile Asn Ser Gly Ser Gly Ala Val Met Asn
            340                 345                 350

Ala Met Glu Thr Asn Leu Val Gly Ser Asp Lys Tyr Ala Ala Arg Phe
            355                 360                 365

Gly Glu Ser Ile Val Asn Leu Gly Asp Ile Asp Asn Asp Gly Phe Glu
            370                 375                 380

Asp Val Ala Ile Gly Ala Pro Gln Glu Asp Asp Leu Gln Gly Ala Ile
385                 390                 395                 400

Tyr Ile Tyr Asn Gly Arg Ala Asp Gly Ile Ser Ser Thr Phe Ser Gln
                405                 410                 415

Arg Ile Glu Gly Leu Gln Ile Ser Lys Ser Leu Ser Met Phe Gly Gln
            420                 425                 430

Ser Ile Ser Gly Gln Ile Asp Ala Asp Asn Asn Gly Tyr Val Asp Val
            435                 440                 445

Ala Val Gly Ala Phe Arg Ser Asp Ser Ala Val Leu Leu Arg Thr Arg
450                 455                 460

Pro Val Val Ile Val Asp Ala Ser Leu Ser His Pro Glu Ser Val Asn
465                 470                 475                 480

Arg Thr Lys Phe Asp Cys Val Glu Asn Gly Trp Pro Ser Val Cys Ile
                485                 490                 495

Asp Leu Thr Leu Cys Phe Ser Tyr Lys Gly Lys Glu Val Pro Gly Tyr
            500                 505                 510

Ile Val Leu Phe Tyr Asn Met Ser Leu Asp Val Asn Arg Lys Ala Glu
            515                 520                 525

Ser Pro Pro Arg Phe Tyr Phe Ser Ser Asn Gly Thr Ser Asp Val Ile
            530                 535                 540

Thr Gly Ser Ile Gln Val Ser Ser Arg Glu Ala Asn Cys Arg Thr His
545                 550                 555                 560

Gln Ala Phe Met Arg Lys Asp Val Arg Asp Ile Leu Thr Pro Ile Gln
                565                 570                 575

Ile Glu Ala Ala Tyr His Leu Gly Pro His Val Ile Ser Lys Arg Ser
            580                 585                 590
```

-continued

Thr Glu Glu Phe Pro Pro Leu Gln Pro Ile Leu Gln Gln Lys Lys Glu
        595                 600                 605
Lys Asp Ile Met Lys Thr Ile Asn Phe Ala Arg Phe Cys Ala His
610                 615                 620
Glu Asn Cys Ser Ala Asp Leu Gln Val Ser Ala Lys Ile Gly Phe Leu
625                 630                 635                 640
Lys Pro His Glu Asn Lys Thr Tyr Leu Ala Val Gly Ser Met Lys Thr
                645                 650                 655
Leu Met Leu Asn Val Ser Leu Phe Asn Ala Gly Asp Asp Ala Tyr Glu
                660                 665                 670
Thr Thr Leu His Val Lys Leu Pro Val Gly Leu Tyr Phe Ile Lys Ile
            675                 680                 685
Leu Glu Leu Glu Glu Lys Gln Ile Asn Cys Glu Val Thr Asp Asn Ser
        690                 695                 700
Gly Val Val Gln Leu Asp Cys Ser Ile Gly Tyr Ile Tyr Val Asp His
705                 710                 715                 720
Leu Ser Arg Ile Asp Ile Ser Phe Leu Leu Asp Val Ser Ser Leu Ser
                725                 730                 735
Arg Ala Glu Glu Asp Leu Ser Ile Thr Val His Ala Thr Cys Glu Asn
                740                 745                 750
Glu Glu Glu Met Asp Asn Leu Lys His Ser Arg Val Thr Val Ala Ile
            755                 760                 765
Pro Leu Lys Tyr Glu Val Lys Leu Thr Val His Gly Phe Val Asn Pro
        770                 775                 780
Thr Ser Phe Val Tyr Gly Ser Asn Asp Glu Asn Glu Pro Glu Thr Cys
785                 790                 795                 800
Met Val Glu Lys Met Asn Leu Thr Phe His Val Ile Asn Thr Gly Asn
                805                 810                 815
Ser Met Ala Pro Asn Val Ser Val Glu Ile Met Val Pro Asn Ser Phe
                820                 825                 830
Ser Pro Gln Thr Asp Lys Leu Phe Asn Ile Leu Asp Val Gln Thr Thr
            835                 840                 845
Thr Gly Glu Cys His Phe Glu Asn Tyr Gln Arg Val Cys Ala Leu Glu
        850                 855                 860
Gln Gln Lys Ser Ala Met Gln Thr Leu Lys Gly Ile Val Arg Phe Leu
865                 870                 875                 880
Ser Lys Thr Asp Lys Arg Leu Leu Tyr Cys Ile Lys Ala Asp Pro His
                885                 890                 895
Cys Leu Asn Phe Leu Cys Asn Phe Gly Lys Met Glu Ser Gly Lys Glu
                900                 905                 910
Ala Ser Val His Ile Gln Leu Glu Gly Arg Pro Ser Ile Leu Glu Met
            915                 920                 925
Asp Glu Thr Ser Ala Leu Lys Phe Glu Ile Arg Ala Thr Gly Phe Pro
        930                 935                 940
Glu Pro Asn Pro Arg Val Ile Glu Leu Asn Lys Asp Glu Asn Val Ala
945                 950                 955                 960
His Val Leu Leu Glu Gly Leu His His Gln Arg Pro Lys Arg Tyr Phe
                965                 970                 975
Thr Ile Val Ile Ile Ser Ser Leu Leu Gly Leu Ile Val Leu
                980                 985                 990
Leu Leu Ile Ser Tyr Val Met Trp Lys Ala Gly Phe Phe Lys Arg Gln
        995                 1000                1005
Tyr Lys Ser Ile Leu Gln Glu Glu Asn Arg Arg Asp Ser Trp Ser

Tyr Ile Asn Ser Lys Ser Asn Asp Asp
    1025                1030

<210> SEQ ID NO 73
<211> LENGTH: 1049
<212> TYPE: PRT
<213> ORGANISM: Homo sapiens

<400> SEQUENCE: 73

Met Gly Ser Arg Thr Pro Glu Ser Pro Leu His Ala Val Gln Leu Arg
1               5                   10                  15

Trp Gly Pro Arg Arg Pro Pro Leu Leu Pro Leu Leu Leu Leu Leu Leu
            20                  25                  30

Leu Pro Pro Pro Pro Arg Val Gly Gly Phe Asn Leu Asp Ala Glu Ala
        35                  40                  45

Pro Ala Val Leu Ser Gly Pro Pro Gly Ser Phe Phe Gly Phe Ser Val
    50                  55                  60

Glu Phe Tyr Arg Pro Gly Thr Asp Gly Val Ser Val Leu Val Gly Ala
65                  70                  75                  80

Pro Lys Ala Asn Thr Ser Gln Pro Gly Val Leu Gln Gly Gly Ala Val
                85                  90                  95

Tyr Leu Cys Pro Trp Gly Ala Ser Pro Thr Gln Cys Thr Pro Ile Glu
            100                 105                 110

Phe Asp Ser Lys Gly Ser Arg Leu Leu Glu Ser Ser Leu Ser Ser Ser
        115                 120                 125

Glu Gly Glu Glu Pro Val Glu Tyr Lys Ser Leu Gln Trp Phe Gly Ala
    130                 135                 140

Thr Val Arg Ala His Gly Ser Ser Ile Leu Ala Cys Ala Pro Leu Tyr
145                 150                 155                 160

Ser Trp Arg Thr Glu Lys Glu Pro Leu Ser Asp Pro Val Gly Thr Cys
                165                 170                 175

Tyr Leu Ser Thr Asp Asn Phe Thr Arg Ile Leu Glu Tyr Ala Pro Cys
            180                 185                 190

Arg Ser Asp Phe Ser Trp Ala Ala Gly Gln Gly Tyr Cys Gln Gly Gly
        195                 200                 205

Phe Ser Ala Glu Phe Thr Lys Thr Gly Arg Val Val Leu Gly Gly Pro
    210                 215                 220

Gly Ser Tyr Phe Trp Gln Gly Gln Ile Leu Ser Ala Thr Gln Glu Gln
225                 230                 235                 240

Ile Ala Glu Ser Tyr Tyr Pro Glu Tyr Leu Ile Asn Leu Val Gln Gly
                245                 250                 255

Gln Leu Gln Thr Arg Gln Ala Ser Ser Ile Tyr Asp Asp Ser Tyr Leu
            260                 265                 270

Gly Tyr Ser Val Ala Val Gly Glu Phe Ser Gly Asp Asp Thr Glu Asp
        275                 280                 285

Phe Val Ala Gly Val Pro Lys Gly Asn Leu Thr Tyr Gly Tyr Val Thr
    290                 295                 300

Ile Leu Asn Gly Ser Asp Ile Arg Ser Leu Tyr Asn Phe Ser Gly Glu
305                 310                 315                 320

Gln Met Ala Ser Tyr Phe Gly Tyr Ala Val Ala Ala Thr Asp Val Asn
                325                 330                 335

Gly Asp Gly Leu Asp Asp Leu Val Gly Ala Pro Leu Leu Met Asp
            340                 345                 350

```
Arg Thr Pro Asp Gly Arg Pro Gln Glu Val Gly Arg Val Tyr Val Tyr
            355                 360                 365

Leu Gln His Pro Ala Gly Ile Glu Pro Thr Pro Thr Leu Thr Leu Thr
        370                 375                 380

Gly His Asp Glu Phe Gly Arg Phe Gly Ser Ser Leu Thr Pro Leu Gly
385                 390                 395                 400

Asp Leu Asp Gln Asp Gly Tyr Asn Asp Val Ala Ile Gly Ala Pro Phe
                405                 410                 415

Gly Gly Glu Thr Gln Gln Gly Val Val Phe Val Phe Pro Gly Gly Pro
            420                 425                 430

Gly Gly Leu Gly Ser Lys Pro Ser Gln Val Leu Gln Pro Leu Trp Ala
            435                 440                 445

Ala Ser His Thr Pro Asp Phe Phe Gly Ser Ala Leu Arg Gly Gly Arg
        450                 455                 460

Asp Leu Asp Gly Asn Gly Tyr Pro Asp Leu Ile Val Gly Ser Phe Gly
465                 470                 475                 480

Val Asp Lys Ala Val Val Tyr Arg Gly Arg Pro Ile Val Ser Ala Ser
                485                 490                 495

Ala Ser Leu Thr Ile Phe Pro Ala Met Phe Asn Pro Glu Glu Arg Ser
            500                 505                 510

Cys Ser Leu Glu Gly Asn Pro Val Ala Cys Ile Asn Leu Ser Phe Cys
            515                 520                 525

Leu Asn Ala Ser Gly Lys His Val Ala Asp Ser Ile Gly Phe Thr Val
        530                 535                 540

Glu Leu Gln Leu Asp Trp Gln Lys Gln Lys Gly Gly Val Arg Arg Ala
545                 550                 555                 560

Leu Phe Leu Ala Ser Arg Gln Ala Thr Leu Thr Gln Thr Leu Leu Ile
                565                 570                 575

Gln Asn Gly Ala Arg Glu Asp Cys Arg Glu Met Lys Ile Tyr Leu Arg
            580                 585                 590

Asn Glu Ser Glu Phe Arg Asp Lys Leu Ser Pro Ile His Ile Ala Leu
        595                 600                 605

Asn Phe Ser Leu Asp Pro Gln Ala Pro Val Asp Ser His Gly Leu Arg
    610                 615                 620

Pro Ala Leu His Tyr Gln Ser Lys Ser Arg Ile Glu Asp Lys Ala Gln
625                 630                 635                 640

Ile Leu Leu Asp Cys Gly Glu Asp Asn Ile Cys Val Pro Asp Leu Gln
                645                 650                 655

Leu Glu Val Phe Gly Glu Gln Asn His Val Tyr Leu Gly Asp Lys Asn
            660                 665                 670

Ala Leu Asn Leu Thr Phe His Ala Gln Asn Val Gly Glu Gly Gly Ala
        675                 680                 685

Tyr Glu Ala Glu Leu Arg Val Thr Ala Pro Pro Glu Ala Glu Tyr Ser
    690                 695                 700

Gly Leu Val Arg His Pro Gly Asn Phe Ser Ser Leu Ser Cys Asp Tyr
705                 710                 715                 720

Phe Ala Val Asn Gln Ser Arg Leu Leu Val Cys Asp Leu Gly Asn Pro
                725                 730                 735

Met Lys Ala Gly Ala Ser Leu Trp Gly Gly Leu Arg Phe Thr Val Pro
            740                 745                 750

His Leu Arg Asp Thr Lys Lys Thr Ile Gln Phe Asp Phe Gln Ile Leu
        755                 760                 765

Ser Lys Asn Leu Asn Asn Ser Gln Ser Asp Val Val Ser Phe Arg Leu
```

```
                770               775               780
Ser Val Glu Ala Gln Ala Gln Val Thr Leu Asn Gly Val Ser Lys Pro
785               790               795               800

Glu Ala Val Leu Phe Pro Val Ser Asp Trp His Pro Arg Asp Gln Pro
                805               810               815

Gln Lys Glu Glu Asp Leu Gly Pro Ala Val His Val Tyr Glu Leu
            820               825               830

Ile Asn Gln Gly Pro Ser Ser Ile Ser Gln Gly Val Leu Glu Leu Ser
            835               840               845

Cys Pro Gln Ala Leu Glu Gly Gln Gln Leu Leu Tyr Val Thr Arg Val
850               855               860

Thr Gly Leu Asn Cys Thr Thr Asn His Pro Ile Asn Pro Lys Gly Leu
865               870               875               880

Glu Leu Asp Pro Glu Gly Ser Leu His His Gln Lys Arg Glu Ala
                885               890               895

Pro Ser Arg Ser Ser Ala Ser Ser Gly Pro Gln Ile Leu Lys Cys Pro
            900               905               910

Glu Ala Glu Cys Phe Arg Leu Arg Cys Glu Leu Gly Pro Leu His Gln
            915               920               925

Gln Glu Ser Gln Ser Leu Gln Leu His Phe Arg Val Trp Ala Lys Thr
            930               935               940

Phe Leu Gln Arg Glu His Gln Pro Phe Ser Leu Gln Cys Glu Ala Val
945               950               955               960

Tyr Lys Ala Leu Lys Met Pro Tyr Arg Ile Leu Pro Arg Gln Leu Pro
                965               970               975

Gln Lys Glu Arg Gln Val Ala Thr Ala Val Gln Trp Thr Lys Ala Glu
            980               985               990

Gly Ser Tyr Gly Val Pro Leu Trp Ile Ile Ile Leu Ala Ile Leu Phe
            995              1000              1005

Gly Leu Leu Leu Leu Gly Leu Leu Ile Tyr Ile Leu Tyr Lys Leu
           1010              1015              1020

Gly Phe Phe Lys Arg Ser Leu Pro Tyr Gly Thr Ala Met Glu Lys
           1025              1030              1035

Ala Gln Leu Lys Pro Pro Ala Thr Ser Asp Ala
           1040              1045

<210> SEQ ID NO 74
<211> LENGTH: 1130
<212> TYPE: PRT
<213> ORGANISM: Homo sapiens

<400> SEQUENCE: 74

Met Ala Ala Ala Gly Gln Leu Cys Leu Leu Tyr Leu Ser Ala Gly Leu
1               5                  10                  15

Leu Ser Arg Leu Gly Ala Ala Phe Asn Leu Asp Thr Arg Glu Asp Asn
                20                  25                  30

Val Ile Arg Lys Tyr Gly Asp Pro Gly Ser Leu Phe Gly Phe Ser Leu
            35                  40                  45

Ala Met His Trp Gln Leu Gln Pro Glu Asp Lys Arg Leu Leu Leu Val
        50                  55                  60

Gly Ala Pro Arg Ala Glu Ala Leu Pro Leu Gln Arg Ala Asn Arg Thr
65                  70                  75                  80

Gly Gly Leu Tyr Ser Cys Asp Ile Thr Ala Arg Gly Pro Cys Thr Arg
                85                  90                  95
```

-continued

```
Ile Glu Phe Asp Asn Asp Ala Asp Pro Thr Ser Glu Ser Lys Glu Asp
                100                 105                 110

Gln Trp Met Gly Val Thr Val Gln Ser Gln Gly Pro Gly Gly Lys Val
            115                 120                 125

Val Thr Cys Ala His Arg Tyr Glu Lys Arg Gln His Val Asn Thr Lys
        130                 135                 140

Gln Glu Ser Arg Asp Ile Phe Gly Arg Cys Tyr Val Leu Ser Gln Asn
145                 150                 155                 160

Leu Arg Ile Glu Asp Met Asp Gly Asp Trp Ser Phe Cys Asp
                165                 170                 175

Gly Arg Leu Arg Gly His Glu Lys Phe Gly Ser Cys Gln Gln Gly Val
            180                 185                 190

Ala Ala Thr Phe Thr Lys Asp Phe His Tyr Ile Val Phe Gly Ala Pro
        195                 200                 205

Gly Thr Tyr Asn Trp Lys Gly Ile Val Arg Val Glu Gln Lys Asn Asn
        210                 215                 220

Thr Phe Phe Asp Met Asn Ile Phe Glu Asp Gly Pro Tyr Glu Val Gly
225                 230                 235                 240

Gly Glu Thr Glu His Asp Glu Ser Leu Val Pro Val Pro Ala Asn Ser
                245                 250                 255

Tyr Leu Gly Leu Leu Phe Leu Thr Ser Val Ser Tyr Thr Asp Pro Asp
            260                 265                 270

Gln Phe Val Tyr Lys Thr Arg Pro Arg Glu Gln Pro Asp Thr Phe
        275                 280                 285

Pro Asp Val Met Met Asn Ser Tyr Leu Gly Phe Ser Leu Asp Ser Gly
        290                 295                 300

Lys Gly Ile Val Ser Lys Asp Glu Ile Thr Phe Val Ser Gly Ala Pro
305                 310                 315                 320

Arg Ala Asn His Ser Gly Ala Val Val Leu Leu Lys Arg Asp Met Lys
                325                 330                 335

Ser Ala His Leu Leu Pro Glu His Ile Phe Asp Gly Glu Gly Leu Ala
            340                 345                 350

Ser Ser Phe Gly Tyr Asp Val Ala Val Val Asp Leu Asn Lys Asp Gly
        355                 360                 365

Trp Gln Asp Ile Val Ile Gly Ala Pro Gln Tyr Phe Asp Arg Asp Gly
        370                 375                 380

Glu Val Gly Gly Ala Val Tyr Val Tyr Met Asn Gln Gln Gly Arg Trp
385                 390                 395                 400

Asn Asn Val Lys Pro Ile Arg Leu Asn Gly Thr Lys Asp Ser Met Phe
                405                 410                 415

Gly Ile Ala Val Lys Asn Ile Gly Asp Ile Asn Gln Asp Gly Tyr Pro
            420                 425                 430

Asp Ile Ala Val Gly Ala Pro Tyr Asp Asp Leu Gly Lys Val Phe Ile
        435                 440                 445

Tyr His Gly Ser Ala Asn Gly Ile Asn Thr Lys Pro Thr Gln Val Leu
        450                 455                 460

Lys Gly Ile Ser Pro Tyr Phe Gly Tyr Ser Ile Ala Gly Asn Met Asp
465                 470                 475                 480

Leu Asp Arg Asn Ser Tyr Pro Asp Val Ala Val Gly Ser Leu Ser Asp
                485                 490                 495

Ser Val Thr Ile Phe Arg Ser Arg Pro Val Ile Asn Ile Gln Lys Thr
            500                 505                 510

Ile Thr Val Thr Pro Asn Arg Ile Asp Leu Arg Gln Lys Thr Ala Cys
```

-continued

```
                515                 520                 525
Gly Ala Pro Ser Gly Ile Cys Leu Gln Val Lys Ser Cys Phe Glu Tyr
530                 535                 540

Thr Ala Asn Pro Ala Gly Tyr Asn Pro Ser Ile Ser Ile Val Gly Thr
545                 550                 555                 560

Leu Glu Ala Glu Lys Glu Arg Arg Lys Ser Gly Leu Ser Ser Arg Val
                565                 570                 575

Gln Phe Arg Asn Gln Gly Ser Glu Pro Lys Tyr Thr Gln Glu Leu Thr
                580                 585                 590

Leu Lys Arg Gln Lys Gln Lys Val Cys Met Glu Glu Thr Leu Trp Leu
                595                 600                 605

Gln Asp Asn Ile Arg Asp Lys Leu Arg Pro Ile Pro Ile Thr Ala Ser
            610                 615                 620

Val Glu Ile Gln Glu Pro Ser Ser Arg Arg Val Asn Ser Leu Pro
625                 630                 635                 640

Glu Val Leu Pro Ile Leu Asn Ser Asp Glu Pro Lys Thr Ala His Ile
                645                 650                 655

Asp Val His Phe Leu Lys Glu Gly Cys Gly Asp Asp Asn Val Cys Asn
                660                 665                 670

Ser Asn Leu Lys Leu Glu Tyr Lys Phe Cys Thr Arg Glu Gly Asn Gln
            675                 680                 685

Asp Lys Phe Ser Tyr Leu Pro Ile Gln Lys Gly Val Pro Glu Leu Val
            690                 695                 700

Leu Lys Asp Gln Lys Asp Ile Ala Leu Glu Ile Thr Val Thr Asn Ser
705                 710                 715                 720

Pro Ser Asn Pro Arg Asn Pro Thr Lys Asp Gly Asp Ala His Glu
                725                 730                 735

Ala Lys Leu Ile Ala Thr Phe Pro Asp Thr Leu Thr Tyr Ser Ala Tyr
                740                 745                 750

Arg Glu Leu Arg Ala Phe Pro Glu Lys Gln Leu Ser Cys Val Ala Asn
                755                 760                 765

Gln Asn Gly Ser Gln Ala Asp Cys Glu Leu Gly Asn Pro Phe Lys Arg
            770                 775                 780

Asn Ser Asn Val Thr Phe Tyr Leu Val Leu Ser Thr Thr Glu Val Thr
785                 790                 795                 800

Phe Asp Thr Pro Asp Leu Asp Ile Asn Leu Lys Leu Glu Thr Thr Ser
                805                 810                 815

Asn Gln Asp Asn Leu Ala Pro Ile Thr Ala Lys Ala Lys Val Val Ile
                820                 825                 830

Glu Leu Leu Leu Ser Val Ser Gly Val Ala Lys Pro Ser Gln Val Tyr
            835                 840                 845

Phe Gly Gly Thr Val Val Gly Glu Gln Ala Met Lys Ser Glu Asp Glu
            850                 855                 860

Val Gly Ser Leu Ile Glu Tyr Glu Phe Arg Val Ile Asn Leu Gly Lys
865                 870                 875                 880

Pro Leu Thr Asn Leu Gly Thr Ala Thr Leu Asn Ile Gln Trp Pro Lys
                885                 890                 895

Glu Ile Ser Asn Gly Lys Trp Leu Leu Tyr Leu Val Lys Val Glu Ser
                900                 905                 910

Lys Gly Leu Glu Lys Val Thr Cys Glu Pro Gln Lys Glu Ile Asn Ser
            915                 920                 925

Leu Asn Leu Thr Glu Ser His Asn Ser Arg Lys Lys Arg Glu Ile Thr
            930                 935                 940
```

Glu Lys Gln Ile Asp Asp Asn Arg Lys Phe Ser Leu Phe Ala Glu Arg
945                 950                 955                 960

Lys Tyr Gln Thr Leu Asn Cys Ser Val Asn Val Cys Val Asn Ile
            965                 970                 975

Arg Cys Pro Leu Arg Gly Leu Asp Ser Lys Ala Ser Leu Ile Leu Arg
            980                 985                 990

Ser Arg Leu Trp Asn Ser Thr Phe Leu Glu Glu Tyr Ser Lys Leu Asn
            995                 1000                1005

Tyr Leu Asp Ile Leu Met Arg Ala Phe Ile Asp Val Thr Ala Ala
    1010                1015                1020

Ala Glu Asn Ile Arg Leu Pro Asn Ala Gly Thr Gln Val Arg Val
    1025                1030                1035

Thr Val Phe Pro Ser Lys Thr Val Ala Gln Tyr Ser Gly Val Pro
    1040                1045                1050

Trp Trp Ile Ile Leu Val Ala Ile Leu Ala Gly Ile Leu Met Leu
    1055                1060                1065

Ala Leu Leu Val Phe Ile Leu Trp Lys Cys Gly Phe Phe Lys Arg
    1070                1075                1080

Ser Arg Tyr Asp Asp Ser Val Pro Arg Tyr His Ala Val Arg Ile
    1085                1090                1095

Arg Lys Glu Glu Arg Glu Ile Lys Asp Glu Lys Tyr Ile Asp Asn
    1100                1105                1110

Leu Glu Lys Lys Gln Trp Ile Thr Lys Trp Asn Glu Asn Glu Ser
    1115                1120                1125

Tyr Ser
    1130

<210> SEQ ID NO 75
<211> LENGTH: 1181
<212> TYPE: PRT
<213> ORGANISM: Homo sapiens

<400> SEQUENCE: 75

Met Ala Gly Ala Arg Ser Arg Asp Pro Trp Gly Ala Ser Gly Ile Cys
1               5                   10                  15

Tyr Leu Phe Gly Ser Leu Leu Val Glu Leu Leu Phe Ser Arg Ala Val
                20                  25                  30

Ala Phe Asn Leu Asp Val Met Gly Ala Leu Arg Lys Glu Gly Glu Pro
            35                  40                  45

Gly Ser Leu Phe Gly Phe Ser Val Ala Leu His Arg Gln Leu Gln Pro
        50                  55                  60

Arg Pro Gln Ser Trp Leu Leu Val Gly Ala Pro Gln Ala Leu Ala Leu
65                  70                  75                  80

Pro Gly Gln Gln Ala Asn Arg Thr Gly Gly Leu Phe Ala Cys Pro Leu
                85                  90                  95

Ser Leu Glu Gln Thr Asp Cys Tyr Arg Val Asp Ile Asp Gln Gly Ala
            100                 105                 110

Asp Met Gln Lys Glu Ser Lys Glu Asn Gln Trp Leu Gly Val Ser Val
            115                 120                 125

Arg Ser Gln Gly Pro Gly Gly Lys Ile Val Thr Cys Ala His Arg Tyr
        130                 135                 140

Glu Ala Arg Gln Arg Val Asp Gln Ile Leu Glu Thr Arg Asp Met Ile
145                 150                 155                 160

Gly Arg Cys Phe Val Leu Ser Gln Asp Leu Ala Ile Arg Asp Glu Leu

```
                165                 170                 175
Asp Gly Gly Glu Trp Lys Phe Cys Glu Gly Arg Pro Gln Gly His Glu
                180                 185                 190

Gln Phe Gly Phe Cys Gln Gln Gly Thr Ala Ala Phe Ser Pro Asp
            195                 200                 205

Ser His Tyr Leu Leu Phe Gly Ala Pro Gly Thr Tyr Asn Trp Lys Gly
        210                 215                 220

Thr Ala Arg Val Glu Leu Cys Ala Gln Gly Ser Ala Asp Leu Ala His
225                 230                 235                 240

Leu Asp Asp Gly Pro Tyr Glu Ala Gly Gly Glu Lys Glu Gln Asp Pro
                245                 250                 255

Arg Leu Ile Pro Val Pro Ala Asn Ser Tyr Phe Gly Leu Leu Phe Val
            260                 265                 270

Thr Asn Ile Asp Ser Ser Asp Pro Asp Gln Leu Val Tyr Lys Thr Leu
                275                 280                 285

Asp Pro Ala Asp Arg Leu Pro Gly Pro Ala Gly Asp Leu Ala Leu Asn
        290                 295                 300

Ser Tyr Leu Gly Phe Ser Ile Asp Ser Gly Lys Gly Leu Val Arg Ala
305                 310                 315                 320

Glu Glu Leu Ser Phe Val Ala Gly Ala Pro Arg Ala Asn His Lys Gly
                325                 330                 335

Ala Val Val Ile Leu Arg Lys Asp Ser Ala Ser Arg Leu Val Pro Glu
            340                 345                 350

Val Met Leu Ser Gly Glu Arg Leu Thr Ser Gly Phe Gly Tyr Ser Leu
                355                 360                 365

Ala Val Ala Asp Leu Asn Ser Asp Gly Trp Pro Asp Leu Ile Val Gly
        370                 375                 380

Ala Pro Tyr Phe Phe Glu Arg Gln Glu Glu Leu Gly Gly Ala Val Tyr
385                 390                 395                 400

Val Tyr Leu Asn Gln Gly Gly His Trp Ala Gly Ile Ser Pro Leu Arg
                405                 410                 415

Leu Cys Gly Ser Pro Asp Ser Met Phe Gly Ile Ser Leu Ala Val Leu
            420                 425                 430

Gly Asp Leu Asn Gln Asp Gly Phe Pro Asp Ile Ala Val Gly Ala Pro
                435                 440                 445

Phe Asp Gly Asp Gly Lys Val Phe Ile Tyr His Gly Ser Ser Leu Gly
        450                 455                 460

Val Val Ala Lys Pro Ser Gln Val Leu Glu Gly Glu Ala Val Gly Ile
465                 470                 475                 480

Lys Ser Phe Gly Tyr Ser Leu Ser Gly Ser Leu Asp Met Asp Gly Asn
                485                 490                 495

Gln Tyr Pro Asp Leu Leu Val Gly Ser Leu Ala Asp Thr Ala Val Leu
            500                 505                 510

Phe Arg Ala Arg Pro Ile Leu His Val Ser His Glu Val Ser Ile Ala
        515                 520                 525

Pro Arg Ser Ile Asp Leu Glu Gln Pro Asn Cys Ala Gly Gly His Ser
        530                 535                 540

Val Cys Val Asp Leu Arg Val Cys Phe Ser Tyr Ile Ala Val Pro Ser
545                 550                 555                 560

Ser Tyr Ser Pro Thr Val Ala Leu Asp Tyr Val Leu Asp Ala Asp Thr
                565                 570                 575

Asp Arg Arg Leu Arg Gly Gln Val Pro Arg Val Thr Phe Leu Ser Arg
            580                 585                 590
```

```
Asn Leu Glu Glu Pro Lys His Gln Ala Ser Gly Thr Val Trp Leu Lys
            595                 600                 605

His Gln His Asp Arg Val Cys Gly Asp Ala Met Phe Gln Leu Gln Glu
    610                 615                 620

Asn Val Lys Asp Lys Leu Arg Ala Ile Val Thr Leu Ser Tyr Ser
625                 630                 635                 640

Leu Gln Thr Pro Arg Leu Arg Arg Gln Ala Pro Gly Gln Gly Leu Pro
                645                 650                 655

Pro Val Ala Pro Ile Leu Asn Ala His Gln Pro Ser Thr Gln Arg Ala
            660                 665                 670

Glu Ile His Phe Leu Lys Gln Gly Cys Gly Asp Lys Ile Cys Gln
    675                 680                 685

Ser Asn Leu Gln Leu Val Arg Ala Arg Phe Cys Thr Arg Val Ser Asp
    690                 695                 700

Thr Glu Phe Gln Pro Leu Pro Met Asp Val Asp Gly Thr Thr Ala Leu
705                 710                 715                 720

Phe Ala Leu Ser Gly Gln Pro Val Ile Gly Leu Glu Leu Met Val Thr
                725                 730                 735

Asn Leu Pro Ser Asp Pro Ala Gln Pro Gln Ala Asp Gly Asp Asp Ala
            740                 745                 750

His Glu Ala Gln Leu Leu Val Met Leu Pro Asp Ser Leu His Tyr Ser
    755                 760                 765

Gly Val Arg Ala Leu Asp Pro Ala Glu Lys Pro Leu Cys Leu Ser Asn
    770                 775                 780

Glu Asn Ala Ser His Val Glu Cys Glu Leu Gly Asn Pro Met Lys Arg
785                 790                 795                 800

Gly Ala Gln Val Thr Phe Tyr Leu Ile Leu Ser Thr Ser Gly Ile Ser
                805                 810                 815

Ile Glu Thr Thr Glu Leu Glu Val Glu Leu Leu Leu Ala Thr Ile Ser
                820                 825                 830

Glu Gln Glu Leu His Pro Val Ser Ala Arg Ala Arg Val Phe Ile Glu
    835                 840                 845

Leu Pro Leu Ser Ile Ala Gly Met Ala Ile Pro Gln Gln Leu Phe Phe
    850                 855                 860

Ser Gly Val Val Arg Gly Glu Arg Ala Met Gln Ser Glu Arg Asp Val
865                 870                 875                 880

Gly Ser Lys Val Lys Tyr Glu Val Thr Val Ser Asn Gln Gly Gln Ser
                885                 890                 895

Leu Arg Thr Leu Gly Ser Ala Phe Leu Asn Ile Met Trp Pro His Glu
                900                 905                 910

Ile Ala Asn Gly Lys Trp Leu Leu Tyr Pro Met Gln Val Glu Leu Glu
            915                 920                 925

Gly Gly Gln Gly Pro Gly Gln Lys Gly Leu Cys Ser Pro Arg Pro Asn
930                 935                 940

Ile Leu His Leu Asp Val Asp Ser Arg Asp Arg Arg Arg Glu Leu
945                 950                 955                 960

Glu Pro Pro Glu Gln Gln Glu Pro Gly Glu Arg Gln Glu Pro Ser Met
                965                 970                 975

Ser Trp Trp Pro Val Ser Ser Ala Glu Lys Lys Lys Asn Ile Thr Leu
            980                 985                 990

Asp Cys Ala Arg Gly Thr Ala Asn Cys Val Val Phe Ser Cys Pro Leu
            995                 1000                1005
```

```
Tyr Ser Phe Asp Arg Ala Ala Val Leu His Val Trp Gly Arg Leu
    1010                1015                1020

Trp Asn Ser Thr Phe Leu Glu Glu Tyr Ser Ala Val Lys Ser Leu
    1025                1030                1035

Glu Val Ile Val Arg Ala Asn Ile Thr Val Lys Ser Ser Ile Lys
    1040                1045                1050

Asn Leu Met Leu Arg Asp Ala Ser Thr Val Ile Pro Val Met Val
    1055                1060                1065

Tyr Leu Asp Pro Met Ala Val Val Ala Glu Gly Val Pro Trp Trp
    1070                1075                1080

Val Ile Leu Leu Ala Val Leu Ala Gly Leu Leu Val Leu Ala Leu
    1085                1090                1095

Leu Val Leu Leu Leu Trp Lys Met Gly Phe Phe Lys Arg Ala Lys
    1100                1105                1110

His Pro Glu Ala Thr Val Pro Gln Tyr His Ala Val Lys Ile Pro
    1115                1120                1125

Arg Glu Asp Arg Gln Gln Phe Lys Glu Glu Lys Thr Gly Thr Ile
    1130                1135                1140

Leu Arg Asn Asn Trp Gly Ser Pro Arg Arg Glu Gly Pro Asp Ala
    1145                1150                1155

His Pro Ile Leu Ala Ala Asp Gly His Pro Glu Leu Gly Pro Asp
    1160                1165                1170

Gly His Pro Gly Pro Gly Thr Ala
    1175                1180

<210> SEQ ID NO 76
<211> LENGTH: 1063
<212> TYPE: PRT
<213> ORGANISM: Homo sapiens

<400> SEQUENCE: 76

Met Ser Pro Gly Ala Ser Arg Gly Pro Arg Gly Ser Gln Ala Pro Leu
1               5                   10                  15

Ile Ala Pro Leu Cys Cys Ala Ala Ala Leu Gly Met Leu Leu Trp
                20                  25                  30

Ser Pro Ala Cys Gln Ala Phe Asn Leu Asp Val Glu Lys Leu Thr Val
                35                  40                  45

Tyr Ser Gly Pro Lys Gly Ser Tyr Phe Gly Tyr Ala Val Asp Phe His
    50                  55                  60

Ile Pro Asp Ala Arg Thr Ala Ser Val Leu Val Gly Ala Pro Lys Ala
65                  70                  75                  80

Asn Thr Ser Gln Pro Asp Ile Val Glu Gly Gly Ala Val Tyr Tyr Cys
                85                  90                  95

Pro Trp Pro Ala Glu Gly Ser Ala Gln Cys Arg Gln Ile Pro Phe Asp
                100                 105                 110

Thr Thr Asn Asn Arg Lys Ile Arg Val Asn Gly Thr Lys Glu Pro Ile
            115                 120                 125

Glu Phe Lys Ser Asn Gln Trp Phe Gly Ala Thr Val Lys Ala His Lys
    130                 135                 140

Gly Lys Val Val Ala Cys Ala Pro Leu Tyr His Trp Arg Thr Leu Lys
145                 150                 155                 160

Pro Thr Pro Glu Lys Asp Pro Val Gly Thr Cys Tyr Val Ala Ile Gln
                165                 170                 175

Asn Phe Ser Ala Tyr Ala Glu Phe Ser Pro Cys Arg Asn Ser Asn Ala
                180                 185                 190
```

```
Asp Pro Glu Gly Gln Gly Tyr Cys Gln Ala Gly Phe Ser Leu Asp Phe
        195                 200                 205

Tyr Lys Asn Gly Asp Leu Ile Val Gly Gly Pro Gly Ser Phe Tyr Trp
        210                 215                 220

Gln Gly Gln Val Ile Thr Ala Ser Val Ala Asp Ile Ile Ala Asn Tyr
225                 230                 235                 240

Ser Phe Lys Asp Ile Leu Arg Lys Leu Ala Gly Glu Lys Gln Thr Glu
            245                 250                 255

Val Ala Pro Ala Ser Tyr Asp Ser Tyr Leu Gly Tyr Ser Val Ala
                260                 265                 270

Ala Gly Glu Phe Thr Gly Asp Ser Gln Gln Glu Leu Val Ala Gly Ile
            275                 280                 285

Pro Arg Gly Ala Gln Asn Phe Gly Tyr Val Ser Ile Ile Asn Ser Thr
        290                 295                 300

Asp Met Thr Phe Ile Gln Asn Phe Thr Gly Glu Gln Met Ala Ser Tyr
305                 310                 315                 320

Phe Gly Tyr Thr Val Val Ser Asp Val Asn Ser Asp Gly Leu Asp
                325                 330                 335

Asp Val Leu Val Gly Ala Pro Leu Phe Met Glu Arg Glu Phe Glu Ser
            340                 345                 350

Asn Pro Arg Glu Val Gly Gln Ile Tyr Leu Tyr Leu Gln Val Ser Ser
        355                 360                 365

Leu Leu Phe Arg Asp Pro Gln Ile Leu Thr Gly Thr Glu Thr Phe Gly
370                 375                 380

Arg Phe Gly Ser Ala Met Ala His Leu Gly Asp Leu Asn Gln Asp Gly
385                 390                 395                 400

Tyr Asn Asp Ile Ala Ile Gly Val Pro Phe Ala Gly Lys Asp Gln Arg
                405                 410                 415

Gly Lys Val Leu Ile Tyr Asn Gly Asn Lys Asp Gly Leu Asn Thr Lys
            420                 425                 430

Pro Ser Gln Val Leu Gln Gly Val Trp Ala Ser His Ala Val Pro Ser
        435                 440                 445

Gly Phe Gly Phe Thr Leu Arg Gly Asp Ser Asp Ile Asp Lys Asn Asp
        450                 455                 460

Tyr Pro Asp Leu Ile Val Gly Ala Phe Gly Thr Gly Lys Val Ala Val
465                 470                 475                 480

Tyr Arg Ala Arg Pro Val Val Thr Val Asp Ala Gln Leu Leu Leu His
                485                 490                 495

Pro Met Ile Ile Asn Leu Glu Asn Lys Thr Cys Gln Val Pro Asp Ser
            500                 505                 510

Met Thr Ser Ala Ala Cys Phe Ser Leu Arg Val Cys Ala Ser Val Thr
        515                 520                 525

Gly Gln Ser Ile Ala Asn Thr Ile Val Leu Met Ala Glu Val Gln Leu
        530                 535                 540

Asp Ser Leu Lys Gln Lys Gly Ala Ile Lys Arg Thr Leu Phe Leu Asp
545                 550                 555                 560

Asn His Gln Ala His Arg Val Phe Pro Leu Val Ile Lys Arg Gln Lys
                565                 570                 575

Ser His Gln Cys Gln Asp Phe Ile Val Tyr Leu Arg Asp Glu Thr Glu
            580                 585                 590

Phe Arg Asp Lys Leu Ser Pro Ile Asn Ile Ser Leu Asn Tyr Ser Leu
        595                 600                 605
```

```
Asp Glu Ser Thr Phe Lys Glu Gly Leu Glu Val Lys Pro Ile Leu Asn
    610                 615                 620

Tyr Tyr Arg Glu Asn Ile Val Ser Glu Gln Ala His Ile Leu Val Asp
625                 630                 635                 640

Cys Gly Glu Asp Asn Leu Cys Val Pro Asp Leu Lys Leu Ser Ala Arg
                645                 650                 655

Pro Asp Lys His Gln Val Ile Ile Gly Asp Glu Asn His Leu Met Leu
            660                 665                 670

Ile Ile Asn Ala Arg Asn Glu Gly Glu Ala Tyr Glu Ala Glu Leu
        675                 680                 685

Phe Val Met Ile Pro Glu Glu Ala Asp Tyr Val Gly Ile Glu Arg Asn
690                 695                 700

Asn Lys Gly Phe Arg Pro Leu Ser Cys Glu Tyr Lys Met Glu Asn Val
705                 710                 715                 720

Thr Arg Met Val Val Cys Asp Leu Gly Asn Pro Met Val Ser Gly Thr
                725                 730                 735

Asn Tyr Ser Leu Gly Leu Arg Phe Ala Val Pro Arg Leu Glu Lys Thr
            740                 745                 750

Asn Met Ser Ile Asn Phe Asp Leu Gln Ile Arg Ser Ser Asn Lys Asp
        755                 760                 765

Asn Pro Asp Ser Asn Phe Val Ser Leu Gln Ile Asn Ile Thr Ala Val
770                 775                 780

Ala Gln Val Glu Ile Arg Gly Val Ser His Pro Gln Ile Val Leu
785                 790                 795                 800

Pro Ile His Asn Trp Glu Pro Glu Glu Pro His Lys Glu Glu
                805                 810                 815

Val Gly Pro Leu Val Glu His Ile Tyr Glu Leu His Asn Ile Gly Pro
            820                 825                 830

Ser Thr Ile Ser Asp Thr Ile Leu Glu Val Gly Trp Pro Phe Ser Ala
        835                 840                 845

Arg Asp Glu Phe Leu Leu Tyr Ile Phe His Ile Gln Thr Leu Gly Pro
    850                 855                 860

Leu Gln Cys Gln Pro Asn Pro Asn Ile Asn Pro Gln Asp Ile Lys Pro
865                 870                 875                 880

Ala Ala Ser Pro Glu Asp Thr Pro Glu Leu Ser Ala Phe Leu Arg Asn
                885                 890                 895

Ser Thr Ile Pro His Leu Val Arg Lys Arg Asp Val His Val Val Glu
            900                 905                 910

Phe His Arg Gln Ser Pro Ala Lys Ile Leu Asn Cys Thr Asn Ile Glu
        915                 920                 925

Cys Leu Gln Ile Ser Cys Ala Val Gly Arg Leu Glu Gly Gly Glu Ser
930                 935                 940

Ala Val Leu Lys Val Arg Ser Arg Leu Trp Ala His Thr Phe Leu Gln
945                 950                 955                 960

Arg Lys Asn Asp Pro Tyr Ala Leu Ala Ser Leu Val Ser Phe Glu Val
                965                 970                 975

Lys Lys Met Pro Tyr Thr Asp Gln Pro Ala Lys Leu Pro Glu Gly Ser
            980                 985                 990

Ile Val Ile Lys Thr Ser Val Ile  Trp Ala Thr Pro Asn  Val Ser Phe
        995                 1000                1005

Ser Ile  Pro Leu Trp Val Ile  Ile Leu Ala Ile Leu  Leu Gly Leu
    1010                1015                1020

Leu Val  Leu Ala Ile Leu Thr  Leu Ala Leu Trp Lys  Cys Gly Phe
```

```
                1025                1030                1035

Phe Asp Arg Ala Arg Pro Pro Gln Glu Asp Met Thr Asp Arg Glu
    1040                1045                1050

Gln Leu Thr Asn Asp Lys Thr Pro Glu Ala
    1055                1060

<210> SEQ ID NO 77
<211> LENGTH: 1035
<212> TYPE: PRT
<213> ORGANISM: Homo sapiens

<400> SEQUENCE: 77

Met Gly Gly Pro Ala Ala Pro Arg Gly Ala Gly Arg Leu Arg Ala Leu
1               5                   10                  15

Leu Leu Ala Leu Val Val Ala Gly Ile Pro Ala Gly Ala Tyr Asn Leu
            20                  25                  30

Asp Pro Gln Arg Pro Val His Phe Gln Gly Pro Ala Asp Ser Phe Phe
        35                  40                  45

Gly Tyr Ala Val Leu Glu His Phe His Asp Asn Thr Arg Trp Val Leu
    50                  55                  60

Val Gly Ala Pro Lys Ala Asp Ser Lys Tyr Ser Pro Ser Val Lys Ser
65                  70                  75                  80

Pro Gly Ala Val Phe Lys Cys Arg Val His Thr Asn Pro Asp Arg Arg
                85                  90                  95

Cys Thr Glu Leu Asp Met Ala Arg Gly Lys Asn Arg Gly Thr Ser Cys
            100                 105                 110

Gly Lys Thr Cys Arg Glu Asp Arg Asp Asp Glu Trp Met Gly Val Ser
        115                 120                 125

Leu Ala Arg Gln Pro Lys Ala Asp Gly Arg Val Leu Ala Cys Ala His
    130                 135                 140

Arg Trp Lys Asn Ile Tyr Tyr Glu Ala Asp His Ile Leu Pro His Gly
145                 150                 155                 160

Phe Cys Tyr Ile Ile Pro Ser Asn Leu Gln Ala Lys Gly Arg Thr Leu
                165                 170                 175

Ile Pro Cys Tyr Glu Glu Tyr Lys Lys Lys Tyr Gly Glu Glu His Gly
            180                 185                 190

Ser Cys Gln Ala Gly Ile Ala Gly Phe Phe Thr Glu Glu Leu Val Val
        195                 200                 205

Met Gly Ala Pro Gly Ser Phe Tyr Trp Ala Gly Thr Ile Lys Val Leu
    210                 215                 220

Asn Leu Thr Asp Asn Thr Tyr Leu Lys Leu Asn Asp Glu Val Ile Met
225                 230                 235                 240

Asn Arg Arg Tyr Thr Tyr Leu Gly Tyr Ala Val Thr Ala Gly His Phe
                245                 250                 255

Ser His Pro Ser Thr Ile Asp Val Val Gly Gly Ala Pro Gln Asp Lys
            260                 265                 270

Gly Ile Gly Lys Val Tyr Ile Phe Arg Ala Asp Arg Arg Ser Gly Thr
        275                 280                 285

Leu Ile Lys Ile Phe Gln Ala Ser Gly Lys Lys Met Gly Ser Tyr Phe
    290                 295                 300

Gly Ser Ser Leu Cys Ala Val Asp Leu Asn Gly Asp Gly Leu Ser Asp
305                 310                 315                 320

Leu Leu Val Gly Ala Pro Met Phe Ser Glu Ile Arg Asp Glu Gly Gln
                325                 330                 335
```

Val Thr Val Tyr Ile Asn Arg Gly Asn Gly Ala Leu Glu Glu Gln Leu
            340                 345                 350

Ala Leu Thr Gly Asp Gly Ala Tyr Asn Ala His Phe Gly Glu Ser Ile
            355                 360                 365

Ala Ser Leu Asp Asp Leu Asp Asn Asp Gly Phe Pro Asp Val Ala Ile
            370                 375                 380

Gly Ala Pro Lys Glu Asp Asp Phe Ala Gly Ala Val Tyr Ile Tyr His
385                 390                 395                 400

Gly Asp Ala Gly Gly Ile Val Pro Gln Tyr Ser Met Lys Leu Ser Gly
                405                 410                 415

Gln Lys Ile Asn Pro Val Leu Arg Met Phe Gly Gln Ser Ile Ser Gly
            420                 425                 430

Gly Ile Asp Met Asp Gly Asn Gly Tyr Pro Asp Val Thr Val Gly Ala
            435                 440                 445

Phe Met Ser Asp Ser Val Val Leu Leu Arg Ala Arg Pro Val Ile Thr
            450                 455                 460

Val Asp Val Ser Ile Phe Leu Pro Gly Ser Ile Asn Ile Thr Ala Pro
465                 470                 475                 480

Gln Cys His Asp Gly Gln Gln Pro Val Asn Cys Leu Asn Val Thr Thr
                485                 490                 495

Cys Phe Ser Phe His Gly Lys His Val Pro Gly Glu Ile Gly Leu Asn
            500                 505                 510

Tyr Val Leu Met Ala Asp Val Ala Lys Lys Glu Lys Gly Gln Met Pro
            515                 520                 525

Arg Val Tyr Phe Val Leu Leu Gly Glu Thr Met Gly Gln Val Thr Glu
530                 535                 540

Lys Leu Gln Leu Thr Tyr Met Glu Glu Thr Cys Arg His Tyr Val Ala
545                 550                 555                 560

His Val Lys Arg Arg Val Gln Asp Val Ile Ser Pro Ile Val Phe Glu
                565                 570                 575

Ala Ala Tyr Ser Leu Ser Glu His Val Thr Gly Glu Glu Glu Arg Glu
            580                 585                 590

Leu Pro Pro Leu Thr Pro Val Leu Arg Trp Lys Lys Gly Gln Lys Ile
            595                 600                 605

Ala Gln Lys Asn Gln Thr Val Phe Glu Arg Asn Cys Arg Ser Glu Asp
610                 615                 620

Cys Ala Ala Asp Leu Gln Leu Gln Gly Lys Leu Leu Leu Ser Ser Met
625                 630                 635                 640

Asp Glu Lys Thr Leu Tyr Leu Ala Leu Gly Ala Val Lys Asn Ile Ser
                645                 650                 655

Leu Asn Ile Ser Ile Ser Asn Leu Gly Asp Asp Ala Tyr Asp Ala Asn
            660                 665                 670

Val Ser Phe Asn Val Ser Arg Glu Leu Phe Phe Ile Asn Met Trp Gln
            675                 680                 685

Lys Glu Glu Met Gly Ile Ser Cys Glu Leu Leu Glu Ser Asp Phe Leu
            690                 695                 700

Lys Cys Ser Val Gly Phe Pro Phe Met Arg Ser Lys Ser Lys Tyr Glu
705                 710                 715                 720

Phe Ser Val Ile Phe Asp Thr Ser His Leu Ser Gly Glu Glu Val
                725                 730                 735

Leu Ser Phe Ile Val Thr Ala Gln Ser Gly Asn Thr Glu Arg Ser Glu
            740                 745                 750

Ser Leu His Asp Asn Thr Leu Val Leu Met Val Pro Leu Met His Glu

```
                     755                 760                 765
Val Asp Thr Ser Ile Thr Gly Ile Met Ser Pro Thr Ser Phe Val Tyr
770                 775                 780

Gly Glu Ser Val Asp Ala Ala Asn Phe Ile Gln Leu Asp Asp Leu Glu
785                 790                 795                 800

Cys His Phe Gln Pro Ile Asn Ile Thr Leu Gln Val Tyr Asn Thr Gly
                    805                 810                 815

Pro Ser Thr Leu Pro Gly Ser Ser Val Ser Ile Ser Phe Pro Asn Arg
                820                 825                 830

Leu Ser Ser Gly Gly Ala Glu Met Phe His Val Gln Glu Met Val Val
                835                 840                 845

Gly Gln Glu Lys Gly Asn Cys Ser Phe Gln Lys Asn Pro Thr Pro Cys
850                 855                 860

Ile Ile Pro Gln Glu Gln Glu Asn Ile Phe His Thr Ile Phe Ala Phe
865                 870                 875                 880

Phe Thr Lys Ser Gly Arg Lys Val Leu Asp Cys Glu Lys Pro Gly Ile
                885                 890                 895

Ser Cys Leu Thr Ala His Cys Asn Phe Ser Ala Leu Ala Lys Glu Glu
                900                 905                 910

Ser Arg Thr Ile Asp Ile Tyr Met Leu Leu Asn Thr Glu Ile Leu Lys
                915                 920                 925

Lys Asp Ser Ser Val Ile Gln Phe Met Ser Arg Ala Lys Val Lys
930                 935                 940

Val Asp Pro Ala Leu Arg Val Val Glu Ile Ala His Gly Asn Pro Glu
945                 950                 955                 960

Glu Val Thr Val Val Phe Glu Ala Leu His Asn Leu Glu Pro Arg Gly
                965                 970                 975

Tyr Val Val Gly Trp Ile Ala Ile Ser Leu Leu Val Gly Ile Leu
                980                 985                 990

Ile Phe Leu Leu Leu Ala Val Leu  Leu Trp Lys Met Gly  Phe Phe Arg
                995                 1000                1005

Arg Arg  Tyr Lys Glu Ile Ile  Glu Ala Glu Lys Asn  Arg Lys Glu
    1010                 1015                 1020

Asn Glu  Asp Ser Trp Asp Trp  Val Gln Lys Asn Gln
    1025                 1030                 1035
```

<210> SEQ ID NO 78
<211> LENGTH: 1167
<212> TYPE: PRT
<213> ORGANISM: Homo sapiens

<400> SEQUENCE: 78

```
Met Glu Leu Pro Phe Val Thr His Leu Phe Leu Pro Leu Val Phe Leu
1               5                   10                  15

Thr Gly Leu Cys Ser Pro Phe Asn Leu Asp Glu His His Pro Arg Leu
                20                  25                  30

Phe Pro Gly Pro Pro Glu Ala Glu Phe Gly Tyr Ser Val Leu Gln His
                35                  40                  45

Val Gly Gly Gly Gln Arg Trp Met Leu Val Gly Ala Pro Trp Asp Gly
50                  55                  60

Pro Ser Gly Asp Arg Arg Gly Asp Val Tyr Arg Cys Pro Val Gly Gly
65                  70                  75                  80

Ala His Asn Ala Pro Cys Ala Lys Gly His Leu Gly Asp Tyr Gln Leu
                85                  90                  95
```

Gly Asn Ser Ser His Pro Ala Val Asn Met His Leu Gly Met Ser Leu
            100                 105                 110

Leu Glu Thr Asp Gly Asp Gly Phe Met Ala Cys Ala Pro Leu Trp
    115                 120                 125

Ser Arg Ala Cys Gly Ser Ser Val Phe Ser Ser Gly Ile Cys Ala Arg
    130                 135                 140

Val Asp Ala Ser Phe Gln Pro Gln Gly Ser Leu Ala Pro Thr Ala Gln
145                 150                 155                 160

Arg Cys Pro Thr Tyr Met Asp Val Val Ile Val Leu Asp Gly Ser Asn
                165                 170                 175

Ser Ile Tyr Pro Trp Ser Glu Val Gln Thr Phe Leu Arg Arg Leu Val
            180                 185                 190

Gly Lys Leu Phe Ile Asp Pro Glu Gln Ile Gln Val Gly Leu Val Gln
            195                 200                 205

Tyr Gly Glu Ser Pro Val His Glu Trp Ser Leu Gly Asp Phe Arg Thr
        210                 215                 220

Lys Glu Glu Val Val Arg Ala Ala Lys Asn Leu Ser Arg Arg Glu Gly
225                 230                 235                 240

Arg Glu Thr Lys Thr Ala Gln Ala Ile Met Val Ala Cys Thr Glu Gly
                245                 250                 255

Phe Ser Gln Ser His Gly Gly Arg Pro Glu Ala Ala Arg Leu Leu Val
            260                 265                 270

Val Val Thr Asp Gly Glu Ser His Asp Gly Glu Glu Leu Pro Ala Ala
            275                 280                 285

Leu Lys Ala Cys Glu Ala Gly Arg Val Thr Arg Tyr Gly Ile Ala Val
    290                 295                 300

Leu Gly His Tyr Leu Arg Arg Gln Arg Asp Pro Ser Ser Phe Leu Arg
305                 310                 315                 320

Glu Ile Arg Thr Ile Ala Ser Asp Pro Asp Glu Arg Phe Phe Phe Asn
                325                 330                 335

Val Thr Asp Glu Ala Ala Leu Thr Asp Ile Val Asp Ala Leu Gly Asp
            340                 345                 350

Arg Ile Phe Gly Leu Glu Gly Ser His Ala Glu Asn Glu Ser Ser Phe
    355                 360                 365

Gly Leu Glu Met Ser Gln Ile Gly Phe Ser Thr His Arg Leu Lys Asp
370                 375                 380

Gly Ile Leu Phe Gly Met Val Gly Ala Tyr Asp Trp Gly Gly Ser Val
385                 390                 395                 400

Leu Trp Leu Glu Gly Gly His Arg Leu Phe Pro Pro Arg Met Ala Leu
                405                 410                 415

Glu Asp Glu Phe Pro Pro Ala Leu Gln Asn His Ala Ala Tyr Leu Gly
            420                 425                 430

Tyr Ser Val Ser Ser Met Leu Leu Arg Gly Gly Arg Arg Leu Phe Leu
    435                 440                 445

Ser Gly Ala Pro Arg Phe Arg His Arg Gly Lys Val Ile Ala Phe Gln
    450                 455                 460

Leu Lys Lys Asp Gly Ala Val Arg Val Ala Gln Ser Leu Gln Gly Glu
465                 470                 475                 480

Gln Ile Gly Ser Tyr Phe Gly Ser Glu Leu Cys Pro Leu Asp Thr Asp
                485                 490                 495

Arg Asp Gly Thr Thr Asp Val Leu Leu Val Ala Ala Pro Met Phe Leu
            500                 505                 510

Gly Pro Gln Asn Lys Glu Thr Gly Arg Val Tyr Val Tyr Leu Val Gly

```
                515                 520                 525
Gln Gln Ser Leu Leu Thr Leu Gln Gly Thr Leu Gln Pro Glu Pro Pro
        530                 535                 540

Gln Asp Ala Arg Phe Gly Phe Ala Met Gly Ala Leu Pro Asp Leu Asn
545                 550                 555                 560

Gln Asp Gly Phe Ala Asp Val Ala Val Gly Ala Pro Leu Glu Asp Gly
                565                 570                 575

His Gln Gly Ala Leu Tyr Leu Tyr His Gly Thr Gln Ser Gly Val Arg
                580                 585                 590

Pro His Pro Ala Gln Arg Ile Ala Ala Ala Ser Met Pro His Ala Leu
            595                 600                 605

Ser Tyr Phe Gly Arg Ser Val Asp Gly Arg Leu Asp Leu Asp Gly Asp
        610                 615                 620

Asp Leu Val Asp Val Ala Val Gly Ala Gln Gly Ala Ala Ile Leu Leu
625                 630                 635                 640

Ser Ser Arg Pro Ile Val His Leu Thr Pro Ser Leu Glu Val Thr Pro
                645                 650                 655

Gln Ala Ile Ser Val Val Gln Arg Asp Cys Arg Arg Gly Gln Glu
            660                 665                 670

Ala Val Cys Leu Thr Ala Ala Leu Cys Phe Gln Val Thr Ser Arg Thr
                675                 680                 685

Pro Gly Arg Trp Asp His Gln Phe Tyr Met Arg Phe Thr Ala Ser Leu
        690                 695                 700

Asp Glu Trp Thr Ala Gly Ala Arg Ala Ala Phe Asp Gly Ser Gly Gln
705                 710                 715                 720

Arg Leu Ser Pro Arg Arg Leu Arg Leu Ser Val Gly Asn Val Thr Cys
                725                 730                 735

Glu Gln Leu His Phe His Val Leu Asp Thr Ser Asp Tyr Leu Arg Pro
            740                 745                 750

Val Ala Leu Thr Val Thr Phe Ala Leu Asp Asn Thr Thr Lys Pro Gly
        755                 760                 765

Pro Val Leu Asn Glu Gly Ser Pro Thr Ser Ile Gln Lys Leu Val Pro
    770                 775                 780

Phe Ser Lys Asp Cys Gly Pro Asp Asn Glu Cys Val Thr Asp Leu Val
785                 790                 795                 800

Leu Gln Val Asn Met Asp Ile Arg Gly Ser Arg Lys Ala Pro Phe Val
                805                 810                 815

Val Arg Gly Gly Arg Arg Lys Val Leu Val Ser Thr Thr Leu Glu Asn
            820                 825                 830

Arg Lys Glu Asn Ala Tyr Asn Thr Ser Leu Ser Leu Ile Phe Ser Arg
        835                 840                 845

Asn Leu His Leu Ala Ser Leu Thr Pro Gln Arg Glu Ser Pro Ile Lys
    850                 855                 860

Val Glu Cys Ala Ala Pro Ser Ala His Ala Arg Leu Cys Ser Val Gly
865                 870                 875                 880

His Pro Val Phe Gln Thr Gly Ala Lys Val Thr Phe Leu Leu Glu Phe
                885                 890                 895

Glu Phe Ser Cys Ser Ser Leu Leu Ser Gln Val Phe Val Lys Leu Thr
            900                 905                 910

Ala Ser Ser Asp Ser Leu Glu Arg Asn Gly Thr Leu Gln Asp Asn Thr
        915                 920                 925

Ala Gln Thr Ser Ala Tyr Ile Gln Tyr Glu Pro His Leu Leu Phe Ser
    930                 935                 940
```

```
Ser Glu Ser Thr Leu His Arg Tyr Glu Val His Pro Tyr Gly Thr Leu
945                 950                 955                 960

Pro Val Gly Pro Gly Pro Glu Phe Lys Thr Thr Leu Arg Val Gln Asn
                965                 970                 975

Leu Gly Cys Tyr Val Val Ser Gly Leu Ile Ile Ser Ala Leu Leu Pro
            980                 985                 990

Ala Val Ala His Gly Gly Asn Tyr Phe Leu Ser Leu Ser Gln Val Ile
        995                 1000                1005

Thr Asn Asn Ala Ser Cys Ile Val Gln Asn Leu Thr Glu Pro Pro
    1010                1015                1020

Gly Pro Pro Val His Pro Glu Glu Leu Gln His Thr Asn Arg Leu
    1025                1030                1035

Asn Gly Ser Asn Thr Gln Cys Gln Val Val Arg Cys His Leu Gly
    1040                1045                1050

Gln Leu Ala Lys Gly Thr Glu Val Ser Val Gly Leu Leu Arg Leu
    1055                1060                1065

Val His Asn Glu Phe Phe Arg Arg Ala Lys Phe Lys Ser Leu Thr
    1070                1075                1080

Val Val Ser Thr Phe Glu Leu Gly Thr Glu Glu Gly Ser Val Leu
    1085                1090                1095

Gln Leu Thr Glu Ala Ser Arg Trp Ser Glu Ser Leu Leu Glu Val
    1100                1105                1110

Val Gln Thr Arg Pro Ile Leu Ile Ser Leu Trp Ile Leu Ile Gly
    1115                1120                1125

Ser Val Leu Gly Gly Leu Leu Leu Leu Ala Leu Leu Val Phe Cys
    1130                1135                1140

Leu Trp Lys Leu Gly Phe Phe Ala His Lys Lys Ile Pro Glu Glu
    1145                1150                1155

Glu Lys Arg Glu Glu Lys Leu Glu Gln
    1160                1165

<210> SEQ ID NO 79
<211> LENGTH: 1188
<212> TYPE: PRT
<213> ORGANISM: Homo sapiens

<400> SEQUENCE: 79

Met Asp Leu Pro Arg Gly Leu Val Val Ala Trp Ala Leu Ser Leu Trp
1               5                   10                  15

Pro Gly Phe Thr Asp Thr Phe Asn Met Asp Thr Arg Lys Pro Arg Val
                20                  25                  30

Ile Pro Gly Ser Arg Thr Ala Phe Phe Gly Tyr Thr Val Gln Gln His
            35                  40                  45

Asp Ile Ser Gly Asn Lys Trp Leu Val Val Gly Ala Pro Leu Glu Thr
50                  55                  60

Asn Gly Tyr Gln Lys Thr Gly Asp Val Tyr Lys Cys Pro Val Ile His
65                  70                  75                  80

Gly Asn Cys Thr Lys Leu Asn Leu Gly Arg Val Thr Leu Ser Asn Val
                85                  90                  95

Ser Glu Arg Lys Asp Asn Met Arg Leu Gly Leu Ser Leu Ala Thr Asn
                100                 105                 110

Pro Lys Asp Asn Ser Phe Leu Ala Cys Ser Pro Leu Trp Ser His Glu
            115                 120                 125

Cys Gly Ser Ser Tyr Tyr Thr Thr Gly Met Cys Ser Arg Val Asn Ser
```

```
            130                 135                 140
Asn Phe Arg Phe Ser Lys Thr Val Ala Pro Ala Leu Gln Arg Cys Gln
145                 150                 155                 160

Thr Tyr Met Asp Ile Val Ile Val Leu Asp Gly Ser Asn Ser Ile Tyr
                165                 170                 175

Pro Trp Val Glu Val Gln His Phe Leu Ile Asn Ile Leu Lys Lys Phe
            180                 185                 190

Tyr Ile Gly Pro Gly Gln Ile Gln Val Gly Val Val Gln Tyr Gly Glu
        195                 200                 205

Asp Val Val His Glu Phe His Leu Asn Asp Tyr Arg Ser Val Lys Asp
    210                 215                 220

Val Val Glu Ala Ala Ser His Ile Glu Gln Arg Gly Gly Thr Glu Thr
225                 230                 235                 240

Arg Thr Ala Phe Gly Ile Glu Phe Ala Arg Ser Glu Ala Phe Gln Lys
                245                 250                 255

Gly Gly Arg Lys Gly Ala Lys Lys Val Met Ile Val Ile Thr Asp Gly
            260                 265                 270

Glu Ser His Asp Ser Pro Asp Leu Glu Lys Val Ile Gln Gln Ser Glu
        275                 280                 285

Arg Asp Asn Val Thr Arg Tyr Ala Val Ala Val Leu Gly Tyr Tyr Asn
    290                 295                 300

Arg Arg Gly Ile Asn Pro Glu Thr Phe Leu Asn Glu Ile Lys Tyr Ile
305                 310                 315                 320

Ala Ser Asp Pro Asp Asp Lys His Phe Phe Asn Val Thr Asp Glu Ala
                325                 330                 335

Ala Leu Lys Asp Ile Val Asp Ala Leu Gly Asp Arg Ile Phe Ser Leu
            340                 345                 350

Glu Gly Thr Asn Lys Asn Glu Thr Ser Phe Gly Leu Glu Met Ser Gln
        355                 360                 365

Thr Gly Phe Ser Ser His Val Val Glu Asp Gly Val Leu Leu Gly Ala
    370                 375                 380

Val Gly Ala Tyr Asp Trp Asn Gly Ala Val Leu Lys Glu Thr Ser Ala
385                 390                 395                 400

Gly Lys Val Ile Pro Leu Arg Glu Ser Tyr Leu Lys Glu Phe Pro Glu
                405                 410                 415

Glu Leu Lys Asn His Gly Ala Tyr Leu Gly Tyr Thr Val Thr Ser Val
            420                 425                 430

Val Ser Ser Arg Gln Gly Arg Val Tyr Val Ala Gly Ala Pro Arg Phe
        435                 440                 445

Asn His Thr Gly Lys Val Ile Leu Phe Thr Met His Asn Asn Arg Ser
    450                 455                 460

Leu Thr Ile His Gln Ala Met Arg Gly Gln Gln Ile Gly Ser Tyr Phe
465                 470                 475                 480

Gly Ser Glu Ile Thr Ser Val Asp Ile Asp Gly Asp Gly Val Thr Asp
                485                 490                 495

Val Leu Leu Val Gly Ala Pro Met Tyr Phe Asn Glu Gly Arg Glu Arg
            500                 505                 510

Gly Lys Val Tyr Val Tyr Glu Leu Arg Gln Asn Leu Phe Val Tyr Asn
        515                 520                 525

Gly Thr Leu Lys Asp Ser His Ser Tyr Gln Asn Ala Arg Phe Gly Ser
    530                 535                 540

Ser Ile Ala Ser Val Arg Asp Leu Asn Gln Asp Ser Tyr Asn Asp Val
545                 550                 555                 560
```

```
Val Val Gly Ala Pro Leu Glu Asp Asn His Ala Gly Ala Ile Tyr Ile
            565                 570                 575

Phe His Gly Phe Arg Gly Ser Ile Leu Lys Thr Pro Lys Gln Arg Ile
            580                 585                 590

Thr Ala Ser Glu Leu Ala Thr Gly Leu Gln Tyr Phe Gly Cys Ser Ile
            595                 600                 605

His Gly Gln Leu Asp Leu Asn Glu Asp Gly Leu Ile Asp Leu Ala Val
            610                 615                 620

Gly Ala Leu Gly Asn Ala Val Ile Leu Trp Ser Arg Pro Val Val Gln
625                 630                 635                 640

Ile Asn Ala Ser Leu His Phe Glu Pro Ser Lys Ile Asn Ile Phe His
            645                 650                 655

Arg Asp Cys Lys Arg Ser Gly Arg Asp Ala Thr Cys Leu Ala Ala Phe
            660                 665                 670

Leu Cys Phe Thr Pro Ile Phe Leu Ala Pro His Phe Gln Thr Thr Thr
            675                 680                 685

Val Gly Ile Arg Tyr Asn Ala Thr Met Asp Glu Arg Arg Tyr Thr Pro
            690                 695                 700

Arg Ala His Leu Asp Glu Gly Gly Asp Arg Phe Thr Asn Arg Ala Val
705                 710                 715                 720

Leu Leu Ser Ser Gly Gln Glu Leu Cys Glu Arg Ile Asn Phe His Val
            725                 730                 735

Leu Asp Thr Ala Asp Tyr Val Lys Pro Val Thr Phe Ser Val Glu Tyr
            740                 745                 750

Ser Leu Glu Asp Pro Asp His Gly Pro Met Leu Asp Asp Gly Trp Pro
            755                 760                 765

Thr Thr Leu Arg Val Ser Val Pro Phe Trp Asn Gly Cys Asn Glu Asp
            770                 775                 780

Glu His Cys Val Pro Asp Leu Val Leu Asp Ala Arg Ser Asp Leu Pro
785                 790                 795                 800

Thr Ala Met Glu Tyr Cys Gln Arg Val Leu Arg Lys Pro Ala Gln Asp
            805                 810                 815

Cys Ser Ala Tyr Thr Leu Ser Phe Asp Thr Thr Val Phe Ile Ile Glu
            820                 825                 830

Ser Thr Arg Gln Arg Val Ala Val Glu Ala Thr Leu Glu Asn Arg Gly
            835                 840                 845

Glu Asn Ala Tyr Ser Thr Val Leu Asn Ile Ser Gln Ser Ala Asn Leu
            850                 855                 860

Gln Phe Ala Ser Leu Ile Gln Lys Glu Asp Ser Asp Gly Ser Ile Glu
865                 870                 875                 880

Cys Val Asn Glu Glu Arg Arg Leu Gln Lys Gln Val Cys Asn Val Ser
            885                 890                 895

Tyr Pro Phe Phe Arg Ala Lys Ala Lys Val Ala Phe Arg Leu Asp Phe
            900                 905                 910

Glu Phe Ser Lys Ser Ile Phe Leu His His Leu Glu Ile Glu Leu Ala
            915                 920                 925

Ala Gly Ser Asp Ser Asn Glu Arg Asp Ser Thr Lys Glu Asp Asn Val
            930                 935                 940

Ala Pro Leu Arg Phe His Leu Lys Tyr Glu Ala Asp Val Leu Phe Thr
945                 950                 955                 960

Arg Ser Ser Ser Leu Ser His Tyr Glu Val Lys Pro Asn Ser Ser Leu
            965                 970                 975
```

```
Glu Arg Tyr Asp Gly Ile Gly Pro Pro Phe Ser Cys Ile Phe Arg Ile
            980                 985                 990

Gln Asn Leu Gly Leu Phe Pro Ile His Gly Met Met Met Lys Ile Thr
        995                 1000                1005

Ile Pro Ile Ala Thr Arg Ser Gly Asn Arg Leu Leu Lys Leu Arg
    1010                1015                1020

Asp Phe Leu Thr Asp Glu Ala Asn Thr Ser Cys Asn Ile Trp Gly
    1025                1030                1035

Asn Ser Thr Glu Tyr Arg Pro Thr Pro Val Glu Glu Asp Leu Arg
    1040                1045                1050

Arg Ala Pro Gln Leu Asn His Ser Asn Ser Asp Val Val Ser Ile
    1055                1060                1065

Asn Cys Asn Ile Arg Leu Val Pro Asn Gln Glu Ile Asn Phe His
    1070                1075                1080

Leu Leu Gly Asn Leu Trp Leu Arg Ser Leu Lys Ala Leu Lys Tyr
    1085                1090                1095

Lys Ser Met Lys Ile Met Val Asn Ala Ala Leu Gln Arg Gln Phe
    1100                1105                1110

His Ser Pro Phe Ile Phe Arg Glu Glu Asp Pro Ser Arg Gln Ile
    1115                1120                1125

Val Phe Glu Ile Ser Lys Gln Glu Asp Trp Gln Val Pro Ile Trp
    1130                1135                1140

Ile Ile Val Gly Ser Thr Leu Gly Gly Leu Leu Leu Leu Ala Leu
    1145                1150                1155

Leu Val Leu Ala Leu Trp Lys Leu Gly Phe Phe Arg Ser Ala Arg
    1160                1165                1170

Arg Arg Arg Glu Pro Gly Leu Asp Pro Thr Pro Lys Val Leu Glu
    1175                1180                1185

<210> SEQ ID NO 80
<211> LENGTH: 1048
<212> TYPE: PRT
<213> ORGANISM: Homo sapiens

<400> SEQUENCE: 80

Met Ala Phe Pro Pro Arg Arg Arg Leu Arg Leu Gly Pro Arg Gly Leu
1               5                   10                  15

Pro Leu Leu Leu Ser Gly Leu Leu Leu Pro Leu Cys Arg Ala Phe Asn
            20                  25                  30

Leu Asp Val Asp Ser Pro Ala Glu Tyr Ser Gly Pro Glu Gly Ser Tyr
        35                  40                  45

Phe Gly Phe Ala Val Asp Phe Phe Val Pro Ser Ala Ser Ser Arg Met
    50                  55                  60

Phe Leu Leu Val Gly Ala Pro Lys Ala Asn Thr Thr Gln Pro Gly Ile
65                  70                  75                  80

Val Glu Gly Gly Gln Val Leu Lys Cys Asp Trp Ser Ser Thr Arg Arg
                85                  90                  95

Cys Gln Pro Ile Glu Phe Asp Ala Thr Gly Asn Arg Asp Tyr Ala Lys
            100                 105                 110

Asp Asp Pro Leu Glu Phe Lys Ser His Gln Trp Phe Gly Ala Ser Val
        115                 120                 125

Arg Ser Lys Gln Asp Lys Ile Leu Ala Cys Ala Pro Leu Tyr His Trp
    130                 135                 140

Arg Thr Glu Met Lys Gln Glu Arg Glu Pro Val Gly Thr Cys Phe Leu
145                 150                 155                 160
```

```
Gln Asp Gly Thr Lys Thr Val Glu Tyr Ala Pro Cys Arg Ser Gln Asp
            165                 170                 175

Ile Asp Ala Asp Gly Gln Gly Phe Cys Gln Gly Gly Phe Ser Ile Asp
            180                 185                 190

Phe Thr Lys Ala Asp Arg Val Leu Leu Gly Pro Gly Ser Phe Tyr
        195                 200                 205

Trp Gln Gly Gln Leu Ile Ser Asp Gln Val Ala Glu Ile Val Ser Lys
210                 215                 220

Tyr Asp Pro Asn Val Tyr Ser Ile Lys Tyr Asn Asn Gln Leu Ala Thr
225                 230                 235                 240

Arg Thr Ala Gln Ala Ile Phe Asp Ser Tyr Leu Gly Tyr Ser Val
                245                 250                 255

Ala Val Gly Asp Phe Asn Gly Asp Gly Ile Asp Asp Phe Val Ser Gly
            260                 265                 270

Val Pro Arg Ala Ala Arg Thr Leu Gly Met Val Tyr Ile Tyr Asp Gly
        275                 280                 285

Lys Asn Met Ser Ser Leu Tyr Asn Phe Thr Gly Glu Gln Met Ala Ala
            290                 295                 300

Tyr Phe Gly Phe Ser Val Ala Ala Thr Asp Ile Asn Gly Asp Asp Tyr
305                 310                 315                 320

Ala Asp Val Phe Ile Gly Ala Pro Leu Phe Met Asp Arg Gly Ser Asp
                325                 330                 335

Gly Lys Leu Gln Glu Val Gly Gln Val Ser Val Ser Leu Gln Arg Ala
            340                 345                 350

Ser Gly Asp Phe Gln Thr Thr Lys Leu Asn Gly Phe Glu Val Phe Ala
            355                 360                 365

Arg Phe Gly Ser Ala Ile Ala Pro Leu Gly Asp Leu Asp Gln Asp Gly
        370                 375                 380

Phe Asn Asp Ile Ala Ile Ala Ala Pro Tyr Gly Gly Glu Asp Lys Lys
385                 390                 395                 400

Gly Ile Val Tyr Ile Phe Asn Gly Arg Ser Thr Gly Leu Asn Ala Val
                405                 410                 415

Pro Ser Gln Ile Leu Glu Gly Gln Trp Ala Ala Arg Ser Met Pro Pro
            420                 425                 430

Ser Phe Gly Tyr Ser Met Lys Gly Ala Thr Asp Ile Asp Lys Asn Gly
        435                 440                 445

Tyr Pro Asp Leu Ile Val Gly Ala Phe Gly Val Asp Arg Ala Ile Leu
450                 455                 460

Tyr Arg Ala Arg Pro Val Ile Thr Val Asn Ala Gly Leu Glu Val Tyr
465                 470                 475                 480

Pro Ser Ile Leu Asn Gln Asp Asn Lys Thr Cys Ser Leu Pro Gly Thr
            485                 490                 495

Ala Leu Lys Val Ser Cys Phe Asn Val Arg Phe Cys Leu Lys Ala Asp
            500                 505                 510

Gly Lys Gly Val Leu Pro Arg Lys Leu Asn Phe Gln Val Glu Leu Leu
        515                 520                 525

Leu Asp Lys Leu Lys Gln Lys Gly Ala Ile Arg Arg Ala Leu Phe Leu
530                 535                 540

Tyr Ser Arg Ser Pro Ser His Ser Lys Asn Met Thr Ile Ser Arg Gly
545                 550                 555                 560

Gly Leu Met Gln Cys Glu Glu Leu Ile Ala Tyr Leu Arg Asp Glu Ser
                565                 570                 575
```

```
Glu Phe Arg Asp Lys Leu Thr Pro Ile Thr Ile Phe Met Glu Tyr Arg
                580                 585                 590

Leu Asp Tyr Arg Thr Ala Ala Asp Thr Thr Gly Leu Gln Pro Ile Leu
            595                 600                 605

Asn Gln Phe Thr Pro Ala Asn Ile Ser Arg Gln Ala His Ile Leu Leu
        610                 615                 620

Asp Cys Gly Glu Asp Asn Val Cys Lys Pro Lys Leu Glu Val Ser Val
625                 630                 635                 640

Asp Ser Asp Gln Lys Lys Ile Tyr Ile Gly Asp Asp Asn Pro Leu Thr
                645                 650                 655

Leu Ile Val Lys Ala Gln Asn Gln Gly Glu Gly Ala Tyr Glu Ala Glu
            660                 665                 670

Leu Ile Val Ser Ile Pro Leu Gln Ala Asp Phe Ile Gly Val Val Arg
            675                 680                 685

Asn Asn Glu Ala Leu Ala Arg Leu Ser Cys Ala Phe Lys Thr Glu Asn
690                 695                 700

Gln Thr Arg Gln Val Val Cys Asp Leu Gly Asn Pro Met Lys Ala Gly
705                 710                 715                 720

Thr Gln Leu Leu Ala Gly Leu Arg Phe Ser Val His Gln Gln Ser Glu
                725                 730                 735

Met Asp Thr Ser Val Lys Phe Asp Leu Gln Ile Gln Ser Ser Asn Leu
            740                 745                 750

Phe Asp Lys Val Ser Pro Val Ser His Lys Val Asp Leu Ala Val
            755                 760                 765

Leu Ala Ala Val Glu Ile Arg Gly Val Ser Ser Pro Asp His Val Phe
770                 775                 780

Leu Pro Ile Pro Asn Trp Glu His Lys Glu Asn Pro Glu Thr Glu Glu
785                 790                 795                 800

Asp Val Gly Pro Val Val Gln His Ile Tyr Glu Leu Arg Asn Asn Gly
                805                 810                 815

Pro Ser Ser Phe Ser Lys Ala Met Leu His Leu Gln Trp Pro Tyr Lys
            820                 825                 830

Tyr Asn Asn Asn Thr Leu Leu Tyr Ile Leu His Tyr Asp Ile Asp Gly
            835                 840                 845

Pro Met Asn Cys Thr Ser Asp Met Glu Ile Asn Pro Leu Arg Ile Lys
850                 855                 860

Ile Ser Ser Leu Gln Thr Thr Glu Lys Asn Asp Thr Val Ala Gly Gln
865                 870                 875                 880

Gly Glu Arg Asp His Leu Ile Thr Lys Arg Asp Leu Ala Leu Ser Glu
                885                 890                 895

Gly Asp Ile His Thr Leu Gly Cys Gly Val Ala Gln Cys Leu Lys Ile
            900                 905                 910

Val Cys Gln Val Gly Arg Leu Asp Arg Gly Lys Ser Ala Ile Leu Tyr
            915                 920                 925

Val Lys Ser Leu Leu Trp Thr Glu Thr Phe Met Asn Lys Glu Asn Gln
930                 935                 940

Asn His Ser Tyr Ser Leu Lys Ser Ser Ala Ser Phe Asn Val Ile Glu
945                 950                 955                 960

Phe Pro Tyr Lys Asn Leu Pro Ile Glu Asp Ile Thr Asn Ser Thr Leu
                965                 970                 975

Val Thr Thr Asn Val Thr Trp Gly Ile Gln Pro Ala Pro Met Pro Val
            980                 985                 990

Pro Val Trp Val Ile Ile Leu Ala  Val Leu Ala Gly Leu  Leu Leu Leu
```

```
            995                 1000                1005
Ala Val Leu Val Phe Val Met Tyr Arg Met Gly Phe Phe Lys Arg
        1010                1015                1020

Val Arg Pro Pro Gln Glu Glu Gln Arg Glu Gln Leu Gln Pro
    1025                1030                1035

His Glu Asn Gly Glu Gly Asn Ser Glu Thr
    1040                1045

<210> SEQ ID NO 81
<211> LENGTH: 1039
<212> TYPE: PRT
<213> ORGANISM: Homo sapiens

<400> SEQUENCE: 81

Met Ala Arg Ala Leu Cys Pro Leu Gln Ala Leu Trp Leu Leu Glu Trp
1               5                   10                  15

Val Leu Leu Leu Leu Gly Pro Cys Ala Ala Pro Pro Ala Trp Ala Leu
            20                  25                  30

Asn Leu Asp Pro Val Gln Leu Thr Phe Tyr Ala Gly Pro Asn Gly Ser
        35                  40                  45

Gln Phe Gly Phe Ser Leu Asp Phe His Lys Asp Ser His Gly Arg Val
    50                  55                  60

Ala Ile Val Val Gly Ala Pro Arg Thr Leu Gly Pro Ser Gln Glu Glu
65                  70                  75                  80

Thr Gly Gly Val Phe Leu Cys Pro Trp Arg Ala Glu Gly Gly Gln Cys
                85                  90                  95

Pro Ser Leu Leu Phe Asp Leu Arg Asp Glu Thr Arg Asn Val Gly Ser
            100                 105                 110

Gln Thr Leu Gln Thr Phe Lys Ala Arg Gln Gly Leu Gly Ala Ser Val
        115                 120                 125

Val Ser Trp Ser Asp Val Ile Val Ala Cys Ala Pro Trp Gln His Trp
    130                 135                 140

Asn Val Leu Glu Lys Thr Glu Glu Ala Glu Lys Thr Pro Val Gly Ser
145                 150                 155                 160

Cys Phe Leu Ala Gln Pro Glu Ser Gly Arg Arg Ala Glu Tyr Ser Pro
                165                 170                 175

Cys Arg Gly Asn Thr Leu Ser Arg Ile Tyr Val Glu Asn Asp Phe Ser
            180                 185                 190

Trp Asp Lys Arg Tyr Cys Glu Ala Gly Phe Ser Ser Val Val Thr Gln
        195                 200                 205

Ala Gly Glu Leu Val Leu Gly Ala Pro Gly Gly Tyr Tyr Phe Leu Gly
    210                 215                 220

Leu Leu Ala Gln Ala Pro Val Ala Asp Ile Phe Ser Ser Tyr Arg Pro
225                 230                 235                 240

Gly Ile Leu Leu Trp His Val Ser Ser Gln Ser Leu Ser Phe Asp Ser
                245                 250                 255

Ser Asn Pro Glu Tyr Phe Asp Gly Tyr Trp Gly Tyr Ser Val Ala Val
            260                 265                 270

Gly Glu Phe Asp Gly Asp Leu Asn Thr Thr Glu Tyr Val Val Gly Ala
        275                 280                 285

Pro Thr Trp Ser Trp Thr Leu Gly Ala Val Glu Ile Leu Asp Ser Tyr
    290                 295                 300

Tyr Gln Arg Leu His Arg Leu Arg Gly Glu Gln Met Ala Ser Tyr Phe
305                 310                 315                 320
```

```
Gly His Ser Val Ala Val Thr Asp Val Asn Gly Asp Gly Arg His Asp
            325                 330                 335

Leu Leu Val Gly Ala Pro Leu Tyr Met Glu Ser Arg Ala Asp Arg Lys
            340                 345                 350

Leu Ala Glu Val Gly Arg Val Tyr Leu Phe Leu Gln Pro Arg Gly Pro
            355                 360                 365

His Ala Leu Gly Ala Pro Ser Leu Leu Leu Thr Gly Thr Gln Leu Tyr
            370                 375                 380

Gly Arg Phe Gly Ser Ala Ile Ala Pro Leu Gly Asp Leu Asp Arg Asp
385                 390                 395                 400

Gly Tyr Asn Asp Ile Ala Val Ala Ala Pro Tyr Gly Gly Pro Ser Gly
                405                 410                 415

Arg Gly Gln Val Leu Val Phe Leu Gly Gln Ser Glu Gly Leu Arg Ser
            420                 425                 430

Arg Pro Ser Gln Val Leu Asp Ser Pro Phe Pro Thr Gly Ser Ala Phe
            435                 440                 445

Gly Phe Ser Leu Arg Gly Ala Val Asp Ile Asp Asp Asn Gly Tyr Pro
            450                 455                 460

Asp Leu Ile Val Gly Ala Tyr Gly Ala Asn Gln Val Ala Val Tyr Arg
465                 470                 475                 480

Ala Gln Pro Val Val Lys Ala Ser Val Gln Leu Leu Val Gln Asp Ser
                485                 490                 495

Leu Asn Pro Ala Val Lys Ser Cys Val Leu Pro Gln Thr Lys Thr Pro
                500                 505                 510

Val Ser Cys Phe Asn Ile Gln Met Cys Val Gly Ala Thr Gly His Asn
            515                 520                 525

Ile Pro Gln Lys Leu Ser Leu Asn Ala Glu Leu Gln Leu Asp Arg Gln
            530                 535                 540

Lys Pro Arg Gln Gly Arg Arg Val Leu Leu Leu Gly Ser Gln Gln Ala
545                 550                 555                 560

Gly Thr Thr Leu Asn Leu Asp Leu Gly Gly Lys His Ser Pro Ile Cys
                565                 570                 575

His Thr Thr Met Ala Phe Leu Arg Asp Glu Ala Asp Phe Arg Asp Lys
            580                 585                 590

Leu Ser Pro Ile Val Leu Ser Leu Asn Val Ser Leu Pro Pro Thr Glu
            595                 600                 605

Ala Gly Met Ala Pro Ala Val Val Leu His Gly Asp Thr His Val Gln
            610                 615                 620

Glu Gln Thr Arg Ile Val Leu Asp Cys Gly Glu Asp Val Cys Val
625                 630                 635                 640

Pro Gln Leu Gln Leu Thr Ala Ser Val Thr Gly Ser Pro Leu Leu Val
                645                 650                 655

Gly Ala Asp Asn Val Leu Glu Leu Gln Met Asp Ala Ala Asn Glu Gly
                660                 665                 670

Glu Gly Ala Tyr Glu Ala Glu Leu Ala Val His Leu Pro Gln Gly Ala
            675                 680                 685

His Tyr Met Arg Ala Leu Ser Asn Val Glu Gly Phe Glu Arg Leu Ile
            690                 695                 700

Cys Asn Gln Lys Lys Glu Asn Glu Thr Arg Val Val Leu Cys Glu Leu
705                 710                 715                 720

Gly Asn Pro Met Lys Lys Asn Ala Gln Ile Gly Ile Ala Met Leu Val
                725                 730                 735

Ser Val Gly Asn Leu Glu Glu Ala Gly Glu Ser Val Ser Phe Gln Leu
```

```
                    740                 745                 750
        Gln Ile Arg Ser Lys Asn Ser Gln Asn Pro Asn Ser Lys Ile Val Leu
                    755                 760                 765
        Leu Asp Val Pro Val Arg Ala Glu Ala Gln Val Glu Leu Arg Gly Asn
                    770                 775                 780
        Ser Phe Pro Ala Ser Leu Val Val Ala Ala Glu Gly Glu Arg Glu
        785                 790                 795                 800
        Gln Asn Ser Leu Asp Ser Trp Gly Pro Lys Val Glu His Thr Tyr Glu
                    805                 810                 815
        Leu His Asn Asn Gly Pro Gly Thr Val Asn Gly Leu His Leu Ser Ile
                    820                 825                 830
        His Leu Pro Gly Gln Ser Gln Pro Ser Asp Leu Leu Tyr Ile Leu Asp
                    835                 840                 845
        Ile Gln Pro Gln Gly Gly Leu Gln Cys Phe Pro Gln Pro Val Asn
                    850                 855                 860
        Pro Leu Lys Val Asp Trp Gly Leu Pro Ile Pro Ser Pro Ser Pro Ile
        865                 870                 875                 880
        His Pro Ala His His Lys Arg Asp Arg Arg Gln Ile Phe Leu Pro Glu
                    885                 890                 895
        Pro Glu Gln Pro Ser Arg Leu Gln Asp Pro Val Leu Val Ser Cys Asp
                    900                 905                 910
        Ser Ala Pro Cys Thr Val Val Gln Cys Asp Leu Gln Glu Met Ala Arg
                    915                 920                 925
        Gly Gln Arg Ala Met Val Thr Val Leu Ala Phe Leu Trp Leu Pro Ser
                    930                 935                 940
        Leu Tyr Gln Arg Pro Leu Asp Gln Phe Val Leu Gln Ser His Ala Trp
        945                 950                 955                 960
        Phe Asn Val Ser Ser Leu Pro Tyr Ala Val Pro Pro Leu Ser Leu Pro
                    965                 970                 975
        Arg Gly Glu Ala Gln Val Trp Thr Gln Leu Leu Arg Ala Leu Glu Glu
                    980                 985                 990
        Arg Ala Ile Pro Ile Trp Trp Val Leu Val Gly Val Leu Gly Gly Leu
                    995                 1000                1005
        Leu Leu Leu Thr Ile Leu Val Leu Ala Met Trp Lys Val Gly Phe
              1010                1015                1020
        Phe Lys Arg Asn Arg Pro Pro Leu Glu Glu Asp Glu Glu Gly
              1025                1030                1035
        Glu

<210> SEQ ID NO 82
<211> LENGTH: 1170
<212> TYPE: PRT
<213> ORGANISM: Homo sapiens

<400> SEQUENCE: 82

Met Lys Asp Ser Cys Ile Thr Val Met Ala Met Ala Leu Leu Ser Gly
        1               5                   10                  15
        Phe Phe Phe Phe Ala Pro Ala Ser Ser Tyr Asn Leu Asp Val Arg Gly
                    20                  25                  30
        Ala Arg Ser Phe Ser Pro Pro Arg Ala Gly Arg His Phe Gly Tyr Arg
                    35                  40                  45
        Val Leu Gln Val Gly Asn Gly Val Ile Val Gly Ala Pro Gly Glu Gly
                    50                  55                  60
        Asn Ser Thr Gly Ser Leu Tyr Gln Cys Gln Ser Gly Thr Gly His Cys
```

```
            65                  70                  75                  80
Leu Pro Val Thr Leu Arg Gly Ser Asn Tyr Thr Ser Lys Tyr Leu Gly
                    85                  90                  95
Met Thr Leu Ala Thr Asp Pro Thr Asp Gly Ser Ile Leu Ala Cys Asp
                100                 105                 110
Pro Gly Leu Ser Arg Thr Cys Asp Gln Asn Thr Tyr Leu Ser Gly Leu
            115                 120                 125
Cys Tyr Leu Phe Arg Gln Asn Leu Gln Gly Pro Met Leu Gln Gly Arg
130                 135                 140
Pro Gly Phe Gln Glu Cys Ile Lys Gly Asn Val Asp Leu Val Phe Leu
145                 150                 155                 160
Phe Asp Gly Ser Met Ser Leu Gln Pro Asp Glu Phe Gln Lys Ile Leu
                165                 170                 175
Asp Phe Met Lys Asp Val Met Lys Lys Leu Ser Asn Thr Ser Tyr Gln
                180                 185                 190
Phe Ala Ala Val Gln Phe Ser Thr Ser Tyr Lys Thr Glu Phe Asp Phe
            195                 200                 205
Ser Asp Tyr Val Lys Arg Lys Asp Pro Asp Ala Leu Leu Lys His Val
        210                 215                 220
Lys His Met Leu Leu Leu Thr Asn Thr Phe Gly Ala Ile Asn Tyr Val
225                 230                 235                 240
Ala Thr Glu Val Phe Arg Glu Glu Leu Gly Ala Arg Pro Asp Ala Thr
                245                 250                 255
Lys Val Leu Ile Ile Ile Thr Asp Gly Glu Ala Thr Asp Ser Gly Asn
                260                 265                 270
Ile Asp Ala Ala Lys Asp Ile Ile Arg Tyr Ile Ile Gly Ile Gly Lys
            275                 280                 285
His Phe Gln Thr Lys Glu Ser Gln Glu Thr Leu His Lys Phe Ala Ser
        290                 295                 300
Lys Pro Ala Ser Glu Phe Val Lys Ile Leu Asp Thr Phe Glu Lys Leu
305                 310                 315                 320
Lys Asp Leu Phe Thr Glu Leu Gln Lys Lys Ile Tyr Val Ile Glu Gly
                325                 330                 335
Thr Ser Lys Gln Asp Leu Thr Ser Phe Asn Met Glu Leu Ser Ser Ser
                340                 345                 350
Gly Ile Ser Ala Asp Leu Ser Arg Gly His Ala Val Val Gly Ala Val
            355                 360                 365
Gly Ala Lys Asp Trp Ala Gly Gly Phe Leu Asp Leu Lys Ala Asp Leu
        370                 375                 380
Gln Asp Asp Thr Phe Ile Gly Asn Glu Pro Leu Thr Pro Glu Val Arg
385                 390                 395                 400
Ala Gly Tyr Leu Gly Tyr Thr Val Thr Trp Leu Pro Ser Arg Gln Lys
                405                 410                 415
Thr Ser Leu Leu Ala Ser Gly Ala Pro Arg Tyr Gln His Met Gly Arg
                420                 425                 430
Val Leu Leu Phe Gln Glu Pro Gln Gly Gly His Trp Ser Gln Val
            435                 440                 445
Gln Thr Ile His Gly Thr Gln Ile Gly Ser Tyr Phe Gly Gly Glu Leu
        450                 455                 460
Cys Gly Val Asp Val Asp Gln Asp Gly Glu Thr Glu Leu Leu Leu Ile
465                 470                 475                 480
Gly Ala Pro Leu Phe Tyr Gly Glu Gln Arg Gly Gly Arg Val Phe Ile
                485                 490                 495
```

-continued

Tyr Gln Arg Arg Gln Leu Gly Phe Glu Glu Val Ser Glu Leu Gln Gly
            500                 505                 510

Asp Pro Gly Tyr Pro Leu Gly Arg Phe Gly Glu Ala Ile Thr Ala Leu
            515                 520                 525

Thr Asp Ile Asn Gly Asp Gly Leu Val Asp Val Ala Val Gly Ala Pro
530                 535                 540

Leu Glu Glu Gln Gly Ala Val Tyr Ile Phe Asn Gly Arg His Gly Gly
545                 550                 555                 560

Leu Ser Pro Gln Pro Ser Gln Arg Ile Glu Gly Thr Gln Val Leu Ser
            565                 570                 575

Gly Ile Gln Trp Phe Gly Arg Ser Ile His Gly Val Lys Asp Leu Glu
            580                 585                 590

Gly Asp Gly Leu Ala Asp Val Ala Val Gly Ala Glu Ser Gln Met Ile
            595                 600                 605

Val Leu Ser Ser Arg Pro Val Val Asp Met Val Thr Leu Met Ser Phe
            610                 615                 620

Ser Pro Ala Glu Ile Pro Val His Glu Val Glu Cys Ser Tyr Ser Thr
625                 630                 635                 640

Ser Asn Lys Met Lys Glu Gly Val Asn Ile Thr Ile Cys Phe Gln Ile
            645                 650                 655

Lys Ser Leu Ile Pro Gln Phe Gln Gly Arg Leu Val Ala Asn Leu Thr
            660                 665                 670

Tyr Thr Leu Gln Leu Asp Gly His Arg Thr Arg Arg Arg Gly Leu Phe
            675                 680                 685

Pro Gly Gly Arg His Glu Leu Arg Arg Asn Ile Ala Val Thr Thr Ser
            690                 695                 700

Met Ser Cys Thr Asp Phe Ser Phe His Phe Pro Val Cys Val Gln Asp
705                 710                 715                 720

Leu Ile Ser Pro Ile Asn Val Ser Leu Asn Phe Ser Leu Trp Glu Glu
            725                 730                 735

Glu Gly Thr Pro Arg Asp Gln Arg Ala Gln Gly Lys Asp Ile Pro Pro
            740                 745                 750

Ile Leu Arg Pro Ser Leu His Ser Glu Thr Trp Glu Ile Pro Phe Glu
            755                 760                 765

Lys Asn Cys Gly Glu Asp Lys Lys Cys Glu Ala Asn Leu Arg Val Ser
            770                 775                 780

Phe Ser Pro Ala Arg Ser Arg Ala Leu Arg Leu Thr Ala Phe Ala Ser
785                 790                 795                 800

Leu Ser Val Glu Leu Ser Leu Ser Asn Leu Glu Glu Asp Ala Tyr Trp
            805                 810                 815

Val Gln Leu Asp Leu His Phe Pro Pro Gly Leu Ser Phe Arg Lys Val
            820                 825                 830

Glu Met Leu Lys Pro His Ser Gln Ile Pro Val Ser Cys Glu Glu Leu
            835                 840                 845

Pro Glu Glu Ser Arg Leu Leu Ser Arg Ala Leu Ser Cys Asn Val Ser
            850                 855                 860

Ser Pro Ile Phe Lys Ala Gly His Ser Val Ala Leu Gln Met Met Phe
865                 870                 875                 880

Asn Thr Leu Val Asn Ser Ser Trp Gly Asp Ser Val Glu Leu His Ala
            885                 890                 895

Asn Val Thr Cys Asn Asn Glu Asp Ser Asp Leu Leu Glu Asp Asn Ser
            900                 905                 910

Ala Thr Thr Ile Ile Pro Ile Leu Tyr Pro Ile Asn Ile Leu Ile Gln
            915                 920                 925

Asp Gln Glu Asp Ser Thr Leu Tyr Val Ser Phe Thr Pro Lys Gly Pro
        930                 935                 940

Lys Ile His Gln Val Lys His Met Tyr Gln Val Arg Ile Gln Pro Ser
945                 950                 955                 960

Ile His Asp His Asn Ile Pro Thr Leu Glu Ala Val Val Gly Val Pro
                965                 970                 975

Gln Pro Pro Ser Glu Gly Pro Ile Thr His Gln Trp Ser Val Gln Met
            980                 985                 990

Glu Pro Pro Val Pro Cys His Tyr Glu Asp Leu Glu Arg Leu Pro Asp
        995                1000                1005

Ala Ala Glu Pro Cys Leu Pro Gly Ala Leu Phe Arg Cys Pro Val
    1010                1015                1020

Val Phe Arg Gln Glu Ile Leu Val Gln Val Ile Gly Thr Leu Glu
    1025                1030                1035

Leu Val Gly Glu Ile Glu Ala Ser Ser Met Phe Ser Leu Cys Ser
    1040                1045                1050

Ser Leu Ser Ile Ser Phe Asn Ser Ser Lys His Phe His Leu Tyr
    1055                1060                1065

Gly Ser Asn Ala Ser Leu Ala Gln Val Val Met Lys Val Asp Val
    1070                1075                1080

Val Tyr Glu Lys Gln Met Leu Tyr Leu Tyr Val Leu Ser Gly Ile
    1085                1090                1095

Gly Gly Leu Leu Leu Leu Leu Ile Phe Ile Val Leu Tyr Lys
    1100                1105                1110

Val Gly Phe Phe Lys Arg Asn Leu Lys Glu Lys Met Glu Ala Gly
    1115                1120                1125

Arg Gly Val Pro Asn Gly Ile Pro Ala Glu Asp Ser Glu Gln Leu
    1130                1135                1140

Ala Ser Gly Gln Glu Ala Gly Asp Pro Gly Cys Leu Lys Pro Leu
    1145                1150                1155

His Glu Lys Asp Ser Glu Ser Gly Gly Gly Lys Asp
    1160                1165                1170

<210> SEQ ID NO 83
<211> LENGTH: 1152
<212> TYPE: PRT
<213> ORGANISM: Homo sapiens

<400> SEQUENCE: 83

Met Ala Leu Arg Val Leu Leu Leu Thr Ala Leu Thr Leu Cys His Gly
1               5                   10                  15

Phe Asn Leu Asp Thr Glu Asn Ala Met Thr Phe Gln Glu Asn Ala Arg
            20                  25                  30

Gly Phe Gly Gln Ser Val Val Gln Leu Gln Gly Ser Arg Val Val Val
        35                  40                  45

Gly Ala Pro Gln Glu Ile Val Ala Ala Asn Gln Arg Gly Ser Leu Tyr
    50                  55                  60

Gln Cys Asp Tyr Ser Thr Gly Ser Cys Glu Pro Ile Arg Leu Gln Val
65                  70                  75                  80

Pro Val Glu Ala Val Asn Met Ser Leu Gly Leu Ser Leu Ala Ala Thr
                85                  90                  95

Thr Ser Pro Pro Gln Leu Leu Ala Cys Gly Pro Thr Val His Gln Thr
            100                 105                 110

Cys Ser Glu Asn Thr Tyr Val Lys Gly Leu Cys Phe Leu Phe Gly Ser
                115                 120                 125

Asn Leu Arg Gln Gln Pro Gln Lys Phe Pro Glu Ala Leu Arg Gly Cys
        130                 135                 140

Pro Gln Glu Asp Ser Asp Ile Ala Phe Leu Ile Asp Gly Ser Gly Ser
145                 150                 155                 160

Ile Ile Pro His Asp Phe Arg Arg Met Lys Glu Phe Val Ser Thr Val
                165                 170                 175

Met Glu Gln Leu Lys Lys Ser Lys Thr Leu Phe Ser Leu Met Gln Tyr
                180                 185                 190

Ser Glu Glu Phe Arg Ile His Phe Thr Phe Lys Glu Phe Gln Asn Asn
                195                 200                 205

Pro Asn Pro Arg Ser Leu Val Lys Pro Ile Thr Gln Leu Leu Gly Arg
        210                 215                 220

Thr His Thr Ala Thr Gly Ile Arg Lys Val Val Arg Glu Leu Phe Asn
225                 230                 235                 240

Ile Thr Asn Gly Ala Arg Lys Asn Ala Phe Lys Ile Leu Val Val Ile
                245                 250                 255

Thr Asp Gly Glu Lys Phe Gly Asp Pro Leu Gly Tyr Glu Asp Val Ile
                260                 265                 270

Pro Glu Ala Asp Arg Glu Gly Val Ile Arg Tyr Val Ile Gly Val Gly
        275                 280                 285

Asp Ala Phe Arg Ser Glu Lys Ser Arg Gln Glu Leu Asn Thr Ile Ala
        290                 295                 300

Ser Lys Pro Pro Arg Asp His Val Phe Gln Val Asn Asn Phe Glu Ala
305                 310                 315                 320

Leu Lys Thr Ile Gln Asn Gln Leu Arg Glu Lys Ile Phe Ala Ile Glu
                325                 330                 335

Gly Thr Gln Thr Gly Ser Ser Ser Phe Glu His Glu Met Ser Gln
                340                 345                 350

Glu Gly Phe Ser Ala Ala Ile Thr Ser Asn Gly Pro Leu Leu Ser Thr
        355                 360                 365

Val Gly Ser Tyr Asp Trp Ala Gly Gly Val Phe Leu Tyr Thr Ser Lys
        370                 375                 380

Glu Lys Ser Thr Phe Ile Asn Met Thr Arg Val Asp Ser Asp Met Asn
385                 390                 395                 400

Asp Ala Tyr Leu Gly Tyr Ala Ala Ala Ile Ile Leu Arg Asn Arg Val
                405                 410                 415

Gln Ser Leu Val Leu Gly Ala Pro Arg Tyr Gln His Ile Gly Leu Val
                420                 425                 430

Ala Met Phe Arg Gln Asn Thr Gly Met Trp Glu Ser Asn Ala Asn Val
                435                 440                 445

Lys Gly Thr Gln Ile Gly Ala Tyr Phe Gly Ala Ser Leu Cys Ser Val
        450                 455                 460

Asp Val Asp Ser Asn Gly Ser Thr Asp Leu Val Leu Ile Gly Ala Pro
465                 470                 475                 480

His Tyr Tyr Glu Gln Thr Arg Gly Gly Gln Val Ser Val Cys Pro Leu
                485                 490                 495

Pro Arg Gly Arg Ala Arg Trp Gln Cys Asp Ala Val Leu Tyr Gly Glu
        500                 505                 510

Gln Gly Gln Pro Trp Gly Arg Phe Gly Ala Ala Leu Thr Val Leu Gly
        515                 520                 525

```
Asp Val Asn Gly Asp Lys Leu Thr Asp Val Ala Ile Gly Ala Pro Gly
    530                 535                 540

Glu Glu Asp Asn Arg Gly Ala Val Tyr Leu Phe His Gly Thr Ser Gly
545                 550                 555                 560

Ser Gly Ile Ser Pro Ser His Ser Gln Arg Ile Ala Gly Ser Lys Leu
            565                 570                 575

Ser Pro Arg Leu Gln Tyr Phe Gly Gln Ser Leu Ser Gly Gly Gln Asp
            580                 585                 590

Leu Thr Met Asp Gly Leu Val Asp Leu Thr Val Gly Ala Gln Gly His
        595                 600                 605

Val Leu Leu Leu Arg Ser Gln Pro Val Leu Arg Val Lys Ala Ile Met
    610                 615                 620

Glu Phe Asn Pro Arg Glu Val Ala Arg Asn Val Phe Glu Cys Asn Asp
625                 630                 635                 640

Gln Val Val Lys Gly Lys Glu Ala Gly Glu Val Arg Val Cys Leu His
            645                 650                 655

Val Gln Lys Ser Thr Arg Asp Arg Leu Arg Glu Gly Gln Ile Gln Ser
            660                 665                 670

Val Val Thr Tyr Asp Leu Ala Leu Asp Ser Gly Arg Pro His Ser Arg
        675                 680                 685

Ala Val Phe Asn Glu Thr Lys Asn Ser Thr Arg Arg Gln Thr Gln Val
    690                 695                 700

Leu Gly Leu Thr Gln Thr Cys Glu Thr Leu Lys Leu Gln Leu Pro Asn
705                 710                 715                 720

Cys Ile Glu Asp Pro Val Ser Pro Ile Val Leu Arg Leu Asn Phe Ser
            725                 730                 735

Leu Val Gly Thr Pro Leu Ser Ala Phe Gly Asn Leu Arg Pro Val Leu
            740                 745                 750

Ala Glu Asp Ala Gln Arg Leu Phe Thr Ala Leu Phe Pro Phe Glu Lys
        755                 760                 765

Asn Cys Gly Asn Asp Asn Ile Cys Gln Asp Asp Leu Ser Ile Thr Phe
    770                 775                 780

Ser Phe Met Ser Leu Asp Cys Leu Val Val Gly Gly Pro Arg Glu Phe
785                 790                 795                 800

Asn Val Thr Val Thr Val Arg Asn Asp Gly Glu Asp Ser Tyr Arg Thr
            805                 810                 815

Gln Val Thr Phe Phe Pro Leu Asp Leu Ser Tyr Arg Lys Val Ser
            820                 825                 830

Thr Leu Gln Asn Gln Arg Ser Gln Arg Ser Trp Arg Leu Ala Cys Glu
        835                 840                 845

Ser Ala Ser Ser Thr Glu Val Ser Gly Ala Leu Lys Ser Thr Ser Cys
    850                 855                 860

Ser Ile Asn His Pro Ile Phe Pro Glu Asn Ser Glu Val Thr Phe Asn
865                 870                 875                 880

Ile Thr Phe Asp Val Asp Ser Lys Ala Ser Leu Gly Asn Lys Leu Leu
            885                 890                 895

Leu Lys Ala Asn Val Thr Ser Glu Asn Asn Met Pro Arg Thr Asn Lys
            900                 905                 910

Thr Glu Phe Gln Leu Glu Leu Pro Val Lys Tyr Ala Val Tyr Met Val
        915                 920                 925

Val Thr Ser His Gly Val Ser Thr Lys Tyr Leu Asn Phe Thr Ala Ser
    930                 935                 940

Glu Asn Thr Ser Arg Val Met Gln His Gln Tyr Gln Val Ser Asn Leu
```

```
                945                 950                 955                 960
       Gly Gln Arg Ser Leu Pro Ile Ser Leu Val Phe Leu Val Pro Val Arg
                           965                 970                 975
       Leu Asn Gln Thr Val Ile Trp Asp Arg Pro Gln Val Thr Phe Ser Glu
                   980                 985                 990
       Asn Leu Ser Ser Thr Cys His Thr Lys Glu Arg Leu Pro Ser His Ser
               995                 1000                1005
       Asp Phe Leu Ala Glu Leu Arg Lys Ala Pro Val Val Asn Cys Ser
           1010                1015                1020
       Ile Ala Val Cys Gln Arg Ile Gln Cys Asp Ile Pro Phe Phe Gly
           1025                1030                1035
       Ile Gln Glu Glu Phe Asn Ala Thr Leu Lys Gly Asn Leu Ser Phe
           1040                1045                1050
       Asp Trp Tyr Ile Lys Thr Ser His Asn His Leu Leu Ile Val Ser
           1055                1060                1065
       Thr Ala Glu Ile Leu Phe Asn Asp Ser Val Phe Thr Leu Leu Pro
           1070                1075                1080
       Gly Gln Gly Ala Phe Val Arg Ser Gln Thr Glu Thr Lys Val Glu
           1085                1090                1095
       Pro Phe Glu Val Pro Asn Pro Leu Pro Leu Ile Val Gly Ser Ser
           1100                1105                1110
       Val Gly Gly Leu Leu Leu Leu Ala Leu Ile Thr Ala Ala Leu Tyr
           1115                1120                1125
       Lys Leu Gly Phe Phe Lys Arg Gln Tyr Lys Asp Met Met Ser Glu
           1130                1135                1140
       Gly Gly Pro Pro Gly Ala Glu Pro Gln
           1145                1150

<210> SEQ ID NO 84
<211> LENGTH: 1163
<212> TYPE: PRT
<213> ORGANISM: Homo sapiens

<400> SEQUENCE: 84

Met Thr Arg Thr Arg Ala Ala Leu Leu Leu Phe Thr Ala Leu Ala Thr
 1               5                   10                  15

Ser Leu Gly Phe Asn Leu Asp Thr Glu Glu Leu Thr Ala Phe Arg Val
                20                  25                  30

Asp Ser Ala Gly Phe Gly Asp Ser Val Val Gln Tyr Ala Asn Ser Trp
            35                  40                  45

Val Val Val Gly Ala Pro Gln Lys Ile Thr Ala Ala Asn Gln Thr Gly
        50                  55                  60

Gly Leu Tyr Gln Cys Gly Tyr Ser Thr Gly Ala Cys Glu Pro Ile Gly
65                  70                  75                  80

Leu Gln Val Pro Pro Glu Ala Val Asn Met Ser Leu Gly Leu Ser Leu
                85                  90                  95

Ala Ser Thr Thr Ser Pro Ser Gln Leu Leu Ala Cys Gly Pro Thr Val
                100                 105                 110

His His Glu Cys Gly Arg Asn Met Tyr Leu Thr Gly Leu Cys Phe Leu
            115                 120                 125

Leu Gly Pro Thr Gln Leu Thr Gln Arg Leu Pro Val Ser Arg Gln Glu
        130                 135                 140

Cys Pro Arg Gln Glu Gln Asp Ile Val Phe Leu Ile Asp Gly Ser Gly
145                 150                 155                 160
```

```
Ser Ile Ser Ser Arg Asn Phe Ala Thr Met Met Asn Phe Val Arg Ala
                165                 170                 175

Val Ile Ser Gln Phe Gln Arg Pro Ser Thr Gln Phe Ser Leu Met Gln
            180                 185                 190

Phe Ser Asn Lys Phe Gln Thr His Phe Thr Phe Glu Glu Phe Arg Arg
        195                 200                 205

Ser Ser Asn Pro Leu Ser Leu Leu Ala Ser Val His Gln Leu Gln Gly
    210                 215                 220

Phe Thr Tyr Thr Ala Thr Ala Ile Gln Asn Val Val His Arg Leu Phe
225                 230                 235                 240

His Ala Ser Tyr Gly Arg Arg Asp Ala Ala Lys Ile Leu Ile Val
                245                 250                 255

Ile Thr Asp Gly Lys Lys Glu Gly Asp Ser Leu Asp Tyr Lys Asp Val
                260                 265                 270

Ile Pro Met Ala Asp Ala Ala Gly Ile Ile Arg Tyr Ala Ile Gly Val
            275                 280                 285

Gly Leu Ala Phe Gln Asn Arg Asn Ser Trp Lys Glu Leu Asn Asp Ile
        290                 295                 300

Ala Ser Lys Pro Ser Gln Glu His Ile Phe Lys Val Glu Asp Phe Asp
305                 310                 315                 320

Ala Leu Lys Asp Ile Gln Asn Gln Leu Lys Glu Lys Ile Phe Ala Ile
                325                 330                 335

Glu Gly Thr Glu Thr Thr Ser Ser Ser Phe Glu Leu Glu Met Ala
                340                 345                 350

Gln Glu Gly Phe Ser Ala Val Phe Thr Pro Asp Gly Pro Val Leu Gly
            355                 360                 365

Ala Val Gly Ser Phe Thr Trp Ser Gly Gly Ala Phe Leu Tyr Pro Pro
        370                 375                 380

Asn Met Ser Pro Thr Phe Ile Asn Met Ser Gln Glu Asn Val Asp Met
385                 390                 395                 400

Arg Asp Ser Tyr Leu Gly Tyr Ser Thr Glu Leu Ala Leu Trp Lys Gly
                405                 410                 415

Val Gln Ser Leu Val Leu Gly Ala Pro Arg Tyr Gln His Thr Gly Lys
            420                 425                 430

Ala Val Ile Phe Thr Gln Val Ser Arg Gln Trp Arg Met Lys Ala Glu
        435                 440                 445

Val Thr Gly Thr Gln Ile Gly Ser Tyr Phe Gly Ala Ser Leu Cys Ser
        450                 455                 460

Val Asp Val Asp Ser Asp Gly Ser Thr Asp Leu Val Leu Ile Gly Ala
465                 470                 475                 480

Pro His Tyr Tyr Glu Gln Thr Arg Gly Gly Gln Val Ser Val Cys Pro
                485                 490                 495

Leu Pro Arg Gly Trp Arg Arg Trp Cys Asp Ala Val Leu Tyr Gly
            500                 505                 510

Glu Gln Gly His Pro Trp Gly Arg Phe Gly Ala Ala Leu Thr Val Leu
        515                 520                 525

Gly Asp Val Asn Gly Asp Lys Leu Thr Asp Val Val Ile Gly Ala Pro
530                 535                 540

Gly Glu Glu Glu Asn Arg Gly Ala Val Tyr Leu Phe His Gly Val Leu
545                 550                 555                 560

Gly Pro Ser Ile Ser Pro Ser His Ser Gln Arg Ile Ala Gly Ser Gln
                565                 570                 575

Leu Ser Ser Arg Leu Gln Tyr Phe Gly Gln Ala Leu Ser Gly Gly Gln
```

-continued

```
            580               585               590
Asp Leu Thr Gln Asp Gly Leu Val Asp Leu Ala Val Gly Ala Arg Gly
            595               600               605
Gln Val Leu Leu Leu Arg Thr Arg Pro Val Leu Trp Val Gly Val Ser
            610               615               620
Met Gln Phe Ile Pro Ala Glu Ile Pro Arg Ser Ala Phe Glu Cys Arg
625               630               635               640
Glu Gln Val Val Ser Glu Gln Thr Leu Val Gln Ser Asn Ile Cys Leu
            645               650               655
Tyr Ile Asp Lys Arg Ser Lys Asn Leu Leu Gly Ser Arg Asp Leu Gln
            660               665               670
Ser Ser Val Thr Leu Asp Leu Ala Leu Asp Pro Gly Arg Leu Ser Pro
            675               680               685
Arg Ala Thr Phe Gln Glu Thr Lys Asn Arg Ser Leu Ser Arg Val Arg
            690               695               700
Val Leu Gly Leu Lys Ala His Cys Glu Asn Phe Asn Leu Leu Leu Pro
705               710               715               720
Ser Cys Val Glu Asp Ser Val Thr Pro Ile Thr Leu Arg Leu Asn Phe
            725               730               735
Thr Leu Val Gly Lys Pro Leu Leu Ala Phe Arg Asn Leu Arg Pro Met
            740               745               750
Leu Ala Ala Asp Ala Gln Arg Tyr Phe Thr Ala Ser Leu Pro Phe Glu
            755               760               765
Lys Asn Cys Gly Ala Asp His Ile Cys Gln Asp Asn Leu Gly Ile Ser
            770               775               780
Phe Ser Phe Pro Gly Leu Lys Ser Leu Leu Val Gly Ser Asn Leu Glu
785               790               795               800
Leu Asn Ala Glu Val Met Val Trp Asn Asp Gly Glu Asp Ser Tyr Gly
            805               810               815
Thr Thr Ile Thr Phe Ser His Pro Ala Gly Leu Ser Tyr Arg Tyr Val
            820               825               830
Ala Glu Gly Gln Lys Gln Gly Gln Leu Arg Ser Leu His Leu Thr Cys
            835               840               845
Asp Ser Ala Pro Val Gly Ser Gln Gly Thr Trp Ser Thr Ser Cys Arg
            850               855               860
Ile Asn His Leu Ile Phe Arg Gly Gly Ala Gln Ile Thr Phe Leu Ala
865               870               875               880
Thr Phe Asp Val Ser Pro Lys Ala Val Leu Gly Asp Arg Leu Leu Leu
            885               890               895
Thr Ala Asn Val Ser Ser Glu Asn Asn Thr Pro Arg Thr Ser Lys Thr
            900               905               910
Thr Phe Gln Leu Glu Leu Pro Val Lys Tyr Ala Val Tyr Thr Val Val
            915               920               925
Ser Ser His Glu Gln Phe Thr Lys Tyr Leu Asn Phe Ser Glu Ser Glu
            930               935               940
Glu Lys Glu Ser His Val Ala Met His Arg Tyr Gln Val Asn Asn Leu
945               950               955               960
Gly Gln Arg Asp Leu Pro Val Ser Ile Asn Phe Trp Val Pro Val Glu
            965               970               975
Leu Asn Gln Glu Ala Val Trp Met Asp Val Glu Val Ser His Pro Gln
            980               985               990
Asn Pro Ser Leu Arg Cys Ser Ser  Glu Lys Ile Ala Pro  Pro Ala Ser
            995               1000              1005
```

```
Asp Phe Leu Ala His Ile Gln  Lys Asn Pro Val Leu  Asp Cys Ser
    1010            1015             1020

Ile Ala Gly Cys Leu Arg Phe  Arg Cys Asp Val Pro  Ser Phe Ser
    1025            1030             1035

Val Gln Glu Glu Leu Asp Phe  Thr Leu Lys Gly Asn  Leu Ser Phe
    1040            1045             1050

Gly Trp Val Arg Gln Ile Leu  Gln Lys Lys Val Ser  Val Val Ser
    1055            1060             1065

Val Ala Glu Ile Thr Phe Asp  Thr Ser Val Tyr Ser  Gln Leu Pro
    1070            1075             1080

Gly Gln Glu Ala Phe Met Arg  Ala Gln Thr Thr Thr  Val Leu Glu
    1085            1090             1095

Lys Tyr Lys Val His Asn Pro  Thr Pro Leu Ile Val  Gly Ser Ser
    1100            1105             1110

Ile Gly Gly Leu Leu Leu Leu  Ala Leu Ile Thr Ala  Val Leu Tyr
    1115            1120             1125

Lys Val Gly Phe Phe Lys Arg  Gln Tyr Lys Glu Met  Met Glu Glu
    1130            1135             1140

Ala Asn Gly Gln Ile Ala Pro  Glu Asn Gly Thr Gln  Thr Pro Ser
    1145            1150             1155

Pro Pro Ser Glu Lys
    1160

<210> SEQ ID NO 85
<211> LENGTH: 4
<212> TYPE: PRT
<213> ORGANISM: Artificial Sequence
<220> FEATURE:
<223> OTHER INFORMATION: Linker sequence

<400> SEQUENCE: 85

Gly Asn Gly Ser
1

<210> SEQ ID NO 86
<211> LENGTH: 6
<212> TYPE: PRT
<213> ORGANISM: Artificial Sequence
<220> FEATURE:
<223> OTHER INFORMATION: TEV Protease

<400> SEQUENCE: 86

Glu Asn Leu Tyr Phe Gln
1               5
```

REAGENTS AND ASSAYS USING MODIFIED INTEGRIN DOMAINS

RELATED APPLICATIONS

This application claims the benefit of the filing date of U.S. Provisional Patent Application No. 62/827,461, filed Apr. 1, 2019, the contents of which is hereby incorporated by reference.

SEQUENCE LISTING

The instant application contains a Sequence Listing which has been submitted electronically in ASCII format and is hereby incorporated by reference in its entirety. The ASCII copy, created on Oct. 9, 2024, is named 42960-317688_Sequence Listing_ST25-10-9-24.txt and is 322 KB in size.

BACKGROUND

1. Technical Field

Modified integrin polypeptides, methods for identifying additional agents that can regulate integrin function via binding to sites away from the ligand binding pocket, such as via binding to allosteric sites and for identifying the additional agents that can regulate integrin function via binding to sites away from the ligand binding pocket are provided.

2. Background Information

Integrins are cell surface molecules that mediate important interactions between cells and between cells and the extracellular environment. Integrins can adopt at least two different conformations on cell surfaces: a non-activated conformation that does not bind to the integrin ligand (the "closed" or "unliganded" conformation") and an activated conformation that can bind the integrin ligand (the "open" or "liganded" conformation). Environmental and cellular signaling can cause integrins to alter their conformation from a non-activated conformation to an activated conformation. After activation, integrins bind in a specific manner to their cognate ligands on the surface of other cells, in the extracellular matrix, or that are assembled in the clotting or complement cascades.

Each integrin heterodimeric receptor includes an α subunit and a β subunit. Eighteen α subunits (α1-α11, αV, αIIb, αD, αE, αM, αL, αX) and eight β subunits (β-β8) have been identified in mammals. Two subfamilies can be identified depending on the presence or absence of an inserted or 'I' domain in the a subunit ('αI'). The I domain includes a central hydrophobic six-stranded β-sheet surrounded by seven α-helices, with a metal-ion dependent adhesion site (MIDAS) in the domain. In each of the nine al-containing integrins (α1, α2, α10, α11, αE, αD, αM, αL, αX), the MIDAS is important for ligand binding. I domains can exist in closed (inactive) or open (active) conformations. A domain sharing the same overall fold as the al domain is present in all β subunits (the I-like or 'βI' domain). Three closely linked metal ion binding sites in the β I domain are especially important in ligand binding. $Mg^{2+}$ at the central, metal ion-dependent adhesion site (MIDAS) site directly coordinates the acidic sidechain shared by the integrin ligands.

Integrins are involved in many cellular processes including, but not limited to inflammation, oncogenic cell transformation, metastasis, and apoptosis. Thus, there is considerable interest in identifying agents that can activate or inhibit the activity of one or more integrins.

Currently, a majority of antibodies and other agents used to regulate integrin binding (typically as antagonists) bind to the ligand binding domain, at a ligand binding site. While useful, many of these antibodies have not been very effective in vivo and in clinic. For example, Vitaxin antibody (a derivative of LM609 antibody that recognizes integrin αVβ3 at the ligand binding site (Borst 2017)) sterically blocks ligand binding, but has not been as effective in clinical trials (Raab-Westphal 2017). Similarly, AL-579 (a modified version of AL-57 antibody, that recognizes an active epitope of LFA-1 (Shimaoka 2006) does not sufficiently block migration of LFA-1 expressing cells in vivo, as it is a blocking antibody (Samy 2017). Additionally, very few cells in circulation express the activation epitope. Such epitopes may also be expressed at very low levels in normal, circulating cells, but are increased at their sites of adhesion or migration, which requires a non-blocking, activation epitope specific agent to bind there.

Since integrins can adopt at least two different conformations, there is a need for identifying agents such as antibodies and other binding agents that preferentially bind one conformation of integrin over other possible conformations. Furthermore, there is a need to identify such agents that do not bind the ligand binding pocket of the integrin or that do not prevent binding of integrins to its one or more different ligands.

Thus, there exists a need for reagents and methods for identifying additional agents that can regulate integrin function via binding to sites away from the ligand binding pocket, such as via binding to allosteric sites and for identifying additional agents that can regulate integrin function via binding to sites away from the ligand binding pocket.

BRIEF SUMMARY

Modified integrin polypeptides are provided. The modified integrin polypeptide includes at least one amino acid substitution in a metal ion binding site, where the metal ion binding site is selected from Metal Ion Dependent Adhesion Site (MIDAS), Adjacent to MIDAS (ADMIDAS) and ligand-associated metal binding site (LIMBS)/synergistic metal binding site (SyMBS) relative to a wild type integrin polypeptide.

Methods of identifying binding agents that bind to a modified integrin polypeptide are provided. The methods include providing a modified integrin polypeptide having at least one amino acid substitution compared to a wild type integrin polypeptide, contacting the modified integrin polypeptide with a plurality of binding agents, and identify binding agents that specifically bind to the modified integrin polypeptide.

BRIEF DESCRIPTION OF THE DRAWINGS

FIG. 1A illustrates traditional approaches to identifying agents that bind integrins.

FIG. 1B illustrates an embodiment of a method to identify agents that bind integrins.

FIG. 3 illustrates alignment of integrin βI-domains showing MIDAS, ADMIDAS and LIMBS/SyMBS sites. (ITB1_Human (SEQ ID NO: 8); ITB2-_Human (SEQ ID NO: 9); ITB3_Human (SEQ ID NO: 10); ITB4_Human (SEQ ID NO: 11); ITB5_Human (SEQ ID NO: 12); ITB6_Human (SEQ ID NO: 13); ITB7-_Human (SEQ ID NO: 14); ITB8_Human (SEQ ID NO: 15)).

DETAILED DESCRIPTION

Figure 2:
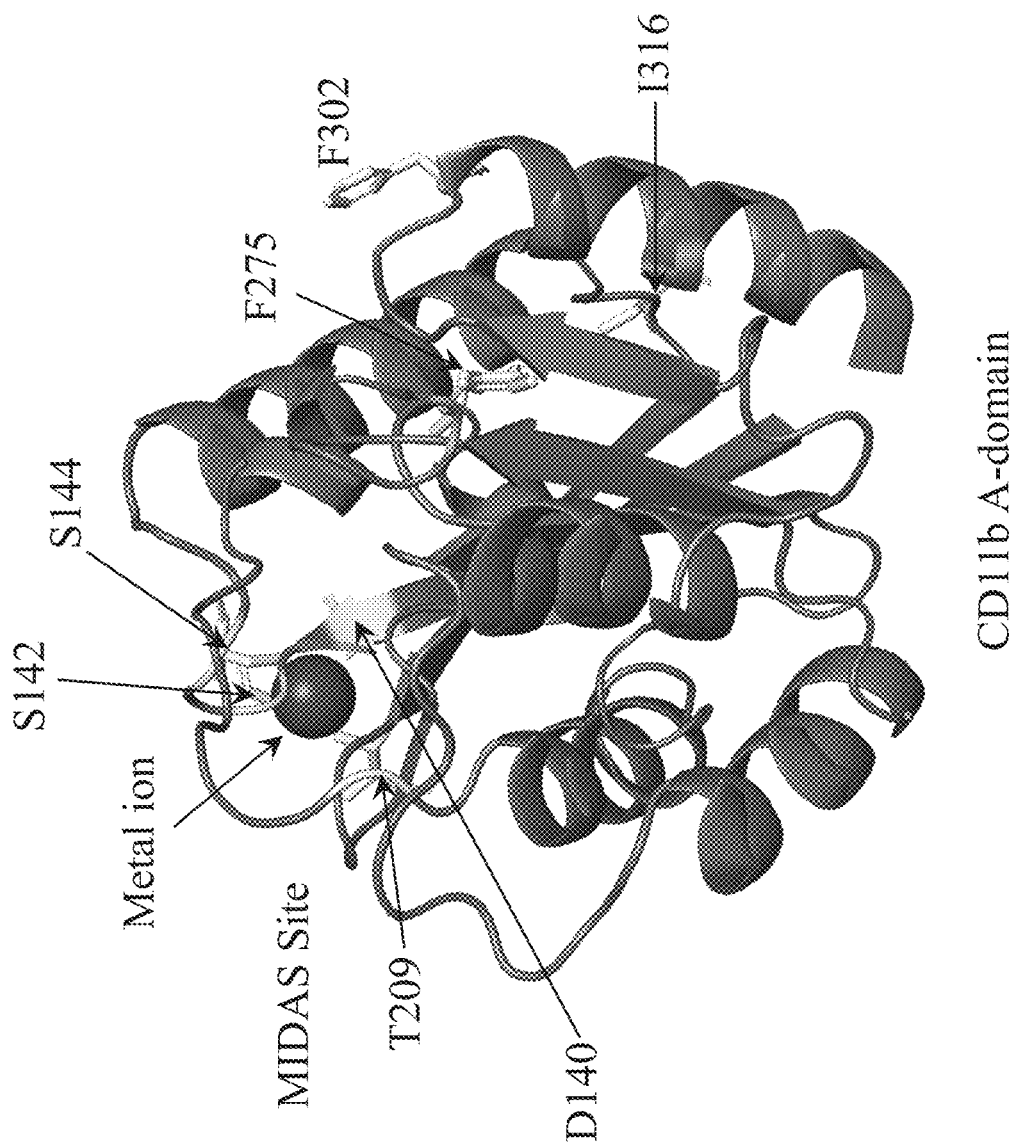
FIG. 2 illustrates the structure of CD11b A-Domain and the amino acid residues at the MIDAS site.

The embodiments disclosed below are not intended to be exhaustive or to limit the scope of the disclosure to the precise form in the following description. Rather, the embodiments are chosen and described as examples so that others skilled in the art may utilize its teachings.

Modified integrin polypeptides, methods for finding additional agents that can regulate integrin function via binding to sites away from the ligand binding pocket, such as via binding to allosteric sites and for identifying additional agents that can regulate integrin function via binding to sites away from the ligand binding pocket are provided.

Polypeptides derived from various domains of integrin chains that adopt a preferred conformation are provided. These integrin polypeptides can be utilized in assays to identify binding agents, such as antibodies and antibody fragments, that bind a pre-selected integrin domain or domain conformation. In some embodiments the binding agent binds to the integrin domain polypeptide at an allosteric site.

Definitions

The term "binding agent" refers to an agent that can interact with a target molecule. An "integrin binding agent" refers to an agent that can interact with an integrin polypeptide or fragment thereof. An integrin binding agent includes agents that preferentially interact with an integrin polypeptide or fragment thereof at a site away from the ligand binding pocket, such as via binding to allosteric sites.

A polypeptide that is "conformationally stabilized" or "fixed" is one that is held in a subset of the possible conformations that it could otherwise assume, generally due to the effects of a change introduced to a wild type polypeptide.

As used herein, the term "stabilizing disulfide bond" is used to describe substitution of at least one cysteine residue that permits the formation of a disulfide bond, which in turn prevents a conformational shift in the integrin polypeptide even in the presence of an activating ligand. The "stabilizing disulfide bond" is introduced to the polypeptide by substitution of a cysteine residue in an existing wild type amino acid and does not reflect a natural or native disulfide bond of the polypeptide.

An antibody or fragment thereof that binds to a specific conformation or conformational state of a polypeptide refers to an antibody or fragment thereof that binds with a higher affinity to a polypeptide in a subset of conformations or conformational states than to other conformations or conformational states that a polypeptide may assume.

The conformational state of a polypeptide is "active" when a subset of conformational states increases, opens, activates, facilitates, enhances activation, enhances binding, or up regulates the activity of the polypeptide by at least 10% over another conformation state of the polypeptide.

The conformational state of a polypeptide is "inactive" when a subset of conformational states decreases, closes, deactivates, hinders, diminishes activation, or diminishes binding, or down regulates the activity of the polypeptide by at least 10% over another conformation state of the polypeptide.

An "antibody" refers to a binding agent that is a polypeptide comprising at least a light chain or heavy chain immunoglobulin variable region which specifically recognizes and binds an epitope of a target antigen, such as a peptide, lipid, polysaccharide, or nucleic acid containing an antigenic determinant, such as those recognized by an immune cell. Antibodies include antigen binding fragments thereof. The term also includes genetically engineered forms such as chimeric antibodies (for example, humanized murine antibodies), hetero-conjugate antibodies (such as, bispecific antibodies) and antigen binding fragments thereof. See also, Pierce Catalog and Handbook, 1994-1995 (Pierce Chemical Co., Rockford, IL); Kuby, J., Immunology, 3rd Ed., W. H. Freeman & Co., New York, 1997.

Light and heavy chain variable regions contain a "framework" region interrupted by three hypervariable regions, also called "complementarity-determining regions" or "CDRs." The CDRs may be defined or identified by conventional methods, such as by sequence according to Kabat et al., (Wu, TT and Kabat, E. A., J Exp Med. 132 (2): 211-50, (1970); Borden, P. and Kabat E. A., PNAS, 84:2440-2443 (1987); (see, Kabat et al., Sequences of Proteins of Immunological Interest, U.S. Department of Health and Human Services, 1991, which is hereby incorporated by reference), or by structure according to Chothia et al (Choithia, C. and Lesk, A M., J Mal. Biol., 196 (4): 901-917 (1987), Choithia, C. et al, Nature, 342:877-883 (1989)).

The sequences of the framework regions of different light or heavy chains are relatively conserved within a species, such as humans. The framework region of an antibody, that is the combined framework regions of the constituent light and heavy chains, serves to position and align the CDRs in three-dimensional space. The CDRs are primarily responsible for binding to an epitope of an antigen. The CDRs of each chain are typically referred to as CDR1, CDR2, and CDR3, numbered sequentially starting from the N-terminus, and are also typically identified by the chain in which the particular CDR is located. Thus, the CDRs located in the variable domain of the heavy chain of the antibody are referred to as CDRH1, CDRH2, and CDRH3, whereas the CDRs located in the variable domain of the light chain of the antibody are referred to as CDRL1, CDRL2, and CDRL3. Antibodies with different specificities (i.e., different combining sites for different antigens) have different CDRs. Although it is the CDRs that vary from antibody to antibody, only a limited number of amino acid positions within the CDRs are directly involved in antigen binding. These positions within the CDRs are called specificity determining residues (SDRs).

References to "VH" or "VH" refer to the variable region of an immunoglobulin heavy chain, including that of an antibody, Fv, scFv, dsFv, Fab, or other antibody fragment as disclosed herein. References to "$V_L$" or "VL" refer to the variable region of an immunoglobulin light chain, including that of an antibody, Fv, scFv, dsFv, Fab, or other antibody fragment as disclosed herein.

A "monoclonal antibody" is an antibody produced by a single clone of B lymphocytes or by a cell into which the light and heavy chain genes of a single antibody have been transfected. Monoclonal antibodies are produced by methods known to those of skill in the art, for instance by making hybrid antibody-forming cells from a fusion of myeloma cells with immune spleen cells. Monoclonal antibodies include humanized monoclonal antibodies.

A "chimeric antibody" has framework residues from one species, such as human, and CDRs (which generally confer antigen binding) from another species, such as a mouse. In some embodiments, a CAR contemplated herein comprises antigen-specific binding domain that is a chimeric antibody or antigen binding fragment thereof.

In certain embodiments, the antibody is a humanized antibody (such as a humanized monoclonal antibody) that specifically binds to a surface protein on a tumor cell. A "humanized" antibody is an immunoglobulin including a human framework region and one or more CDRs from a non-human (for example a mouse, rat, or synthetic) immunoglobulin. Humanized antibodies may be constructed by means of genetic engineering (see for example, U.S. Pat. No. 5,585,089).

"Camel Ig" or "camelid VHH" as used herein refers to the smallest known antigen binding unit of a heavy chain antibody (Koch-Nolte, et al., FASEB J, 21:3490-3498 (2007)). A "heavy chain antibody" or a "camelid antibody" refers to an antibody that contains two VH domains and no light chains (Riechmann L. et al., J Immunol. Methods 231:25-38 (1999); WO94/04678; WO94/25591; U.S. Pat. No. 6,005,079).

"IgNAR" of "immunoglobulin new antigen receptor" refers to class of antibodies from the shark immune repertoire that consist of homodimers of one variable new antigen receptor (VNAR) domain and five constant new antigen receptor (CNAR) domains.

Papain digestion of antibodies produces two identical antigen-binding fragments, called "Fab" fragments, each with a single antigen-binding site, and a residual "Fc" fragment, whose name reflects its ability to crystallize readily. The Fab fragment contains the heavy- and light chain variable domains and also contains the constant domain of the light chain and the first constant domain (CH1) of the heavy chain. Fab' fragments differ from Fab fragments by the addition of a few residues at the carboxy terminus of the heavy chain CH1 domain including one or more cysteines from the antibody hinge region. Fab'-SH is the designation herein for Fab' in which the cysteine residue(s) of the constant domains bear a free thiol group. F(ab') 2 antibody fragments originally were produced as pairs of Fab' fragments which have hinge cysteines between them. Other chemical couplings of antibody fragments are also known.

"Fv" is the minimum antibody fragment which contains a complete antigen-binding site. In a single-chain Fv (scFv) species, one heavy- and one light-chain variable domain may be covalently linked by a flexible peptide linker such that the light and heavy chains may associate in a "dimeric" structure analogous to that in a two-chain Fv species.

The term "diabodies" refers to antibody fragments with two antigen-binding sites, which fragments comprise a heavy-chain variable domain (VH) connected to a light-chain variable domain (VL) in the same polypeptide chain (VH-VL). By using a linker that is too short to allow pairing between the two domains on the same chain, the domains are forced to pair with the complementary domains of another chain and create two antigen-binding sites. Diabodies may be bivalent or bispecific. Diabodies are described more fully in, for example, EP 404,097; WO 1993/01161; Hudson et al., Nat. Med. 9:129-134 (2003); and Hollinger et al., PNAS USA 90:6444-6448 (1993). Triabodies and tetrabodies are also described in Hudson et al., Nat. Med. 9:129-134 (2003).

"Single domain antibody" or "sdAb" or "nanobody" refers to an antibody fragment that consists of the variable region of an antibody heavy chain (VH domain) or the variable region of an antibody light chain (VL domain) (Holt, L., et al., Trends in Biotechnology, 21 (11): 484-490).

"Single-chain Fv" or "scFv" antibody fragments comprise the VH and VL domains of antibody, wherein these domains are present in a single polypeptide chain and in either orientation (e.g., VL-VH or VH-VL). Generally, the scFv polypeptide further comprises a polypeptide linker between the VH and VL domains which enables the scFv to form the desired structure for antigen binding. For a review of scFv, see, e.g., Pluckthin, in The Pharmacology of Monoclonal Antibodies, vol. 113, Rosenburg and Moore eds., (Springer-Verlag, New York, 1994), pp. 269-315.

The practice of the disclosure will employ, unless indicated specifically to the contrary, conventional methods of chemistry, biochemistry, organic chemistry, molecular biology, microbiology, recombinant DNA techniques, genetics, immunology, and cell biology that are within the skill of the art, many of which are described below for the purpose of illustration. Such techniques are explained fully in the literature. See, e.g., Sambrook, et al., *Molecular Cloning: A Laboratory Manual* (3rd Edition, 2001); *Sambrook, et al., Molecular Cloning: A Laboratory Manual* (2nd Edition, 1989); *Maniatis et al., Molecular Cloning: A Laboratory Manual* (1982); Ausubel et al., *Current Protocols in Molecular Biology* (John Wiley and Sons, updated July 2008); *Short Protocols in Molecular Biology: A Compendium of Methods from Current Protocols in Molecular Biology*, Greene Pub. Associates and Wiley—Interscience; Glover, *DNA Cloning: A Practical Approach*, vol. I & II (IRL Press, Oxford, 1985); Anand, Techniques for the Analysis of Complex Genomes, (Academic Press, New York, 1992); *Transcription and Translation* (B. Hames & S. Higgins, Eds., 1984); Perbal, *A Practical Guide to Molecular Cloning* (1984); Harlow and Lane, *Antibodies*, (Cold Spring Harbor Laboratory Press, Cold Spring Harbor, N.Y., 1998) *Current Protocols in Immunology* Q. E. Coligan, A. M. Kruisbeek, D. H. Margulies, E. M. Shevach and W. Strober, eds., 1991); *Annual Review of Immunology*; as well as monographs in journals such as Advances in Immunology.

All publications, patents and patent applications cited herein are hereby incorporated by reference in their entirety.

Modified Integrin Polypeptides

Current approaches for identifying antibodies against various integrin domains rely on using either polypeptides, purified proteins or cell-expressed proteins. Approaches also involve in vitro methods, in vivo methods or a combination of both. The integrin beta chain A-domain (βA, also known as beta I-like domain (βI)) is the primary ligand binding domain in most integrins, except for the αA-domain containing integrins, where the alpha chain A-domain (αA, also known as I-domain (αI)) is the primary ligand binding domain. Thus, these domains are also ideal target for agents to regulate integrin function. Many approaches have also utilized the integrin alpha chain A-domain (αA, also known as I-domain (αI)) or the beta chain A-domain (βA, also known as beta I-like domain (βI)). These domains contain the metal ion binding sites MIDAS, ADMIDAS, and LIMBS/SyMBS. Integrins typically use their Metal Ion Dependent Adhesion Site (MIDAS) to engage and bind their ligands. Previous approaches have utilized recombinant or cell expressed protein domains (whether wild type or mutant) with their metal ion binding amino acids intact. As described above, these residues coordinate a metal ion and use to engage their respective ligands.

However, the metal ions are highly antigenic. Therefore, in many cases, in screening assays to identify antibodies, a metal coordinating site acts as an antigen and leads to a higher number of agents recognizing that site versus other sites (FIG. 1A). A recent study screening showed that MIDAS site was the key epitope for enriched binders from a phage-display library (Hu 2010). This makes identification of allosteric binders (to other sites) more difficult. This is also reflected in the literature, where one finds a prevalence of antibodies against the ligand binding sites of integrin domains, versus other regions of the protein. For example, mAb AL-57 against αA-domain of CD11a; mAbs 107, AM01 and AM17 against αA domain of CD11b all bind the MIDAS site and block ligand binding.

In the present disclosure, a novel approach is disclosed for designing modified integrin domains for screening assays to identify allosteric modulators. The modified integrin domains may include just a modified integrin I-domain from an integrin a subunit, or the entire mature a subunit extracellular domain, or the entire mature a subunit, and/or may be further associated with an integrin β subunit extracellular domain and/or entire subunit. In one embodiment, a modified integrin I-domain polypeptide is a soluble protein, e.g., a heterodimeric soluble protein, or a monomeric soluble protein. In some embodiments, the modified integrin domains may be conformationally biased integrin polypeptides. In some embodiments, the approach uses recombinant or cell-expressed polypeptides containing the αA or βA domains of integrins, where the domains include substituted amino acids compared to the wild type integrin domains and in some embodiments the modified integrin polypeptides are stabilized into preferred conformations using site directed mutagenesis, as exemplified below. Additionally, the integrin domains are designed such that their ability to coordinate metal ions in the MIDAS, ADMIDAS, LIMBS/SyMBS sites are significantly modified. Literature reports describe crystal structure of many of these domains and the exact residues that coordinate metal ion binding. Thus, these variants also have no or highly reduced capacity for ligand binding via metal ion engagement. Examples of such substitutions are changing one or more amino acids that coordinate metal ion binding via the amino acid side chain. Non-limiting examples include changing Glutamate (D), Aspartate (E), Serine(S), Threonine (T) to Alanine (A), Glycine (G), leucine (L), isoleucine (I) or Valine (V), such that the amino acid side chains at these sites do not have polar atoms available for coordinating to metal ions. In accordance with the present disclosure, an intact metal ion binding is not necessary for an integrin/domain to adopt a pre-specified conformation (closed or open) and that removing metal ion binding site, which is highly antigenic, allows for identification of binders/antibodies to other sites on the integrin/domain.

In some embodiments, the variant integrin polypeptides described herein selectively impair binding of metal ions to the metal-ion dependent binding sites and, thus, reduce the increased antigenicity of those sites. This allows for identification of agents that bind and potentially regulate integrin function, especially agents that bind allosteric sites. Thus, these polypeptides are useful in screening assays.

Conformationally Stabilized Integrin Polypeptides

In some embodiments, methods for stabilizing a polypeptide, e.g., a polypeptide comprising a functional domain of a protein, in a desired conformation, while missing metal ion coordination sites are provided. Such methods include introducing disulfide bond(s) into the polypeptide, or mutation of certain residues, such that the polypeptide is stabilized in a desired conformation. These approaches can be applied to human integrins as well as integrins from other species. Additionally, it can be applied to other integrin like proteins (e.g.; Wang 2017).

Screening Assays polypeptides of the present disclosure may be altered in various ways including amino acid substitutions, deletions, truncations, and insertions. Methods for such manipulations are generally known in the art. For example, amino acid sequence variants of a reference polypeptide may be prepared by mutations in the DNA. Methods for mutagenesis and nucleotide sequence alterations are well known in the art. See, for example, Kunkel (1985, Proc. Natl. Acad. Sci. USA. 82:488-492), Kunkel et al., (1987, Methods in Enzymol, 154:367-382), U.S. Pat. No. 4,873,192, Watson, J. D. et al., (Molecular Biology of the Gene, Fourth Edition, Benjamin/Cummings, Menlo Park, Calif., 1987) and the references cited therein. Guidance as to appropriate amino acid substitutions that do not affect biological activity of the protein of interest may be found in the model of Dayhoff et al., (1978) Atlas of Protein Sequence and Structure (Natl. Biomed. Res. Found., Washington, D.C.).

Recombinant Expression Vectors and Host Cells

In some embodiments, vectors, for example, recombinant expression vectors, containing a nucleic acid encoding a modified integrin polypeptide (or a portion thereof), e.g., an integrin I-domain or I-like domain polypeptide or fusion protein are disclosed. The term "vector" is used herein to refer to a nucleic acid molecule capable transferring or transporting another nucleic acid molecule. The transferred nucleic acid is generally linked to, e.g., inserted into, the vector nucleic acid molecule. A vector may include sequences that direct autonomous replication in a cell, or may include sequences sufficient to allow integration into host cell DNA. Examples of vectors are plasmids (e.g., DNA plasmids or RNA plasmids), autonomously replicating sequences, and transposable elements. Additional exemplary vectors include, without limitation, plasmids, phagemids, cosmids, artificial chromosomes such as yeast artificial chromosome (YAC), bacterial artificial chromosome (BAC), or PI-derived artificial chromosome (PAC), bacteriophages such as lambda phage or M13 phage, and animal viruses. Examples of categories of animal viruses useful as vectors include, without limitation, retrovirus (including lentivirus), adenovirus, adeno-associated virus, herpesvirus (e.g., herpes simplex virus), poxvirus, baculovirus, papillomavirus, and papovavirus (e.g., SV40). Examples of expression vectors are pClneo vectors (Promega) for expression in mammalian cells; pLenti4N5-DEST™, pLenti6N5-DEST™, and pLenti6.2N5-GW/lacZ (Invitrogen) for lentivirus-mediated gene transfer and expression in mammalian cells. In certain embodiments, useful viral vectors include, e.g., replication defective retroviruses and lentiviruses.

The term "viral vector" may refer either to a virus (e.g., a transfer plasmid that includes virus-derived nucleic acid elements that typically facilitate transfer of the nucleic acid molecule or integration into the genome of a cell; e.g. virus-associated vector), or viral particle capable of transferring a nucleic acid construct into a cell, or to the transferred nucleic acid itself. Constructs may be integrated and packaged into non-replicating, defective viral genomes like Adenovirus, Adeno-associated virus (AAV), or Herpes simplex virus (HSV) or others, including retroviral and lentiviral vectors, for infection or transduction into cells. The vector may or may not be incorporated into the cell's genome. Viral vectors and transfer plasmids contain structural and/or functional genetic elements that are primarily derived from a virus. Exemplary viruses used as vectors include retroviruses, adenoviruses, adeno-associated viruses, lentiviruses, pox viruses, alphaviruses, and herpes viruses. For example, the term "retroviral vector" refers to a viral vector or plasmid containing structural and functional genetic elements, or portions thereof, that are primarily derived from a retrovirus; the term "lentiviral vector" refers to a viral vector or plasmid containing structural and functional genetic elements, or portions thereof, including LTRs that are primarily derived from a lentivirus. The term "hybrid vector" refers to a vector, LTR or other nucleic acid containing both retroviral, e.g., lentiviral, sequences and non-lentiviral viral sequences. In one embodiment, a hybrid vector refers to a vector or transfer plasmid comprising retroviral e.g., lentiviral, sequences for reverse transcription, replication, integration and/or packaging.

The recombinant expression vectors can include a nucleic acid encoding a modified integrin polypeptide described herein in a form suitable for expression of the nucleic acid in a host cell, which means that the recombinant expression vectors include one or more regulatory sequences, selected on the basis of the host cells to be used for expression, which is operatively linked to the nucleic acid sequence to be expressed.

The "control elements" or "regulatory sequences" present in an expression vector are those non-translated regions of the vector-origin of replication, selection cassettes, promoters, enhancers, translation initiation signals (Shine Dalgarno sequence or Kozak sequence) introns, a polyadenylation sequence, 5' and 3' untranslated regions—which interact with host cellular proteins to carry out transcription and translation. Such elements may vary in their strength and specificity. Depending on the vector system and host utilized, any number of suitable transcription and translation elements, including ubiquitous promoters and inducible promoters maybe used.

In particular embodiments, a vector for use in practicing the embodiments described herein including, but not limited to expression vectors and viral vectors, will include exogenous, endogenous, or heterologous control sequences such as promoters and/or enhancers. An "endogenous" control sequence is one which is naturally linked with a given gene in the genome. An "exogenous" control sequence is one which is placed in juxtaposition to a gene by means of genetic manipulation (i.e., molecular biological techniques) such that transcription of that gene is directed by the linked enhancer/promoter. A "heterologous" control sequence is an exogenous sequence that is from a different species than the cell being genetically manipulated.

The term "promoter" as used herein refers to a recognition site of a polynucleotide (DNA or RNA) to which an RNA polymerase binds. An RNA polymerase initiates and transcribes polynucleotides operably linked to the promoter. In particular embodiments, promoters operative in mammalian cells comprise an AT-rich region located approximately 25 to 30 bases upstream from the site where transcription is initiated and/or another sequence found 70 to 80 bases upstream from the start of transcription, a CNCAAT region where N may be any nucleotide.

The term "enhancer" refers to a segment of DNA which contains sequences capable of providing enhanced transcription and in some instances may function independent of their orientation relative to another control sequence. An enhancer may function cooperatively or additively with promoters and/or other enhancer elements. The term "promoter/enhancer" refers to a segment of DNA which contains sequences capable of providing both promoter and enhancer functions.

The term "operably linked", refers to a juxtaposition wherein the components described are in a relationship permitting them to function in their intended manner. In one embodiment, the term refers to a functional linkage between a nucleic acid expression control sequence (such as a promoter, and/or enhancer) and a second polynucleotide sequence, e.g., a polynucleotide—of interest, wherein the expression control sequence directs transcription of the nucleic acid corresponding to the second sequence.

As used herein, the term "constitutive expression control sequence" refers to a promoter, enhancer, or promoter/enhancer that continually or continuously allows for transcription of an operably linked sequence. A constitutive expression control sequence may be a "ubiquitous" promoter, enhancer, or promoter/enhancer that allows expression in a wide variety of cell and tissue types or a "cell specific," "cell type specific," "cell lineage specific," or "tissue specific" promoter, enhancer, or promoter/enhancer that allows expression in a restricted variety of cell and tissue types, respectively.

Illustrative ubiquitous expression control sequences suitable for use in particular embodiments of the disclosure include, but are not limited to, a cytomegalovirus (CMV) immediate early promoter, a viral simian virus 40 (SV40) (e.g., early or late), a Moloney murine leukemia virus (MoMLV) LTR promoter, a Rous sarcoma virus (RSV) LTR, a herpes simplex virus (HSV) (thymidine kinase) promoter, HS, P7.5, and P11 promoters from vaccinia virus, an elongation factor I-alpha (EFla) promoter, early growth response 1 (EGRI), ferritin H (FerH), ferritin L (FerL), Glyceraldehyde 3-phosphate dehydrogenase (GAPDH), eukaryotic translation initiation factor 4AI (EIF4AI), heat shock 70 kDa protein 5 (HSPA5), heat shock protein 90 kDa beta, member 1 (HSP90B 1), heat shock protein 70 kDa (HSP70), β-kinesin (β-KIN), the human ROSA 26 locus (Irions et al., Nature Biotechnology 25, 1477-1482 (2007)), a Ubiquitin C promoter (UBC), a phosphoglycerate kinase-I (PGK) promoter, a cytomegalovirus enhancer/chicken β-actin (CAG) promoter, a β-actin promoter and a myeloproliferative sarcoma virus enhancer, negative control region deleted, dl587rev primer-binding site substituted (MND) promoter (Challita et al., J Virol. 69 (2): 748-55 (1995)).

As used herein, "conditional expression" may refer to any type of conditional expression including, but not limited to, inducible expression; repressible expression; expression in cells or tissues having a particular physiological, biological, or disease state, etc. This definition is not intended to exclude cell type or tissue specific expression. Certain embodiments described herein provide conditional expression of a polynucleotide-of-interest, e.g., expression is controlled by subjecting a cell, tissue, organism, etc., to a treatment or condition that causes the polynucleotide to be expressed or that causes an increase or decrease in expression of the polynucleotide encoded by the polynucleotide-of-interest.

Illustrative examples of inducible promoters/systems include, but are not limited to, steroid-inducible promoters such as promoters for genes encoding glucocorticoid or estrogen receptors (inducible by treatment with the corresponding hormone), metallothionine promoter (inducible by treatment with various heavy metals), MX-1 promoter (inducible by interferon), the "GeneSwitch" mifepristone-regulatable system (Sirin et al., 2003, Gene, 323:67), the cumate inducible gene switch (WO 2002/088346), tetracycline-dependent regulatory systems, etc.

Conditional expression may also be achieved by using a site specific DNA recombinase. According to certain embodiments of the disclosure the vector comprises at least one (typically two) site(s) for recombination mediated by a site specific recombinase. As used herein, the terms "recombinase" or "site specific recombinase" include excisive or integrative proteins, enzymes, cofactors or associated proteins that are involved in recombination reactions involving one or more recombination sites (e.g., two, three, four, five, seven, ten, twelve, fifteen, twenty, thirty, fifty, etc.), which may be wild-type proteins (see Landy, Current Opinion in Biotechnology 3:699-707 (1993)), or mutants, derivatives (e.g., fusion proteins containing the recombination protein sequences or fragments thereof), fragments, and variants thereof. Illustrative examples of recombinases suitable for use in particular embodiments of the present disclosure include, but are not limited to: Cre, Int, IHF, Xis, Flp, Fis, Hin, Gin, ΦC31, Cin, Tn3 resolvase, TndX, XerC, XerD, TnpX, Hjc, Gin, SpCCEI, and ParA.

Expression of proteins in prokaryotes is most often carried out in *E. coli* with vectors containing constitutive or inducible promoters directing the expression of either fusion or non-fusion proteins. Fusion vectors add a number of amino acids to a protein encoded therein, usually to the amino terminus of the recombinant protein. Such fusion vectors typically serve three purposes: 1) to increase expression of recombinant protein; 2) to increase the solubility and/or stability of the recombinant protein; and 3) to aid in the purification of the recombinant protein by acting as a ligand in affinity purification. Often, in fusion expression vectors, a proteolytic cleavage site is introduced at the junction of the fusion moiety and the recombinant protein to enable separation of the recombinant protein from the fusion moiety subsequent to purification of the fusion protein. Such enzymes, and their cognate recognition sequences, include Factor Xa, thrombin and enterokinase. Typical fusion expression vectors include pGEX (Pharmacia Biotech Inc; Smith, D. B. and Johnson, K. S. (1988) *Gene* 67:31-40), pMAL (New England Biolabs, Beverly, Mass.) and pRIT5 (Pharmacia, Piscataway, N.J.) which fuse glutathione S-transferase (GST), maltose E binding protein, or protein A, respectively, to the target recombinant protein. Purified modified integrin I-domain fusion proteins (e.g., soluble I-domain-Ig) can be utilized to modulate integrin activity, as described herein.

Examples of suitable inducible non-fusion *E. coli* expression vectors include pTrc (Amann et al., (1988) *Gene* 69:301-315) and pET 11d (Studier et al., *Gene Expression Technology Methods in Enzymology* 185, Academic Press, San Diego, Calif. (1990) 60-89). Target gene expression from the pTrc vector relies on host RNA polymerase transcription from a hybrid trp-lac fusion promoter. Target gene expression from the pET 11d vector relies on transcription from a T7 gn10-lac fusion promoter mediated by a coexpressed viral RNA polymerase (T7 gn1). This viral polymerase is supplied by host strains BL21 (DE3) or HMS174 (DE3) from a resident prophage harboring a T7 gn1 gene under the transcriptional control of the lacUV 5 promoter.

One strategy to maximize recombinant protein expression in *E. coli* is to express the protein in a host bacteria with an impaired capacity to proteolytically cleave the recombinant protein (Gottesman, S., *Gene Expression Technology: Methods in Enzymology* 185, Academic Press, San Diego, Calif. (1990) 119-128). Another strategy is to alter the nucleic acid sequence of the nucleic acid to be inserted into an expression vector so that the individual codons for each amino acid are those preferentially utilized in *E. coli* (Wada et al., (1992) *Nucleic Acids Res.* 20:2111-2118). Such alteration of nucleic acid sequences of the invention can be carried out by standard DNA synthesis techniques.

In another embodiment, the expression vector is a yeast expression vector. Examples of vectors for expression in yeast *S. cerevisiae* include pYepSec1 (Baldari, et al., (1987) *EMBO J.* 6:229-234), pMFa (Kurjan and Herskowitz, (1982) *Cell* 30:933-943), pJRY88 (Schultz et al., (1987) *Gene* 54:113-123), pYES2 (Invitrogen Corporation, San Diego, Calif.), and picZ (InVitrogen Corp, San Diego, Calif.).

Alternatively, modified integrin polypeptides can be expressed in insect cells using baculovirus expression vectors. Baculovirus vectors available for expression of proteins in cultured insect cells (e.g., Sf9 cells) include the pAc series (Smith et al. (1983) *Mol. Cell. Biol.* 3:2156-2165) and the pVL series (Lucklow and Summers (1989) *Virology* 170: 31-39).

In some embodiments, host cells into which a nucleic acid molecule encoding a modified integrin polypeptide is introduced may be used. The terms "host cell" and "recombinant host cell" are used interchangeably herein. It is understood that such terms refer not only to the particular subject cell but to the progeny or potential progeny of such a cell. Because certain modifications may occur in succeeding generations due to either mutation or environmental influences, such progeny may not, in fact, be identical to the parent cell, but are still included within the scope of the term as used herein.

A host cell can be any prokaryotic or eukaryotic cell. For example, a modified integrin polypeptide or fusion protein can be expressed in bacterial cells such as *E. coli*, insect cells, yeast or mammalian cells (such as hematopoietic cells, leukocytes, K562 cells, 293T cells, human umbilical vein endothelial cells (HUVEC), human microvascular endothelial cells (HMVEC), Chinese hamster ovary cells (CHO) or COS cells). Other suitable host cells are known to those skilled in the art. A host cell, such as a prokaryotic or eukaryotic host cell in culture, may be used to produce (i.e., express) a modified integrin polypeptide.

In some embodiments, modified/unnatural amino acids may be incorporated into the integrin polypeptides during their recombinant production in eukaryotic and prokaryotic systems (mammalian, yeast, bacterial systems). In some embodiments, the incorporation of modified/unnatural amino acids may help make certain sites on the integrins more antigenic for discovery of binding agents targeting those sites on integrins. (Chin, 2014 Annu Rev Biochem. 2014; 83:379-408. Suchanek et al., 2005 Nat Methods, Apr; 2 (4): 261-7.)

In some embodiments, methods for identifying binding agents which modulate integrin activity are provided. These assays are designed to identify binding agents, for example, that bind to a modified integrin polypeptide and/or that bind to a wild type integrin polypeptide that is the same family member as the modified integrin polypeptide. The binding agents may be identified by binding to the modified integrin polypeptide and further screened for binding to wild type integrin polypeptides. In some embodiments, the methods may be used to identify integrin binding agents that bind to allosteric sites on the modified integrin polypeptide and/or the wild type integrin polypeptide. In some embodiments, the methods may be used identify binding agents that bind to allosteric sites on the modified integrin polypeptide and/or the wild type integrin polypeptide and modulate integrin activity. By way of non-limiting example, the methods include identifying binding agents that bind to a modified integrin α subunit or β subunit (α1-α11, αV, αIIb, αD, αE, αM, αL, αX or β-β8) and/or that bind to the wild type a subunit or β subunit (α1-α11, αV, αIIb, αD, αE, αM, αL, αX or β1-β8), respectively. In some embodiments, I domain containing integrins may be used for identifying binding agents which modulate integrin activity. For example, each of the nine α1-containing integrins (α1, α2, α10, α11, αE, αD, αM, αL, αX), and all β subunits (the I-like or 'βI' domain) may be used for identifying binding agents which modulate integrin activity.

As used interchangeably herein, an "integrin activity", or an "integrin-mediated activity" refers to an activity exerted by an integrin polypeptide or nucleic acid molecule on an integrin responsive cell, or on integrin ligand or receptor, as determined in vitro and in vivo, according to standard techniques. In one embodiment, an integrin activity is the ability to mediate cell adhesion events, e.g, cell to cell or cell to extracellular matrix adhesion. In another embodiment, an integrin activity is the ability to transduce cellular signaling events. In yet another embodiment, an integrin activity is the ability to bind a ligand, e.g., ICAM.

In some embodiments, soluble, recombinant modified integrin polypeptides can be used to screen for binding agents that do not interfere with integrin ligand binding. In some embodiments, antagonists with direct/competitive and indirect/noncompetitive modes of inhibition can be discriminated, based on comparison with effects on wild-type integrin polypeptides which show minimal ligand binding activity.

In other embodiments, cell-based assays may be used to screen for binding agents the bind to modified integrin polypeptides and in some cases that do not interfere with integrin ligand binding. Cell based assays include contacting a cell expressing a modified integrin polypeptide on the cell surface with a test agent and determining the ability of the test agent to bind to the modified integrin polypeptide. By way of non-limiting example, a cell expressing a modified integrin polypeptide stabilized in an open configuration or a closed configuration and/or with the metal ion binding domain modified on the cell surface is contacted with a test agent, and the ability of the test agent to bind to the modified integrin polypeptide is determined.

Antibody Selection Assays Using Phage Display libraries

Figure 4:
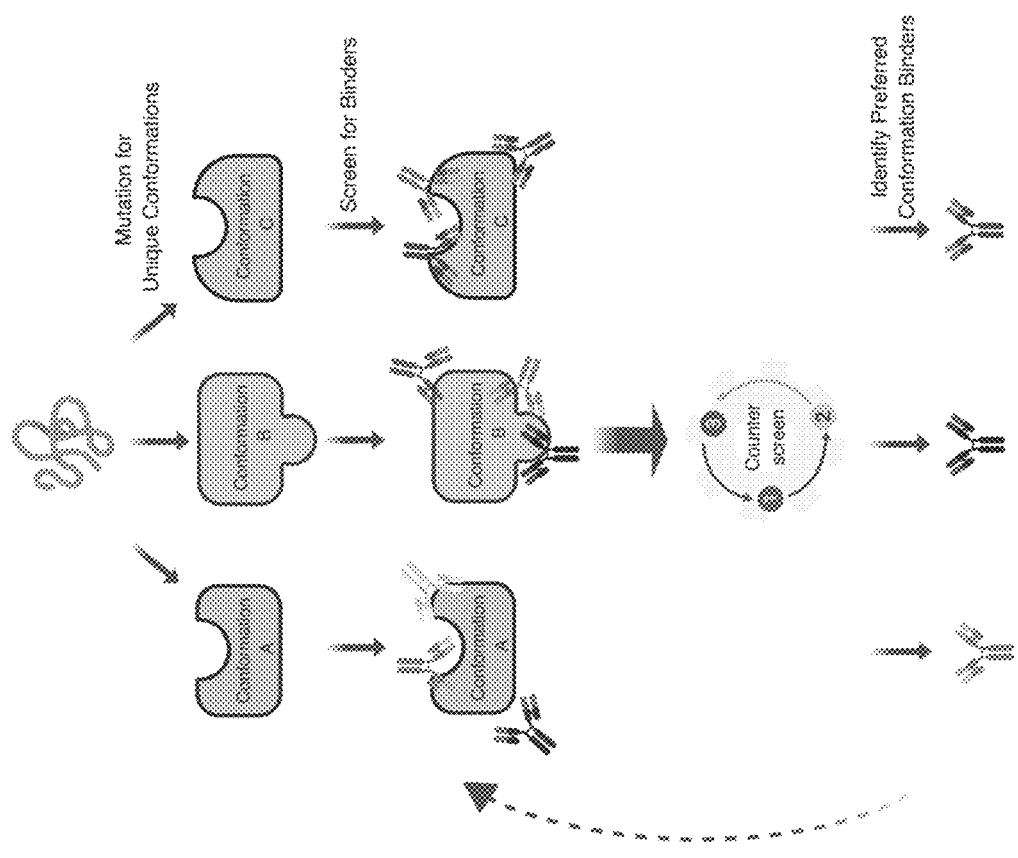
FIG. 4 illustrates an embodiment of a screening assay for identifying binding agents that bind to selected polypeptide conformations.

Assays can be performed in many different formats. For example, one could use assays similar to as described in Hu 2010. For example, wild type and mutant recombinant proteins can be expressed on yeast or mammalian cell (e.g.; K562) surface. They can also be expressed as a recombinant protein and bound to a solid-surface for screening. They can then be used in sequential or parallel screening against a phage display library (FIG. 4). After depleting non-specific binders by screening against cells not expressing the protein domain, remaining clones can be screened against one or more clones expressing protein locked in a preferred conformation. After enrichment, the clones can be further enriched or screened against the cells expressing protein in a different conformation. The selected clones can be tested in purified protein based in vitro assays, cell based in vitro assays, ligand binding assays, in vivo assays, or other assays and further developed. Sequencing of clones can be used to identify and further improve their activity.

Other Assays

As an example, for testing isolated domain ligand binding, CD11b A-domain assays (using recombinant A-domains) can be performed using recombinant C3d domain (Bajic 2013).

Betal domains can be recombinantly expressed as α/β-chain ectodomains, headpiece, or head domains, as described in literature (Su 2016; Takagi 2002 Biochemistry, 41, 4339-4347 etc). Allosteric regions or sequences of the BI domain can also be grafted onto αA domain(s) for recombinant expression and use in assays.

For identifying specific allosteric antibodies, known allosteric antibodies, such as 12G10 again integrin beta1, that binds β1 as an agonist (Humphries 2005; Su 2016), can also be modified, humanized or mutagenized.

The assays can also be useful in identifying antibodies that, for example, selectively (and allosterically) bind activated integrin molecules but are substantially incapable of binding non-activated molecules. For example, antibody 12G10 against BI domain of integrin beta1, mAb24 against βI domain of CD18.

Diagnostic Assays

Binding agents that bind to modified integrin polypeptides or wild type polypeptides can also be used for diagnostics in vitro and in vivo. In one aspect, a diagnostic method for detecting the presence of an integrin polypeptide in vitro or in vivo is provided using the binding agent. In some embodiments, the binding agent binds to the allosteric site on a modified integrin polypeptide. In some embodiments, the binding agent binds to a wild type integrin at one or more sites, including for example, allosteric sites. In some embodiments, the binding agent can bind to a modified integrin a subunit or β subunit (α1-α11, αV, αIIb, αD, αE, αM, αL, αX or β1-β8) and/or a wild type α subunit or β subunit of the same type (α1-α11, αV, αIIb, αD, αE, αM, αL, αX or β1-β8), respectively. In some embodiments, binding agents that bind I domain containing integrins may be used in diagnostic assays. For example, each of the nine α1-containing integrins (α1, α2, α10, α11, αE, αD, αM, αL, αX), and all β subunits (the I-like or 'βI' domain) may be used in diagnostic assays.

In some embodiments, the modified integrin polypeptides described herein may be used for diagnostics in vitro and in vivo.

In some embodiments, the integrin binding agent is used to evaluate a sample in vitro (e.g., a biological sample). The method includes: (i) contacting a sample with binding agent that specifically binds an integrin polypeptide; and (ii) detecting formation of a complex between the integrin binding agent and the sample. The method can also include contacting a reference sample (e.g., a control sample) with the binding agent, and determining the extent of formation of the complex between the binding agent and the sample, relative to the same for the reference sample. A change, e.g., a statistically significant change, in the formation of the complex in the sample or subject relative to the control sample or subject can be indicative of the presence of an integrin in the sample. Samples can be obtained by surgical or non-surgical methods.

Another method includes: (i) administering the integrin binding agent to a subject; and (ii) detecting formation of a complex between the integrin binding agent, and the subject. The detecting can include determining location or time of formation of the complex. In one embodiment, the subject has, is suspected of having, or is at risk for a disorder described herein, e.g., an integrin associated disorder.

Therapeutic Binding Agents

Binding agents identified by the above-described screening assays or modified integrin polypeptides may be used as therapeutic treatments. By way of non-limiting example, any treatments which modulate integrin activity and/or inflammatory activity should be considered as candidates for human therapeutic intervention.

As used herein "treatment" or "treating," includes any beneficial or desirable effect on the symptoms or pathology of a disease or pathological condition, and may include even minimal reductions in one or more measurable markers of the disease or condition being treated, e.g., an integrin-mediated disorder. Treatment may involve optionally either the reduction or amelioration of symptoms of the disease or condition, or the delaying of the progression of the disease or condition. "Treatment" does not necessarily indicate complete eradication or cure of the disease or condition, or associated symptoms thereof.

The binding agents identified from the assays or the modified integrin polypeptides may be able to enhance ligand binding by integrins, have no effect on ligand binding by integrins or occlude ligand binding by a subset of ligands of a particular integrin.

Additional embodiments include compositions comprising binding agents that selectively bind an integrin polypeptide or a modified integrin polypeptide described herein, and a pharmaceutically acceptable carrier. The compositions may be used in therapeutic methods. For example, some embodiments provide methods for treating or preventing an integrin-mediated disorder (e. g., an inflammatory or autoimmune disorder or cancer) in a subject, or for inhibiting the binding of an integrin to its ligand in a subject or for enhancing the binding of an integrin to its ligand comprising administering to a therapeutically effective amount of an anti-integrin antibody or an antigen binding fragment thereof which specifically binds to an integrin polypeptide. In some embodiments, the binding agent, such as an antibody or fragment thereof binds to an allosteric site on the integrin polypeptide. In some embodiments, the binding agent binds to the integrin polypeptide in the open conformation or in the closed conformation.

As used herein, an integrin mediated disorder includes, for example, an inflammatory or immune system disorder, and/or a cellular proliferative disorder.

Examples of integrin-mediated disorders include myocardial infarction, stroke, restenosis, transplant rejection, graft versus host disease or host versus graft disease, and reperfusion injury, fibrosis, alport's syndrome, pain, chronic pain, ophthalmic diseases, alzheimers, parkinsons disease. An inflammatory or immune system disorder includes, but is not limited to adult respiratory distress syndrome (ARDS), multiple organ injury syndromes secondary to septicemia or trauma, viral infection, inflammatory bowel disease, ulcerative colitis, Crohn's disease, leukocyte adhesion deficiency II syndrome, thermal injury, hemodialysis, leukapheresis, peritonitis, chronic obstructive pulmonary disease, lung inflammation, asthma, acute appendicitis, dermatoses with acute inflammatory components, wound healing, septic shock, acute glomerulonephritis, nephritis, amyloidosis, reactive arthritis, rheumatoid arthritis, chronic bronchitis, diabetes, Sjorgen's syndrome, sarcoidosis, scleroderma, lupus, polymyositis, Reiter's syndrome, psoriasis, dermatitis, pelvic inflammatory disease, inflammatory breast disease, orbital inflammatory disease, immune deficiency disorders (e. g., HIV, common variable immunodeficiency, congenital X-linked infantile hypogammaglobulinemia, transient hypogammaglobulinemia, selective IgA deficiency, necrotizing enterocolitis, granulocyte transfusion associated syndromes, cytokine-induced toxicity, chronic mucocutaneous candidiasis, severe combined immunodeficiency), autoimmune disorders, and acute purulent meningitis or other central nervous system inflammatory disorders.

A "cellular proliferative disorder" includes those disorders that affect cell proliferation, activation, adhesion, growth, differentiation, or migration processes. As used herein, a "cellular proliferation, activation, adhesion, growth, differentiation, or migration process" is a process by which a cell increases in number, size, activation state, or content, by which a cell develops a specialized set of characteristics which differ from that of other cells, or by which a cell moves closer to or further from a particular location or stimulus. Disorders characterized by aberrantly regulated growth, activation, adhesion, differentiation, or migration. Such disorders include cancer, e. g., carcinoma, sarcoma, lymphoma or leukemia, examples of which include, but are not limited to, breast, endometrial, ovarian, uterine, hepatic, gastrointestinal, prostate, colorectal, and lung cancer, melanoma, neurofibromatosis, adenomatous polyposis of the colon, Wilms' tumor, nephroblastoma, teratoma, rhabdomyosarcoma; tumor invasion, angiogenesis and metastasis; skeletal dysplasia; hematopoietic and/or myeloproliferative disorders.

As used herein, the term "amount" refers to "an amount effective" or "therapeutically effective amount" of an integrin binding agent, to achieve a beneficial or desired prophylactic or therapeutic result, including clinical results. A "therapeutically effective amount" of an integrin binding agent may vary according to factors such as the disease state, age, sex, and weight of the individual, and the ability of the integrin binding agent to elicit a desired response in the individual. A therapeutically effective amount is also one in which any toxic or detrimental effects of the therapy are outweighed by the therapeutically beneficial effects. The term "therapeutically effective amount" includes an amount that is effective to "treat" a subject (e.g., a patient). When a therapeutic amount is indicated, the precise amount of the compositions of the present disclosure to be administered may be determined by a physician with consideration of individual differences in age, weight, extent of the integrin mediated disorder, and condition of the patient (subject).

Formulations of therapeutic and diagnostic agents can be prepared by mixing with physiologically acceptable carriers, excipients, or stabilizers in the form of, e.g., lyophilized powders, slurries, aqueous solutions, lotions, or suspensions (see, e.g., Hardman et al., (2001) Goodman and Gilman's The Pharmacological Basis of Therapeutics, McGraw-Hill, New York, N.Y.; Gennaro (2000) Remington: The Science and Practice of Pharmacy, Lippincott, Williams, and Wilkins, New York, N.Y.; Avis, et al. (eds.) (1993) Pharmaceutical Dosage Forms: Parenteral Medications, Marcel Dekker, NY; Lieberman, et al. (eds.) (1990) Pharmaceutical Dosage Forms: Tablets, Marcel Dekker, NY; Lieberman, et al. (eds.) (1990) Pharmaceutical Dosage Forms: Disperse Systems, Marcel Dekker, NY; Weiner and Kotkoskie (2000) Excipient Toxicity and Safety, Marcel Dekker, Inc., New York, N.Y.).

Selecting an administration regimen for a therapeutic depends on several factors, including the serum or tissue turnover rate of the entity, the level of symptoms, the immunogenicity of the entity, and the accessibility of the target cells in the biological matrix. In certain embodiments, an administration regimen maximizes the amount of therapeutic delivered to the patient consistent with an acceptable level of side effects. Accordingly, the amount of biologic delivered depends in part on the particular entity and the severity of the condition being treated. Guidance in selecting appropriate doses of antibodies, cytokines, and small molecules are available (see, e.g., Wawrzynczak (1996) Antibody Therapy, Bios Scientific Pub. Ltd, Oxfordshire, UK; Kresina (ed.) (1991) Monoclonal Antibodies, Cytokines and Arthritis, Marcel Dekker, New York, N.Y.; Bach (ed.) (1993)

Monoclonal Antibodies and Peptide Therapy in Autoimmune Diseases, Marcel Dekker, New York, N.Y.; Baert et al, (2003) New Engl. J. Med. 348:601-608; Milgrom et al, (1999) New Engl. J. Med. 341:1966-1973; Slamon et al, (2001) New Engl. J. Med. 344:783-792; Beniaminovitz et al, (2000) New Engl. J. Med. 342:613-619; Ghosh et al, (2003) New Engl. J. Med. 348:24-32; Lipsky et al, (2000) New Engl. J. Med. 343:1594-1602).

Determination of the appropriate dose is made by the clinician, e.g., using parameters or factors known or suspected in the art to affect treatment or predicted to affect treatment. Generally, the dose begins with an amount somewhat less than the optimum dose and it is increased by small increments thereafter until the desired or optimum effect is achieved relative to any negative side effects. Important diagnostic measures include those of symptoms of, e.g., the inflammation or level of inflammatory cytokines produced.

Actual dosage levels of the active ingredients in the pharmaceutical compositions of the present invention may be varied so as to obtain an amount of the active ingredient which is effective to achieve the desired therapeutic response for a particular patient, composition, and mode of administration, without being toxic to the patient. The selected dosage level will depend upon a variety of pharmacokinetic factors including the activity of the particular compositions of the present invention employed, or the ester, salt or amide thereof, the route of administration, the time of administration, the rate of excretion of the particular compound being employed, the duration of the treatment, other drugs, compounds and/or materials used in combination with the particular compositions employed, the age, sex, weight, condition, general health and prior medical history of the patient being treated, and like factors known in the medical arts. Compositions comprising binding agents such as antibodies or fragments thereof can be provided by continuous infusion, or by doses at intervals of, e.g., one day, one week, or 1-7 times per week. Doses may be provided intravenously, subcutaneously, topically, orally, nasally, rectally, intramuscular, intracerebrally, or by inhalation. A specific dose protocol is one involving the maximal dose or dose frequency that avoids significant undesirable side effects. A total weekly dose may be at least 0.05 µ/kg body weight, at least 0.2 µg/kg, at least 0.5 µg/kg, at least 1 µg/kg, at least 10 µg/kg, at least 100 µg/kg, at least 0.2 mg/kg, at least 1.0 mg/kg, at least 2.0 mg/kg, at least 10 mg/kg, at least 25 mg/kg, at least 30 mg/kg, at least 40 mg/kg or at least 50 mg/kg (see, e.g., Yang et al, (2003) New Engl. J. Med. 349:427-434; Herold et al, (2002) New Engl. J. Med. 346:1692-1698; Liu et al, (1999) J. Neurol. Neurosurg. Psych. 67:451-456; Portielji et al, (2003) Cancer Immunol. Immunother. 52:133-144). The desired dose of antibodies or fragments thereof is about the same as for an antibody or polypeptide, on a moles/kg body weight basis. The desired plasma concentration of the antibodies or fragments thereof is about, on a moles/kg body weight basis. The dose may be at least 15 µg at least 20 µg, at least 25 µg, at least 30 µg, at least 35 µg, at least 40 µg, at least 45 µg, at least 50 µg, at least 55 µg, at least 60 µg, at least 65 µg, at least 70 µg, at least 75 µg, at least 80 µg, at least 85 µg, at least 90 µg, at least 95 µg, or at least 100 µg. The doses administered to a subject may number at least 1, 2, 3, 4, 5, 6, 7, 8, 9, 10, 11, or 12, or more. For antibodies or fragments thereof of the invention, the dosage administered to a patient may be 0.0001 mg/kg to 100 mg/kg of the patient's body weight. The dosage may be between 0.0001 mg/kg and 20 mg/kg, 0.0001 mg/kg and 10 mg/kg, 0.0001 mg/kg and 5 mg/kg, 0.0001 and 2 mg/kg, 0.0001 and 1 mg/kg, 0.0001 mg/kg and 0.75 mg/kg, 0.0001 mg/kg and 0.5 mg/kg, 0.0001 mg/kg to 0.25 mg/kg, 0.0001 to 0.15 mg/kg, 0.0001 to 0.10 mg/kg, 0.001 to 0.5 mg/kg, 0.01 to 0.25 mg/kg or 0.01 to 0.10 mg/kg of the patient's body weight.

The dosage of the antibodies or fragments thereof of the invention may be calculated using the patient's weight in kilograms (kg) multiplied by the dose to be administered in mg/kg. The dosage of the antibodies or fragments thereof of the invention may be 150 µg/kg or less, 125 µg/kg or less, 100 µg/kg or less, 95 µg/kg or less, 90 µg/kg or less, 85 µg/kg or less, 80 µg/kg or less, 75 µg/kg or less, 70 µg/kg or less, 65 µg/kg or less, 60 µg/kg or less, 55 µg/kg or less, 50 µg/kg or less, 45 µg/kg or less, 40 µg/kg or less, 35 µg/kg or less, 30 µg/kg or less, 25 µg/kg or less, 20 µg/kg or less, 15 µg/kg or less, 10 µg/kg or less, 5 µg/kg or less, 2.5 µg/kg or less, 2 µg/kg or less, 1.5 µg/kg or less, 1 µg/kg or less, 0.5 g/kg or less, or 0.5 µg/kg or less of a patient's body weight.

Unit dose of the antibodies or fragments thereof of the invention may be 0.1 mg to 20 mg, 0.1 mg to 15 mg, 0.1 mg to 12 mg, 0.1 mg to 10 mg, 0.1 mg to 8 mg, 0.1 mg to 7 mg, 0.1 mg to 5 mg, 0.1 to 2.5 mg, 0.25 mg to 60 mg, 0.25 mg to 40 mg, 0.25 mg to 20 mg, 0.25 to 15 mg, 0.25 to 12 mg, 0.25 to 10 mg, 0.25 to 8 mg, 0.25 mg to 7 mg, 0.25 mg to 5 mg, 0.5 mg to 2.5 mg, 1 mg to 20 mg, 1 mg to 15 mg, 1 mg to 12 mg, 1 mg to 10 mg, 1 mg to 8 mg, 1 mg to 7 mg, 1 mg to 5 mg, or 1 mg to 2.5 mg.

The dosage of the antibodies or fragments thereof of the invention may achieve a serum titer of at least 0.1 µg/ml, at least 0.5 µg/ml, at least 1 µg/ml, at least 2 µg/ml, at least 5 µg/ml, at least 6 µg/ml, at least 10 µg/ml, at least 15 µg/ml, at least 20 µg/ml, at least 25 µg/ml, at least 50 µg/ml, at least 100 µg/ml, at least 125 µg/ml, at least 150 µg/ml, at least 175 µg/ml, at least 200 µg/ml, at least 225 µg/ml, at least 250 µg/ml, at least 275 µg/ml, at least 300 µg/ml, at least 325 µg/ml, at least 350 µg/ml, at least 375 µg/ml, or at least 400 µg/ml in a subject. Alternatively, the dosage of the antibodies or fragments thereof of the invention may achieve a serum titer of at least 0.1 µg/ml, at least 0.5 µg/ml, at least 1 µg/ml, at least, 2 µg/ml, at least 5 µg/ml, at least 6 µg/ml, at least 10 µg/ml, at least 15 µg/ml, at least 20 µg/ml, at least 25 µg/ml, at least 50 µg/ml, at least 100 µg/ml, at least 125 µg/ml, at least 150 µg/ml, at least 175 µg/ml, at least 200 µg/ml, at least 225 µg/ml, at least 250 µg/ml, at least 275 µg/ml, at least 300 µg/ml, at least 325 µg/ml, at least 350 µg/ml, at least 375 µg/ml, or at least 400 µg/ml in the subject.

Doses of antibodies or fragments thereof of the invention may be repeated and the administrations may be separated by at least 1 day, 2 days, 3 days, 5 days, 7 days, 10 days, 15 days, 30 days, 45 days, 2 months, 75 days, 3 months, or at least 6 months.

An effective amount for a particular patient may vary depending on factors such as the condition being treated, the overall health of the patient, the method route and dose of administration and the severity of side effects (see, e.g., Maynard et al., (1996) A Handbook of SOPs for Good Clinical Practice, Interpharm Press, Boca Raton, Fla.; Dent (2001) Good Laboratory and Good Clinical Practice, Urch PubL, London, UK).

The route of administration may be by, e.g., topical or cutaneous application, injection or infusion by intravenous, intraperitoneal, intracerebral, intramuscular, intraocular, intraarterial, intracerebrospinal, intralesional, or by sustained release systems or an implant (see, e.g., Sidman et al., (1983) Biopolymers 22:547-556; Langer et al., (1981) J. Biomed. Mater. Res. 15:167-277; Langer (1982) Chem. Tech. 12:98-105; Epstein et al, (1985) Proc. Natl. Acad. Sci. USA 82:3688-3692; Hwang et al., (1980) Proc. Natl. Acad.

Sci. USA 77:4030-4034; U.S. Pat. Nos. 6,350,466 and 6,316,024). Where necessary, the composition may also include a solubilizing agent and a local anesthetic such as lidocaine to ease pain at the site of the injection. In addition, pulmonary administration can also be employed, e.g., by use of an inhaler or nebulizer, and formulation with an aerosolizing agent. See, e.g., U.S. Pat. Nos. 6,019,968, 5,985,320, 5,985,309, 5,934,272, 5,874,064, 5,855,913, 5,290,540, and 4,880,078; and PCT Publication Nos. WO 92/19244, WO 97/32572, WO 97/44013, WO 98/31346, and WO 99/66903, each of which is incorporated herein by reference their entirety.

A composition of the integrin binding agent described herein may also be administered via one or more routes of administration using one or more of a variety of methods known in the art. As will be appreciated by the skilled artisan, the route and/or mode of administration will vary depending upon the desired results. Selected routes of administration for antibodies or fragments thereof of the invention include intravenous, intramuscular, intradermal, intraperitoneal, subcutaneous, spinal or other parenteral routes of administration, for example by injection or infusion. Parenteral administration may represent modes of administration other than enteral and topical administration, usually by injection, and includes, without limitation, intravenous, intramuscular, intraarterial, intrathecal, intracapsular, intraorbital, intracardiac, intradermal, intraperitoneal, transtracheal, subcutaneous, subcuticular, intraarticular, subcapsular, subarachnoid, intraspinal, epidural and intrasternal injection and infusion. Alternatively, a composition of the invention can be administered via a non-parenteral route, such as a topical, epidermal or mucosal route of administration, for example, intranasally, orally, vaginally, rectally, sublingually or topically. In one embodiment, the antibodies or fragments thereof of the invention is administered by infusion. In another embodiment, the multispecific epitope binding protein of the invention is administered subcutaneously. If the antibodies or fragments thereof of the invention are administered in a controlled release or sustained release system, a pump may be used to achieve controlled or sustained release (see Langer, supra; Sefton, (1987) CRC Crit. Ref Biomed. Eng. 14:20; Buchwald et al., (1980), Surgery 88:507; Saudek et al, (1989) N. Engl. J. Med. 321:574). Polymeric materials can be used to achieve controlled or sustained release of the therapies of the invention (see e.g., Medical Applications of Controlled Release, Langer and Wise (eds.), CRC Pres., Boca Raton, Fla. (1974); Controlled Drug Bioavailability, Drug Product Design and Performance, Smolen and Ball (eds.), Wiley, New York (1984); Ranger and Peppas, (1983) J. Macromol. Sci. Rev. Macromol. Chem. 23:61; see also Levy et al., (1985) Science 228:190; During et al, (1989) Ann. Neurol. 25:351; Howard et al, (1989) J. Neurosurg. 7 1:105); U.S. Pat. Nos. 5,679,377; 5,916,597; 5,912,015; 5,989,463; 5,128,326; PCT Publication No. WO 99/15154; and PCT Publication No. WO 99/20253. Examples of polymers used in sustained release formulations include, but are not limited to, poly(2-hydroxy ethyl methacrylate), poly(methyl methacrylate), poly(acrylic acid), poly(ethylene-co-vinyl acetate), poly (methacrylic acid), polyglycolides (PLG), polyanhydrides, poly(N-vinyl pyrrolidone), poly(vinyl alcohol), polyacrylamide, poly(ethylene glycol), polylactides (PLA), poly(lactide-co-glycolides) (PLGA), and polyorthoesters. In one embodiment, the polymer used in a sustained release formulation is inert, free of leachable impurities, stable on storage, sterile, and biodegradable. A controlled or sustained release system can be placed in proximity of the prophylactic or therapeutic target, thus requiring only a fraction of the systemic dose (see, e.g., Goodson, in Medical Applications of Controlled Release, supra, vol. 2, pp. 115-138 (1984)).

Controlled release systems are discussed in the review by Langer, (1990), Science 249:1527-1533). Any technique known to one of skill in the art can be used to produce sustained release formulations comprising one or more antibodies or fragments thereof of the invention. See, e.g., U.S. Pat. No. 4,526,938, PCT publication WO 91/05548, PCT publication WO 96/20698, Ning et al, (1996), Radiotherapy & Oncology 39:179-189, Song et al, (1995) PDA Journal of Pharmaceutical Science & Technology 50:372-397, Cleek et al., (1997) Pro. Int'l. Symp. Control. Rel. Bioact. Mater. 24:853-854, and Lam et al, (1997) Proc. Int'l. Symp. Control Rel. Bioact. Mater. 24:759-760, each of which is incorporated herein by reference in their entirety.

If the antibodies or fragments thereof are administered topically, they can be formulated in the form of an ointment, cream, transdermal patch, lotion, gel, shampoo, spray, aerosol, solution, emulsion, or other form well-known to one of skill in the art. See, e.g., Remington's Pharmaceutical Sciences and Introduction to Pharmaceutical Dosage Forms, 19th ed., Mack Pub. Co., Easton, Pa. (1995). For non-sprayable topical dosage forms, viscous to semi-solid or solid forms comprising a carrier or one or more excipients compatible with topical application and having a dynamic viscosity, in some instances, greater than water are typically employed. Suitable formulations include, without limitation, solutions, suspensions, emulsions, creams, ointments, powders, liniments, salves, and the like, which are, if desired, sterilized or mixed with auxiliary agents (e.g., preservatives, stabilizers, wetting agents, buffers, or salts) for influencing various properties, such as, for example, osmotic pressure. Other suitable topical dosage forms include sprayable aerosol preparations wherein the active ingredient, in some instances, in combination with a solid or liquid inert carrier, is packaged in a mixture with a pressurized volatile (e.g., a gaseous propellant, such as freon) or in a squeeze bottle. Moisturizers or humectants can also be added to pharmaceutical compositions and dosage forms if desired. Examples of such additional ingredients are well-known in the art.

If the compositions comprising antibodies or fragments thereof are administered intranasally, it can be formulated in an aerosol form, spray, mist or in the form of drops. In particular, prophylactic or therapeutic agents for use according to the present invention can be conveniently delivered in the form of an aerosol spray presentation from pressurized packs or a nebuliser, with the use of a suitable propellant (e.g., dichlorodifluoromethane, trichlorofluoromethane, dichlorotetrafluoroethane, carbon dioxide or other suitable gas). In the case of a pressurized aerosol the dosage unit may be determined by providing a valve to deliver a metered amount. Capsules and cartridges (composed of, e.g., gelatin) for use in an inhaler or insufflator may be formulated containing a powder mix of the compound and a suitable powder base such as lactose or starch.

Methods for co-administration or treatment with a second therapeutic agent, e.g., a cytokine, steroid, chemotherapeutic agent, antibiotic, or radiation, are known in the art (see, e.g., Hardman et al., (eds.) (2001) Goodman and Gilman's The Pharmacological Basis of Therapeutics, IO.sup.th ed., McGraw-Hill, New York, N.Y.; Poole and Peterson (eds.) (2001) Pharmacotherapeutics for Advanced Practice: A Practical Approach, Lippincott, Williams & Wilkins, Phila., Pa.; Chabner and Longo (eds.) (2001) Cancer Chemotherapy and Biotherapy, Lippincott, Williams & Wilkins, Phila., Pa.). An effective amount of therapeutic may decrease the symptoms by at least 10%; by at least 20%; at least about 30%>; at least 40%>, or at least 50%.

Additional therapies (e.g., prophylactic or therapeutic agents), which can be administered in combination with the integrin binding agent may be administered less than 5 minutes apart, less than 30 minutes apart, 1 hour apart, at about 1 hour apart, at about 1 to about 2 hours apart, at about 2 hours to about 3 hours apart, at about 3 hours to about 4 hours apart, at about 4 hours to about 5 hours apart, at about 5 hours to about 6 hours apart, at about 6 hours to about 7 hours apart, at about 7 hours to about 8 hours apart, at about 8 hours to about 9 hours apart, at about 9 hours to about 10 hours apart, at about 10 hours to about 11 hours apart, at about 11 hours to about 12 hours apart, at about 12 hours to 18 hours apart, 18 hours to 24 hours apart, 24 hours to 36 hours apart, 36 hours to 48 hours apart, 48 hours to 52 hours apart, 52 hours to 60 hours apart, 60 hours to 72 hours apart, 72 hours to 84 hours apart, 84 hours to 96 hours apart, or 96 hours to 120 hours apart from the antibodies or fragments thereof of the invention. The two or more therapies may be administered within one same patient visit.

The integrin binding agents and the other therapies may be cyclically administered. Cycling therapy involves the administration of a first therapy (e.g., a first prophylactic or therapeutic agent) for a period of time, followed by the administration of a second therapy (e.g., a second prophylactic or therapeutic agent) for a period of time, optionally, followed by the administration of a third therapy (e.g., prophylactic or therapeutic agent) for a period of time and so forth, and repeating this sequential administration, i.e., the cycle in order to reduce the development of resistance to one of the therapies, to avoid or reduce the side effects of one of the therapies, and/or to improve the efficacy of the therapies.

In certain embodiments, the integrin binding agents can be formulated to ensure proper distribution in vivo. For example, the blood-brain barrier (BBB) excludes many highly hydrophilic compounds. To ensure that the therapeutic compounds of the invention cross the BBB (if desired), they can be formulated, for example, in liposomes. For methods of manufacturing liposomes, see, e.g., U.S. Pat. Nos. 4,522,811; 5,374,548; and 5,399,331. The liposomes may comprise one or more moieties which are selectively transported into specific cells or organs, thus enhance targeted drug delivery (see, e.g., Ranade, (1989) J. Clin. Pharmacol. 29:685). Exemplary targeting moieties include folate or biotin (see, e.g., U.S. Pat. No. 5,416,016 to Low et al); mannosides (Umezawa et al, (1988) Biochem. Biophys. Res. Commun. 153:1038); antibodies (Bloeman et al, (1995) FEBS Lett. 357:140; Owais et al., (1995) Antimicrob. Agents Chemother. 39:180); surfactant protein A receptor (Briscoe et al, (1995) Am. J. Physiol. 1233:134); p 120 (Schreier et al, (1994) J. Biol. Chem. 269:9090); see also K. Keinanen; M. L. Laukkanen (1994) FEBS Lett. 346:123; J. J. Killion; I. J. Fidler (1994) Immunomethods 4:273.

Protocols for the administration of pharmaceutical composition comprising integrin binding agents alone or in combination with other therapies to a subject in need thereof are provided. The therapies (e.g., prophylactic or therapeutic agents) of the combination therapies can be administered concomitantly or sequentially to a subject. The therapy (e.g., prophylactic or therapeutic agents) of the combination therapies of the present invention can also be cyclically administered. Cycling therapy involves the administration of a first therapy (e.g., a first prophylactic or therapeutic agent) for a period of time, followed by the administration of a second therapy (e.g., a second prophylactic or therapeutic agent) for a period of time and repeating this sequential administration, i.e., the cycle, in order to reduce the development of resistance to one of the therapies (e.g., agents) to avoid or reduce the side effects of one of the therapies (e.g., agents), and/or to improve, the efficacy of the therapies.

The therapies (e.g., prophylactic or therapeutic agents) of the combination therapies can be administered to a subject concurrently. The term "concurrently" is not limited to the administration of therapies (e.g., prophylactic or therapeutic agents) at exactly the same time, but rather it is meant that a pharmaceutical composition comprising antibodies or fragments thereof of the invention are administered to a subject in a sequence and within a time interval such that the antibodies of the invention can act together with the other therapy (ies) to provide an increased benefit than if they were administered otherwise. For example, each therapy may be administered to a subject at the same time or sequentially in any order at different points in time; however, if not administered at the same time, they should be administered sufficiently close in time so as to provide the desired therapeutic or prophylactic effect. Each therapy can be administered to a subject separately, in any appropriate form and by any suitable route. In various embodiments, the therapies (e.g., prophylactic or therapeutic agents) are administered to a subject less than 15 minutes, less than 30 minutes, less than 1 hour apart, at about 1 hour apart, at about 1 hour to about 2 hours apart, at about 2 hours to about 3 hours apart, at about 3 hours to about 4 hours apart, at about 4 hours to about 5 hours apart, at about 5 hours to about 6 hours apart, at about 6 hours to about 7 hours apart, at about 7 hours to about 8 hours apart, at about 8 hours to about 9 hours apart, at about 9 hours to about 10 hours apart, at about 10 hours to about 11 hours apart, at about 11 hours to about 12 hours apart, 24 hours apart, 48 hours apart, 72 hours apart, or 1 week apart. In other embodiments, two or more therapies (e.g., prophylactic or therapeutic agents) are administered to a within the same patient visit.

The prophylactic or therapeutic agents of the combination therapies can be administered to a subject in the same pharmaceutical composition. Alternatively, the prophylactic or therapeutic agents of the combination therapies can be administered concurrently to a subject in separate pharmaceutical compositions. The prophylactic or therapeutic agents may be administered to a subject by the same or different routes of administration.

Examples of modified integrin polypeptides

CD11b A-domain (αA domain of CD11b) modifications (FIG. 2).

By way of non-limiting example, changes to the CD11b A-domain are described below. The changes made to the MIDAS domain residues of the CD11b A-domain described herein may also be made to any of the integrin beta domains shown in FIG. 3. Additionally, changes to any of the MIDAS, ADMIDAS, LIMBS/SyMBS residues may also be made and used to identify integrin binding agents.

The amino acid residues below are numbered according to the mature integrin CD11b A-domain after the 16 amino acid signaling N-terminus has been cleaved. The Uniprot P11215 sequence of the protein contains the additional N-terminal 16 amino acid signaling peptide sequence that is cleaved in mature protein (thus the residue number 209 below corresponds to residue number 225 in the Uniprot sequence).

The mature wild type human Integrin alpha-M (CD 11b) A-domain is shown below with the 16 amino acid signal peptide removed.

(SEQ ID NO: 1)
FNLDTENAMTFQENARGFGQSVVQLQGSRVVVGAPQEIVAANQRGSLYQCD

YSTGSCEPIRLQVPVEAVNMSLGLSLAATTSPPQLLACGPTVHQTCSENTY

VKGLCFLFGSNLRQQPQKFPEALRGCPQEDSDIAFLIDGSGSIIPHDFRRM

KEFVSTVMEQLKKSKTLFSLMQYSEEFRIHFTFKEFQNNPNPRSLVKPITQ

LLGRTHTATGIRKVVRELFNITNGARKNAFKILVVITDGEKFGDPLGYEDV

IPEADREGVIRYVIGVGDAFRSEKSRQELNTIASKPPRDHVFQVNNFEALK

TIQNQLREKIFAIEGTQTGSSSSFEHEMSQEGFSAAITSNGPLLSTVGSYD

WAGGVFLYTSKEKSTFINMTRVDSDMNDAYLGYAAAIILRNRVQSLVLGAP

RYQHIGLVAMFRQNTGMWESNANVKGTQIGAYFGASLCSVDVDSNGSTDLV

LIGAPHYYEQTRGGQVSVCPLPRGRARWQCDAVLYGEQGQPWGRFGAALTV

LGDVNGDKLTDVAIGAPGEEDNRGAVYLFHGTSGSGISPSHSQRIAGSKLS

PRLQYFGQSLSGGQDLTMDGLVDLTVGAQGHVLLLRSQPVLRVKAIMEFNP

REVARNVFECNDQVVKGKEAGEVRVCLHVQKSTRDRLREGQIQSVVTYDLA

LDSGRPHSRAVFNETKNSTRRQTQVLGLTQTCETLKLQLPNCIEDPVSPIV

LRLNFSLVGTPLSAFGNLRPVLAEDAQRLFTALFPFEKNCGNDNICQDDLS

ITFSFMSLDCLVVGGPREFNVTVTVRNDGEDSYRTQVTFFFPLDLSYRKVS

TLQNQRSQRSWRLACESASSTEVSGALKSTSCSINHPIFPENSEVTFNITF

DVDSKASLGNKLLLKANVTSENNMPRTNKTEFQLELPVKYAVYMVVTSHGV

STKYLNFTASENTSRVMQHQYQVSNLGQRSLPISLVFLVPVRLNQTVIWDR

PQVTFSENLSSTCHTKERLPSHSDFLAELRKAPVVNCSIAVCQRIQCDIPF

FGIQEEFNATLKGNLSFDWYIKTSHNHLLIVSTAEILFNDSVFTLLPGQGA

FVRSQTETKVEPFEVPNPLPLIVGSSVGGLLLLALITAALYKLGFFKRQYK

DMMSEGGPPGAEQ

SEQ ID NO: 2 shows CD11b wild type, mature, residues 129-320 with the MIDAS residues D140, S142, S144 and T209 (underlined) of SEQ ID NO: 1.

(SEQ ID NO: 2)
PQEDSDIAFLIDGSGSIIPHDFRRMKEFVSTVMEQLKKSKTLFSLMQYSEE

FRIHFTFKEFQNNPNPRSLVKPITQLLGRTHTATGIRKVVRELFNITNGAR

KNAFKILVVITDGEKFGDPLGYEDVIPEADREGVIRYVIGVGDAFRSEKSR

QELNTIASKPPRDHVFQVNNFEALKTIQNQLREKIFAIE

SEQ ID NO: 3 shows CD11b mature protein residues 129-320 of SEQ ID NO: 1, where MIDAS residue D140 is replaced with Alanine (to remove one MIDAS site metal ion coordinating side chain) D140A.

(SEQ ID NO: 3)
PQEDSDIAFLIAGSGSIIPHDFRRMKEFVSTVMEQLKKSKTLFSLMQYSEE

FRIHFTFKEFQNNPNPRSLVKPITQLLGRTHTATGIRKVVRELFNITNGAR

KNAFKILVVITDGEKFGDPLGYEDVIPEADREGVIRYVIGVGDAFRSEKSR

QELNTIASKPPRDHVFQVNNFEALKTIQNQLREKIFAIE

SEQ ID NO: 4 shows CD11b residues 129-320 of SEQ ID NO: 1, where MIDAS residue D140 is replaced with Alanine (to remove one MIDAS site metal ion coordinating side chain) and 1316 is replaced with Alanine (to create more active conformation of this domain) D140A/1316A.

(SEQ ID NO: 4)
PQEDSDIAFLIAGSGSIIPHDFRRMKEFVSTVMEQLKKSKTLFSLMQYSEE

FRIHFTFKEFQNNPNPRSLVKPITQLLGRTHTATGIRKVVRELFNITNGAR

KNAFKILVVITDGEKFGDPLGYEDVIPEADREGVIRYVIGVGDAFRSEKSR

QELNTIASKPPRDHVFQVNNFEALKTIQNQLREKAFAIE

SEQ ID NO: 5 shows CD11b residues 129-320 of SEQ ID NO: 1, where MIDAS residue D140 is replaced with Alanine (to remove one MIDAS site metal ion coordinating side chain) and F302 is replaced with Tryptophan (to create more active conformation of this domain) D140A/F302W.

(SEQ ID NO: 5)
PQEDSDIAFLIAGSGSIIPHDFRRMKEFVSTVMEQLKKSKTLFSLMQYSEE

FRIHFTFKEFQNNPNPRSLVKPITQLLGRTHTATGIRKVVRELFNITNGAR

KNAFKILVVITDGEKFGDPLGYEDVIPEADREGVIRYVIGVGDAFRSEKSR

QELNTIASKPPRDHVFQVNNWEALKTIQNQLREKIFAIE

SEQ ID NO: 6 shows CD11b residues 129-320 of SEQ ID NO: 1, where four MIDAS site residues are replaced with Alanine (to remove MIDAS site metal ion coordinating side chains) D140A/S140A/S142A/T209A.

(SEQ ID NO: 6)
PQEDSDIAFLIAGAGAIIPHDFRRMKEFVSTVMEQLKKSKTLFSLMQYSEE

FRIHFTFKEFQNNPNPRSLVKPITQLLGRAHTATGIRKVVRELFNITNGAR

KNAFKILVVITDGEKFGDPLGYEDVIPEADREGVIRYVIGVGDAFRSEKSR

QELNTIASKPPRDHVFQVNNFEALKTIQNQLREKIFAIE

SEQ ID NO: 7 shows CD11b residues 128-320 of SEQ ID NO: 1, where residue 128 is replaced with Serine C128S. The C128S substitution may be used in combination with any of the substitutions described above for SEQ ID NOS: 2-6 or any other modification to CD11b.

(SEQ ID NO: 7)
SPQEDSDIAFLIDGSGSIIPHDFRRMKEFVSTVMEQLKKSKTLFSLMQYSE

EFRIHFTFKEFQNNPNPRSLVKPITQLLGRTHTATGIRKVVRELFNITNGA

RKNAFKILVVITDGEKFGDPLGYEDVIPEADREGVIRYVIGVGDAFRSEKS

RQELNTIASKPPRDHVFQVNNFEALKTIQNQLREKIFAIE

Other variants are also possible, including single or a combination of amino acid modifications for any of the integrins described herein.

Examples of other modifications include the changes listed below to the mature form of CD11b (ITGAM, full length with signal peptide shown in SEQ ID NO: 30). (publications Jin 2006; Xiong 2000; Li 1998; Gupta 2007; Shimaoka 2002; McCleverty 2003; Arnaout 2016; Hu 2010).

I316A; I316G Activating/Open
F302W; F302A; F302G; F302L Activating/Open
F275S; F275R Activating/Open
F275S/F302G Activating/Open
Q163C/Q309C; D294C/Q311C; D132C/K315C Activating/Open Q163C/R313C Inactive/Closed
F156A Inactive/Closed Additional mutations in CD11a (ITGAL) that are activating or inactivating mutations referring to the mature protein are shown below (e.g.; Jin 2006; Shimaoka 2001; Lu 2001).
K287C/K294C Activating/Open
L289C/K294C Inactive/Closed
F153A Inactive/Closed Integrin beta3 mutations are shown below referring to the mature protein (e.g.; Luo 2004, Luo 2009; Zhang 2013).
L138I; E206T; S243E; K417E; K417D Activating/Open
G135A Activating/Open
L134G Closed/inactive Integrin beta1 mutations are shown below referring to the mature protein.
V142A Activating/Open
G146A Activating/Open Integrin beta2 mutations are shown below referring to the mature protein.
G128A Activating/Open
NGTD Activating/Open Metal ions can also be preferentially removed from polypeptide and protein preparations by treatment with chelating agents, such as EDTA.

Figure 3:
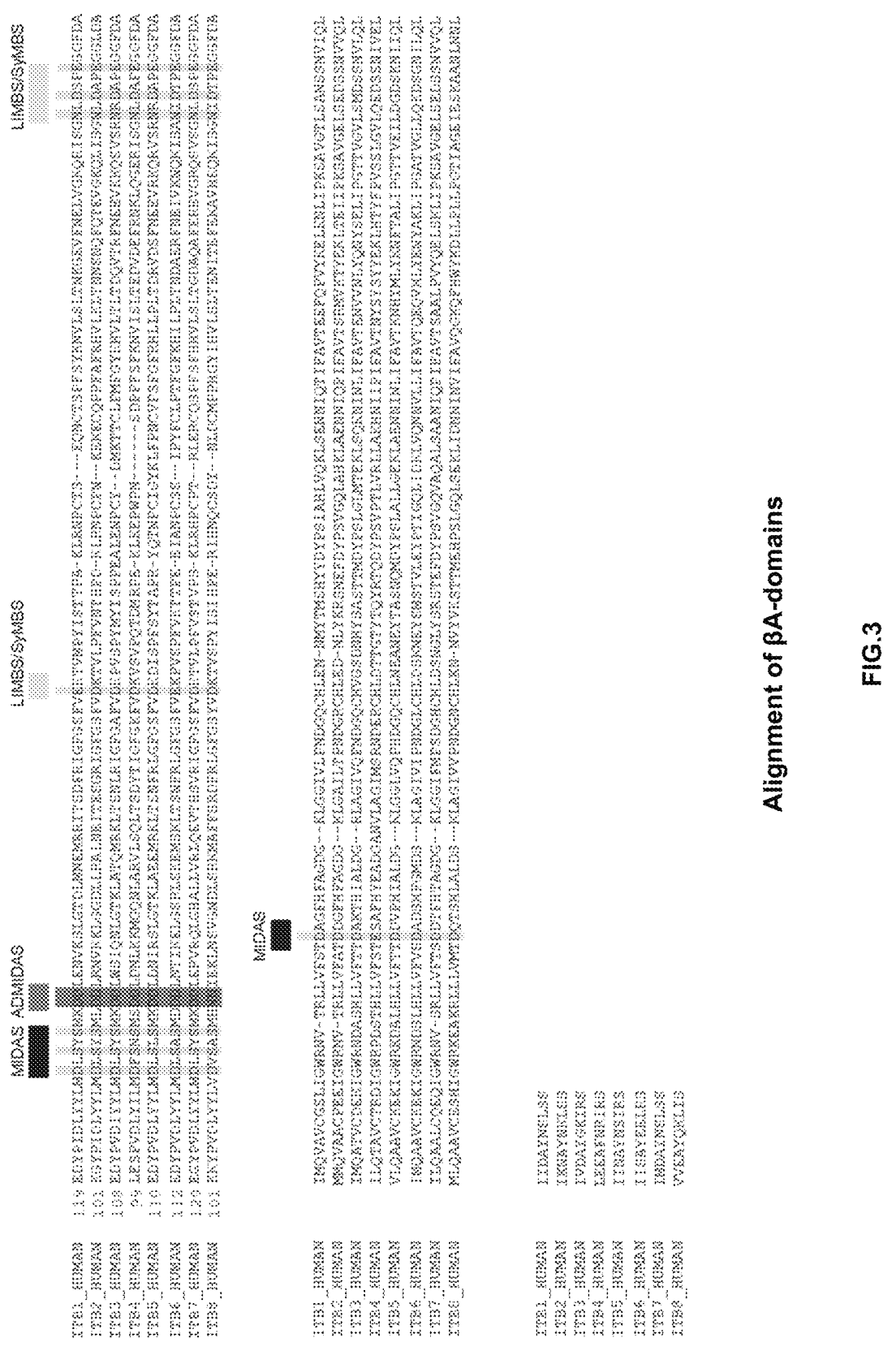

Similar modifications can be made in MIDAS, ADMIDAS, and LIMBS/SyMBS residues in the integrin beta chains 1-8. One or more of the residues identified in each of the integrin beta chains 1-8 suitable for use in identifying binding agents described herein are shown in FIG. 3. Additionally, specificity determining loop 1 (SDL1) and specificity determining loop 2 (SDL2) can be modified or deleted.

Additional integrins that may be modified as described herein are shown in SEQ ID NO: 69-84 and include but are not limited to human integrin alpha-1-11, human integrin alpha-V, human integrin alpha-11b, human integrin alpha-L, human integrin alpha-M and human integrin alpha-X.

Dataset 1. Design and generation of plasmids for expression of various integrin domain constructs (Conformationally Stabilized Integrin Polypeptides).

Integrin domains were cloned into pET-11d expression vector system for *E. Coli* based expression and purification. Inserts for cloning were synthetically prepared and inserted into pET-11d vector. DNA sequencing was used to verify sequences of the cloned inserts. Some of the inserts contained an N-terminal HIS-tag sequence and or MBP-tag sequence, separated with a few amino acid linker. Additionally, some of the sequences also contained a protease cleavage site (such as TEV, SUMO), for easy removal of the tag.

These constructs had the following design:

N-Term MGS-8XHis-S G-PROTEASE-LINKER-INTEGRINDOMAIN-STOP, where LINKER sequence was either=GS or GNGS (SEQ ID NO: 85), PROTEASE was either TEV or SUMO, TEV sequence was ENLYFQ (SEQ ID NO: 86). The constructs described below are summarized in Table 1.

TABLE 1

| Construct ID | Integrin Domain | Tags | Linker Sequence | Incorporated Mutations compared to primary sequence |
|---|---|---|---|---|
| BZ348001 | CD11b | 8XHis-Sumo- | GS | none |
| BZ348002 | CD11a | 8XHis-Sumo- | GS | none |
| BZ348003 | CD11c | 8XHis-Sumo- | GS | none |
| BZ348004 | CD11d | 8XHis-Sumo- | GS | none |
| BZ348005 | ITGB7 | 8XHis-Sumo- | GS | none |
| BZ348006 | CD11b | 8XHis-MBP-TEV- | GS | none |
| BZ348007 | CD11b | 8XHis-TEV- | GS | none |
| BZ348008 | CD11b | 8XHis-TEV- | GS | D140A |
| BZ348009 | CD11b | 8XHis-TEV- | GS | D140A/F275S |
| BZ348010 | CD11b | 8XHis-TEV- | GS | D140A/F275S/F302G |
| BZ348011 | CD11b | 8XHis-TEV- | GS | D242A |
| BZ348012 | CD11b | 8XHis-TEV- | GS | F275S |
| BZ348013 | CD11b | 8XHis-TEV- | GS | F275S/F302G |
| BZ348014 | CD11b | 8XHis-TEV- | GS | D242A/F275S/F302G |
| BZ348015 | CD11b | 8XHis-TEV- | GNGS (SEQ ID NO: 85) | none |
| BZ348016 | CD11a | 8XHis-TEV- | GNGS (SEQ ID NO: 85) | none |
| BZ348017 | CD11c | 8XHis-TEV- | GNGS (SEQ ID NO: 85) | none |
| BZ348018 | CD11d | 8XHis-TEV- | GNGS (SEQ ID NO: 85) | none |
| BZ348019 | ITGB7 | 8XHis-TEV- | GNGS (SEQ ID NO: 85) | C272S-delSDL1-delSDL2 (beta7Protein1) |
| BZ348020 | ITGB4 | 8XHis-TEV- | GNGS (SEQ ID NO: 85) | Beta4-C244S-delSDL1-delSDL2 (beta4Protein1) |
| BZ348021 | ITGB5 | 8XHis-TEV- | GNGS (SEQ ID NO: 85) | Beta5-C257S-delSDL1-delSDL2 (beta5Protein1) |
| BZ348022 | ITGB6 | 8XHis-TEV- | GNGS (SEQ ID NO: 85) | Beta6-C247S-delSDL1-SDL2 (beta6Protein1) |
| BZ348023 | ITGB8 | 8XHis-TEV- | GNGS (SEQ ID NO: 85) | Beta8-C265S-delSDL1-SDL2 (beta8Protein1) |
| BZ348024 | CD11b | 8XHis-TEV- | GNGS (SEQ ID NO: 85) | D140A |
| BZ348025 | CD11b | 8XHis-TEV- | GNGS (SEQ ID NO: 85) | D140A/F275S/F302G |
| BZ348026 | CD11b | 8XHis-TEV- | GNGS (SEQ ID NO: 85) | D242A |
| BZ348027 | CD11b | 8XHis-TEV- | GNGS (SEQ ID NO: 85) | F275S/F302G |

TABLE 1-continued

| Construct ID | Integrin Domain Tags | | Linker Sequence | Incorporated Mutations compared to primary sequence |
|---|---|---|---|---|
| BZ348028 | CD11b | 8XHis-TEV- | GNGS (SEQ ID NO: 85) | D242A/F275S/F302G |
| BZ348029 | CD11a | 8XHis-TEV- | GNGS (SEQ ID NO: 85) | CD11Aa-D137A |
| BZ348030 | CD11a | 8XHis-TEV- | GNGS (SEQ ID NO: 85) | CD11Aa-D238A |
| BZ348031 | CD11a | 8XHis-TEV- | GNGS (SEQ ID NO: 85) | CD11Aa-F264S |
| BZ348032 | CD11a | 8XHis-TEV- | GNGS (SEQ ID NO: 85) | F264S/F291G |
| BZ348033 | CD11a | 8XHis-TEV- | GNGS (SEQ ID NO: 85) | D137A/F264S/F291G |
| BZ348034 | CD11a | 8XHis-TEV- | GNGS (SEQ ID NO: 85) | D238A/F264S/F291G |
| BZ348035 | CD11c | 8XHis-TEV- | GNGS (SEQ ID NO: 85) | D138A |
| BZ348036 | CD11c | 8XHis-TEV- | GNGS (SEQ ID NO: 85) | D240A |
| BZ348037 | CD11c | 8XHis-TEV- | GNGS (SEQ ID NO: 85) | F275S |
| BZ348038 | CD11c | 8XHis-TEV- | GNGS (SEQ ID NO: 85) | F275S/F302G |
| BZ348039 | CD11c | 8XHis-TEV- | GNGS (SEQ ID NO: 85) | D138A/F275S/F302G |
| BZ348040 | CD11c | 8XHis-TEV- | GNGS (SEQ ID NO: 85) | D240A/F275S/F302G |
| BZ348041 | ITGB7 (beta7Protein1) | 8XHis-TEV- | GNGS (SEQ ID NO: 85) | D159A |
| BZ348042 | ITGB7 (beta7Protein1) | 8XHis-TEV- | GNGS (SEQ ID NO: 85) | V171A |
| BZ348043 | ITGB7 (beta7Protein1) | 8XHis-TEV- | GNGS (SEQ ID NO: 85) | L381A |
| BZ348044 | ITGB7 (beta7Protein1) | 8XHis-TEV- | GNGS (SEQ ID NO: 85) | D159A/V171A |
| BZ348045 | ITGB7 (beta7Protein1) | 8XHis-TEV- | GNGS (SEQ ID NO: 85) | D159A/L381A |
| BZ348046 | ITGB7 (beta7Protein1) | 8XHis-TEV- | GNGS (SEQ ID NO: 85) | V379A |
| BZ348047 | ITGB7 (beta7Protein1) | 8XHis-TEV- | GNGS (SEQ ID NO: 85) | D159A/V379A |
| BZ348048 | CD11d | 8XHis-TEV- | GNGS (SEQ ID NO: 85) | D156A |
| BZ348049 | CD11d | 8XHis-TEV- | GNGS (SEQ ID NO: 85) | D156A/F291S/F318G |
| BZ348050 | CD11d | 8XHis-TEV- | GNGS (SEQ ID NO: 85) | D258A |
| BZ348051 | CD11d | 8XHis-TEV- | GNGS (SEQ ID NO: 85) | F291S/F318G |
| BZ348052 | CD11d | 8XHis-TEV- | GNGS (SEQ ID NO: 85) | D258A/F291S/F318G |

1. Protein: CD11b A-domain CD11bA WT (WT residues 132-321)

Constructs: BZ348001, BZ348006, BZ348007, BZ348015

(SEQ ID NO: 16)
132-DSDIAFLIDGSGSIIPHDFRRMKEFVSTVMEQLKKSKTLFSLMQYSE

EFRIHFTFKEFQNNPNPRSLVKPITQLLGRTHTATGIRKVVRELFNITNGA

RKNAFKILVVITDGEKFGDPLGYEDVIPEADREGVIRYVIGVGDAFRSEKS

RQELNTIASKPPRDHVFQVNNFEALKTIQNQLREKIFAIEG-321

2. Protein: CD11b A-domain with designed point mutation (underlined) CD11bA-D140A Feature(s): MIDAS residue D140 is replaced with Alanine (to remove one MIDAS site metal ion coordinating side chain)

Constructs: BZ348008, BZ348024

(SEQ ID NO: 17)
132-DSDIAFLIAGSGSIIPHDFRRMKEFVSTVMEQLKKSKTLFSLMQYS

EFRIHFTFKEFQNNPNPRSLVKPITQLLGRTHTATGIRKVVRELFNITNEG

ARKNAFKILVVITDGEKFGDPLGYEDVIPEADREGVIRYVIGVGDAFRSEK

SRQELNTIASKPPRDHVFQVNNFEALKTIQNQLREKIFAIEG-321

3. Protein: CD11b A-domain with designed point mutations (highlighted) CD11bA-D140A/F275S Feature(s): MIDAS residue D140 is replaced with Alanine (to remove one MIDAS site metal ion coordinating side chain) and F275 is replaced with Serine (to create more active conformation of this domain)

Constructs: BZ348009

(SEQ ID NO: 18)
132-DSDIAFLI<u>A</u>GSGSIIPHDFRRMKEFVSTVMEQLKKSKTLFSLMQY

SEEFRIHFTFKEFQNNPNPRSLVKPITQLLGRTHTATGIRKVVRELFNITN

GARKNAFKILVVITDGEKFGDPLGYEDVIPEADREGVIRYVIGVGDA<u>S</u>RS

EKSRQELNTIASKPPRDHVFQVNN<u>F</u>EALKTIQNQLREKIFAIEG-321

4. Protein: CD11b A-domain with designed point mutations (underlined) CD11bA-D140A/F275S/F302G Feature(s): MIDAS residue D140 is replaced with Alanine (to remove one MIDAS site metal ion coordinating side chain) and F275 is replaced with Serine as well as F302 is replaced with glycine (to create more active conformation of this domain)

Constructs: BZ348010, BZ348025

(SEQ ID NO: 19)
132-DSDIAFLI<u>A</u>GSGSIIPHDFRRMKEFVSTVMEQLKKSKTLFSLMQY

SEEFRIHFTFKEFQNNPNPRSLVKPITQLLGRTHTATGIRKVVRELFNITN

GARKNAFKILVVITDGEKFGDPLGYEDVIPEADREGVIRYVIGVGDA<u>S</u>R

SEKSRQELNTIASKPPRDHVFQVNN<u>G</u>EALKTIQNQLREKIFAIEG-321

5. Protein: CD11b A-domain with designed point mutation (underlined) CD11bA-D242A Feature(s): MIDAS residue D242 is replaced with Alanine (to remove one MIDAS site metal ion coordinating side chain) Constructs: BZ348011, BZ348026

(SEQ ID NO: 20)
132-DSDIAFLIDGSGSIIPHDFRRMKEFVSTVMEQLKKSKTLFSLMQYSE

EFRIHFTFKEFQNNPNPRSLVKPITQLLGRTHTATGIRKVVRELFNITNGA

RKNAFKILVVIT<u>A</u>GEKFGDPLGYEDVIPEADREGVIRYVIGVGDAFRSE

KSRQELNTIASKPPRDHVFQVNNFEALKTIQNQLREKIFAIEG-321

6. Protein: CD11b A-domain with designed point mutation (underlined) CD11bA-F275S Feature(s): F275 is replaced with Serine (to create more active conformation of this domain)

Constructs: BZ348012

(SEQ ID NO: 21)
132-DSDIAFLIDGSGSIIPHDFRRMKEFVSTVMEQLKKSKTLFSLMQYSE

EFRIHFTFKEFQNNPNPRSLVKPITQLLGRTHTATGIRKVVRELFNITNGA

RKNAFKILVVITDGEKFGDPLGYEDVIPEADREGVIRYVIGVGDA<u>A</u>RSE

KSRQELNTIASKPPRDHVFQVNNFEALKTIQNQLREKIFAIEG-321

7. Protein: CD11b A-domain with designed point mutations (underlined) CD11bA-F275S/F302G Feature(s): F275 is replaced with Serine and F302 is replaced with Glycine (to create more active conformation of this domain)

Constructs: BZ348013, BZ348027

(SEQ ID NO: 22)
132-DSDIAFLIDGSGSIIPHDFRRMKEFVSTVMEQLKKSKTLFSLMQYSE

EFRIHFTFKEFQNNPNPRSLVKPITQLLGRTHTATGIRKVVRELFNITNGA

RKNAFKILVVITDGEKFGDPLGYEDVIPEADREGVIRYVIGVGDA<u>S</u>RSE

KSRQELNTIASKPPRDHVFQVNN<u>G</u>EALKTIQNQLREKIFAIEG-321

8. Protein: CD11b A-domain with designed point mutations (underlined) CD11bA-D242A/F275S/F302G Feature(s): MIDAS residue D242 is replaced with Alanine (to remove one MIDAS site metal ion coordinating side chain) and F275 is replaced with Serine (to create more active conformation of this domain) Constructs: BZ348014, BZ348028

(SEQ ID NO: 23)
132-DSDIAFLIDGSGSIIPHDFRRMKEFVSTVMEQLKKSKTLFSLMQYSE

EFRIHFTFKEFQNNPNPRSLVKPITQLLGRTHTATGIRKVVRELFNITNGA

RKNAFKILVVIT<u>A</u>GEKFGDPLGYEDVIPEADREGVIRYVIGVGDA<u>S</u>R

SEKSRQELNTIASKPPRDHVFQVNN<u>G</u>EALKTIQNQLREKIFAIEG-321

9. Protein: CD11a A-domain CD11aA WT, WT residues 128-321

Constructs: BZ348002, BZ348016

(SEQ ID NO: 24)
128-GNVDLVFLFDGSMSLQPDEFQKILDFMKDVMKKLSNTSYQFAAVQFS

TSYKTEFDFSDYVKRKDPDALLKHVKHMLLLTNTFGAINYVATEVFREELG

ARPDATKVLIIITDGEATDSGNIDAAKDIIRYIIGIGKHFQTKESQETLHK

FASKPASEFVKILDTFEKLKDLFTELQKKIYVIEG-321

10. Protein: CD11a A-domain with designed point mutation (underlined) CD11aA-D137A Feature(s): MIDAS residue D137 is replaced with Alanine (to remove one MIDAS site metal ion coordinating side chain)

Constructs: BZ348029

(SEQ ID NO: 25)
128-GNVDLVFLF<u>A</u>GSMSLQPDEFQKILDFMKDVMKKLSNTSYQFAAVQ

FSTSYKTEFDFSDYVKRKDPDALLKHVKHMLLLTNTFGAINYVATEVFRE

ELGARPDATKVLIIITDGEATDSGNIDAAKDIIRYIIGIGKHFQTKESQE

HTLKFASKPASEFVKILDTFEKLKDLFTELQKKIYVIEG-321

11. Protein: CD11a A-domain with designed point mutation (underlined) CD11aA-D238A Feature(s): MIDAS residue D238 is replaced with Alanine (to remove one MIDAS site metal ion coordinating side chain)

Constructs: BZ348030

(SEQ ID NO: 26)
128-GNVDLVFLFDGSMSLQPDEFQKILDFMKDVMKKLSNTSYQFAAVQFS

TSYKTEFDFSDYVKRKDPDALLKHVKHMLLLTNTFGAINYVATEVFREELG

12. Protein: CD11a A-domain with designed point mutation (underlined) CD11aA-F264S Feature(s): F264 is replaced with Serine (to create more active conformation of this domain)

Constructs: BZ348031

(SEQ ID NO: 27)
128-GNVDLVFLFDGSMSLQPDEFQKILDFMKDVMKKLSNTSYQFAAVQFS
TSYKTEFDFSDYVKRKDPDALLKHVKHMLLLTNTFGAINYVATEVFREELG
ARPDATKVLIIITDGEATDSGNIDAAKDIIRYIIGIGKHSQTKESQETLH
KFASKPASEFVKILDTFEKLKDLFTELQKKIYVIEG-321

13. Protein: CD11a A-domain with designed point mutations (underlined) CD11aA-F264S/F291G Feature(s): F264 is replaced with Serine and F 291 is replaced with Glycine (to create more active conformation of this domain)

Constructs: BZ348032

(SEQ ID NO: 28)
128-GNVDLVFLFDGSMSLQPDEFQKILDFMKDVMKKLSNTSYQFAAVQF
STSYKTEFDFSDYVKRKDPDALLKHVKHMLLLTNTFGAINYVATEVFREEL
GARPDATKVLIIITDGEATDSGNIDAAKDIIRYIIGIGKHSQTKESQET
LHKFASKPASEFVKILDTGEKLKDLFTELQKKIYVIEG-321

14. Protein: CD11a A-domain with designed point mutations (underlined) CD11aA-D137A/F264S/F291G Feature(s): MIDAS residue D137 is replaced with Alanine (to remove one MIDAS site metal ion coordinating side chain) and F264 is replaced with Serine as well as F291 is replaced with Glycine (to create more active conformation of this domain)

Constructs: BZ348033

(SEQ ID NO: 29)
128-GNVDLVFLFAGSMSLQPDEFQKILDFMKDVMKKLSNTSYQFAAVQ
FSTSYKTEFDFSDYVKRKDPDALLKHVKHMLLLTNTFGAINYVATEVFRE
ELGARPDATKVLIIITDGEATDSGNIDAAKDIIRYIIGIGKHSQTKESQ
ETLHKFASKPASEFVKILDTGEKLKDLFTELQKKIYVIEG-321

15. Protein: CD11a A-domain with designed point mutations (underlined) CD11aA-D238A/F264S/F291G Feature(s): MIDAS residue D238 is replaced with Alanine (to remove one MIDAS site metal ion coordinating side chain) and F264 is replaced with Serine as well as F291 is replaced with Glycine (to create more active conformation of this domain)

Constructs: BZ348034

(SEQ ID NO: 30)
128-GNVDLVFLFDGSMSLQPDEFQKILDFMKDVMKKLSNTSYQFAAVQFS
GTSYKTEFDFSDYVKRKDPDALLKHVKHMLLLTNTFGAINYVATEVFREEL
GARPDATKVLIIITAGEATDSGNIDAAKDIIRYIIGIGKHSQTKESQ
ETLHKFASKPASEFVKILDTGEKLKDLFTELQKKIYVIEG-321

16. Protein: CD11c A-domain WT 129-319

Constructs: BZ348017 (Tag: His-TEV-)

(SEQ ID NO: 31)
129-QEQDIVFLIDGSGSISSRNFATMMNFVRAVISQFQRPSTQFSLMQFS
NKFQTHFTFEEFRRSSNPLSLLASVHQLQGFTYTATAIQNVVHRLFHASYG
ARRDAAKILIVITDGKKEGDSLDYKDVIPMADAAGIIRYAIGVGLAFQNRN
SWKELNDIASKPSQEHIFKVEDFDALKDIQNQLKEKIFAIEG-319

17. Protein: CD11c A-domain with designed point mutation (underlined) CD11cA-D138A Feature(s): MIDAS residue D138 is replaced with Alanine (to remove one MIDAS site metal ion coordinating side chain)

Constructs: BZ348035

(SEQ ID NO: 32)
129-QEQDIVFLIAGSGSISSRNFATMMNFVRAVISQFQRPSTQFSLM
QFSNKFQTHFTFEEFRRSSNPLSLLASVHQLQGFTYTATAIQNVVHRLFHA
SYGARRDAAKILIVITDGKKEGDSLDYKDVIPMADAAGIIRYAIGVGLAFQ
NRNSWKELNDIASKPSQEHIFKVEDFDALKDIQNQLKEKIFAIEG-319

18. Protein: CD11c A-domain with designed point mutation (underlined) CD11cA-D240A Feature(s): MIDAS residue D240 is replaced with Alanine (to remove one MIDAS site metal ion coordinating side chain)

Constructs: BZ348036

(SEQ ID NO: 33)
129-QEQDIVFLI DGSGSISSRNFATMMNFVRAVISQFQRPSTQFSLMQ
FSNKFQTHFTFEEFRRSSNPLSLLASVHQLQGFTYTATAIQNVVHRLFHAS
YGARRDAAKILIVITAGKKEGDSLDYKDVIPMADAAGIIRYAIGVGLAF
QNRNSWKELNDIASKPSQEHIFKVEDFDALKDIQNQLKEKIFAIEG-319

18. Protein: CD11c A-domain with designed point mutation (underlined) CD11cA-F275S Feature(s): F275 is replaced with Serine (to create more active conformation of this domain)

Constructs: BZ348037

(SEQ ID NO: 34)
129-QEQDIVFLIDGSGSISSRNFATMMNFVRAVISQFQRPSTQFSLMQFS
NKFQTHFTFEEFRRSSNPLSLLASVHQLQGFTYTATAIQNVVHRLFHASYG
ARRDAAKILIVITDGKKEGDSLDYKDVIPMADAAGIIRYAIGVGLASQN
RNSWKELNDIASKPSQEHIFKVEDFDALKDIQNQLKEKIFAIEG-319

19. Protein: CD11c A-domain with designed point mutations (underlined) CD11cA-F275S/F302G Feature(s): F275 is replaced with Serine as well as F302 is replaced with Glycine (to create more active conformation of this domain)

Constructs: BZ348038

```
                                           (SEQ ID NO: 35)
129-QEQDIVFLIDGSGSISSRNFATMMNFVRAVISQFQRPSTQFSLMQFS

NKFQTHFTFEEFRRSSNPLSLLASVHQLQGFTYTATAIQNVVHRLFHASYG

ARRDAAKILIVITDGKKEGDSLDYKDVIPMADAAGIIRYAIGVGLASQN

RNSWKELNDIASKPSQEHIFKVEDGDALKDIQNQLKEKIFAIEG-319
```

20. Protein: CD11c A-domain with designed point mutations (underlined) CD11cA-D240A/F275S/F302G Feature(s): MIDAS residue D240 is replaced with Alanine (to remove one MIDAS site metal ion coordinating side chain) and F275 is replaced with Serine as well as F302 is replaced with Glycine (to create more active conformation of this domain)

Constructs: BZ348040

```
                                           (SEQ ID NO: 36)
129-QEQDIVFLIDGSGSISSRNFATMMNFVRAVISQFQRPSTQFSLMQFS

NKFQTHFTFEEFRRSSNPLSLLASVHQLQGFTYTATAIQNVVHRLFHASYG

ARRDAAKILIVITAGKKEGDSLDYKDVIPMADAAGIIRYAIGVGLAS

QNRNSWKELNDIASKPSQEHIFKVEDGDALKDIQNQLKEKIFAIEG-319
```

21. Protein: CD11c A-domain with designed point mutations (underlined) CD11cA-D138A/F275S/F302G Feature(s): MIDAS residue D138 is replaced with Alanine (to remove one MIDAS site metal ion coordinating side chain) and F275 is replaced with Serine as well as F302 is replaced with Glycine (to create more active conformation of this domain)

Constructs: BZ348039

```
                                           (SEQ ID NO: 37)
129-QEQDIVFLIAGSGSISSRNFATMMNFVRAVISQFQRPSTQFSLMQ

FSNKFQTHFTFEEFRRSSNPLSLLASVHQLQGFTYTATAIQNVVHRLFHAS

YGARRDAAKILIVITDGKKEGDSLDYKDVIPMADAAGIIRYAIGVGLAS

QNRNSWKELNDIASKPSQEHIFKVEDGDALKDIQNQLKEKIFAIEG-

319
```

22. Protein: CD11d A-domain WT: residues 147-337

Constructs: BZ348018

```
                                           (SEQ ID NO: 38)
147-QEMDIVFLIDGSGSIDQNDFNQMKGFVQAVMGQFEGTDTLFALMQYS

NLLKIHFTFTQFRTSPSQQSLVDPIVQLKGLTFTATGILTVVTQLFHHKNG

ARKSAKKILIVITDGQKYKDPLEYSDVIPQAEKAGIIRYAIGVGHAFQGPT

ARQELNTISSAPPQDHVFKVDNFAALGSIQKQLQEKIYAVEG-337
```

23. Protein: CD11d A-domain with designed point mutation (underlined) CD11dA-D156A Feature(s): MIDAS residue D156 is replaced with Alanine (to remove one MIDAS site metal ion coordinating side chain Constructs: BZ348048

```
                                           (SEQ ID NO: 39)
147-QEMDIVFLIAGSGSIDQNDFNQMKGFVQAVMGQFEGTDTLFALMQ

YSNLLKIHFTFTQFRTSPSQQSLVDPIVQLKGLTFTATGILTVVTQLFHHK

NGARKSAKKILIVITDGQKYKDPLEYSDVIPQAEKAGIIRYAIGVGHAFQG

PTARQELNTISSAPPQDHVFKVDNFAALGSIQK QLQEKIYAVEG-337
```

24. Protein: CD11d A-domain with designed point mutations (underlined) CD11dA-F291S/F318G Feature(s): F291 is replaced with Serine as well as F318 is replaced with Glycine (to create more active conformation of this domain)

Constructs: BZ348051

```
                                           (SEQ ID NO: 40)
147-QEMDIVFLIDGSGSIDQNDFNQMKGFVQAVMGQFEGTDTLFALMQYS

NLLKIHFTFTQFRTSPSQQSLVDPIVQLKGLTFTATGILTVVTQLFHHKNG

ARKSAKKILIVITDGQKYKDPLEYSDVIPQAEKAGIIRYAIGVGHASQG

PTARQELNTISSAPPQDHVFKVDNGAALGSIQKQLQEKIYAVEG-337
```

25. Protein: CD11d A-domain with designed point mutation (underlined) CD11dA-D258A Feature(s): MIDAS residue D258 is replaced with Alanine (to remove one MIDAS site metal ion coordinating side chain Constructs: BZ348050

```
                                           (SEQ ID NO: 41)
147-QEMDIVFLIDGSGSIDQNDFNQMKGFVQAVMGQFEGTDTLFALMQYS

NLLKIHFTFTQFRTSPSQQSLVDPIVQLKGLTFTATGILTVVTQLFHHKNG

ARKSAKKILIVITAGQKYKDPLEYSDVIPQAEKAGIIRYAIGVGHAFQG

PTARQELNTISSAPPQDHVFKVDNFAALGSIQKQLQEKIYAVEG-337
```

26. Protein: CD11d A-domain with designed point mutations (underlined) CD11dA-D258A/F291S/F318G Feature(s): MIDAS residue D258 is replaced with Alanine (to remove one MIDAS site metal ion coordinating side chain) and F291 is replaced with Serine as well as F318 is replaced with Glycine (to create more active conformation of this domain)

Constructs: BZ348052

```
                                           (SEQ ID NO: 42)
147-QEMDIVFLIDGSGSIDQNDFNQMKGFVQAVMGQFEGTDTLFALMQYS

NLLKIHFTFTQFRTSPSQQSLVDPIVQLKGLTFTATGILTVVTQLFHHKNG

ARKSAKKILIVITAGQKYKDPLEYSDVIPQAEKAGIIRYAIGVGHASQ

GPTARQELNTISSAPPQDHVFKVDNGAALGSIQKQLQEKIYAVEG-337
```

27. Protein: CD11d A-domain with designed point mutations (underlined) CD11dA-D156A/F291S/F318G Feature(s): MIDAS residue D156 is replaced with Alanine (to remove one MIDAS site metal ion coordinating side chain) and F291 is replaced with Serine as well as F318 is replaced with Glycine (to create more active conformation of this domain)

Constructs: BZ348049

(SEQ ID NO: 43)
147-QEMDIVFLI<u>A</u>GSGSIDQNDFNQMKGFVQAVMGQFEGTDTLFALMQY

SNLLKIHFTFTQFRTSPSQQSLVDPIVQLKGLTFTATGILTVVTQLFHHK

NGARKSAKKILIVITDGQKYKDPLEYSDVIPQAEKAGIIRYAIGVGHA<u>S</u>

QGPTARQELNTISSAPPQDHVFKVDN<u>G</u>AALGSIQKQLQEKIYAVEG-

337

28. Protein: Integrin beta7 (ITGB7) beta1-domain with designed point mutation (highlighted) and deletions: Beta7-C272S-delSDL1-delSDL2 (beta7Protein1)
Note: ITGB7 beta1 domain WT Sequence:
B7WT (with SDL1 (K200-F228) and SDL2 (A296-P329) 148-393; Cysteine residues are bolded.

(SEQ ID NO: 44)
148-EGYPVDLYYLMDLSYSMKDDLERVRQLGHALLVRLQEVTHSVRIGFG

SFVD<u>KTVLPFVSTVPSKLRHPCPTRLERCQSPFS</u>FHHVLSLTGDAQAFERE

VGRQSVSGNLDSPEGGFDAILQAAL<u>C</u>QEQIGWRNVSRLLVFTSDDTFHT<u>AG

DGKLGGIFMPSDGHCHLDSNGLYSRSTEFDYP</u>SVGQVAQALSAANIQPIFA

VTSAALPVYQELSKLIPKSAVGELSEDSSNVVQLIMDAYNSLSSTV-393

Feature(s): residue C272 is replaced with Serine (to remove one Cysteine site) and SDL1 (K200-F228) and SDL2 (A296-P329) residues are deleted from the WT sequence (as shown above).
Constructs: BZ348019

(SEQ ID NO: 45)
148-EGYPVDLYYLMDLSYSMKDDLERVRQLGHALLVRLQEVTHSVRIGFG

SFVDSFHHVLSLTGDAQAFEREVGRQSVSGNLDSPEGGFDAILQAAL<u>SQ</u>

EQIGWRNVSRLLVFTSDDTFHTSVGQVAQALSAANIQPIFAVTSAALPVYQ

ELSKLIPKSAVGELSEDSSNVVQLIMDAYNSLSSTV

29. Protein: beta7Protein1 with additional designed point mutation (underlined): beta7Protein1-D159A
Feature(s): MIDAS residue D159 is replaced with Alanine (to remove one MIDAS site metal ion coordinating side chain) and residue C272 is replaced with Serine (to remove one Cysteine site) and SDL1 (K200-F228) and SDL2 (A296-P329) residues are deleted from the WT sequence (as shown above).
Constructs: BZ348041

(SEQ ID NO: 46)
148-EGYPVDLYYLM<u>A</u>LSYSMKDDLERVRQLGHALLVRLQEVTHSVRI

GFGSFVDSFHHVLSLTGDAQAFEREVGRQSVSGNLDSPEGGFDAILQAAL

<u>S</u>QEQIGWRNVSRLLVFTSDDTFHTSVGQVAQALSAANIQPIFAVTSAALP

VYQELSKLIPKSAVGELSEDSSNVVQLIMDAYNSLSSTV

30. Protein: beta7Protein1 with additional designed point mutation (underlined): beta7Protein1-V171A
Feature(s): residue C272 is replaced with Serine (to remove one Cysteine site) and SDL1 (K200-F228) and SDL2 (A296-P329) residues are deleted from the WT sequence (as shown above). Additionally, Valine 171 is replaced with alanine (to create more active conformation of this domain).

Constructs: BZ348042

(SEQ ID NO: 47)
148-EGYPVDLYYLMDLSYSMKDDLER<u>A</u>RQLGHALLVRLQEVTHSVRIG

FGSFVDSFHHVLSLTGDAQAFEREVGRQSVSGNLDSPEGGFDAILQAAL<u>S</u>

QEQIGWRNVSRLLVFTSDDTFHTSVGQVAQALSAANIQPIFAVTSAALPVY

QELSKLIPKSAVGELSEDSSNVVQLIMDAYNSLSSTV

31. Protein: beta7Protein1 with additional designed point mutation (underlined): beta7Protein1-L381A
Feature(s): residue C272 is replaced with Serine (to remove one Cysteine site) and SDL1 (K200-F228) and SDL2 (A296-P329) residues are deleted from the WT sequence (as shown above). Additionally, Leucine 381 is replaced with alanine (to create more active conformation of this domain).
Constructs: BZ348043

(SEQ ID NO: 48)
148-EGYPVDLYYLMDLSYSMKDDLERVRQLGHALLVRLQEVTHSVRIGFG

SFVDSFHHVLSLTGDAQAFEREVGRQSVSGNLDSPEGGFDAILQAAL<u>SQ</u>

EQIGWRNVSRLLVFTSDDTFHTSVGQVAQALSAANIQPIFAVTSAALPVYQ

ELSKLIPKSAVGELSEDSSNVVQ<u>A</u>IMDAYNSLSSTV

32. Protein: beta7Protein1 with additional designed point mutation (underlined): beta7Protein1-D159A/V171A
Feature(s): MIDAS residue D159 is replaced with Alanine (to remove one MIDAS site metal ion coordinating side chain) and residue C272 is replaced with Serine (to remove one Cysteine site) and SDL1 (K200-F228) and SDL2 (A296-P329) residues are deleted from the WT sequence (as shown above). Additionally, Valine 171 is replaced with alanine (to create more active conformation of this domain).
Constructs: BZ348044

(SEQ ID NO: 49)
148-EGYPVDLYYLM<u>A</u>LSYSMKDDLER<u>A</u>RQLGHALLVRLQEVTHSVR

IGFGSFVDSFHHVLSLTGDAQAFEREVGRQSVSGNLDSPEGGFDAILQAAL

<u>S</u>QEQIGWRNVSRLLVFTSDDTFHTSVGQVAQALSAANIQPIFAVTSAALP

VYQELSKLIPKSAVGELSEDSSNVVQLIMDAYNSLSSTV

33. Protein: beta7Protein1 with additional designed point mutation (underlined): beta7Protein1-D159A/L381A
Feature(s): MIDAS residue D159 is replaced with Alanine (to remove one MIDAS site metal ion coordinating side chain) and residue C272 is replaced with Serine (to remove one Cysteine site) and SDL1 (K200-F228) and SDL2 (A296-P329) residues are deleted from the WT sequence (as shown above). Additionally, Leucine 381 is replaced with alanine (to create more active conformation of this domain).
Constructs: BZ348045

(SEQ ID NO: 50)
148-EGYPVDLYYLM<u>A</u>LSYSMKDDLERVRQLGHALLVRLQEVTHSVRIG

FGSFVDSFHHVLSLTGDAQAFEREVGRQSVSGNLDSPEGGFDAILQAAL<u>S</u>

QEQIGWRNVSRLLVFTSDDTFHTSVGQVAQALSAANIQPIFAVTSAALPVY

QELSKLIPKSAVGELSEDSSNVVQ<u>A</u>IMDAYNSLSSTV

34. Protein: beta7Protein1 with additional designed point mutation (underlined): beta7Protein1-V379A Feature(s): residue C272 is replaced with Serine (to remove one Cysteine site) and SDL1 (K200-F228) and SDL2 (A296-P329) residues are deleted from the WT sequence (as shown above). Additionally, Valine 379 is replaced with alanine (to create less active conformation of this domain).

Constructs: BZ348046

(SEQ ID NO: 51)
148-EGYPVDLYYLMDLSYSMKDDLERVRQLGHALLVRLQEVTHSVRIGFG

SFVDSFHHVLSLTGDAQAFEREVGRQSVSGNLDSPEGGFDAILQAAL<u>SQ</u>

EQIGWRNVSRLLVFTSDDTFHTSVGQVAQALSAANIQPIFAVTSAALPVYQ

ELSKLIPKSAVGELSEDSSNV<u>A</u>QLIMDAYNSLSSTV

35. Protein: beta7Protein1 with additional designed point mutation (underlined): beta7Protein1-D159A/V379A Feature(s): MIDAS residue D159 is replaced with Alanine (to remove one MIDAS site metal ion coordinating side chain) and residue C272 is replaced with Serine (to remove one Cysteine site) and SDL1 (K200-F228) and SDL2 (A296-P329) residues are deleted from the WT sequence (as shown above). Additionally, Valine 379 is replaced with alanine (to create less active conformation of this domain).

Constructs: BZ348047

(SEQ ID NO: 52)
148-EGYPVDLYYLM<u>A</u>LSYSMKDDLERVRQLGHALLVRLQEVTHSVRIGF

GSFVDSFHHVLSLTGDAQAFEREVGRQSVSGNLDSPEGGFDAILQAAL<u>SQ</u>

EQIGWRNVSRLLVFTSDDTFHTSVGQVAQALSAANIQPIFAVTSAALPVYQ

ELSKLIPKSAVGELSEDSSNV<u>A</u>QLIMDAYNSLSSTV

36. Protein: Integrin beta4 (ITGB4) beta1-domain with designed point mutation (underlined) and deletions: Beta4-C244S-delSDL1-delSDL2 (beta4Protein1)

Note: ITGB4 beta1 domain WT Sequence:

B4WT (with SDL1 (K177-F201) and SDL2 (E269-P305); Cysteine residues are bolded.

(SEQ ID NO: 53)
126 LESPVDLYILMDFSNSMSDDLDNLKKMGQNLARVLSQLTSDYTIGFG

KFVD<u>KVSVPQTDMRPEKLKEPWPNSDPPFS</u>FKNVISLTEDVDEFRNKLQGE

RISGNLDAPEGGFDAILQTAVCTRDIGWRPDSTHLLVFSTESAFHY<u>EADGA</u>

<u>NVLAGIMSRNDER</u>CHLDTTGTYTQYRTQDYPSVPTLVRLLAKHNIIPIFAV

TNYSYSYYEKLHTYFPVSSLGVLQEDSSNIVELLEEAFNRIRSNL-370

Feature(s): residue C244 is replaced with Serine (to remove one Cysteine site) and SDL1 (K177-F201) and SDL2 (E269-P305) residues are deleted from the WT sequence (as shown above).

Constructs: BZ348020

(SEQ ID NO: 54)
126 LESPVDLYILMDFSNSMSDDLDNLKKMGQNLARVLSQLTSDYTIGFG

KFVDSFKNVISLTEDVDEFRNKLQGERISGNLDAPEGGFDAILQTAV<u>S</u>TR

-continued
DIGWRPDSTHLLVFSTESAFHYSVPTLVRLLAKHNIIPIFAVTNYSYSYYE

KLHTYFPVSSLGVLQEDSSNIVELLEEAFNRIRSNL

37. Protein: Integrin beta5 (ITGB5) beta1-domain with designed point mutation (bolded) and deletions: Beta5-C257S-delSDL1-delSDL2 (beta5Protein1) Note: ITGB5 beta1 domain WT Sequence:

B5WT (SDL1 (K184-F214) and SDL2 (A282-P315) 133-380; Cysteine residues are bolded.

(SEQ ID NO: 55)
133 EDYPVDLYYLMDLSLSMKDDLDNIRSLGTKLAEEMRKLTSNFRLGFG

SFVD<u>KDISPFSYTAPRYQTNPCIGYKLFPNCVPSF</u>GFRHLLPLTDRVDSFN

EEVRKQRVSRRDAPEGGFDAVLQAAVCKEKIGWRKDALHLLVFTTDDVPHI

ALDGKLGGLVQPHDGQCHLNEANEYTASNQMDYPSLALLGEKLAENNINLI

FAVTKNHYMLYKNFTALIPGTTVEILDGDSKNIIQLIINAYNSIRSKV

Feature(s): residue C257 is replaced with Serine (to remove one Cysteine site) and SDL1 (K184-F214) and SDL2 (A282-P315) residues are deleted from the WT sequence (as shown above).

Constructs: BZ348021

(SEQ ID NO: 56)
133-EDYPVDLYYLMDLSLSMKDDLDNIRSLGTKLAEEMRKLTSNFRLGFG

SFVDGFRHLLPLTDRVDSFNEEVRKQRVSRRDAPEGGFDAVLQAAV<u>S</u>KEKI

GWRKDALHLLVFTTDDVPHISLALLGEKLAENNINLIFAVTKNHYMLYKNF

TALIPGTTVEILDGDSKNIIQLIINAYNSIRSKV

38. Protein: Integrin beta6 (ITGB6) beta1-domain with designed point mutation (underlined) and deletions: Beta6-C247S-delSDL1-SDL2 (beta6Protein1)

Note: ITGB6 beta1 domain WT Sequence:

B6WT (SDL1 (K174-F202) and SDL2 (G272-P305); Cysteine residues are bolded.

(SEQ ID NO: 57)
121 TEDYPVDLYYLMDLSASMDDDLNTIKELGSRLSKEMSKLTSNFRLGF

GSFVE<u>KPVSPFVKTTPEEIANPCSSIPYFCLPTF</u>GFKHILPLTNDAERFNE

IVKNQKISANIDTPEGGFDAIMQAAVCKEKIGWRNDSLHLLVFVSDADS

HFGMDSKLAGIVIPNDGLCHLDSKNEYSMSTVLEYPTIGQLIDKLVQNNVL

LIFAVTQEQVHLYENYAKLIPGATVGLLQKDSGNILQLIISAYEELRSEV

Feature(s): residue C247 is replaced with Serine (to remove one Cysteine site) and SDL1 (K174-F202) and SDL2 (G272-P305) residues are deleted from the WT sequence (as shown above).

Constructs: BZ348022

(SEQ ID NO: 58)
121 TEDYPVDLYYLMDLSASMDDDLNTIKELGSRLSKEMSKLTSNFRLGF

GSFVEGFKHILPLTNDAERFNEIVKNQKISANIDTPEGGFDAIMQAAV<u>S</u>

KEKIGWRNDSLHLLVFVSDADSHFTIGQLIDKLVQNNVLLIFAVTQEQVHL

YENYAKLIPGATVGLLQKDSGNILQLIISAYEELRSEV

39. Protein: Integrin beta8 (ITGB8) beta1-domain with designed point mutation (underlined) and deletions: Beta8-C265S-delSDL1-SDL2 (beta8Protein1)

Note: ITGB8 beta1 domain WT Sequence:
B8WT (SDL1 (K193-H221) and SDL2 (A290-P322) 142-388; Cysteine residues are bolded.

(SEQ ID NO: 59)
142 LKKYPVDLYYLVDVSASMHNNIEKLNSVGNDLSRKMAFFSRDFRLGF

GSYVDKTVSPYISIHPERIHNQCSDYNLDCMPPHGYIHVLSLTENITEFEK

AVHRQKISGNIDTPEGGFDAMLQAAVCESHIGWRKEAKRLLLVMTDQTS

HLALDSKLAGIVVPNDGNCHLKNNVYVKSTTMEHPSLGQLSEKLIDNNINV

IFAVQGKQFHWYKDLLPLLPGTIAGEIESKAANLNNLVVEAYQKLISEV

388

Feature(s): residue C265 is replaced with Serine (to remove one Cysteine site) and SDL1 (K193-H221) and SDL2 (A290-P322) residues are deleted from the WT sequence (as shown above).

Constructs: BZ348023

(SEQ ID NO: 60)
142-LKKYPVDLYYLVDVSASMHNNIEKLNSVGNDLSRKMAFFSRDFRLGF

GSYVDGYIHVLSLTENITEFEKAVHRQKISGNIDTPEGGFDAMLQAAVS

ESHIGWRKEAKRLLLVMTDQTSHLSLGQLSEKLIDNNINVIFAVQGKQFHW

YKDLLPLLPGTIAGEIESKAANLNNLVVEAYQKLISEV

Dataset 2. Recombinant protein expression
Table 2 shows typical expression for the plasmids listed.

TABLE 2

| Plasmid used | Culture Scale | Yield of purified protein |
|---|---|---|
| BZ348007 | 6 L | 13 mg |
| BZ348008 | 6 L | 30 mg |
| BZ348010 | 1 L | 1.5 mg |
| BZ348011 | 6 L | 18 mg |
| BZ348013 | 1 L | 3 mg |
| BZ348014 | 6 L | 4.8 mg |

Protocols

Recombinant proteins were expressed in BL21DE3 bacterial strain and grown in TB at 37° C. Induction of expression was at 30° C. for 4 hours with a starting OD600 nm at induction of 1.0-1.2 using 0.5 mM IPTG.

Protein Purification: Preparation of soluble fractions followed by affinity column purification and dialysis in storage buffer. (Optionally) The tag was removed via protease digestion and repurification using an affinity column according to literature protocols. Further purification, if needed, was performed using size exclusion or ion-exchange chromatography.

The E. coli Processed Fraction was purified in a first chromatography step as follows. The soluble fraction was prepared by lysing the cells by sonication, lysozyme treatment and a freeze/thaw cycle followed by centrifugation (20,000 g/30 min/4° C.). The soluble fraction was loaded on to a Ni-IMAC column (Ni-NTA) having a column volume of 2 ml. The Ni-IMAC Lysis Buffer used was 50 mM Tris-HCl pH 8.0, 300 mM NaCl, 10% glycerol, 15 mM imidazole, 2 mM bME. The Ni-IMAC Wash Buffer used was 50 mM Tris-HCl pH 8.0, 600 mM NaCl, 10% glycerol, 40 mM imidazole, 0.002% Triton X-100, 2 mM bME. The Ni-IMAC Elution Buffer used was 25 mM Tris-HCl pH 7.5, 300 mM NaCl, 10% glycerol, 500 mM imidazole, 2 mM bME. The pooled sample volume was 8 mL. The sample was dialyzed overnight in 500 mL and then followed by a 6 hour dialysis in 500 mL.

Screening for optimal conditions for expression of recombinant CD11bA domain using construct number BZ348001.

PAGE based analysis of various expression conditions listed in Table 3 showed that the recombinant His-Sumo-CD11b is expressed in the IMAC elution of all tested conditions without significant differences among conditions. Two lower bands which most likely correspond to a cleavage in the CD11bA can also be seen in all conditions.

Comparison of two different constructs for expression of recombinant CD11bA domain-using construct numbers BZ348006 (N-term tag: His-MBP-TEV-) and BZ348007 (N-term tag: His-TEV-).

PAGE based analysis of various expression conditions listed in Table 3 show that both constructs produce recombinant protein. The MBP containing construct produces a larger amount of protein.

Expression of various recombinant CD11bA domains. PAGE based analysis of various expression conditions. The recombinant His-TEV-CD11b can be readily expressed and purified. His-tag can be cleaved off. Nonlimiting examples of expressed constructs include BZ348008, BZ348011 and BZ348015.

Expression of various recombinant CD11bA domains. PAGE based analysis of various expression conditions. The recombinant His-TEV-CD11b can be readily expressed and purified. Nonlimiting examples of expressed constructs include BZ348010, BZ348013 and BZ348014.

TABLE 3

| | Screening conditions tested | | | | |
|---|---|---|---|---|---|
| Condition | Induction Temp. (° C.) | Induction Time (h) | Medium | IPTG (mM) | OD$_{600\,nm}$ at Induction | IMAC |
| A | 18 | 16 | LB | 0.25 | 0.6-0.8 | Co |
| B | 25 | 16 | LB | 0.25 | 0.6-0.8 | Co |
| C | 30 | 4 | TB | 0.5 | 1.0-1.2 | Co |
| D | 18 | 16 | LB | 0.25 | 0.6-0.8 | Ni |
| E | 25 | 16 | LB | 0.25 | 0.6-0.8 | Ni |
| F | 30 | 4 | TB | 0.5 | 1.0-1.2 | Ni |

Dataset 3. Use of various integrin domains (Conformationally Stabilized Integrin Polypeptides) to identify conformation specific polypeptide binders.

The following polypeptides expressing various CD11b A-domain sequences (WT and mutant) were used in a phage display screening effort to identify conformation specific binders:

TABLE 4

| Construct used | Note |
|---|---|
| BZ348007 | Wild type sequence |
| BZ348008 | MIDAS residue mutation D140A to remove metal binding at MIDAS site |
| BZ348010 | MIDAS residue mutation D140A to remove metal binding at MIDAS site and F275 is replaced with Serine as well as F302 is replaced with glycine (to create more active conformation of this domain) (No MIDAS metal + Active conformation) |

TABLE 4-continued

| Construct used | Note |
|---|---|
| BZ348011 | MIDAS residue mutation D242A to remove metal binding at MIDAS site |
| BZ348013 | F275 is replaced with Serine as well as F302 is replaced with glycine (to create more active conformation of this domain) |
| BZ348014 | MIDAS residue mutation D242A to remove metal binding at MIDAS site and F275 is replaced with Serine as well as F302 is replaced with glycine (to create more active conformation of this domain) (No MIDAS metal + Active conformation) |

Goal: To identify polypeptides (e.g.; scFVs, or any other binding fragments described herein) that selectively bind constructs with no MIDAS metal binding and mutationally stabilized in active conformation over other constructs. By way of non-limiting example, polypeptides that selectively bind to construct BZ348010 or BZ348014 or both (constructs with no MIDAS metal binding and mutationally stabilized in active conformation) over other constructs are identified. Similarly, the protocols used below may be used with any of the constructs described herein.

Protocols

A naïve human scFv phage display library and VHH phage display library were screened against several integrin targets of interest. The screen involved phage ELISA followed by sequencing. The most active clones were then scaled up for further evaluation.

Naïve Human scFv Phage Display Library Screening

Example experiment: A diverse naïve human scFv phage display library (Neoclone, LLC, Madison, WI) was enriched on BZ348014.

After 2 rounds of enrichment against the primary target, positive binders were identified by phage ELISA and analyzed by restriction mapping & sequencing for identification of unique clones. Small scale phage growths were diluted 1:5 in TBS+casein. Nunc Maxi-Sorp strip wells were coated at ~5 µg/ml of each test protein overnight at 4° C. and blocked with TBS+casein. The diluted phage were applied and allowed to bind for 1 hour with shaking. The wells were washed 4 times with TBS+0.05% Tween20 and twice with TBS. Bound phage were detected by incubation for 1 hour with anti-M13-HRP and after washing as above, developed with TMB. Absorbance at 450 nM was read after acidification of the wells.

The table below shows the ELISA data indicating positive binders against the BZ348014 antigen associated with this effort:

TABLE 5

| Clone ID | BZ348014 | Clone ID | Blocked well |
|---|---|---|---|
| 1 | 1.229 | 1 | 0.050 |
| 2 | 1.176 | 2 | 0.049 |
| 3 | 1.267 | 3 | 0.049 |
| 4 | 1.289 | 4 | 0.043 |
| 5 | 1.374 | 5 | 0.045 |
| 6 | 0.641 | 6 | 0.041 |
| 7 | 1.131 | 7 | 0.042 |
| 8 | 0.060 | 8 | 0.047 |
| 9 | 1.012 | 9 | 0.048 |
| 10 | 0.107 | 10 | 0.041 |
| 11 | 0.628 | 11 | 0.043 |
| 12 | 0.045 | 12 | 0.041 |
| 13 | 0.499 | 13 | 0.043 |
| 14 | 0.598 | 14 | 0.044 |
| 15 | 0.044 | 15 | 0.044 |
| 16 | 1.686 | 16 | 0.041 |

High binding clones were included in a counterscreen ELISA against other CD11b A-domain polypetides which produced the following data:

TABLE 6

| Clone ID | BZ348014 | BZ348011 | BZ348008 | BZ348010 | BZ348013 | BZ348007 |
|---|---|---|---|---|---|---|
| 2 | 1.576 | 1.735 | 1.696 | 1.723 | 1.700 | 1.674 |
| 3 | 1.777 | 1.791 | 1.829 | 1.683 | 1.685 | 1.788 |
| 5 | 1.693 | 1.766 | 1.852 | 1.739 | 1.654 | 1.780 |
| 6 | 1.249 | 0.169 | 0.058 | 1.508 | 1.304 | 0.567 |
| 13 | 0.866 | 0.183 | 0.228 | 0.495 | 0.954 | 0.169 |
| 14 | 1.063 | 0.259 | 0.380 | 0.659 | 0.953 | 0.220 |

To confirm binding, a dilution series experiment was carried out. Select clones were subjected to a dilution series which generated the following data:

TABLE 7

| Clone ID | BZ348014 | BZ348007 | BZ348008 | BZ348010 | BZ348011 | BZ348013 |
|---|---|---|---|---|---|---|
| Clone 2 1:5 | 1.822 | 1.868 | 1.827 | 1.840 | 1.856 | 1.832 |
| Clone 2 1:16 | 1.183 | 1.808 | 1.672 | 1.633 | 1.813 | 1.533 |
| Clone 2 1:50 | 0.205 | 0.635 | 0.558 | 0.229 | 0.390 | 0.461 |
| BLOCK ONLY | 0.045 | 0.049 | 0.046 | 0.045 | 0.041 | 0.043 |
| Clone 14 1:5 | 0.782 | 0.557 | 0.372 | 0.046 | 0.200 | 1.377 |
| Clone 14 1:16 | 0.356 | 0.101 | 0.080 | 0.038 | 0.054 | 0.278 |

TABLE 7-continued

| Clone ID | BZ348014 | BZ348007 | BZ348008 | BZ348010 | BZ348011 | BZ348013 |
|---|---|---|---|---|---|---|
| Clone 14 1:50 | 0.059 | 0.060 | 0.047 | 0.040 | 0.045 | 0.078 |
| BLOCK ONLY | 0.043 | 0.046 | 0.046 | 0.040 | 0.045 | 0.050 |

Results: The data suggests that clones 6, 13 and 14 bound selectively to the CD11b A-domain polypeptides mutationally stabilized in active conformation over the other conformations. Clones 2, 3 and 5 showed limited or no selectivity in binding to the various CD11b A-domain polypeptides.

The sequences of the identified clones are shown below.

Clone 2 149-014-2 (VL-Linker-VH)
(SEQ ID NO: 61)
TCTTCTGAGCTGACTCAGGACCCTGCTGTGTCTGTGGCCTTGGGACAGACA

GTCAGGATCACATGCCAAGGAGACAGCCTCAGAAGCTATTATGCAAGCTGG

TACCAGCAGAAGCCAGGACAGGCCCCTGTACTTGTCATCTATGGTAAAAAC

AACCGGCCCTCAGGGATCCCAGACCGATTCTCTGGCTCCAGCTCAGGAAAC

ACAGCTTCCTTGACCATCACTGGGGCTCAGGCGGAAGATGAGGCTGACTAT

TACTGTAACTCCCGGGACAGCAGTGGTAACCATCTGGTATTCGGCGGAGGG

ACCAAGCTGACCGTCCTAGGTGAGGGTAAATCTTCCGGATCTGGTTCCGAA

TCCAAAGCTAGCCAGGTTCAGCTGGTGCAGTCTGGGGCTGAGGTGAAGAAG

CCTGGGGCCTCAGTGAAGGTCTCCTGCAAGGCTTCTGGATACACCTTCACC

GGCTACTATATGCACTGGGTGCGACAGGCCCCTGGACAAGGGCTTGAGTGG

ATGGGATGGATCAACCCTAACAGTGGTGGCACAAACTATGCACAGAAGTTT

CAGGGCTGGGTCACCATGACCAGGGACACGTCCATCAGCACAGCCTACATG

GAGCTGAGCAGGCTGAGATCTGACGACACGGCCGTGTATTACTGTGCGCGC

TACATGGTTCGGGGAGGAGGGATTGACTACTGGGGCCAGGGCACCCTGGTC

ACCGTCTCCTCA

Clone 3 149-014-3 (VL-Linker-VH)
(SEQ ID NO: 62)
TCTTCTGAGCTGACTCAGGACCCTGCTGTGTCTGTGGCCTTGGGACAGACA

GTCAGGATCACATGCCAAGGAGACAGCCTCAGAAGCTATTATGCAAGCTGG

TACCAGCAGAAGCCAGGACAGGCCCCTGTACTTGTCATCTATGGTAAAAAC

AACCGGCCCTCAGGGATCCCAGACCGATTCTCTGGCTCCACCTCAGGAAAT

ACAGCTTCCTTGACCATCACTGGGGCTCAGGCGGAGGATGAGGCTGACTAT

TACTGTAACTCCCGGGACAGCAGTGGTAACCATCTGGTATTCGGCGGAGGG

ACCAAGCTCACCGTCCTAGGTGAGGGTAAATCTTCCGGATCTGGTTCCGAA

TCCAAAGCTAGCCAGGTGCAGCTGCAGGAGTCGGGCCCAGGACTGGTGAAC

CCTTCACAGACCCTGTCCCTCACCTGCACTGTCTCTGGTGGCTCCATCAGC

AGTGGTGGTTACTACTGGAGCTGGATCCGCCAGCACCCAGGGAAGGGCCTG

GAGTGGATTGGGTACATCTCTTACAGTGGGAGCACCTACTACAACCCCTCC

CTCAAGAGTCGAGTTACCATATCAGTAGACACATCTAAGAACCAGTTCTCC

CTGAAGCTGAGCTCTGTGACTGCCGCGGACACGGCCGTGTATTACTGTGCG

AGAGGTCGGACTTGGTTCGACCCCTGGGGCCANGGCACCCTGGTCACCGTC

TCCTCA

Clone 5 149-014-5 (VL-Linker-VH)
(SEQ ID NO: 63)
TCTTCTGAGCTGACTCAGGACCCTGCTGTGTCTGTGGCCTTGGGACAGACA

GTCAGGATCACATGCCAAGGAGACAGCCTCAGAAGCTATTATGCAAGCTGG

TACCAGCAGAAGCCAGGACAGGCCCCTGTACTTGTCATCTATGGTAAAAAC

AACCGGCCCTCAGGGATCCCAGACCGATTCTCTGGCTCCACCTCGGGAAAT

TTTGCTTCCTTGACCATCACGGGGGCTCAGGCGGAAGATGGGGCTGACTAT

TACTGTCACTCCCGGGACAGCAGTGGCAACCATCTGGTTTTCGGCGGGGGG

ACCAAGCTCACCGTCCTAGGTGAGGGTAAATCTTCCGGATCTGGTTCCGAA

TCCAAAGCTAGCGAGGTGCAGCTGGTGCAGTCTGGGGCAGAGGTGAAAAAG

CCGGGGGAGTCTCTGAAGATCTCCTGTAAGGGTTCTGGATACAGCTTTACC

AGCTACTGGATCGGCTGGGTGCGCCAGATGCCCGGGAAAGGCCTGGAGTGG

ATGGGGATCATCTATCCTGGTGACTCTGATACCAGATACAGCCCGTCCTTC

CAAGGCCAGGTCACCATCTCAGCCGACAAGTCCATCAGCACCGCCTACCTG

CAGTGGAGCAGCCTGAAGGCCTCGGACACCGCCATGTATTACTGTGCGAGA

CGTGCTAGGGGTGCTTTTGATATCTGGGGCCAAGGAACCCTGGTCACCGTC

TCCTCA

Clone 6 149-014-6 (VL-linker-VH)
(SEQ ID NO: 64)
CAGTCTGTGCTGACTCAGCCACCCTCAGCGTCTGGGACCCCCGGGCAGAGG

GTCACCATCTCTTGTTCTGGAAGCAGCTCCAACATCGGAAGTAATTATGTA

TCCTGGTACCAGCAGCTCCCAGGAACAGCCCCCAAACTCCTCATTTATGAC

AATAATAAGCGACCCTCAGGGATTCCTGACCGATTCTCTGGCTCCAAGTCT

GGCACGTCAGCCACCCTGGGCATCACCGGACTCCAGACTGGGGACGAGGCC

GATTATTACTGCGGAACATGGGATAGCAGCCTGAGTGCTCTTTATGTCTTC

GGAGCTGGGACCAAGCTGACCGTCCTAGGTGAGGGTAAATCTTCCGGATCT

GGTTCCGAATCCAAAGCTAGCCAGGTGCAGCTGCAGGAGTCGGGCCCAGGA

CTGGTGAAGCCTTCGGAGACCCTGTCCCTCACGTGCAGTGTCTCTGGTGGC

TCCACCAGTAGTTACTACTGGAGCTGGATCCGGCAGCCCCCAGGGAAGGGG

CTGGAGTGGATTGGGTATATCTCGAACAGTGGGAGCACCAACTACAACCCC

TCCCTCAAGAGTCGAGTCACCATGTCAATAGACACGTCCAACAACCAGTTC

TCCCTGAAGTTGAGTTCTGTGACCGCCGCAGACACGGCCGTCTATTACTGT

GCGAGCCACTTGGGAGCTACCTGGCGGTGGGGCCAGGGAACCCTGGTCACC

GTCTCCTCA

Clone 11 149-014-11 VH-linker-VK
(SEQ ID NO: 65)
GAGGTGCAGCTGGTGGAGTCTGGGGGAGGCGTGGTCCAGCCTGGGAGGTCC

CTGAGACTCTCCTGTGCAGCCACTGGATTCACCTTCAGTAACTATGGCATA

CACTGGGTCCGCCAGGCTCCAGGCAAGGGGCTGGAGTGGGTGGCAGTTACA

TCATATGATGGAAGTAATAAATATTATGCAGACTCCGTGAAGGGCCGATTC

ACCATCTCCAGAGACAATTCCAAGAACACGCTGTATCTGCAAATGAACAGC

CTGAGAGTTGAGGACACGGCTGTGTATTACTGTGCCAAAGATCGTGGTTAC

TACACATACGTATTTGACTATTGGGGCCGGGGAACCCTGGTCACCGTCTCC

TCAGGCGAGGGTAAATCTTCCGGATCTGGTTCCGAATCCAAAGCTAGCGAT

GTTGTGATGACCCAGAGTCCACTCTCCCTGCCCGTCACCCCTGGAGAGCCG

GCCGCCATCTCCTGCAGGTCTAGTCAGAGCCTCCTGCATAGTAATGGATAC

AACTATTTGGATTGGTACCTGCAGAAGCCAGGGCAGTCTCCACAGCTCCTG

ATCTATTTGGGTTCTAATCGGGCCTCCGGGGTCCCTGACAGGTTCAGTGGC

AGTGGATCAGGCACAGATTTTACACTGAAAATCAGCAGAGTGGAGGCTGAG

GATGTTGGGGTTTATTACTGCATGCAAGCTGTACAAACTGTCGAC

Clone 13 149-014-13 VH only
(SEQ ID NO: 66)
GAAGTGCAGCTGCTGGAAAGCGGCGGTGGTCTGGTTCAGCCGGGTGGCAGC

CTGCGTCTGAGCTGTGCGGCGAGCGGCTTTACCTTTAGCAGCGATTTAATG

AGCTGGGTGCGTCAGGCACCGGGCAAAGGCCTGGAATGGGTGAGCGCGATT

AGCGGCAGCGGCGGCAGCACCTATTATGCGGATAGCGTGAAAGGCCGTTTT

ACCATTAGCCGTGATAACAGCAAAAACACCCTGTATCTGCAGATGAACAGC

CTGCGTGCGGAAGATACCGCGGTGTATTATTGCGCGAAAAATGAGGTTATC

TTTGATTATTGGGGCCAGGGCACCCTGGTTACCGTTAGCAGCGCGAGCACC

AAAGGCCTGAGCATGTTTGATTATTGGGGCCAGGGCACCAAAGTGGAAATT

AAA

Clone 14 149-014-14 (VK-Linker-VH)
(SEQ ID NO: 67)
GATGTTGTGATGACCCAGTCTCCACTCTCCCTGCCCGCCACCCTTGGACAG

CCGGCCTCCATCTCCTGCAGGTCTAGTCAAAGCCTCGTATACACTGATGGA

AACACCTACTTGAATTGGTTTCAGCAGAGGCCCGGCCAATCTCCAAGGCGC

CTAATTTATAAGGTTTCTAACCGGGACTCTGGGGTCCCAGACAGATTCAGC

GGCAGTGGGTCAGGCACTCATTTCACACTGAAAATCAGCAGGGTGGAGGCT

GAGGATGTTGGAGTTTATTACTGCATGCAAGGTACACACTGGCCTCCGACG

TTCGGCCAAGGGACCAAGGTGGAAATCAAAGAGGGTAAATCTTCCGGATCT

GGTTCCGAATCCAAAGCTAGCGAGGTGCAGCTGGTGCAGTCTGGGGCTGAG

GTGAAGAAGCCTGGGGCCTCAGTGAAGGTCTCCTGCAAGGCTTCTGGAGGC

ACCTTCAGCAGCTATGCTATCAGCTGGGTGCGACAGGCCCCTGGACAAGGG

CTTGAGTGGATGGGAGGGATCATCCCTATCTTTGGTACAGCAAACTACGCA

CAGAAGTTCCAGGGCAGAGTCACGATTACCGCGGACGAATCCACGAGCACA

GCCTACATGGAGCTGAGCAGCCTGAGATCTGAGGACACGGCCGTGTATTAC

TGTGCGAGTAGCGGGGTTGACTACTGGGGCCAGGGCACCCTGGTCACCGTC

TCCTCA

VHH Phage Display Library Screening

VHH Phage Display Library Screening

A panning and enrichment of the BZ348014 antigen against a VHH phage display library (Neoclone, LLC, Madison, WI) was also conducted in an identical manner to the human scFv phage display library screen. One unique binder was identified, clone 8.

Clone 8 149-014-VHH-2-8
(SEQ ID NO: 68)
GATGTGCAGCTGGTGGAGTCTGGGGGAGGCTTGGTGCAGCCTGGGGGGTCT

CTGAGACTCTCCTGTACAGCCTCTGGATTCACCTTCAGTAACTATGCCATG

AACTGGGTCCGCCAGGCTCCAGGAAAGGGGCTCGAGTGGGTCTCAGTTATT

TCAAGTAGTGGTAGTCGCCGAAACTATGCAGACTCCGTGAAAGGCCGATTC

ACCATCTCCAGAGACAACGCCAAGAGCACGCTGTATCTGCAAATGAACAGC

CTGAAACCTGAGGATACGGCCGTATATTACTGTGCAAAGGTTCGAGATGCA

GGCTACTACAGATGGAACCTGAATGACCTTGATTACCGGGGCCAGGGGACC

CAGGTCACCGTCTCCTCA

The above Figures and disclosure are intended to be illustrative and not exhaustive. This description will suggest many variations and alternatives to one of ordinary skill in the art. All such variations and alternatives are intended to be encompassed within the scope of the attached claims. Those familiar with the art may recognize other equivalents to the specific embodiments described herein which equivalents are also intended to be encompassed by the attached claims.

REFERENCES

1. Hynes R O. Integrins: versatility, modulation, and signaling in cell adhesion. Cell. 1992 Apr. 3; 69 (1): 11-25.
2. Bajic G, Yatime L, Sim R B, Vorup-Jensen T, Andersen G R. Structural insight on the recognition of surface-bound opsonins by the integrin I domain of complement receptor 3. PNAS. 2013; 110:16426-16431.
3. Dong X, et al. (2017) Force interacts with macromolecular structure in activation of TGF-β. Nature 542:55-59.
4. Luo B-H, Carman C V, Springer T A (2007) Structural basis of integrin regulation and signaling. Annu Rev Immunol 25:619-647.
5. Chen J, Salas A, Springer T A (2003) Bistable regulation of integrin adhesiveness by a bipolar metal ion cluster. Nat Struct Biol 10:995-1001.
6. Su Y, et al. (2016) Relating conformation to function in integrin α5β1. Proc Natl Acad Sci USA 113: E3872-E3881.
7. Xia W, Springer T A (2014) Metal ion and ligand binding of integrin $α_5β_1$. Proc Natl Acad Sci USA 111:17863-17868.
8. Sen M, Springer T A (2016) Leukocyte integrin αLβ2 headpiece structures: The αI domain, the pocket for the internal ligand, and concerted movements of its loops. Proc Natl Acad Sci USA 113:2940-2945.
9. Xu S, Wang J, Wang J H, Springer T A (2017) Distinct recognition of complement iC3b by integrins αXβ2 and αMβ2. Proc Natl Acad Sci USA 114:3403-3408.

10. Xie C, et al. (2010) Structure of an integrin with an aI domain, complement receptor type 4. EMBO J 29:666-679.
11. Takagi J, Erickson H P, Springer T A (2001)C-terminal opening mimics 'inside-out' activation of integrin $\alpha_5\beta_1$. Nat Struct Biol 8:412-416.
12. Zhang K, Chen J, The regulation of integrin function by divalent cations, Cell Adh Migr. 2012 January-Feb; 6 (1): 20-9.
13. Chen J, Yang W, Kim M, Carman C V, Springer T A Regulation of outside—in signaling and affinity by the beta2 I domain of integrin alphaLbeta2, Proc Natl Acad Sci USA. 2006 Aug. 29; 103 (35): 13062-7. Epub 2006 Aug. 18.
14. Humphries, J. D., Schofield, N. R., Mostafavi-Pour, Z., Green, L. J., Garratt, A. N., Mould, A. P. and Humphries, M. J. (2005). Dual functionality of the anti-beta1 integrin antibody, 12G10, exemplifies agonistic signalling from the ligand binding pocket of integrin adhesion receptors. J. Biol. Chem. 280, 10234-10243.
15. Directed evolution to probe protein allostery and integrin I domains of 200,000-fold higher affinity. Jin M, Song G, Carman C V, Kim Y S, Astrof N S, Shimaoka M, Wittrup D K, Springer T A. Proc. Natl. Acad. Sci. U.S.A. 103 5758-5763 (2006).
16. Xiong J P, Li R, Essafi M, Stehle T, Arnaout M A. An isoleucine-based allosteric switch controls affinity and shape shifting in integrin CD11b A-domain. J Biol Chem. 2000; 275:38762-38767.
17. Li R, Rieu P, Griffith D L, Scott D, Arnaout M A. Two functional states of the CD11b A-domain: correlations with key features of two Mn2+-complexed crystal structures. J Cell Biol 1998; 143 (6): 1523-1534.
18. Chafen Lu, Motomu Shimaoka, Qun Zang, Junichi Takagi, and Timothy A. Springer, Locking in alternate conformations of the integrin $\alpha L\beta 2$ I domain with disulfide bonds reveals functional relationships among integrin domains, PNAS Feb. 27, 2001 98 (5) 2393-2398.
19. Luo B H, Takagi J, Springer T A, Locking the beta3 integrin I-like domain into high and low affinity conformations with disulfides, J Biol Chem. 2004 Mar. 12; 279 (11): 10215-21. Epub 2003 Dec. 16.
20. Luo B H, Karanicolas J, Harmacek L D, Baker D, Springer T A, Rationally designed integrin beta3 mutants stabilized in the high affinity conformation. J Biol Chem. 2009 Feb. 6; 284 (6): 3917-24. doi: 10.1074/jbc.M806312200. Epub 2008 Nov. 19.
21. Gupta V., Gylling A., Alonso, J.-L., Sugimori T., Ianakiev, P., Xiong J.-P. and Arnaout M. A., The β-tail domain (BTD) regulates physiologic ligand binding to integrin CD11b/CD18, Blood, 2007 Apr. 15; 109 (8): 3513-20. Epub 2006 Dec. 14 (DOI 10.1182/blood-2005-11-056689).
22. Shimaoka M, Lu C, Palframan R T, von Andrian U H, McCormack A, Takagi J, Springer T A. Reversibly locking a protein fold in an active conformation with a disulfide bond: integrin alphaL I domains with high affinity and antagonist activity in vivo. Proc Natl Acad Sci USA. 2001 May 22; 98 (11): 6009-14. Epub 2001 May 15.
23. Shimaoka M, Lu C, Salas A, Xiao T, Takagi J, Springer T A. Stabilizing the integrin alpha M inserted domain in alternative conformations with a range of engineered disulfide bonds. Proc Natl Acad Sci USA. 2002 Dec. 24; 99 (26): 16737-41. Epub 2002 Dec. 4.
24. Arnaout M A, Biology and structure of leukocyte @ 2 integrins and their role in inflammation. F1000Res. 2016 Oct. 4; 5. pii: F1000 Faculty Rev-2433.
25. Mahalingam B, Ajroud K, Alonso J L, Anand S, Adair B D, Horenstein A L, Malavasi F, Xiong J P, Arnaout M A. Stable coordination of the inhibitory Ca2+ ion at the metal ion-dependent adhesion site in integrin CD11b/CD18 by an antibody-derived ligand aspartate: implications for integrin regulation and structure-based drug design. J Immunol. 2011 Dec. 15; 187 (12): 6393-401.
26. Lahti M, Bligt E, Niskanen H, Parkash V, Brandt A M, Jokinen J, Patrikainen P, Käpylä J, Heino J, Salminen T A. Structure of collagen receptor integrin $\alpha(1)$I domain carrying the activating mutation E317A. J Biol Chem. 2011 Dec. 16; 286 (50): 43343-51.
27. Barton S J, Travis M A, Askari J A, Buckley P A, Craig S E, Humphries M J, Mould A P. Novel activating and inactivating mutations in the integrin beta 1 subunit A domain. Biochem J. 2004 Jun. 1; 380 (Pt 2): 401-7.
28. McCleverty C J, Liddington R C. Engineered allosteric mutants of the integrin alphaMbeta2 I domain: structural and functional studies. Biochem J. 2003 May 15; 372 (Pt 1): 121-7.
29. Hu X, Kang S, Lefort C, Kim M, Jin M M. Combinatorial libraries against libraries for selecting neoepitope activation-specific antibodies. Proc Natl Acad Sci USA. 2010 Apr. 6; 107 (14): 6252-7. doi: 10.1073/pnas.0914358107. Epub 2010 Mar. 22.
30. Shimaoka M, Kim M, Cohen E H, Yang W, Astrof N, Peer D, Salas A, Ferrand A, Springer T A. AL-57, a ligand-mimetic antibody to integrin LFA-1, reveals chemokine-induced affinity up-regulation in lymphocytes. Proc Natl Acad Sci USA. 2006 Sep. 19; 103 (38): 13991-6. Epub 2006 Sep. 8.
31. Samy K P, Anderson D J, Lo D J, Mulvihill M S, Song M, Farris A B, Parker B S, MacDonald A L, Lu C, Springer T A, Kachlany S C, Reimann K A, How T, Leopardi F V, Franke K S, Williams K D, Collins B H, Kirk A D. Selective Targeting of High-Affinity LFA-1 Does Not Augment Costimulation Blockade in a Nonhuman Primate Renal Transplantation Model. Am J Transplant. 2017 May; 17 (5): 1193-1203. doi: 10.1111/ajt.14141. Epub 2017 Jan. 27.
32. Zhengli Wang, Aye Myat Myat Thinn, and Jieqing Zhu A pivotal role for a conserved bulky residue at the α1-helix of the αI integrin domain in ligand binding, J Biol Chem. 2017 Dec. 15; 292 (50): 20756-20768.
33. Zhang C., Liu J., Jiang X., Haydar N., Zhang C., Shan H., and Zhu J. (2013) Modulation of integrin activation and signaling by α1/α1'-helix unbending at the junction. J. Cell Sci. 126, 5735-5747.
34. Chin J W, Expanding and reprogramming the genetic code of cells and animals. Annu Rev Biochem. 2014; 83:379-408. doi: 10.1146/annurev-biochem-060713-035737. Epub 2014 Feb. 10.
35. Suchanek M, Radzikowska A, Thiele C. Photo-leucine and photo-methionine allow identification of protein-protein interactions in living cells. Nat Methods. 2005 April; 2 (4): 261-7. Epub 2005 Mar. 23.

The invention claimed is:

1. A modified integrin polypeptide comprising at least one amino acid substitution in a metal ion binding site, and at least one conformation specific amino acid substitution selected from the group consisting of F156A, F275S, F275R, F302L and F302W of a wild type integrin polypeptide;
   wherein the wild type integrin polypeptide comprises SEQ ID NO: 1; and
   wherein the metal ion binding site is selected from the group consisting of metal ion dependent adhesion site (MIDAS), adjacent to MIDAS (ADMIDAS) and ligand-associated metal binding site (LIMBS)/synergistic metal binding site (SyMBS).

2. The modified integrin polypeptide according to claim 1, wherein the at least one amino acid substitution in the metal ion binding site is selected from glutamate (E), aspartate (D), serine(S), or threonine (T) in the wild type integrin polypeptide.

3. The modified integrin polypeptide according to claim 2, wherein the at least one amino acid substitution in the metal ion binding site is replacing the amino acid with an amino selected from alanine (A), glycine (G), leucine (L), isoleucine (I) or valine (V).

4. The modified integrin polypeptide according to claim 1, wherein the modified integrin polypeptide further comprises additional conformation specific amino acid substitutions.

5. The modified integrin polypeptide according to claim 4, wherein the additional conformation specific amino acid substitutions are replacing conformation specific amino acids with cysteine residues to form a disulfide bond.

6. The modified integrin polypeptide according to claim 1, wherein the at least one amino acid substitution in the metal ion binding site is selected from the group consisting of D140, D242, S142, S144 and T209 of SEQ ID NO:1.

7. The modified integrin polypeptide according to claim 6, wherein the at least one amino acid substitution in the metal ion binding site is D140A of SEQ ID NO: 1.

8. The modified integrin polypeptide according to claim 6, wherein the at least one amino acid substitution in the metal ion binding site is D140A of SEQ ID NO: 1, and the conformation specific amino acid substitution is a plurality of substitutions selected from F156A, 1316G, 1316A, F275S, F275R, F302L and F302W of SEQ ID NO: 1.

9. The modified integrin polypeptide according to claim 6, wherein the at least one amino acid substitution in the metal ion binding site is a plurality of substitutions selected from D140A, S142A, S144A and T209A of SEQ ID NO: 1.

* * * * *

UNITED STATES PATENT AND TRADEMARK OFFICE
CERTIFICATE OF CORRECTION

| | |
|---|---|
| PATENT NO. | : 12,291,562 B2 |
| APPLICATION NO. | : 17/599625 |
| DATED | : May 6, 2025 |
| INVENTOR(S) | : Vineet Gupta |

Page 1 of 1

It is certified that error appears in the above-identified patent and that said Letters Patent is hereby corrected as shown below:

In the Claims

Column 251, Line 14, delete "1316G, 1316A" and insert therefore --I316G, I316A--

Signed and Sealed this
Thirtieth Day of September, 2025

John A. Squires
*Director of the United States Patent and Trademark Office*